US012291714B2

(12) United States Patent
Bovet et al.

(10) Patent No.: US 12,291,714 B2
(45) Date of Patent: May 6, 2025

(54) MODULATING REDUCING SUGAR CONTENT IN A PLANT (INV)

(71) Applicant: PHILIP MORRIS PRODUCTS S.A., Neuchatel (CH)

(72) Inventors: Lucien Bovet, La Chaux-de-Fonds (CH); Aurore Hilfiker, Salavaux (CH)

(73) Assignee: Philip Morris Products S.A., Neuchatel (CH)

( * ) Notice: Subject to any disclaimer, the term of this patent is extended or adjusted under 35 U.S.C. 154(b) by 186 days.

(21) Appl. No.: 17/765,748

(22) PCT Filed: Sep. 28, 2020

(86) PCT No.: PCT/EP2020/077048
§ 371 (c)(1),
(2) Date: Mar. 31, 2022

(87) PCT Pub. No.: WO2021/063860
PCT Pub. Date: Apr. 8, 2021

(65) Prior Publication Data
US 2022/0348944 A1   Nov. 3, 2022

(30) Foreign Application Priority Data

Oct. 1, 2019 (EP) .................... 19200865

(51) Int. Cl.
*C12N 15/82* (2006.01)
*C12N 9/26* (2006.01)

(52) U.S. Cl.
CPC ....... *C12N 15/8245* (2013.01); *C12N 9/2431* (2013.01); *C12N 15/8213* (2013.01); *C12N 15/8218* (2013.01); *C12Y 302/01026* (2013.01)

(58) Field of Classification Search
None
See application file for complete search history.

(56) References Cited

U.S. PATENT DOCUMENTS

| 9,045,766 | B2 | 6/2015 | Meade |
| 9,683,240 | B2 | 6/2017 | Bovet et al. |
| 10,501,732 | B2 | 12/2019 | Bovet |
| 10,513,698 | B2 | 12/2019 | Mathis |
| 2005/0120418 | A1* | 6/2005 | Fuerstenberg ........... A01H 1/00 435/6.15 |
| 2016/0037742 | A1* | 2/2016 | Mathis .................. C12N 15/01 435/417 |

FOREIGN PATENT DOCUMENTS

| CN | 105120656 | 12/2015 |
| CN | 105686070 | 6/2016 |
| RU | 2608500 | 1/2017 |
| RU | 2681497 | 3/2019 |
| RU | 2689719 | 5/2019 |
| WO | WO 2007/038566 | 4/2007 |
| WO | WO 2010/072210 | 7/2010 |
| WO | WO 2010/091018 | 8/2010 |
| WO | WO 2015/184007 | 12/2015 |

OTHER PUBLICATIONS

Elliott, Kathryn J., et al. "Isolation and characterization of fruit vacuolar invertase genes from two tomato species and temporal differences in mRNA levels during fruit ripening." Plant molecular biology 21 (1993): 515-524. (Year: 1993).*
Cheng, Lingtong, et al. "Genome-wide identification and analysis of the invertase gene family in tobacco (Nicotiana tabacum) reveals NtNINV10 participating the sugar metabolism." Frontiers in Plant Science 14 (2023): 1164296. (Year: 2023).*
Jutta Essmann, et al., RNA Interference-Mediated Repression of Cell Wall Invertase Impairs Defense in Source Leaves of Tobacco, Plant Physiology, vol. 147, Issue 3, Jul. 2008, pp. 1288-1299 (Year: 2008).*
PCT Search Report and Written Opinion for Application No. PCT/EP2020/077048 dated Oct. 14, 2020 (11 pages).
Extended European Search Report for Application No. 19200865.4 dated Feb. 14, 2020 (6 pages).
Database Geneseq [Online] May 31, 2007, "Potato Invertase Protein SEQ ID No. 19", XP00279249, retrieved from EBI Accession No. GSP:AFQ98211, Database accession no. AFQ98211 84.4% sequence identify to SEQ ID No. 8.
Essmann et al., "RNA Interference-Mediated Repression of Cell Wall Invertase Impairs Defense in Source Leaves of Tobacco", Plant Physiology, vol. 147, No. 3, May 23, 2008.
Office Action issued in China for Application No. 202080069448.2 dated Aug. 19, 2023 (11 pages). English translation included.
Tang Huang, "Starch and Sucrose Lyases in Tobaccos from Four Main Producing Areas in Sichuan Province and Gene Differential Expression Analysis Thereof", Chinese Master's Theses Full-text Database, Agricultural Science and Technology serials, pp. D047-352, Jul. 15, 2016.

(Continued)

*Primary Examiner* — Weihua Fan
(74) *Attorney, Agent, or Firm* — Mueting Raasch Group

(57) ABSTRACT

There is described herein a plant cell comprising: (i) a polynucleotide comprising, consisting or consisting essentially of a sequence having at least 81% sequence identity to SEQ ID NO: 5 (NtINV4-S) or at least 62% sequence identity to SEQ ID NO: 7 (NtINV4-T); (ii) a polypeptide encoded by the polynucleotide set forth in (i); (iii) a polypeptide comprising, consisting or consisting essentially of a sequence having at least 85% sequence identity to SEQ ID NO: 6 (NtINV4-S) or at least 85% sequence identity to SEQ ID NO: 8 (NtINV4-T); or (iv) a construct, vector or expression vector comprising the isolated polynucleotide set forth in (i), wherein said plant cell comprises at least one modification which modulates (a) the expression or activity of the polynucleotide or (b) the expression or activity of the polynucleotide the polypeptide, as compared to a control plant cell in which the expression or activity of the polynucleotide or polypeptide has not been modified.

18 Claims, 6 Drawing Sheets
Specification includes a Sequence Listing.

(56) References Cited

OTHER PUBLICATIONS

"Nicotiana tabacum cultivar TN90 unplaced genomic scaffold, Ntab-TN90 Ntab-TN90_scaffold92491, whole genome shotgun sequence", NCBI Reference Sequence: NW 015959542.1, NCBI, May 4, 2016.
"Nicotiana tomentosiformis unplaced genomic scaffold, Ntom_v01 Ntom_scaffold24298, whole genome shotgun sequence", NCBI Reference Sequence: NW_008903928.1, NCBI, Oct. 24, 2016.
Office Action issued in Russia for Application No. 2022111862/10 dated Oct. 16, 2024 (8 pages). English translation included.

\* cited by examiner

SEQUENCE LISTING

<160> NUMBER OF SEQ ID NOS: 33

<210> SEQ ID NO 1
<211> LENGTH: 4237
<212> TYPE: DNA
<213> ORGANISM: Nicotiana tabacum

<400> SEQUENCE: 1
atggcggaaa caacaatag cgttccttac acccaattac cggcggagga caataacacc    60
tccgttaatt ctccggccgg atgccggcta cgacccaaaa gagtgtcgtt tatagtatta   120

```
acagggctgg tggcagcttt gttactttt gtggcagtga aatatgggaa aaacgaggcg      180
gaggatgtga atccagggcc agtaccacca caagaaaccg tgtgcaatat gcttggttct      240
aatctaatgc cgctgaccag catgaagacg gtggcgcgtg gggtggcaga aggtgtctcc      300
gccaagtcac gcggtcgttt cttgggatta cggccgtttc catggaccaa acaaatgttg      360
gcttggcaaa gaacatcctt ccactttcaa cctaagaaga attggatgaa tggttagtaa      420 ttcttttct cttatgttat taattttcat aaatcaactt tattattatt attatacaat       480
aaatcaacat tgcttattga tgaattttaa cataaacccg ccttatgctt gacgagatta      540
actagaacta tatatacaat gaatgattat ctccattcca ttacataacc atgaattatg      600
tttcttaatt aattaaagat ttgacatgac attatatttc gtttatagtt taagaaaagc      660
tttgtattga tgtaaaagaa accattacag cttcgaatat gggatacctt gtcttttct       720 tttcctaaga tggatctttg attgcaagaa cagagtttga attactcagg aaacttattt      780 gcttattat tatttttga ggtgaacatt aatgatttat tcttatttgg catgtgttgg        840
attatttggc ttggattgcg ctgatcacgg aaattgcctg attcttttcg tcagatccta      900
atggtaaagt ccatatattt ctacttgtta ttgttgttgt tcttcttatt attatattat      960
tattgaaaat tatcgacata atcgggacct caaaacatac tagtcgtagc agttttaag      1020 tagacagatt gtcaatatga tgaagacagt tgttttcaga caattgcatg tgaattttct      1080
aggagcaaac acaaattcct agaatggtaa gcaacttcca ccctgtctgt tccaattata     1140
acctcgctac ttttgatcca cttaatctta ttcaaccaac agtggatcac ttatttaatt     1200
atatgtgacc tagtttattg agacattttt acattaagcc ctttcgtatt tacacttcaa     1260
tatgcatcat acaaaaaaaa atgtacttca aagttatacg ttatattaat ttctaactcc     1320 aattttaaa aaaaaatata ttttaggtcc cttattctac aaaggatggt accatttgtt      1380
ctatcaatac aatccagagg ctgcagtatg gggaaatatt gtatggggac atgcagtttc     1440
aagagactta attcactggc aacaccttcc agttgctatg gttgcggatc aatggtacga     1500
cattaatggt gtatggaccg gatccgcaac cattttaccc gatggtaaac tcgtcatgtt     1560
gtatactggg tcaaccaacg agtcagtaca ggttcaaaat ttagcgtacc cggctgaccc     1620
atcggatcct ctcctaataa aatgggtcaa gtatgagggc aacccggttc ttgtaccacc     1680
acccggaatt gctgctaagg atttccgtga ccccaccact gcatgaccca caccacaagg     1740
caaatggcgg attactattg gttcaaaagt taataaaact ggaatttcat tggtctatga     1800
cactattgat tttaagaatt ttgagttgct ggatggggtg ctccatggtg tatcgggtac     1860
gggtatgtgg gaatgtgtgg atttttaccc ggtttcgaaa gttgttgaaa atgggcttga     1920
cacttcagat aatgggcctg cagtaaaaca tgtgttaaag tccagtcttg atgatgatag     1980
aaatgattat tatgcacttg gaacttatga tgctgtggct ggaaaatggg ttcctgataa     2040
tcccactatt gatgttggta ttggattaag atatgattat ggaaatttt atgcatcaaa      2100 aacattttat gaccaagaga aaaagagaag agtcctttgg gcttggatta ctgaaagtga     2160
tagtgaagct gctgatattt gcaaaggttg ggcatcactt caggtacaat tcaattgtgt     2220
caagctagcg cttgcacata gatttagttg aaacctaaaa aatgagtatt tgaaattccg     2280
tagaaaaata attttgaaa gttgaagttg tgtttgaata tgcattttat ttgaaaaaaa      2340
aaacagttct aattttatga gaagaaaaa ttcacctaaa aactgcccta aaccagattt      2400
taggaacttg aaaaaaaaat aaacttttc aaaaactgat tatattctat gaacaaacaa      2460
```

-continued

```
tattatcaaa aatctatttt ttttttgcca aaatctatgg ccaaacagga gctaatttcc    2520 tttattttt ttttcaaact tcatgtcata tttgaatttt ggtctcattt aacactttgg    2580
taacgtgtga tgtaacacag cccattccaa ggactataaa atatgacaag aagacaggaa    2640
gcaatataat tacttggcca gtggcagagg ttgagaattt gagatttaac agcaaggaat    2700
tcgacaaggt ggaggtcaag ccaggaaatg ttgttccact agaagttggc actgccactc    2760
aggtttgttc attaaattta gcttatatac actgactgcc taaaagaatt ttttgacat    2820 tattagtgta ttttaagcta ttatagcacg taacatgcta atgctcgaat aagtttaact    2880
tactataact tgaattgttg atgattacag ttggacataa tggctgagtt tgaagtagac    2940
cctaaggtct tggagaaatt agaaggaagt aatgctacat atgagtgcag aagcagcggt    3000
ggatctgctg aacgtggtgc cttaggacca tttggtttat tggttttaac agataaggga    3060
ttgtccgagc aaactccaat ttacttctac attgctaaag acgctgctgg aaatttcacc    3120
acattcttct gcaatgatct taccaggttc taatttctcc tctcttgcat tttcatctca    3180
tcaatgaagt tttagccctt cacccctcc cccaaaacca aactaataaa ttggagaaaa    3240
ccctttattg gttcagtgct taatagcagt acggaattca ggattttaag tcagtgggtt    3300
ctgcgatcta tatatata ataatatttt tctgcacata catatagtcc gagctagaca    3360
tagtgagttc cgttgaacct gttgcattta gtctgagtcc gccactgctt aagcacatcc    3420
ttctcataac aaccgagctt ccaaaaact taagtatttc tcatgtccat acttttattc    3480
atgtttgaaa atgaagtcac attttgtttt ataaccgaaa atcccgagg gcaagtggcc    3540 agtacatggt tcgaagctca atggacactg caccgcccc tttatcgtgc tccacttaaa    3600
tactaagatt ttgtccgtgg cagggtttca accaatcacg tacgtttaac tcatatatta    3660
ggaatagctt ttaccactag accaaaactc ggggacaatg tatgaagccg atatttgtt    3720 gcaattcttt ttaaattaaa atggggacaa gatccgagac aaatcttgaa aatgcattac    3780
gaagtattgt taagtaagta tgaaaatggt gattctcatc tttttacttc cttttttagg    3840
tcatctgaag caacagatgt tcgcaaacta atctacggaa gcacagttcc agtcctccaa    3900
ggagagaagc tttctctaag aacactggta atatcccctt tttctttctt aatttcttaa    3960
tccaaattct taattagtgc ttgttttcct ttgtgcgtat aattaagttt actaagtatc    4020
aattaatggg gtattttgt caatgtaata ggtggatcat tcaatagtag aaagttttgc    4080
acaaaatgga aggacagcaa taacatcaag gttatatcca acaaaggcaa tatatgaaga    4140
tgctaagctc tacttgttta acaatgctac agatgttacc attactgcct cggtcaagat    4200
ttggcaaata cattctgcaa atatacaatc tagttaa                            4237
```

<210> SEQ ID NO 2
<211> LENGTH: 649
<212> TYPE: PRT
<213> ORGANISM: Nicotiana tabacum

<400> SEQUENCE: 2

```
Met Ala Glu Thr Asn Asn Ser Val Pro Tyr Thr Gln Leu Pro Ala Glu
1               5                   10                  15

Asp Asn Asn Thr Ser Val Asn Ser Pro Ala Gly Cys Arg Leu Arg Pro
            20                  25                  30

Lys Arg Val Ser Phe Ile Val Leu Thr Gly Leu Val Ala Ala Leu Leu
        35                  40                  45

Leu Phe Val Ala Val Lys Tyr Gly Lys Asn Glu Ala Glu Asp Val Asn
    50                  55                  60
```

-continued

```
Pro Gly Pro Val Pro Pro Gln Glu Thr Val Cys Asn Met Leu Gly Ser
 65                  70                  75                  80

Asn Leu Met Pro Leu Thr Ser Met Lys Thr Val Ala Arg Gly Val Ala
                 85                  90                  95

Glu Gly Val Ser Ala Lys Ser Arg Gly Arg Phe Leu Gly Leu Arg Pro
            100                 105                 110

Phe Pro Trp Thr Lys Gln Met Leu Ala Trp Gln Arg Thr Ser Phe His
        115                 120                 125

Phe Gln Pro Lys Lys Asn Trp Met Asn Asp Pro Asn Gly Pro Leu Phe
    130                 135                 140

Tyr Lys Gly Trp Tyr His Leu Phe Tyr Gln Tyr Asn Pro Glu Ala Ala
145                 150                 155                 160

Val Trp Gly Asn Ile Val Trp Gly His Ala Val Ser Arg Asp Leu Ile
                165                 170                 175

His Trp Gln His Leu Pro Val Ala Met Val Ala Asp Gln Trp Tyr Asp
            180                 185                 190

Ile Asn Gly Val Trp Thr Gly Ser Ala Thr Ile Leu Pro Asp Gly Lys
        195                 200                 205

Leu Val Met Leu Tyr Thr Gly Ser Thr Asn Glu Ser Val Gln Val Gln
    210                 215                 220

Asn Leu Ala Tyr Pro Ala Asp Pro Ser Asp Pro Leu Leu Ile Lys Trp
225                 230                 235                 240

Val Lys Tyr Glu Gly Asn Pro Val Leu Val Pro Pro Gly Ile Ala
                245                 250                 255

Ala Lys Asp Phe Arg Asp Pro Thr Thr Ala Trp Thr Thr Pro Gln Gly
            260                 265                 270

Lys Trp Arg Ile Thr Ile Gly Ser Lys Val Asn Lys Thr Gly Ile Ser
        275                 280                 285

Leu Val Tyr Asp Thr Ile Asp Phe Lys Asn Phe Glu Leu Leu Asp Gly
    290                 295                 300

Val Leu His Gly Val Ser Gly Thr Gly Met Trp Glu Cys Val Asp Phe
305                 310                 315                 320

Tyr Pro Val Ser Lys Val Val Glu Asn Gly Leu Asp Thr Ser Asp Asn
                325                 330                 335

Gly Pro Ala Val Lys His Val Leu Lys Ser Ser Leu Asp Asp Asp Arg
            340                 345                 350

Asn Asp Tyr Tyr Ala Leu Gly Thr Tyr Asp Ala Val Ala Gly Lys Trp
        355                 360                 365

Val Pro Asp Asn Pro Thr Ile Asp Val Gly Ile Gly Leu Arg Tyr Asp
    370                 375                 380

Tyr Gly Asn Phe Tyr Ala Ser Lys Thr Phe Tyr Asp Gln Glu Lys Lys
385                 390                 395                 400

Arg Arg Val Leu Trp Ala Trp Ile Thr Glu Ser Asp Ser Glu Ala Ala
                405                 410                 415

Asp Ile Cys Lys Gly Trp Ala Ser Leu Gln Pro Ile Pro Arg Thr Ile
            420                 425                 430

Lys Tyr Asp Lys Lys Thr Gly Ser Asn Ile Ile Thr Trp Pro Val Ala
        435                 440                 445

Glu Val Glu Asn Leu Arg Phe Asn Ser Lys Glu Phe Asp Lys Val Glu
    450                 455                 460

Val Lys Pro Gly Asn Val Val Pro Leu Glu Val Gly Thr Ala Thr Gln
465                 470                 475                 480
```

-continued

```
Leu Asp Ile Met Ala Glu Phe Glu Val Asp Pro Lys Val Leu Glu Lys
            485                 490                 495

Leu Glu Gly Ser Asn Ala Thr Tyr Glu Cys Arg Ser Ser Gly Gly Ser
        500                 505                 510

Ala Glu Arg Gly Ala Leu Gly Pro Phe Gly Leu Leu Val Leu Thr Asp
        515                 520                 525

Lys Gly Leu Ser Glu Gln Thr Pro Ile Tyr Phe Tyr Ile Ala Lys Asp
        530                 535                 540

Ala Ala Gly Asn Phe Thr Thr Phe Phe Cys Asn Asp Leu Thr Arg Ser
545                 550                 555                 560

Ser Glu Ala Thr Asp Val Arg Lys Leu Ile Tyr Gly Ser Thr Val Pro
                565                 570                 575

Val Leu Gln Gly Glu Lys Leu Ser Leu Arg Thr Leu Val Asp His Ser
            580                 585                 590

Ile Val Glu Ser Phe Ala Gln Asn Gly Arg Thr Ala Ile Thr Ser Arg
        595                 600                 605

Leu Tyr Pro Thr Lys Ala Ile Tyr Glu Asp Ala Lys Leu Tyr Leu Phe
        610                 615                 620

Asn Asn Ala Thr Asp Val Thr Ile Thr Ala Ser Val Lys Ile Trp Gln
625                 630                 635                 640

Ile His Ser Ala Asn Ile Gln Ser Ser
                645

<210> SEQ ID NO 3
<211> LENGTH: 5883
<212> TYPE: DNA
<213> ORGANISM: Nicotiana tabacum

<400> SEQUENCE: 3
atggcggaaa caaacaatag cgttccttac acccaattac cggcggagga caataacacc      60
tccagtaatt ctccggccaa atgccggcga cgacccaaaa gagtgtcgtt catagtatta     120
acagggctgg tggcagcttt gttacttttt gtggcagtga aatatgggaa taacgaggcg     180
gaggatgtaa atccagggcc agtaccacca caagaaaccg tgtgtaacat gcttggttct     240
aatctaatgc cgctgaccac catgaggacg gtggcgcgtg gggtggcaga aggtgtctcc     300
gccaagtcac gcggtcgttt cttgggatta cggccgtttc catggaccaa acaaatgttg     360
gcttggcaaa gaacatcctt ccactttcaa cctaagaaga attggatgaa tggttagtaa     420
ttctttttct cttatgttat tttcataaat cagctttgtt tttattaaac aataaatcaa     480
cagcttattg ataattttaa acataaaacc gccttatgct tgacgagatt aactagaact     540
ttatgtacaa tgaatggtta tctccattcc attacatgcc catgaatttt atgtgtctta     600
atttaaagat tgacaggac attacattac gtttatagtt taagaaaagc ttggtattga     660
tataaaaaaa accattacag cttcgaatat gggataccst tgtcttttct ttgcctaaga     720
tggatctttg attgcaagaa cagagtttga attactcagg aaaaatatga atcgttttg      780 gaacttattt gcttgtttat tattttttga ggtgaacatt aatgatttat tcttatttgg     840
catgtgttgg attctttggc tttggactgc gttgctcacg gaaattaccct gattctgttc     900 gtcagatcct aatggtaagt ccatattttc tgccggtatt attattatta ttattgttat     960
tgttattatt attattatta ttattaattt attttgatat attggaaacc atcgacaaaa    1020
cggggacctc aaaacatact agtcggggta gtttgtaagt agacagattg acaatatgat    1080
gaagacagtt gtctttagac aattgcatgt gaattttgta ggagcaaaca caaattccta    1140
```

```
gaatggtata caacttcaat cctgtctgtc caattataac ctcgctactt tgatccact    1200 acacctttt cgatcaacag gggatcactt atttaattat acggaacct ttatataaca     1260 atcatatttg ttcccgtatt ttttaggttt tatattgagt ggttgttatg caaatattac   1320
aggatttgac gttaaatat tttttggtt gttatagata aaattatct ataaataaat      1380 aatcattcct ttttcatgt tacatataaa aaataaggaa attatttaaa tttaaaatct    1440
cacaagctat gcatatttca ctaattaaat attaaagaaa gttaatacat tattaataaa   1500
ttcataacta aaatataaa gatttaaact ctaaggcaga cattttaagg ctaccaaaaa    1560
aataattttt ttcaagattg atggaagtgg aacaactttg taattgtagc ttgtttcgta   1620
gatttcattc tcttactagc gatataacac ttgaattggc aaagatccgt gtctaaattt   1680
tcagcaaaaa ggtatccaat agttttcct tgaatacaat ctaagagttt aaccgttaaa    1740
ttttctatcc aagtattttt taaatttatc caataaaaaa gatatcatgt gcaaatctat   1800
aaatcttata ttttatgcaa gatagaaact ttatttattt ttagaattat tattagcaat   1860
cttaaagatt ttatatggct gttatagagg ggtaattta caaaaagcgt tctgctataa    1920
atatggttgt tgctgttata ggtaaaaagt tgttataaaa ttgttatga aagtcacttt    1980 actttatttt ttaactgaaa agtcactata ctttgcacat tgtaactcaa aagtcaatca   2040
acacttttag ggcgttatta aacattattt ttcatatttc ttttcagccc aaccatttaa   2100
aaaataaaaa aaaatattta aatcatgact cgacggttcc atgacctgac ccatttctc    2160 ttatttatgt tataaaaaac ataaatatta ctttgttgta gtgtattata ttggttctca   2220
atatagttat actaaatgta tacattggtt taagcaaagt attaaataga gaataaggaa   2280
ttaatcttaa caaactagag gagttagatt tgaaactgaa acaagaaaat tagtagcgtt   2340
gaagtgaaaa aaaataaaaa ggaggaagaa aaaataaaaa aagtatttat gcttgaaatt   2400
ttgactgaga atattaata taagagtaaa ttaaaagaca atatccttga tgtttagaa     2460 caagaacgcg catttagta aagataatgt tactagacga ccattttag tcgaactaat     2520 ttaatacttt gcttaaatca atatgttgaa aatcaagaca attaacagta aagtaatatt   2580 tacgttttt tgtaacaaaa ataagagagt gggtcgagtt aaagagcggg ttgagtcacg    2640
gtttaaatgg gtatttttt attgtttaaa tgattgagtt aaaaaaata tgaaaaaaa      2700 aatttaatat ggcctaaatg tattgagtga cttttgagtt acaatgtgta aagtatgatg   2760
actttccttt tacaaaacaa agtaaagtga ctttcataaa caattttcat tagttcaatg   2820
acttctgaga aatggactcc ttaaaaaatt gattctgaag aaaacttggt ttttacggtg   2880
aatgactgtt atatatgaat gttgttatcg aaaggtctga ctgtatgtga cctagtttat   2940
tgagacgttt ttacattaaa gcccttcgt atttacactt caatatgcat catacaaaaa    3000
atatgtgctt cataattata cattacattc atttctaact ccacttttac aaaaaatatt   3060
ttaggtccat tattctacaa aggatggtac catttgttct atcaatacaa tccagaggct   3120
gcagtatggg gaaatattgt atggggccat gcagtttcaa gagacttaat tcactggcaa   3180 cacctttccag ttgctatggt tgcggatcaa tggtacgaca ttaacggtgt atggaccgga  3240
tccgcaacca ttttacccga tggtaaactc gtcatgttat ataccgggtc aaccaacgag   3300
tcagtacagg ttcaaaatct agcgtacccg gctgacccat cggatcctct cctaagaaaa   3360
tgggtcaaat atgagggcaa cccggtactt gtaccaccac ccggaattgc tactaaagat   3420
tttcgtgacc ccaccactgc atggaccaca ccacaaggca aatggaggat tactattggt   3480
tcaaaggtta ataaaactgg aatttcattg gtctatgaca ctattgattt taagaaattt   3540
```

```
gagttgttgg atggggtgct ccatggtgta ccgggtacgg gtatgtggga atgtgtggac    3600
ttttacccgg tttcgaaagt tgttgaaaat gggcttgaca catcagataa tgggcctgca    3660
gtaaaacatg tgttaaagtc cagtctagat gatgatagaa atgattatta tgcacttgga    3720
acttatgatg cagtggctgg taaatggatt cctgataatc ccacaattga tgttggtatt    3780
ggattaagat atgattatgg aaattttttac gcatcaaaaa cattttatga ccaagaaaaa    3840
aagagaagag tcctttgggc ttggattact gaaggtgata gtgaagctgc tgatatttgc    3900
aaaggttggg catcacttca ggtacaattc aattgtgtcg aagacaattt agctagtgtt    3960
gggatataga tttggttgaa acttaaaaaa aaaatatttt aaaattatgg acatgtattt    4020
tatttgaaaa aaattaaaat tctgtgagtg aagaaaaacc ttttacccaa aaactaccct    4080
aaaccagatt tgggaatgt aaaaaaaaga atcagatcat attctatgaa caaacaatat    4140
tatcaaaagt ttttttaaaaa caattttcaa aatctatggt caatttcctc ttttatttta    4200
cttcattttg tcatatttga attttggtct catttaacac ttggtaacgt gtgatgtaaa    4260
acagcctatt ccaaggacta taaaatatga caagaagaca ggaagcaaca taattacttg    4320
gccagtggcg gaggttgaga atttgagatt aaacagtaag gaattcgaca aggtggaggt    4380
aaaaccaggg tcagtttttc cactagaagt tggcactgcc actcaggttt gttgattgaa    4440
tttaactata cacgtgtaaa agaatttctt tacgttatcg gtctatttta aactattata    4500
gcacgtaaca tgctaatatt cgataagttt aacttactat aatttgaatt gttgatgatt    4560
atagttggac ataatggctg agtttgaaat agaccctaag gtcttggaga gattagaagg    4620
aaataatgct acatatgagt gcagaagcag tgggggatct gctgaacgtg gtgccttagg    4680
accatttggt ttattggttt taacagataa gggcttgtcc gagcaaactc caatttactt    4740
ctacattgca aaagacgctg ctggaaattt caccacattc ttctgcaatg atcttaccag    4800
gttctaattt ctcctctctt gcattttcat ctcatcaatg aagttttagc ccctcccccc    4860
caccaaaacc aaactaagaa attggagaaa aacctttatt ggttcactgc ttaatagcag    4920 tacgaattc aggattttga gtcattaggt tctgctctat atatatatat ataataatat    4980
ttttctacac atatatatag ttcgagctaa acataatgag ttccgtcgaa cctgttgcat    5040
ctagtctgaa tccgccactg ctttaacaca tcttctctcat aataaccact atttccaaga    5100
gcttaagtat ttctcatgtc catacttcta tccacgttta aaaatgaagt cagatttgt    5160 tttatatccg agaaatcccg agggcaagtg gccagtacat ggttcgaagc tcaatggaca    5220
ctggcaccgc cctttatcgt gctctactta aatattaaga ttttgtctgt tgcagggttt    5280
taaccaagga cgtacgttta acccatatat aacgagtagc ttttaccact agaccaaaac    5340
tcggggcaat atatgaagcc agatatttgt tgcaattctc tttaattaaa ttaaaatggt    5400
gacaagatcc gagacaaatc ttggaagtgc attacgtagt attttttaagt aagtatgata    5460 atggtgattc tcatcttttt acttcctttt ttttaggtca tctgaagcaa cagatgttcg    5520
caaactaatc tacggaagca cagttccagt cctccaagga gagaagcttt ctctaagaac    5580
actggtaatt ttcattttc ttcttttttt aattgcttat tcaaaattct tgattatatt    5640
gcgtacactt aagtttacca aatataaatt aatggggtat ttttgtgaat gtaataggtg    5700
gatcattcaa tagtagaaag ttttgcacaa agtggaagga cagcaataac gtcaagggta    5760
tatccaacaa aggcaatata tgaagatgct aagctctact tatttaacaa tgctacagat    5820
gttagcatta ctgcctcact caagatttgg caaatgaatt ctgcaaatat acaatctagt    5880
```

```
taa                                                                      5883

<210> SEQ ID NO 4
<211> LENGTH: 645
<212> TYPE: PRT
<213> ORGANISM: Nicotiana tabacum

<400> SEQUENCE: 4

Met Ala Glu Thr Asn Asn Ser Val Pro Tyr Thr Gln Leu Pro Ala Glu
1               5                   10                  15

Asp Asn Asn Thr Ser Ser Asn Ser Pro Ala Lys Cys Arg Arg Arg Pro
            20                  25                  30

Lys Arg Val Ser Phe Ile Val Leu Thr Gly Leu Val Ala Ala Leu Leu
        35                  40                  45

Leu Phe Val Ala Val Lys Tyr Gly Asn Asn Glu Ala Glu Asp Val Asn
    50                  55                  60

Pro Gly Pro Val Pro Pro Gln Glu Thr Val Cys Asn Met Leu Gly Ser
65                  70                  75                  80

Asn Leu Met Pro Leu Thr Thr Met Arg Thr Val Ala Arg Gly Val Ala
                85                  90                  95

Glu Gly Val Ser Ala Lys Ser Arg Gly Arg Phe Leu Gly Leu Arg Pro
            100                 105                 110

Phe Pro Trp Thr Lys Gln Met Leu Ala Trp Gln Arg Thr Ser Phe His
        115                 120                 125

Phe Gln Pro Lys Lys Asn Trp Met Asn Gly Pro Leu Phe Tyr Lys Gly
    130                 135                 140

Trp Tyr His Leu Phe Tyr Gln Tyr Asn Pro Glu Ala Ala Val Trp Gly
145                 150                 155                 160

Asn Ile Val Trp Gly His Ala Val Ser Arg Asp Leu Ile His Trp Gln
                165                 170                 175

His Leu Pro Val Ala Met Val Ala Asp Gln Trp Tyr Asp Ile Asn Gly
            180                 185                 190

Val Trp Thr Gly Ser Ala Thr Ile Leu Pro Asp Gly Lys Leu Val Met
        195                 200                 205

Leu Tyr Thr Gly Ser Thr Asn Glu Ser Val Gln Val Gln Asn Leu Ala
    210                 215                 220

Tyr Pro Ala Asp Pro Ser Asp Pro Leu Leu Arg Lys Trp Val Lys Tyr
225                 230                 235                 240

Glu Gly Asn Pro Val Leu Val Pro Pro Gly Ile Ala Thr Lys Asp
                245                 250                 255

Phe Arg Asp Pro Thr Thr Ala Trp Thr Thr Pro Gln Gly Lys Trp Arg
            260                 265                 270

Ile Thr Ile Gly Ser Lys Val Asn Lys Thr Gly Ile Ser Leu Val Tyr
        275                 280                 285

Asp Thr Ile Asp Phe Lys Lys Phe Glu Leu Leu Asp Gly Val Leu His
    290                 295                 300

Gly Val Pro Gly Thr Gly Met Trp Glu Cys Val Asp Phe Tyr Pro Val
305                 310                 315                 320

Ser Lys Val Val Glu Asn Gly Leu Asp Thr Ser Asp Asn Gly Pro Ala
                325                 330                 335

Val Lys His Val Leu Lys Ser Ser Leu Asp Asp Arg Asn Asp Tyr
            340                 345                 350

Tyr Ala Leu Gly Thr Tyr Asp Ala Val Ala Gly Lys Trp Ile Pro Asp
        355                 360                 365
```

```
Asn Pro Thr Ile Asp Val Gly Ile Gly Leu Arg Tyr Asp Tyr Gly Asn
    370                 375                 380
Phe Tyr Ala Ser Lys Thr Phe Tyr Asp Gln Glu Lys Lys Arg Arg Val
385                 390                 395                 400
Leu Trp Ala Trp Ile Thr Glu Gly Asp Ser Glu Ala Ala Asp Ile Cys
                405                 410                 415
Lys Gly Trp Ala Ser Leu Gln Pro Ile Pro Arg Thr Ile Lys Tyr Asp
                420                 425                 430
Lys Lys Thr Gly Ser Asn Ile Ile Thr Trp Pro Val Ala Glu Val Glu
            435                 440                 445
Asn Leu Arg Leu Asn Ser Lys Glu Phe Asp Lys Val Glu Val Lys Pro
450                 455                 460
Gly Ser Val Phe Pro Leu Glu Val Gly Thr Ala Thr Gln Leu Asp Ile
465                 470                 475                 480
Met Ala Glu Phe Glu Ile Asp Pro Lys Val Leu Glu Arg Leu Glu Gly
                485                 490                 495
Asn Asn Ala Thr Tyr Glu Cys Arg Ser Ser Gly Gly Ser Ala Glu Arg
                500                 505                 510
Gly Ala Leu Gly Pro Phe Gly Leu Leu Val Leu Thr Asp Lys Gly Leu
            515                 520                 525
Ser Glu Gln Thr Pro Ile Tyr Phe Tyr Ile Ala Lys Asp Ala Ala Gly
            530                 535                 540
Asn Phe Thr Thr Phe Phe Cys Asn Asp Leu Thr Arg Ser Ser Glu Ala
545                 550                 555                 560
Thr Asp Val Arg Lys Leu Ile Tyr Gly Ser Thr Val Pro Val Leu Gln
                565                 570                 575
Gly Glu Lys Leu Ser Leu Arg Thr Leu Val Asp His Ser Ile Val Glu
                580                 585                 590
Ser Phe Ala Gln Ser Gly Arg Thr Ala Ile Thr Ser Arg Val Tyr Pro
            595                 600                 605
Thr Lys Ala Ile Tyr Glu Asp Ala Lys Leu Tyr Leu Phe Asn Asn Ala
            610                 615                 620
Thr Asp Val Ser Thr Ala Ser Leu Lys Ile Trp Gln Met Asn Ser Ala
625                 630                 635                 640
Asn Ile Gln Ser Ser
            645

<210> SEQ ID NO 5
<211> LENGTH: 4155
<212> TYPE: DNA
<213> ORGANISM: Nicotiana tabacum

<400> SEQUENCE: 5
atggccaccc accattccca ttatgacccg gaaaactcca cgacccatta cactgtccta      60
ccggatcaac ccgaatccgc cggcgccggg cgccggaagt ctcttaaagt tgtctccggc     120
attttgctct cctctttctt tttgctttct ttagtctttg tgatcctcaa ccagtcttca     180
gatttatcac aagaaaactc ccgctcgtcg gagactttga cgccggcgtt gtcacgaggt     240
gtatctcagg gagtttccga gaagactttc aaggatgttt ccgtagaag ctttcgtac      300 tacccgtgga ctaatgctat gcttacttgg caaaggactg cttaccattt tcaacctcaa     360
aagaattgga tgaacggtaa atttttggc ttatctttct cttattaatt cttttaataa      420
aacatgaatt ttaagatact tatactggct ttttcttatt gattcttatg ctatttttgt     480
tggggtatcc tatggattct gattggatga tatgctgcag atcctaatgg tgagtttact     540
```

```
tattaccata attactttt attatttatt attcccaaac catgattagt gcatccggct    600
attggttaaa gattcacaaa accaataaaa tagtaatctt gtcatagttt ccataataat    660
ctacacgtac gctattgttt aatgacaaga aatttgacgc tcagcatagt taattctctc    720
atatttgtat tgtttacttt atagcctttg agctaattaa ttctgggttt ctttgaacta    780
aacctttata agttacaatc acacatagat gagttggcac attattcagg ctaataatga    840
aagaaattgg attacttgac taatatggca aatgcggcca atttaatttg gattaacacg    900
atatatgtgt ggtaataatg cttttgtgca acatctctca tacaaggaca catgattagg    960
tgattttgta ccaagtctcg ggaccaatca caatatatgg gtcacacctt atatattatt   1020
gtaagagttg ggacccacca aggatttgtc tgtcttcca actagccact tgtctttttc    1080
tcttttttat atttttaaat gaatggtgt gggtttttta ttttgggtc gatctaaccg    1140 cttctgccta ttatcaattt agccttgtga ttgtgagaat agaagagaga aatagaggat   1200
aataataata aggataagaa ttaagaacgt accttcttat tgtcgaaatt atttgagaag   1260
actattcatt gttctgatta gtgtccatcg atgtcccttt cctccttttt ctatcttgga   1320
gaggtttcct cttcttgtt ttactttcc tttttctaaa tatgcattcc aaaatcttaa    1380
cactactcga acgtccattc ttggaaagtc tctttgaaag tttagggcaa catcattcgg   1440
acaacttaat tagcattcac tattaaaaat taatagaaca gaaaagttca tgtatttttt   1500
tagggagagt aagaggcgga ttcagaattt aaatcttatg tgtttagttt ttaaaatttt   1560
taggattgat aactgaacat ggcgagaaac atgaacatgt gacataaatt ccgtgtttca   1620
acactaaaca ggtccattat accacaaagg atggtaccat cttttttatc aatacaatcc   1680
tgattcagct gtttgggaa atatcacatg gggccatgca atatccacgg acttgatcca    1740
ctggctttac ttgcctttcg ccatggttcc gatcaatggt acgatatcaa cggtgtctgg   1800
accgggtccg cgaccatctt gcccgacggt cagatcatga tgctatacac cggtgatacc   1860
aatgattacg tgcaggtgca aaatcttgca taccctgcta acttatcgga tcctctcctc   1920
atcgactggg tcaagtacca ggacaatccg gtcatggttc ccccacccgg cattggtgtc   1980
aaggacttca gagacccgac aactgcttgg accggacccc aaaacgggca gtggctgcta   2040
accatcgggt ccaagattgg taaaacgggt attgcacttg tttatgatac gtccaacttc   2100
acaaacttta agctattgga tggagttttg catgcggttc cgggtacggg tatgtgggag   2160
tgtgtggact tttacccggt atcaaccgtt gaggcaaacg ggttggacac atcatataac   2220
gggccaggta taagcatgtg ttaaaagcaa gtttagatga cgataagcat gattactatg   2280
ctattgggac atatgacccg gtaaagaaca aatggactcc tgataacccg gaattggatg   2340
tgggtatcgg gttgagactg gactacggga aatactatgc gtcaaagaca ttttatgacc   2400
cgaaagaaca aagaagaata ttgtggggat ggattggaga aactgacagt gaagctgctg   2460
atctgctgaa gggatgggca tctgtacagg tatggactct tttaagtaca ctacctcagc   2520
atccgaagag cattacactt ttattttgt tttacattag accacatgaa tgggtgtttt   2580
ggcataactg gtaaagttgt tgccatgtga ccctgaggtc acgggttcga gccgtagaaa   2640
tagcctcttg cagtaatgta ataaactctt agtgcatagg gttgccttt ttattagacc    2700 acacacatgt tcaagttatg tcatgttagt cgtgtcaatt ttttgtggaa atcaatttac   2760
tgcacctcaa tcttgaatta gttgagacta gctataggaa cctttgtatt gagaggactt   2820
atcataattt gatcattttt gcactaactg tcacactatg atattcactt tctttatcca   2880
```

```
gtttagtagt gtgccaatac accttaagca cgtgacaaga atttattagc agggtcatct    2940
cgattttatg taggagtaca gaattgaatt gaatcttttc ttctagtaaa ttctcaattg    3000
caacttgaca atgaagtttt tcagatgcaa aaagatgaa atatctctaa taatttcctt    3060
ttccaataac agagtattcc aaggactctg ctttatgaca aggagacaag gacacatgta    3120
cttcagtggc cagttaaaga aattgagagc ttaagaattg gtgatcctct agtgaaacag    3180
gtcaatcttc aaccaggctc aattgagctt gtccatgttg actcagccgc acaggtttgc    3240
tttctcatcc ttcgaaattg aaaacgtttc acttatatgt gcttgatgta cagtcctaaa    3300
acttgtatgc gcaatggtgc agttggatgt agaagcctca tttgaagtgg acaaagcagc    3360
actcgcggga acaattgaag cagatgtggt ttcaactgca gtactagtgg aggtgctgct    3420
aaaagaggca ttttgggacc atttggtgtc gttgtaattg ctgatcaaac gctttctgag    3480
ctaaccccag tttacttcta cattgccaaa ggaactggtg gccgagctga aacctacttc    3540
tgcgctgatg aaactaggtt tgcttctact atgtttatct tgtatactct atcttaatag    3600
tccttgtcaa agtatagagg aataacatag cggcgtgatc tgatgcagat cctcagaggc    3660
tcctggagtt gctaaacaag tgtatggtag ttcagtacca gtgttagatg gtgaacaaca    3720
ctcaatgaga ttattggtaa gtgataatcc ctttattctg actttcttca aatcaagaat    3780
aatatcaagc ttattagttc ttccagtcat cttacttaat ttgtggaaat gctccaaagt    3840
agtcaatttg gtaactattc aagataatgt ggttcagaat aatttgtgtt atgaatgtat    3900
ttgacagttg ggatgatctg tttttagta aatttcttaa aaacttaat tcaggtggac    3960 cactcaattg tggaaagctt tgctcaagga ggaagaacag tcataacatc gcgaatttac    4020
ccaacaaaag caatcaatgg agcagcacga ctgttcgttt tcaacaatgc caccggggct    4080
agtgtgactg cctccctcaa gatttggtca ctcaaatcag ctgatattcg atccttcccc    4140
ttggaccagt tgtaa                                                     4155
```

<210> SEQ ID NO 6
<211> LENGTH: 642
<212> TYPE: PRT
<213> ORGANISM: Nicotiana tabacum

<400> SEQUENCE: 6

```
Met Ala Thr His His Ser His Tyr Asp Pro Glu Asn Ser Thr Thr His
1               5                   10                  15

Tyr Thr Val Leu Pro Asp Gln Pro Glu Ser Ala Gly Ala Gly Arg Arg
            20                  25                  30

Lys Ser Leu Lys Val Val Ser Gly Ile Leu Leu Ser Ser Phe Phe Leu
        35                  40                  45

Leu Ser Leu Val Phe Val Ile Leu Asn Gln Ser Asp Leu Ser Gln
    50                  55                  60

Glu Asn Ser Arg Ser Ser Glu Thr Leu Thr Pro Ala Leu Ser Arg Gly
65                  70                  75                  80

Val Ser Gln Gly Val Ser Glu Lys Thr Phe Lys Asp Val Ser Gly Arg
                85                  90                  95

Ser Leu Ser Tyr Tyr Pro Trp Thr Asn Ala Met Leu Thr Trp Gln Arg
            100                 105                 110

Thr Ala Tyr His Phe Gln Pro Gln Lys Asn Trp Met Asn Asp Pro Asn
        115                 120                 125

Gly Pro Leu Tyr His Lys Gly Trp Tyr His Leu Phe Tyr Gln Tyr Asn
    130                 135                 140
```

Pro Asp Ser Ala Val Trp Gly Asn Ile Thr Trp Gly His Ala Ile Ser
145                 150                 155                 160

Thr Asp Leu Ile His Trp Leu Tyr Leu Pro Phe Ala Met Val Pro Asp
            165                 170                 175

Gln Trp Tyr Asp Ile Asn Gly Val Trp Thr Gly Ser Ala Thr Ile Leu
            180                 185                 190

Pro Asp Gly Gln Ile Met Met Leu Tyr Thr Gly Asp Thr Asn Asp Tyr
            195                 200                 205

Val Gln Val Gln Asn Leu Ala Tyr Pro Ala Asn Leu Ser Asp Pro Leu
    210                 215                 220

Leu Ile Asp Trp Val Lys Tyr Gln Asp Asn Pro Val Met Val Pro Pro
225                 230                 235                 240

Pro Gly Ile Gly Val Lys Asp Phe Arg Asp Pro Thr Thr Ala Trp Thr
            245                 250                 255

Gly Pro Gln Asn Gly Gln Trp Leu Leu Thr Ile Gly Ser Lys Ile Gly
            260                 265                 270

Lys Thr Gly Ile Ala Leu Val Tyr Asp Thr Ser Asn Phe Thr Asn Phe
            275                 280                 285

Lys Leu Leu Asp Gly Val Leu His Ala Val Pro Gly Thr Gly Met Trp
    290                 295                 300

Glu Cys Val Asp Phe Tyr Pro Val Ser Thr Val Glu Ala Asn Gly Leu
305                 310                 315                 320

Asp Thr Ser Tyr Asn Gly Pro Gly Ile Lys His Val Leu Lys Ala Ser
            325                 330                 335

Leu Asp Asp Asp Lys His Asp Tyr Tyr Ala Ile Gly Thr Tyr Asp Pro
            340                 345                 350

Val Lys Asn Lys Trp Thr Pro Asp Asn Pro Glu Leu Asp Val Gly Ile
    355                 360                 365

Gly Leu Arg Leu Asp Tyr Gly Lys Tyr Tyr Ala Ser Lys Thr Phe Tyr
    370                 375                 380

Asp Pro Lys Glu Gln Arg Arg Ile Leu Trp Gly Trp Ile Gly Glu Thr
385                 390                 395                 400

Asp Ser Glu Ala Ala Asp Leu Leu Lys Gly Trp Ala Ser Val Gln Ser
            405                 410                 415

Ile Pro Arg Thr Leu Leu Tyr Asp Lys Glu Thr Arg Thr His Val Leu
            420                 425                 430

Gln Trp Pro Val Lys Glu Ile Glu Ser Leu Arg Ile Gly Asp Pro Leu
            435                 440                 445

Val Lys Gln Val Asn Leu Gln Pro Gly Ser Ile Glu Leu Val His Val
    450                 455                 460

Asp Ser Ala Ala Gln Leu Asp Val Glu Ala Ser Phe Glu Val Asp Lys
465                 470                 475                 480

Ala Ala Leu Ala Gly Thr Ile Glu Ala Asp Val Gly Phe Asn Cys Ser
            485                 490                 495

Thr Ser Gly Gly Ala Ala Lys Arg Gly Ile Leu Gly Pro Phe Gly Val
            500                 505                 510

Val Val Ile Ala Asp Gln Thr Leu Ser Glu Leu Thr Pro Val Tyr Phe
    515                 520                 525

Tyr Ile Ala Lys Gly Thr Gly Arg Ala Glu Thr Tyr Phe Cys Ala
    530                 535                 540

Asp Glu Thr Arg Ser Ser Glu Ala Pro Gly Val Ala Lys Gln Val Tyr
545                 550                 555                 560

Gly Ser Ser Val Pro Val Leu Asp Gly Glu Gln His Ser Met Arg Leu

```
                     565                 570                 575
Leu Val Asp His Ser Ile Val Glu Ser Phe Ala Gln Gly Gly Arg Thr
                 580                 585                 590

Val Ile Thr Ser Arg Ile Tyr Pro Thr Lys Ala Ile Asn Gly Ala Ala
             595                 600                 605

Arg Phe Val Phe Asn Asn Ala Thr Gly Ala Ser Val Thr Ala Ser Leu
         610                 615                 620

Lys Ile Trp Ser Leu Lys Ser Ala Asp Ile Arg Ser Phe Pro Leu Asp
625                 630                 635                 640

Gln Leu

<210> SEQ ID NO 7
<211> LENGTH: 1919
<212> TYPE: DNA
<213> ORGANISM: Nicotiana tabacum

<400> SEQUENCE: 7
```

| | | | | | |
|---|---|---|---|---|---|
| atgatgttat | acaccggtga | taccaatgat | tacgtgcagg | tgcaaaatct | tgcgtacccc | 60 |
| gccaacttat | cggatcccct | cctcatcgac | tgggtcaagt | accggggcaa | cccggtcatg | 120 |
| gttccaccac | ccgcattgg | tgtcaaggac | tttagagacc | caacgactgc | ttggaccgga | 180 |
| ccacaaaacg | ggcagtggct | gcttaccatc | gggtccaaga | ttggtaaaac | gggtattgca | 240 |
| attgtttatg | gtacttccaa | cttcacaaac | tttaagctat | ggatggagt | tttgcatgcg | 300 |
| gttccgggta | cgggtatgtg | ggagtgtgtg | gacttttacc | cggtatcaac | cgatgaggca | 360 |
| aacgggttgg | acacatcata | taacgggcca | ggtataaagc | atgtgttaaa | agcaagttta | 420 |
| gatgacgata | agcatgatta | ctatgctatt | gggacatatg | accggtaaag | aacaaatgga | 480 |
| ctcctgataa | cccgcaattg | gatgtgggta | tcgggttgag | actggactac | gggaaatact | 540 |
| atgcgtcaaa | gacattttat | gacccgaagg | aacaagaag | aatattgtgg | ggatggattg | 600 |
| gggaaactga | cagtgaagct | gctgatctgc | tgaagggatg | gcatctgta | caggtatgga | 660 |
| cacttttcaa | gtacactacc | tcagcttccg | aagagcatta | cacatttatt | tttgtattac | 720 |
| attagggtgc | cttggcgtaa | ctctggtaaa | gtaagttctg | aattgcaacg | tgaaaatgga | 780 |
| ggttttaga | tgcaaagaga | tgatatatcc | ctaatagttt | tcctgtttta | ataacagagt | 840 |
| attccaagga | ctgtgctta | tgataaggag | actaggacac | atgttcttca | gtggccagtt | 900 |
| aaagaaattg | agagcttaag | aattggtgat | cctctagtga | aacgggtcaa | tcttcaacca | 960 |
| ggctcaattg | agctagtcca | tgttgactca | gccgcacagg | ttgctttctc | atccttggaa | 1020 |
| attgaaaacg | tttcacttat | atgtgcttaa | tgtgcagtcc | taaaacttgt | atgtgcaatg | 1080 |
| gtgcagttgg | atgtagaagc | ctcatttgaa | gtggacaaag | cagcactcga | gggaacaatt | 1140 |
| gaagcagatg | ttggtttcaa | ctgcagtact | agtggaggtg | ctgctaaaag | aggcattttg | 1200 |
| ggaccatttg | tgtcgttgt | aattgctgat | caaacgcttt | ctgagctaac | tccagtttac | 1260 |
| ttctacattg | ccaaaggacc | tgatggccga | gctgaaacct | acttctgtgc | tgatgaaact | 1320 |
| aggtttgctt | ctactatgtt | tatcttgtat | actctatctt | aatagtcctt | gtcaaagtat | 1380 |
| agatgaataa | catagcggcg | tgatctgatg | cagatcctca | gaggctcctg | gagttgctaa | 1440 |
| acaagtgtat | ggtagttcag | taccagtgtt | agatgatgaa | caacactcaa | tgagattatt | 1500 |
| ggtaagtgat | aatcccgtta | ttctgacctt | cgtcaaatca | gaataatatc | aagcttatta | 1560 |
| gttcttccag | tcatccttatt | aaatttatgg | aaatgctcca | agtagtcaa | tttggtaact | 1620 |
| attcaagata | atgtggttca | gaataatttg | tgttatgaat | gtatttgaca | gttgggatga | 1680 |

```
tctgtgtttt tgagtaaaat ttcttaaaac tgaactcagg tggaccactc aattgtggag    1740
agctttgctc aaggaggaag aacagtcata acatcgcgaa tttacccaac aaaggcaatc    1800
aatggagcag cacgactgtt cgttttcaac aatgccacga gggcaaggtg actgcctccc    1860
tgaagatttg gtcactcgaa tcagctgata ttcgatcctt ccccttggac cagttgtaa     1919

<210> SEQ ID NO 8
<211> LENGTH: 638
<212> TYPE: PRT
<213> ORGANISM: Nicotiana tabacum

<400> SEQUENCE: 8

Met Ala Thr His His Ser His Tyr Asp Pro Glu Asn Ser Thr Thr His
1               5                   10                  15

Tyr Thr Val Leu Pro Asp Gln Pro Glu Ser Ala Gly Ser Gly His Arg
            20                  25                  30

Lys Ser Leu Lys Val Val Ser Gly Ile Leu Ser Ser Phe Phe Leu
        35                  40                  45

Leu Ser Leu Val Phe Val Ile Val Asn Gln Ser Ser Asp Leu Ser Gln
    50                  55                  60

Lys Asn Ser His Ser Ser Glu Thr Leu Thr Pro Ala Leu Ser Arg Gly
65                  70                  75                  80

Val Ser Gln Gly Val Ser Glu Lys Thr Phe Arg Asp Val Ser Gly Gly
                85                  90                  95

Ser Leu Ser Tyr Tyr Pro Trp Thr Asn Ala Met Leu Thr Trp Gln Arg
            100                 105                 110

Thr Ala Tyr His Phe Gln Pro Gln Lys Asn Trp Met Asn Gly Pro Leu
        115                 120                 125

Tyr His Lys Gly Trp Tyr His Leu Phe Tyr Gln Tyr Asn Pro Asp Ser
    130                 135                 140

Ala Ile Trp Gly Asn Ile Thr Trp Gly His Ala Ile Ser Thr Asp Leu
145                 150                 155                 160

Ile His Trp Leu Tyr Leu Pro Phe Ala Leu Val Pro Asp Gln Trp Tyr
                165                 170                 175

Asp Ile Asn Gly Val Trp Thr Gly Ser Ala Thr Phe Leu Pro Asp Gly
            180                 185                 190

Gln Ile Met Met Leu Tyr Thr Gly Asp Thr Asn Asp Tyr Val Gln Val
        195                 200                 205

Gln Asn Leu Ala Tyr Pro Ala Asn Leu Ser Asp Pro Leu Leu Ile Asp
    210                 215                 220

Trp Val Lys Tyr Arg Gly Asn Pro Val Met Val Pro Pro Pro Gly Ile
225                 230                 235                 240

Gly Val Lys Asp Phe Arg Asp Pro Thr Thr Ala Trp Thr Gly Pro Gln
                245                 250                 255

Asn Gly Gln Trp Leu Leu Thr Ile Gly Ser Lys Ile Gly Lys Thr Gly
            260                 265                 270

Ile Ala Ile Val Tyr Gly Thr Ser Asn Phe Thr Asn Phe Lys Leu Leu
        275                 280                 285

Asp Gly Val Leu His Ala Val Pro Gly Thr Gly Met Trp Glu Cys Val
    290                 295                 300

Asp Phe Tyr Pro Val Ser Thr Asp Glu Ala Asn Gly Leu Asp Thr Ser
305                 310                 315                 320

Tyr Asn Gly Pro Gly Ile Lys His Val Leu Lys Ala Ser Leu Asp Asp
                325                 330                 335
```

Asp Lys His Asp Tyr Tyr Ala Ile Gly Thr Tyr Asp Pro Val Lys Asn
                340                 345                 350

Lys Trp Thr Pro Asp Asn Pro Gln Leu Asp Val Gly Ile Gly Leu Arg
            355                 360                 365

Leu Asp Tyr Gly Lys Tyr Tyr Ala Ser Lys Thr Phe Tyr Asp Pro Lys
370                 375                 380

Glu Gln Arg Arg Ile Leu Trp Gly Trp Ile Gly Glu Thr Asp Ser Glu
385                 390                 395                 400

Ala Ala Asp Leu Leu Lys Gly Trp Ala Ser Val Gln Ser Ile Pro Arg
                405                 410                 415

Thr Val Leu Tyr Asp Lys Glu Thr Arg Thr His Val Leu Gln Trp Pro
            420                 425                 430

Val Lys Glu Ile Glu Ser Leu Arg Ile Gly Asp Pro Leu Val Lys Arg
        435                 440                 445

Val Asn Leu Gln Pro Gly Ser Ile Glu Leu Val His Val Asp Ser Ala
    450                 455                 460

Ala Gln Leu Asp Val Glu Ala Ser Phe Glu Val Asp Lys Ala Ala Leu
465                 470                 475                 480

Glu Gly Thr Ile Glu Ala Asp Val Gly Phe Asn Cys Ser Thr Ser Gly
                485                 490                 495

Gly Ala Ala Lys Arg Gly Ile Leu Gly Pro Phe Gly Val Val Ile
            500                 505                 510

Ala Asp Gln Thr Leu Ser Glu Leu Thr Pro Val Tyr Phe Tyr Ile Ala
        515                 520                 525

Lys Gly Pro Asp Gly Arg Ala Glu Thr Tyr Phe Cys Ala Asp Glu Thr
    530                 535                 540

Arg Ser Ser Glu Ala Pro Gly Val Ala Lys Gln Val Tyr Gly Ser Ser
545                 550                 555                 560

Val Pro Val Leu Asp Asp Glu Gln His Ser Met Arg Leu Leu Val Asp
                565                 570                 575

His Ser Ile Val Glu Ser Phe Ala Gln Gly Gly Arg Thr Val Ile Thr
            580                 585                 590

Ser Arg Ile Tyr Pro Thr Lys Ala Ile Asn Gly Ala Ala Arg Leu Phe
        595                 600                 605

Val Phe Asn Asn Ala Thr Arg Ser Val Thr Ala Ser Leu Lys Ile Trp
    610                 615                 620

Ser Leu Glu Ser Ala Asp Ile Arg Ser Phe Pro Leu Asp Gln
625                 630                 635

<210> SEQ ID NO 9
<211> LENGTH: 98
<212> TYPE: DNA
<213> ORGANISM: Artificial Sequence
<220> FEATURE:
<223> OTHER INFORMATION: Nucleotide sequence for silencing NtINV4-T and
      NtINV4-S

<400> SEQUENCE: 9
ggtttcaact gcagtactag tggaggtgct gctaaaagag gcattttggg accatttggt      60
gtcgttgtaa ttgctgatca aacgctttct gagctaac                              98

<210> SEQ ID NO 10
<211> LENGTH: 4384
<212> TYPE: DNA
<213> ORGANISM: Nicotiana tabacum
<220> FEATURE:

```
<221> NAME/KEY: misc_feature
<222> LOCATION: (1520)..(1520)
<223> OTHER INFORMATION: n is a, c, g, or t

<400> SEQUENCE: 10
```

| | | | | | |
|---|---|---|---|---|---|
| atggcagcta | gtggtcttag | cattaagaaa | agtttggagg | aatccatttt | ggctcatcca | 60 |
| gatgaaattt | tggctctcaa | gtcaaggtac | attactacat | ataatgatat | taagaactag | 120 |
| aggcttatcc | aaggttttgt | tacattttg | aaattataag | tttagaacct | aatagtactt | 180 |
| ggtagcactt | gtttccttat | tatctagctg | ttgttactgc | ttgttgctac | tgctttctgt | 240 |
| tcatctttcc | ttgagcccgg | tctatcggaa | acaacctctc | tattctcaaa | gtataaggtt | 300 |
| tgcgtacata | ctacctcccc | agactctact | tgtggaattt | actgttttg | ttgtgttgtt | 360 |
| gtaatctaat | atttattaga | attttactga | tttttcacat | atatatatct | atgtcccctg | 420 |
| tcgaaaattc | tatagctcat | gttagctaaa | tacattagta | ccattgtttt | taattgtttt | 480 |
| ggttttggca | caggattgaa | actgaaggga | aagggtaat | gaaaccactt | gatctcttga | 540 |
| accatttggt | ttctgttact | agtaagacaa | atggagtaaa | tattgtacct | agtgcacttg | 600 |
| tggaagttct | cagttgcagc | caagaagctg | tgattgtacc | accaaaacta | gcactagctg | 660 |
| tacgtccgag | gcccggtgta | tgggagtact | tgtcactgaa | tcttaagaca | aagaaagtgg | 720 |
| ctgaattaag | cattcctgaa | taccttcaat | tgaaagagaa | cactgttgat | gaaaggtaaa | 780 |
| gtattagtct | gcgatttcgc | tttgtgaaat | tgaagttttt | gttttgattc | ataatgtttt | 840 |
| gtgtatcaat | tatgttacca | gtggaaacat | attggagttg | gattttgagc | catttacaac | 900 |
| agttacacca | ccaaaaacac | tttctgactc | tattggcaat | ggtttggagt | ttcttaatcg | 960 |
| ccacattgct | tcgaaaatgt | ttcatgataa | ggagatttcc | agatgcctcc | ttgacttcct | 1020 |
| cagaaaccat | aactacaaag | gaaaggtaat | aaaaaaaagt | gtttctttaa | acaagttgta | 1080 |
| tgattatgtg | tatatttcta | agtatgttaa | cttgaaaaca | gtcattgatg | gtgaaagaaa | 1140 |
| gcattcaaag | cctagagagt | ttccaacttg | ttctgaaaaa | agcagaggaa | catttgtgca | 1200 |
| cattgaatcc | agaaactcca | tactccaatt | ttgaatcaaa | gtttgaagag | attggcttgg | 1260 |
| aaagagggtg | gggaaacacc | gctgaacgcg | tgcaagacac | tatcagtcat | cttttgcatc | 1320 |
| tccttgaggc | tcctaacgcg | tcttctttgg | aaaatttcct | tggtagaatc | ccattggttt | 1380 |
| tcaatgttgt | gattctaact | ccacatggtt | attttgctca | agataatgtc | ttgggctatc | 1440 |
| ctgacactgg | tggccaggtt | tgtgtccaat | attttgcatt | cttgatcaag | ttctttatac | 1500 |
| catttgaacc | aacaatcttn | aacattcttt | ttttggttgt | gaaatgttga | ataggttgtt | 1560 |
| tacattcttg | atcaagttcc | agctatggag | cgtgagatgc | ttcatcgtat | gaagcttcaa | 1620 |
| ggactcgatg | atatcatccc | tcgcatcctt | gttgtaagtg | gccttaattt | tcctagtttc | 1680 |
| atttacacct | ctaaatgaaa | ttgatctttt | ttgttgtttt | atatcaggta | acaaggctgc | 1740 |
| tgcctgatgc | agtaggaacc | acctgtggcg | agcggatgga | gaaagtatat | ggggcagaac | 1800 |
| attctcatat | aattcgtgtt | ccatttagaa | ctgagaaggg | aatgttgcgc | aaatggatct | 1860 |
| cacgattcga | agtctggcca | tacatggaaa | ctttcactga | ggttggaaca | taaaaacaaa | 1920 |
| taaaatccat | tggaatgttc | cttctgcaat | tgaaaatgtc | ttgctaactg | aagacccatt | 1980 |
| tttaaattga | tcatcaggat | gttgcagaag | aacttgtcaa | agaattgcaa | gctaaaccag | 2040 |
| acttgatcat | tggaaactac | agtgagggaa | atcttgctgc | ctcttttgctt | gcgaagaaat | 2100 |
| ttggggctac | tcagtgtact | attgctcatg | ccttggaaaa | aactaagtat | ccaaactctg | 2160 |
| accttaattg | gaagaagttt | gatgacaagt | atcatttctc | aagtcagttc | actgctgatc | 2220 |

```
tctttgccat gaatcacact gatttcatca tcaccagcac tttccaagaa attgctggaa    2280
ggtaaaagca aatgcacacc atcatagtat ttcatatttt tacccttgtt tatactattt    2340
ccattcaccg accccgactt gtttaggatt gagccatagt tgttgttgtt gtttgtttat    2400
actatttcca tttgccgacc acaacttgtt taggactgag gtatagttgt tgttgttggt    2460
ttgttcatat tattttcatt cgctaaccct aacttgtttg ggactgaggc atagtagtag    2520
tagtagttgt tgctattagt ttatactatt tccatttgcc aaccccaact tgtttggtac    2580
tgagacatag ttgttgttgt tgttgttgt ttatactatt tccatttgcc gaccccaact    2640
tgtttaggac tgaggtatag ttgttgttgt tggtttgttc atattatttt cattcgctaa    2700
ccccaacttg tttgggactg aggcatagta gtagtagtag tagttgttgc tattagttta    2760
tactatttcc atttgccaac cccaacttgt tggtactga gacatagttg ttgttgttgt    2820
ttgtttatac tatttcaatt tgtcgacccc aatttgtttg ggaccaaggc atggttgttg    2880
ttgttgtttg tttgtttta ctgtttccat tgatattgga acatttgtta tttgcagcaa    2940
aaacactgta ggacagtatg agagtcatac tgcttttacc atgcctggat tgtaccgagt    3000
agtccatgga atcgattcgt ttgatccaaa gttcaacatt gtctcccctg ggctgatat    3060 gtcaatctac ttcccttaca ctgagaagga gaaaaggcta accaacttcc acccggaaat    3120
tgaagaactc ctctacagtc ctgttgagaa taaggaccac ttgttagtct ccttaatttg    3180
cttttatttc atcccattta tgatcgcttt tatcccaaca gatcgattaa tcatttgtta    3240
tcaacataaa cagatgtgtg ttgaaggacc ggaacaagcc aattctcttt accatggcaa    3300
ggctagatcg cgtgaagaat ctaacagggc tcgtggaatg gtatgctaag aatgcaaggc    3360
tgagggagct tgttaacctt gtggttgtag gcggagacag aaggaaagaa tccaaagatt    3420
tagaagagca agcagagatg aagaagatgt atgatcttat cgaaacctat aacctgaacg    3480
gccaattcag gtggatttct tcccaaatga atcgtgtgag gaacggagaa ctctatcgtt    3540
acattgcaga cacgaggggt gctttcgttc aaccagcatt ctacgaggct tttggtttga    3600
cagttgtaga gtctatgact tgtggttttgc caactttgc tacttgtaat ggtggaccat    3660
ttgagattat agtgaatgga aaatctggtt tccatattga tcctaatcaa ggtgacaagg    3720
ctgctgatat gttggtaaat ttcttttgaaa aatctaaaga agatccaagt tattgggatg    3780
ctatttccaa gggaggtctg caacgtattc ttgaaaagta agcttttgca tttgattagc    3840
acaagtgcac aaccaagatt taacttttga acaaactaaa actaacccctt ttttgtattt    3900 tcttttgcta ggtatacatg gcaaatttat tcacagaaag tgatcacact atctgggatt    3960
tatggattct ggaagtatgc aaccaagaat gataaagttg ctagtgcaaa gaagcgctat    4020
cttgagatgt tttatgaact tggatttaag aaatcagtaa gtgtcaattt taaagggaa    4080 ccttggatca acggttaagt tgtctttgtg caacctatag gtcagggggtt tgagccgtag    4140 aagtagccac taatatttac attagggtag actgtgtaca tatcacaccc cttggggtac    4200 ggcccttcc tggatcctgt atgaacgcgg gatgccttgt gcaccgggct gtattttttt    4260
ttttagtgtc acttctgtat tttgtttgag cttgtttata agtttggaa atctgctgct    4320 aatttgtata tttgttggtt gtgtatttca ggctgagaaa gttccattgg ctattgatga    4380
atag                                                                4384
```

<210> SEQ ID NO 11
<211> LENGTH: 803
<212> TYPE: PRT

-continued

<213> ORGANISM: Nicotiana tabacum

<400> SEQUENCE: 11

```
Met Ala Ala Ser Gly Leu Ser Ile Lys Lys Ser Leu Glu Glu Ser Ile
1               5                   10                  15

Leu Ala His Pro Asp Glu Ile Leu Ala Leu Lys Ser Arg Ile Glu Thr
            20                  25                  30

Glu Gly Lys Gly Val Met Lys Pro Leu Asp Leu Leu Asn His Leu Val
        35                  40                  45

Ser Val Thr Ser Lys Thr Asn Gly Val Asn Ile Val Pro Ser Ala Leu
    50                  55                  60

Val Glu Val Leu Ser Cys Ser Gln Glu Ala Val Ile Val Pro Pro Lys
65                  70                  75                  80

Leu Ala Leu Ala Val Arg Pro Arg Pro Gly Val Trp Glu Tyr Leu Ser
                85                  90                  95

Leu Asn Leu Lys Thr Lys Lys Val Ala Glu Leu Ser Ile Pro Glu Tyr
            100                 105                 110

Leu Gln Leu Lys Glu Asn Thr Val Asp Glu Ser Gly Asn Ile Leu Glu
        115                 120                 125

Leu Asp Phe Glu Pro Phe Thr Thr Val Thr Pro Lys Thr Leu Ser
    130                 135                 140

Asp Ser Ile Gly Asn Gly Leu Glu Phe Leu Asn Arg His Ile Ala Ser
145                 150                 155                 160

Lys Met Phe His Asp Lys Glu Ile Ser Arg Cys Leu Leu Asp Phe Leu
                165                 170                 175

Arg Asn His Asn Tyr Lys Gly Lys Ser Leu Met Val Lys Glu Ser Ile
            180                 185                 190

Gln Ser Leu Glu Ser Phe Gln Leu Val Leu Lys Ala Glu Glu His
        195                 200                 205

Leu Cys Thr Leu Asn Pro Glu Thr Pro Tyr Ser Asn Phe Glu Ser Lys
    210                 215                 220

Phe Glu Glu Ile Gly Leu Glu Arg Gly Trp Gly Asn Thr Ala Glu Arg
225                 230                 235                 240

Val Gln Asp Thr Ile Ser His Leu Leu His Leu Leu Glu Ala Pro Asn
                245                 250                 255

Ala Ser Ser Leu Glu Asn Phe Leu Gly Arg Ile Pro Leu Val Phe Asn
            260                 265                 270

Val Val Ile Leu Thr Pro His Gly Tyr Phe Ala Gln Asp Asn Val Leu
        275                 280                 285

Gly Tyr Pro Asp Thr Gly Gly Gln Val Val Tyr Ile Leu Asp Gln Val
    290                 295                 300

Pro Ala Met Glu Arg Glu Met Leu His Arg Met Lys Leu Gln Gly Leu
305                 310                 315                 320

Asp Asp Ile Ile Pro Arg Ile Leu Val Val Thr Arg Leu Leu Pro Asp
                325                 330                 335

Ala Val Gly Thr Thr Cys Gly Glu Arg Met Glu Lys Val Tyr Gly Ala
            340                 345                 350

Glu His Ser His Ile Ile Arg Val Pro Phe Arg Thr Glu Lys Gly Met
        355                 360                 365

Leu Arg Lys Trp Ile Ser Arg Phe Glu Val Trp Pro Tyr Met Glu Thr
    370                 375                 380

Phe Thr Glu Asp Val Ala Glu Glu Leu Val Lys Glu Leu Gln Ala Lys
385                 390                 395                 400
```

```
Pro Asp Leu Ile Ile Gly Asn Tyr Ser Glu Gly Asn Leu Ala Ala Ser
                405                 410                 415

Leu Leu Ala Lys Lys Phe Gly Ala Thr Gln Cys Thr Ile Ala His Ala
        420                 425                 430

Leu Glu Lys Thr Lys Tyr Pro Asn Ser Asp Leu Asn Trp Lys Lys Phe
        435                 440                 445

Asp Asp Lys Tyr His Phe Ser Ser Gln Phe Thr Ala Asp Leu Phe Ala
    450                 455                 460

Met Asn His Thr Asp Phe Ile Ile Thr Ser Thr Phe Gln Glu Ile Ala
465                 470                 475                 480

Gly Ser Lys Asn Thr Val Gly Gln Tyr Glu Ser His Thr Ala Phe Thr
                485                 490                 495

Met Pro Gly Leu Tyr Arg Val Val His Gly Ile Asp Ser Phe Asp Pro
            500                 505                 510

Lys Phe Asn Ile Val Ser Pro Gly Ala Asp Met Ser Ile Tyr Phe Pro
        515                 520                 525

Tyr Thr Glu Lys Glu Lys Arg Leu Thr Asn Phe His Pro Glu Ile Glu
    530                 535                 540

Glu Leu Leu Tyr Ser Pro Val Glu Asn Lys Asp His Leu Cys Val Leu
545                 550                 555                 560

Lys Asp Arg Asn Lys Pro Ile Leu Phe Thr Met Ala Arg Leu Asp Arg
                565                 570                 575

Val Lys Asn Leu Thr Gly Leu Val Glu Trp Tyr Ala Lys Asn Ala Arg
            580                 585                 590

Leu Arg Glu Leu Val Asn Leu Val Val Gly Gly Asp Arg Arg Lys
        595                 600                 605

Glu Ser Lys Asp Leu Glu Glu Gln Ala Glu Met Lys Lys Met Tyr Asp
    610                 615                 620

Leu Ile Glu Thr Tyr Asn Leu Asn Gly Gln Phe Arg Trp Ile Ser Ser
625                 630                 635                 640

Gln Met Asn Arg Val Arg Asn Gly Glu Leu Tyr Arg Tyr Ile Ala Asp
                645                 650                 655

Thr Arg Gly Ala Phe Val Gln Pro Ala Phe Tyr Glu Ala Phe Gly Leu
            660                 665                 670

Thr Val Val Glu Ser Met Thr Cys Gly Leu Pro Thr Phe Ala Thr Cys
        675                 680                 685

Asn Gly Gly Pro Phe Glu Ile Ile Val Asn Gly Lys Ser Gly Phe His
    690                 695                 700

Ile Asp Pro Asn Gln Gly Asp Lys Ala Ala Asp Met Leu Val Asn Phe
705                 710                 715                 720

Phe Glu Lys Ser Lys Glu Asp Pro Ser Tyr Trp Asp Ala Ile Ser Lys
                725                 730                 735

Gly Gly Leu Gln Arg Ile Leu Glu Lys Tyr Thr Trp Gln Ile Tyr Ser
            740                 745                 750

Gln Lys Val Ile Thr Leu Ser Gly Ile Tyr Gly Phe Trp Lys Tyr Ala
        755                 760                 765

Thr Lys Asn Asp Lys Val Ala Ser Ala Lys Lys Arg Tyr Leu Glu Met
    770                 775                 780

Phe Tyr Glu Leu Gly Phe Lys Lys Ser Ala Glu Lys Val Pro Leu Ala
785                 790                 795                 800

Ile Asp Glu

<210> SEQ ID NO 12
```

<211> LENGTH: 3926
<212> TYPE: DNA
<213> ORGANISM: Nicotiana tabacum

<400> SEQUENCE: 12

```
atggcaggca gtggtcttag cattaaggaa agtttggagg aatccatttt ggctcatcca      60
gatgaaattt tggctctcaa gtcaaggtac attactgcat aatgatatta agacctagaa     120
gcggatccaa gattttgtta cattttgaa attataagtt tagaatctaa tatttgttat      180
cgcttgtttc cttattatct tgctgttgtt actgcctgtt gctactagtt tctgttcatc     240
cttccttgag ctgagtttct atcggaaaca acctctctac tctcaaagta ggaataagtt     300
atgcgtacac actaccctcc ccagactcca cttgtgtaat ttactgagtt tgttgttgtt     360
gttgttgtaa tctaatactt gttagaattt tactgatttt tcacatatat atctatgacc     420
catgtcgaaa atactatagc tcatgtgcta aatacattag taccattgtt ttgtaattgt     480
tttggttttg gaacaggatt gaaactgaag ggaaaggggt aatgaaacca gttgatctct     540
tgaaccattt ggtttctgtt actagtaaaa caaatggagt aaatgttgta cctagtgcac     600
ttgtggaagt tctcagttgc agccaagaag ctgtgattgt accaccaaaa ctagcactag     660
ctgtacgtcc gaggcccggt gtatgggagt acttgtcact gaatcttaag acaaagaaag     720
tggctgaatt gagcattcct gagtaccttc aattgaaaga gaatactgtt gatgaaaggt     780
aaagtaatag tctgcgattt cgcttttgtga aattgaagtt ttttgtttga ttcttaatgt     840
tttgtgtatc aattatgtta ccagtggaaa catcttggag ttggattttg agccatttac     900
aactgttaca acaccaaaaa cactttctga ctctattggc aatggtttgg agtttcttaa     960
tcgccacatt gcttcgaaaa tgtttcttga taggagatt gccaagtgcc tccttgactt    1020
tctcagaaac cataactaca aaggaaaggt agtaaaaaaa gtgtttcttt aaacaagttg    1080
tatgattatg tgtgtatttc taaatatgtc aatttgaaaa cagtcattga tggtgaaaga    1140
aagcattcaa agcctggaga gtttccaact tgttctgaaa aaagcagagg aatatttgca    1200
cacactgaat ccagaaactc catactccaa atttgaatcc aagtttgaag agattggctt    1260
ggaaagaggg tggggaaaca ccgctgaacg cgtgcaagac accattagtc atcttttgca    1320
tctccttgag gctcctaacg cgtcttcctt ggaaaatttc cttggtagaa tcccattggt    1380
tttcaatgtt gtgattctca ccccacatgg ttatttgct caagataatg tcttgggcta    1440
tcctgacact ggtggccagg tttgtgtccg atataacata tcaagaaatt ttgcattctt    1500
gatcatgttc tttataccat ttgaaccaac attcttttt tggttgtgaa atgttgaata    1560
ggttgtttac attcttgatc aagttccagc tatggagcgt gagatgcttc atcgtatgaa    1620
gcttcaagga ctcgacgata tcatccctcg catccttgtt gtaagtgccc ttaatttttcc   1680
tggtttggtt tacctctaaa tgaaattgat tttctggctt tctaactttt ttggattgat    1740
cttttttgttg ttttatatca ggtaactagg ctgctgcctg atgctgtagg aaccacttgt    1800
ggcgagtgga tggagaaagt atatgggca gaacattctc atataattcg tgttccattt    1860
agaactgaga aggaatgtt gcgcaaatgg atctcacgat tcgaagtctg gccatacatg    1920
gaaactttca ctgaggttgg aacataaaaa caaataaaaa tcattggaat gttcttctgc    1980
atttgaaaat gtcttgctaa ctaaagactc atttttaaat taatcatcag gatgttgcag    2040
aagaacttgt caaagaattg caagctaaac cagactgat aattggaaac tacagtgagg     2100
gaaatcttgc tgcctcattg cttgctaaga aatttggggc tactcagtgt actattgctc    2160
atgccttgga aaaaactaag tatccaaaact ctgaccttaa ttggaagaag tttgatgaca    2220
```

-continued

```
agtatcattt ctcaagtcag ttcactgctg atcttttgc catgaatcac actgatttca      2280
ttatcaccag cactttccaa gaaattgctg aaggtaaaa gcaaatgcac accatcatag      2340
tatttcatat ttttacccta gtttatacta tttccatttg tcaactccaa cttgtttggg    2400
attgaaccat agttgttgtt tgtttatact atttccattc gccgacccca acttatttgg   2460
gactgagaca taattgttgt tattattgtt tgtttgttta tactatttcc attctcagac    2520
cccaacttct ttgggactga gccgtagatt gttgttgttg ttgttgttgt tgtttgttta    2580
tgctatttcc gttcaccgac cccaacttat ttgggactga ggtgtagaag tagtcgttgt    2640
tgtttgttta tacgacttcc aattgatatt cgaatgtttt tattttgca gcaagaacac     2700
tgtaggacag tatgagagtc atactgcttt taccatgcct ggattgtatc gagtagtcca   2760
tggaatcaat tcgtttgatc caaagttcaa cattgtctcc cctggggctg atatgtcaat    2820
ctacttccct tacactgaga aggagaaag actaaccaac ttccacccgg aaattgaaga    2880
actcctctac agtcctgttg agaataagga ccacttgtta gtcttcttta tttcattcat   2940
ttttctacac cttttttttc aacagattga ttgattggtt cttatcaacg taaacagatg   3000
tgtgttgaag gaccgaaaca agccaattct ctttaccatg gcaaggctag atcgcgtgaa   3060
gaatctaaca gggctcgtgg aatggtatgc aaagaatgca aggctaaggg agctcgttaa   3120
ccttgtggtt gtaggcggag acagaaggaa agaatccaaa gatttagaag agcaagcaga   3180
gatgaagaag atgtatgatc ttatcgaaac atacaacctg aatggccaat tcaggtggat   3240
ttcttcccaa atgaatcgtg tgaggaacgg agaactttat cgatacattg cagacacgag    3300
gggtgctttc gttcaaccag catttatga ggcatttggt ttgacagttg ttgagtctat    3360
gacttgtggt ttgccaactt ttgctacttg taatggtgga ccatttgaga ttatagtgaa    3420
tggaaaatct ggtttccata ttgatcctaa tcaaggtgac aaggctgctg atatgttggt    3480
taatttcttc gaaaaatcta agaagatcc aagttattgg gatactattt ccaagggtgg    3540
tctgcagcgt attcttgaaa agtaagcttt tgcatttgat tagcacaagt gtacaaccaa    3600
gatttaactt atgaacaaac taaaactaac cctttttta ttttcttttg ctaggtatac    3660
atggcaaatt tattcacaga aagtgatcac attatctggg atttatggat ctggaaata    3720
tgcaaccaag aatgacaaag ttgctagtgc gaagaagcgc tatcttgaaa tgttttatga    3780
atttgggttt aagaaatcag taagtgtcac ttctgtattt tgtttgagct tgtttgtaaa    3840
gtttggcaat cttctgctaa tttgtactat atttgttgac ttgtgcattt caggctgaga   3900
aagttccatt ggctattgat gaatag                                          3926
```

<210> SEQ ID NO 13
<211> LENGTH: 803
<212> TYPE: PRT
<213> ORGANISM: Nicotiana tabacum

<400> SEQUENCE: 13

Met Ala Gly Ser Gly Leu Ser Ile Lys Glu Ser Leu Glu Glu Ser Ile
1               5                   10                  15

Leu Ala His Pro Asp Glu Ile Leu Ala Leu Lys Ser Arg Ile Glu Thr
            20                  25                  30

Glu Gly Lys Gly Val Met Lys Pro Val Asp Leu Leu Asn His Leu Val
        35                  40                  45

Ser Val Thr Ser Lys Thr Asn Gly Val Asn Val Val Pro Ser Ala Leu
    50                  55                  60

```
Val Glu Val Leu Ser Cys Ser Gln Glu Ala Val Ile Val Pro Pro Lys
 65                  70                  75                  80

Leu Ala Leu Ala Val Arg Pro Arg Pro Gly Val Trp Glu Tyr Leu Ser
                 85                  90                  95

Leu Asn Leu Lys Thr Lys Lys Val Ala Glu Leu Ser Ile Pro Glu Tyr
            100                 105                 110

Leu Gln Leu Lys Glu Asn Thr Val Asp Glu Ser Gly Asn Ile Leu Glu
            115                 120                 125

Leu Asp Phe Glu Pro Phe Thr Thr Val Thr Thr Pro Lys Thr Leu Ser
130                 135                 140

Asp Ser Ile Gly Asn Gly Leu Glu Phe Leu Asn Arg His Ile Ala Ser
145                 150                 155                 160

Lys Met Phe Leu Asp Lys Glu Ile Ala Lys Cys Leu Leu Asp Phe Leu
                165                 170                 175

Arg Asn His Asn Tyr Lys Gly Lys Ser Leu Met Val Lys Glu Ser Ile
                180                 185                 190

Gln Ser Leu Glu Ser Phe Gln Leu Val Leu Lys Ala Glu Glu Tyr
            195                 200                 205

Leu His Thr Leu Asn Pro Glu Thr Pro Tyr Ser Lys Phe Glu Ser Lys
210                 215                 220

Phe Glu Glu Ile Gly Leu Glu Arg Gly Trp Gly Asn Thr Ala Glu Arg
225                 230                 235                 240

Val Gln Asp Thr Ile Ser His Leu Leu His Leu Leu Glu Ala Pro Asn
                245                 250                 255

Ala Ser Ser Leu Glu Asn Phe Leu Gly Arg Ile Pro Leu Val Phe Asn
                260                 265                 270

Val Val Ile Leu Thr Pro His Gly Tyr Phe Ala Gln Asp Asn Val Leu
                275                 280                 285

Gly Tyr Pro Asp Thr Gly Gly Gln Val Val Tyr Ile Leu Asp Gln Val
                290                 295                 300

Pro Ala Met Glu Arg Glu Met Leu His Arg Met Lys Leu Gln Gly Leu
305                 310                 315                 320

Asp Asp Ile Ile Pro Arg Ile Leu Val Val Thr Arg Leu Leu Pro Asp
                325                 330                 335

Ala Val Gly Thr Thr Cys Gly Glu Trp Met Glu Lys Val Tyr Gly Ala
                340                 345                 350

Glu His Ser His Ile Ile Arg Val Pro Phe Arg Thr Glu Lys Gly Met
                355                 360                 365

Leu Arg Lys Trp Ile Ser Arg Phe Glu Val Trp Pro Tyr Met Glu Thr
                370                 375                 380

Phe Thr Glu Asp Val Ala Glu Glu Leu Val Lys Glu Leu Gln Ala Lys
385                 390                 395                 400

Pro Asp Leu Ile Ile Gly Asn Tyr Ser Glu Gly Asn Leu Ala Ala Ser
                405                 410                 415

Leu Leu Ala Lys Lys Phe Gly Ala Thr Gln Cys Thr Ile Ala His Ala
                420                 425                 430

Leu Glu Lys Thr Lys Tyr Pro Asn Ser Asp Leu Asn Trp Lys Lys Phe
                435                 440                 445

Asp Asp Lys Tyr His Phe Ser Ser Gln Phe Thr Ala Asp Leu Phe Ala
                450                 455                 460

Met Asn His Thr Asp Phe Ile Ile Thr Ser Thr Phe Gln Glu Ile Ala
465                 470                 475                 480

Gly Ser Lys Asn Thr Val Gly Gln Tyr Glu Ser His Thr Ala Phe Thr
```

```
                    485               490                   495
Met Pro Gly Leu Tyr Arg Val Val His Gly Ile Asn Ser Phe Asp Pro
                500                   505                   510

Lys Phe Asn Ile Val Ser Pro Gly Ala Asp Met Ser Ile Tyr Phe Pro
                515                   520                   525

Tyr Thr Glu Lys Glu Lys Arg Leu Thr Asn Phe His Pro Glu Ile Glu
            530                   535                   540

Glu Leu Leu Tyr Ser Pro Val Glu Asn Lys Asp His Leu Cys Val Leu
545                 550                   555                   560

Lys Asp Gln Asn Lys Pro Ile Leu Phe Thr Met Ala Arg Leu Asp Arg
                565                   570                   575

Val Lys Asn Leu Thr Gly Leu Val Glu Trp Tyr Ala Lys Asn Ala Arg
                580                   585                   590

Leu Arg Glu Leu Val Asn Leu Val Val Gly Gly Asp Arg Arg Lys
            595                   600                   605

Glu Ser Lys Asp Leu Glu Glu Gln Ala Glu Met Lys Lys Met Tyr Asp
        610                   615                   620

Leu Ile Glu Thr Tyr Asn Leu Asn Gly Gln Phe Arg Trp Ile Ser Ser
625                 630                   635                   640

Gln Met Asn Arg Val Arg Asn Gly Glu Leu Tyr Arg Tyr Ile Ala Asp
                    645                   650                   655

Thr Arg Gly Ala Phe Val Gln Pro Ala Phe Tyr Glu Ala Phe Gly Leu
                660                   665                   670

Thr Val Val Glu Ser Met Thr Cys Gly Leu Pro Thr Phe Ala Thr Cys
                675                   680                   685

Asn Gly Gly Pro Phe Glu Ile Ile Val Asn Gly Lys Ser Gly Phe His
                690                   695                   700

Ile Asp Pro Asn Gln Gly Asp Lys Ala Ala Asp Met Leu Val Asn Phe
705                 710                   715                   720

Phe Glu Lys Ser Lys Glu Asp Pro Ser Tyr Trp Asp Thr Ile Ser Lys
                725                   730                   735

Gly Gly Leu Gln Arg Ile Leu Glu Lys Tyr Thr Trp Gln Ile Tyr Ser
                740                   745                   750

Gln Lys Val Ile Thr Leu Ser Gly Ile Tyr Gly Phe Trp Lys Tyr Ala
            755                   760                   765

Thr Lys Asn Asp Lys Val Ala Ser Ala Lys Arg Tyr Leu Glu Met
        770                   775                   780

Phe Tyr Glu Phe Gly Phe Lys Lys Ser Ala Glu Lys Val Pro Leu Ala
785                 790                   795                   800

Ile Asp Glu

<210> SEQ ID NO 14
<211> LENGTH: 4532
<212> TYPE: DNA
<213> ORGANISM: Nicotiana tabacum

<400> SEQUENCE: 14
atggctgaac gtgctctgac tcgtgttcac agccttcgtg aacgtcttga tgccactttg      60
gctgcacatc gcaatgagat attgctgttt ctttcaaggt attgcctaag tagtgttctt     120
gtttcctaca aaagattcag ttggtgttca aaaaacgata tgtgatttga tttatctgcc     180
taagtcttgg tagtcataat tatccggtac ctgtgctggt gcgagttagc tggttcggaa     240
actactctta tgaaaacgag agatttagtt ggtgttgtct gcaattctgt agtatggact     300
```

-continued

| | | | | | |
|---|---|---|---|---|---|
| attaagcaga | tagatcatgt | ttgatatcga | aaaggaatgt | atatgtgatg | ttacttgaac | 360 |
| tggttttggt | tattacagga | ttgaaagcca | tggaaaaggg | atcttgaaac | ctcaccagct | 420 |
| attggctgag | ttcgatgcaa | ttcgccaaga | tgacaaaaag | aagctgaatg | atcatgcatt | 480 |
| tgaagaactc | ctgaaatcta | ctcaggtaat | tttgattttg | gctaaatgtg | ttaccaagct | 540 |
| gaatgatcat | gcatttgagt | ttgtgtccga | ctactacaat | gatatgttat | accaggaagc | 600 |
| gattgttctg | ccaccttggg | ttgcacttgc | cattcgtttg | aggcctggtg | tgtgggaata | 660 |
| tgtccgtgtg | aatgttaatg | ctctagtcgt | tgaggagctg | accgtccctg | agtatttgca | 720 |
| ttttaaggaa | gaacttgttg | atggaacgta | agttttagtc | tcttatttga | tactatgtta | 780 |
| gagaataggc | agtggattca | atttatcagt | gttgtttttt | acctaatgca | gctccaatgg | 840 |
| aaatttcgtt | ctcgagttgg | attttgagcc | cttcactgca | tcctttccta | aaccgaccct | 900 |
| caccaaatct | attgggaatg | gagttgaatt | cctcaatagg | cacctttctg | cgaaaatgtt | 960 |
| ccatgacaag | gaaagcatga | ccccgcttct | tgaatttctt | cgggttcaca | attataaggg | 1020 |
| caaggtaact | ttgttattcc | cattcatata | tatgttcagt | ttgtgcttat | catgcgccca | 1080 |
| atgatgtatg | aatatgtact | aaaggataga | tgtacgattt | cgtttgcaga | caatgatgct | 1140 |
| gaatgacaga | atacagaatt | taaccactct | gcaaaatgtc | ctaaggaagg | cagaggaata | 1200 |
| ccttattatg | cttcccctg | aaactccatt | ttccgaattc | gaacacaagt | tccaagaaat | 1260 |
| tggattggag | aagggatggg | gcgacactgc | ggagcgcgtg | ctagagatga | tatgcatgct | 1320 |
| tcttgatcta | cttgaggctc | ccgactcctg | tactcttgag | aagttcctag | ggagaattcc | 1380 |
| tatggtgttc | aacgtggtta | tcctttcccc | ccatggatat | ttcgcccagg | aaaatgtctt | 1440 |
| gggttatccc | gacactggtg | gccaggtgca | ttactttagt | ctttgtccgt | gagtctatgt | 1500 |
| tgctcagatc | ctctacaatg | ccactgtacc | cgtgtaggat | actccaaata | taatgcattt | 1560 |
| ttggaggatc | tgtcaccggt | gcaatggcat | tttggaggtc | ggagcaacaa | acaactgcta | 1620 |
| gtatgcttct | aaagcttgct | tccataaatg | ctaaggtcct | tcacccgtaa | tgtgcaggtt | 1680 |
| gtctacatat | tagatcaagt | tccagccttg | gagcgtgaaa | tgcttaaacg | cctaaaggag | 1740 |
| caaggacttg | atataacacc | gcgtattctt | attgttagta | tttcttgtac | ttgtaattgc | 1800 |
| tgcggattac | acaaaatttt | ctctttattg | gcaacttatc | ttgatattat | tcccaggtta | 1860 |
| ctcgtctgct | gcctgatgca | gttggaacaa | cttgtggtca | gcggcttgag | aaggtgtatg | 1920 |
| gagccgagca | ctcacatatt | cttagggtcc | cctttaggac | cgagaagggc | attgttcgca | 1980 |
| aatggatatc | tcgctttgaa | gtgtggccat | acatggagac | tttcactgag | gtgacactaa | 2040 |
| gcttccttgt | atttgtctat | cttctaattg | gtattaggaa | caatttgcta | attattaacg | 2100 |
| ctttggcttt | tcgtacatca | ggatgttgca | aaagaacttg | ctgcagaact | gcaggccaag | 2160 |
| ccagatttga | taattggcaa | ctatagcgag | ggaaatcttg | tggcttcatt | gctggctcac | 2220 |
| aagttaggcg | taacgcaggt | ctgtgttatt | tttcacctct | tataaatctg | attgtatttc | 2280 |
| cattagtctg | gaactaaaag | tactaaaatt | ttcttttctt | cgctgtgtta | tttgccttct | 2340 |
| gcagtgcacc | attgcccatg | cattggagaa | acaaagtat | cctgattctg | acatctactg | 2400 |
| gaaaaattt | gacgaaaaat | accatttctc | gtcccagttt | accgctgatc | ttattgcaat | 2460 |
| gaatcacacc | gattttatca | tcaccagcac | tttccaggag | atagcaggaa | ggtataacat | 2520 |
| caattgctaa | ttcggttgca | gtaacatttt | gttcgatttc | ttcccttat | gcttaaccta | 2580 |
| ataccctaat | gaattttcca | gcaaggacac | tgtcggacag | tacgagagtc | accaggcatt | 2640 |
| cacaatgcct | ggattgtaca | gagtcgttca | cggcattgat | gtgttcgatc | ccaaattcaa | 2700 |

-continued

```
cattgtctca cctggagctg atataaacct gtatttccca tattccgaga aggaaaagag    2760
attgacagca cttcacccag aaattgagga gcttctgtac agtgatgttg agaacgagga    2820
acatctgtaa gtttctaact tactcgtacc gtcagtggca gagccagaat tttcattaaa    2880
atggggtcaa aatataaaga cataaattca caaagaagcc aagggggtgtc aatatgtagt   2940 ataaatatat taaaaaaatt acctagctac acaatgtaat tttccgacaa aggggtatcg    3000
gttgcacttc ttgaatacat gtggctctgc cactgggtac agttacaaag tcctgttacc    3060
tatgtagatg agcttgtgct gaacatgttg tgattttggt aggtgtgtgc taaaggacag    3120
gaataagcca atcttattca caatggcgag attggatcgt gtgaagaact taaccggact    3180
tgttgagtgg tacgccaaga acgcacggct aagggagttg gttaaccttg ttgtcgttgg    3240
tggagaccga aggaaggaat ccaaagattt ggaagagcaa gcagagatga agaagatgta    3300
tgagctaata aagactcaca acttaaatgg ccaattcaga tggatttctt cacagatgaa    3360
ccgagtaagg aacggcgaac tctaccgata cattgccgac actaggggag ctttcgtgca    3420
gcctgcattc tatgaggctt tcggtttgac tgttgttgag gccatgaccct gtggtttgcc   3480 tacatttgca actaatcatg gcggtccagc tgagatcatc gttaacgaaa atccggctt     3540 ccatatcgat ccatatcacg gtgagcaagc tgctgatctg ctagctgatt tctttgagaa    3600
atgtaagacg gaaccttctc attgggaaac tatttcaacc ggtggcctga gcgcatcca    3660 agagaagtaa gcaactcttt cttgactcta gtcattcaaa ttaacttggg atttgaggca    3720
tagttgattg ataatttatc gcgtctctac tactatatac aggtacacgt ggcaaatcta    3780
ctcggagaga ttattgacgt tggctgctgt ttacggtttc tggaaacatg tttctaagct    3840
tgatcgtcta gaaatccgtc gatatctaga aatgttttat gctctcaaat accggaagat    3900
ggtgagttct tctgcttcct gctcttctca tagtgtttaa tatacacttg attgattgca    3960
ttcacttaga ctaagttgct cggacacggg tgtggatgtc cgacacgagt gcggatctag    4020
agttcagatc cttcaagatg taaattataa gattcgggga tatggatcct agtacggata    4080
cgggtgcgag aatccggcta aaataattt taaaaaaat tatctctaaa ttatgagata     4140
ttatgtggaa tacttacgta taacttgtaa agtgtagatt tttttaatt ctcaagttgt     4200 agattagtaa atgattgatt tcctagataa gtatgctatt tcttcaaat ttactcttct    4260 gatttcgaaa atcaaattgt atctcgtctc gaattttcc gtccgttatg gtcaaagtac     4320
ccaaaatcgt tgaccaaat cggtacggat cccatacca cacccacact agtgtcgtat      4380
tgacacgggt gccgcaccta aactgctatg tcggagcaac ttagcactta gagaatcatt    4440
gatgttaaat tttcttaatt cttgaatctg ctaatgaaga ttttatcttg gtttttgttt    4500
aggctgaagc tgttccattg gctgctgaat ga                                  4532
```

<210> SEQ ID NO 15
<211> LENGTH: 805
<212> TYPE: PRT
<213> ORGANISM: Nicotiana tabacum

<400> SEQUENCE: 15

Met Ala Glu Arg Ala Leu Thr Arg Val His Ser Leu Arg Glu Arg Leu
1               5                   10                  15

Asp Ala Thr Leu Ala Ala His Arg Asn Glu Ile Leu Leu Phe Leu Ser
            20                  25                  30

Arg Ile Glu Ser His Gly Lys Gly Ile Leu Lys Pro His Gln Leu Leu
        35                  40                  45

-continued

```
Ala Glu Phe Asp Ala Ile Arg Gln Asp Asp Lys Lys Leu Asn Asp
    50                  55                  60

His Ala Phe Glu Glu Leu Leu Lys Ser Thr Gln Glu Ala Ile Val Leu
65                  70                  75                  80

Pro Pro Trp Val Ala Leu Ala Ile Arg Leu Arg Pro Gly Val Trp Glu
                85                  90                  95

Tyr Val Arg Val Asn Val Asn Ala Leu Val Val Glu Glu Leu Thr Val
                100                 105                 110

Pro Glu Tyr Leu His Phe Lys Glu Glu Leu Val Asp Gly Thr Ser Asn
            115                 120                 125

Gly Asn Phe Val Leu Glu Leu Asp Phe Glu Pro Phe Thr Ala Ser Phe
    130                 135                 140

Pro Lys Pro Thr Leu Thr Lys Ser Ile Gly Asn Gly Val Glu Phe Leu
145                 150                 155                 160

Asn Arg His Leu Ser Ala Lys Met Phe His Asp Lys Glu Ser Met Thr
                165                 170                 175

Pro Leu Leu Glu Phe Leu Arg Val His Asn Tyr Lys Gly Lys Thr Met
            180                 185                 190

Met Leu Asn Asp Arg Ile Gln Asn Leu Thr Thr Leu Gln Asn Val Leu
    195                 200                 205

Arg Lys Ala Glu Glu Tyr Leu Ile Met Leu Pro Pro Glu Thr Pro Phe
210                 215                 220

Ser Glu Phe Glu His Lys Phe Gln Glu Ile Gly Leu Glu Lys Gly Trp
225                 230                 235                 240

Gly Asp Thr Ala Glu Arg Val Leu Glu Met Ile Cys Met Leu Leu Asp
                245                 250                 255

Leu Leu Glu Ala Pro Asp Ser Cys Thr Leu Glu Lys Phe Leu Gly Arg
            260                 265                 270

Ile Pro Met Val Phe Asn Val Val Ile Leu Ser Pro His Gly Tyr Phe
    275                 280                 285

Ala Gln Glu Asn Val Leu Gly Tyr Pro Asp Thr Gly Gly Gln Val Val
    290                 295                 300

Tyr Ile Leu Asp Gln Val Pro Ala Leu Glu Arg Glu Met Leu Lys Arg
305                 310                 315                 320

Leu Lys Glu Gln Gly Leu Asp Ile Thr Pro Arg Ile Leu Ile Val Thr
                325                 330                 335

Arg Leu Leu Pro Asp Ala Val Gly Thr Thr Cys Gly Gln Arg Leu Glu
            340                 345                 350

Lys Val Tyr Gly Ala Glu His Ser His Ile Leu Arg Val Pro Phe Arg
    355                 360                 365

Thr Glu Lys Gly Ile Val Arg Lys Trp Ile Ser Arg Phe Glu Val Trp
370                 375                 380

Pro Tyr Met Glu Thr Phe Thr Glu Asp Val Ala Lys Glu Leu Ala Ala
385                 390                 395                 400

Glu Leu Gln Ala Lys Pro Asp Leu Ile Ile Gly Asn Tyr Ser Glu Gly
            405                 410                 415

Asn Leu Val Ala Ser Leu Leu Ala His Lys Leu Gly Val Thr Gln Cys
            420                 425                 430

Thr Ile Ala His Ala Leu Glu Lys Thr Lys Tyr Pro Asp Ser Asp Ile
    435                 440                 445

Tyr Trp Lys Lys Phe Asp Glu Lys Tyr His Phe Ser Ser Gln Phe Thr
450                 455                 460
```

```
Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Gln Ala Phe Thr Met Pro Gly Leu Tyr Arg Val Val His Gly Ile
            500                 505                 510

Asp Val Phe Asp Pro Lys Phe Asn Ile Val Ser Pro Gly Ala Asp Ile
        515                 520                 525

Asn Leu Tyr Phe Pro Tyr Ser Glu Lys Glu Lys Arg Leu Thr Ala Leu
    530                 535                 540

His Pro Glu Ile Glu Glu Leu Leu Tyr Ser Asp Val Glu Asn Glu Glu
545                 550                 555                 560

His Leu Cys Val Leu Lys Asp Arg Asn Lys Pro Ile Leu Phe Thr Met
                565                 570                 575

Ala Arg Leu Asp Arg Val Lys Asn Leu Thr Gly Leu Val Glu Trp Tyr
                580                 585                 590

Ala Lys Asn Ala Arg Leu Arg Glu Leu Val Asn Leu Val Val Val Gly
            595                 600                 605

Gly Asp Arg Arg Lys Glu Ser Lys Asp Leu Glu Glu Gln Ala Glu Met
        610                 615                 620

Lys Lys Met Tyr Glu Leu Ile Lys Thr His Asn Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Ala Asp Thr Arg Gly Ala Phe Val Gln Pro Ala Phe Tyr
            660                 665                 670

Glu Ala Phe Gly Leu Thr Val Val Glu Ala Met Thr Cys Gly Leu Pro
        675                 680                 685

Thr Phe Ala Thr Asn His Gly Gly Pro Ala Glu Ile Ile Val Asn Gly
690                 695                 700

Lys Ser Gly Phe His Ile Asp Pro Tyr His Gly Glu Gln Ala Ala Asp
705                 710                 715                 720

Leu Leu Ala Asp Phe Phe Glu Lys Cys Lys Thr Glu Pro Ser His Trp
                725                 730                 735

Glu Thr Ile Ser Thr Gly Gly Leu Lys Arg Ile Gln Glu Lys Tyr Thr
            740                 745                 750

Trp Gln Ile Tyr Ser Glu Arg Leu Leu Thr Leu Ala Ala Val Tyr Gly
        755                 760                 765

Phe Trp Lys His Val Ser Lys Leu Asp Arg Leu Glu Ile Arg Arg Tyr
770                 775                 780

Leu Glu Met Phe Tyr Ala Leu Lys Tyr Arg Lys Met Ala Glu Ala Val
785                 790                 795                 800

Pro Leu Ala Ala Glu
                805

<210> SEQ ID NO 16
<211> LENGTH: 5901
<212> TYPE: DNA
<213> ORGANISM: Nicotiana tabacum

<400> SEQUENCE: 16 atgctttta tgggagtaaa ttttatggcc ggtcattcaa ctttgtgttc attacgcaaa      60 agtcatttt cttggtgttt attacgcaag tcattttct ttttttttg ttacgtaaaa     120 atcattcaac tatgtgttta ttatctaaaa ttcaattttt ttttccttt tgttacacaa     180
```

```
aaatcatttt actttactct atttatcaca aaagtcacct tggccagatt ttataatagg    240
cttttatctt ttgttacaca aaaattattt tactttactc tatttatcac aaagtcacc     300 ttggccagat tttataatag gcttttatct tttgttacac aaaaattatt ttactttact    360
ctatttatca caaaagtcac cttggccaga ttttacaata cttttacctt aaaagactat    420
tatgcccttg acattataaa tcctctcatt tatataatac cttctatatg atacactata    480
taatatattt ttacctaggt attttactta taattaaaat aatattaaat tattttattt    540
atctatttta taatatattc atacatttaa ttttttcatg gcaaatcact ttgtttaatc    600
atatttaaac atgaacaaat tttaaatatc aaaaaaataa aaaaataaaa aaaatattta    660
tttgaaataa taacaaacag atttgtttaa caaatgatag ttttttttta tagtcaataa    720 aattttttaaa aaaattcaaa gatatttgtt tttaatatta atattttttaa agctttatct   780 gttaatatta tttatttgaa agtattaatc tgatgtgtca ttgtgttaaa tgtgagtatt    840
ttatttattg gattaatgag tatggcttgg ctgataaaaa gctttgattt tataattttc    900
attaaaaata ttttattaag ctagtacctg acaaatttaa tatcttgaaa attaacgtta    960
agaaaaaatt aaatataaaa atatattata aaaataataa ataaataata tcaagttatt   1020
ttaattataa ataaaataca tggttaaaaa tatattatat agcatataat atagaaggta   1080
ttacataaat gagatgattt aaagggcata atagactttt caggtgaatg atttgtaaaa   1140
tatggttaaa gtgattattg tgataattag agcatagtaa aataattttt atgtaacaaa   1200
agaaaaaaaa aatgactttt gggtaatgaa cataaatttg aataacttttt acgtaacaaa   1260 agaataaaat aaattttgga taataaacat aaaattgaat gaccacctat aaaatttatt   1320 attttttttgg gctcttcttg atttgatttt ttagtttagc ctttgcagta atcttggttg   1380
tcacgcgtag cgttgtgctt tcgccacata agtatttagt agacttaatt aatgtcatta   1440
tatcggttgg tgtggtttta attacttaac tgtactatta tattaggtgg aaggtttgaa   1500
aatttatagt agtaacattc tagatcattg aaaatattgg tgtttcagtg acttttttagt   1560 atgtcatttt catttttctaa gtggttgtac taatatagta tattaaaatt ttgattggtt   1620
gagaaacaat ctctctcacc tacacggtac gggtaaggta tgcgtatacg cttatcctcc   1680
ctacactcca tttgtgggac tattgttgtt attttggata agctgaggta tccatcttct   1740
actaactgca ctagtttatt ttttttgctg tttacagttg aaacaattgt ctgaggattt   1800
ctcacctgct gaatcaactg caatggctga acgtgtgctg actcgtgttc acagccttcg   1860
tgaacgtctt gatgctactt tggctgctca tcgcaatgag atattactgt ttctttcaag   1920
gtatagccaa agatagtatt cttgttaact aaaaaagatt cagttggtgt tcaaaaaacg   1980
atacgtttat ctgcctaagt cttggtagtc agaattatcc ggtacctatg ctggtgtgag   2040
ttagctggct aggaaaccac tcttatgaaa acaagagatt tagttagagt tgtctgtaat   2100
tctgtagtat ggactatgta tgtgatgcta tttgaactgg ttttggttat tataggattg   2160
aaagccatgg aaaagggatc ttgaaaccgc atcagctatt ggctgagttt gatgcaattc   2220
gccaagatga caaaaagaaa ctgaatgatc atgcatttga agaactcctg aagtccactc   2280
aggtaatatg gttttggcta tatttgtcgc caacgccaag ctcatatttt tatattattt   2340
tgagcttgtg tctgaatacg acgatgatat gttatactag gaagcaattg ttctgccacc   2400
ttgggttgca cttgcgattc gtttgaggcc tggtgtgtgg gaatatgtcc gtgtgaatgt   2460
caatgcgcta gtcgttgagg agctgactgt ccctgagtat ttgcatttca aggaagaact   2520
```

```
tgtcgatgga acgtaagtgt tagtcttcaa tttgatgcta tgttagagaa taggctgtgg    2580
aatttattga tcaatgctgt gctttgtcct gatacagctc caatggaaat ttcgttctcg    2640
agttggattt tgagcccttc accgcatcct ttcctaaacc aaccctcacc aaatctatcg    2700
gaaatggagt tgaattcctc aataggcacc tctctgcgaa aatgttccat gacaaggaaa    2760
gcatgacccc gcttcttgaa tttcttcggg ttcacaatta taagggcaag gtgacttgct    2820
atttccattt atctataggt tcggtttgtg cttatcatgc gcccaatgac atatgaatat    2880
gcgctaaagg atagatatat gatttccttt gcagacaatg atgctgaacg acagaataca    2940
gaatttaacc acactgcaaa atgtcctaag gaaggcagag gaatacctca ttatgcttcc    3000
ccctgaaact ccattttccg aattcgaaca caagttccaa gaaattggat tggagaaggg    3060
atggggcgac actgcagagc gcgtgctgga gatgatatgc atgcttcttg atctcctcga    3120
ggctcccgat tcctgtactc ttgagaagtt cttggggaga attcctatgg tgttcaatgt    3180
ggttatcctt tccccccacg atatttcgc ccaggaaaat gtcttgggtt atcccgacac    3240
tggtggccag gtgcattact ttaatcttta tccgtgagtc tatgtttgtt cgaatcctct    3300
agaaatgtca ctgtacctat gtaggatact ccaaatataa tgcattttgg ggggatctgt    3360
tatgggtgcg atggcatttt tggaggtcgg agcaacaaac aattgctatg tattcttcta    3420
aagcttgctt tcataaatgc taaggtcctt caccttaat gtgcaggttg tctatatatt    3480
agatcaagtt ccagccttgg agcgtgaaat gcttaagcgc ctaaaggagc aaggacttga    3540
tatcacaccg cgtattctta ttgttagtat ttcctgtact tgtaattact gcggattaca    3600
caaaatttcc tttttatctt cttaacaact tatcttgatg gtattcccag gttactcgtc    3660
tgctacctga tgcagttgga acgacttgtg gtcagcggct tgagaaggtg tatggagccg    3720
agcactcaca tattctgagg gtccccttta ggactgagaa gggcattgtt cgtaaatgga    3780
tctctcgctt tgaagtgtgg ccatatatgg agactttcac tgaggtgaca ctaaaacttc    3840 cttatattg tctatcttct aattggtatt aggaataatt tgttaattgt taactctttg    3900
tcttttcgta catcaggatg tcgcaaaaga acttgctgca gaattgcagg ccaagccaga    3960
tttgataata ggcaactata gcgagggaaa tcttgtggct tcattgctcg ctcataagtt    4020
aggcgtaaca caggtctgtg ttgttttca ctctcttaaa gatctgattg catttccatt    4080
agtctggaac tagaagtact aaaaagttct tttcttcact gtgttatttg ccgtcggcag    4140
tgcaccatag ctcatgcatt ggagaaaaca aagtatcctg attctgacat ctactggaaa    4200
aaattcgatg aaaaatacca tttctcgtcc cagtttaccg ctgatcttat tgcaatgaat    4260
cacaccgatt ttatcatcac cagcactttc caggagatag caggaaggta aacatcaat    4320 ttgctacttc gactgcaaca gcattgtgtt cccatttctt tcccttatgc ttaacctaat    4380
accgtcatga attttccagc aaggacactg tcggacagta cgagagtcat caggcattca    4440
caatgcccgg attgtacaga gttgttcacg gcattgatgt gttcgacccc aaattcaaca    4500
ttgtctcacc tggagctgac ataaacctct atttcccata ttccgagaag gaaagagac    4560 tgacagcact tcaccctgaa atcgaggagc tgctgtacag tgacattgag aacgaggaac    4620
atctgtaagt ttctacctta ctcgtacagt cagtggcgga gccagaattt tcactaaaat    4680
aaggtcaaaa tataaagaca taaatccaca agaagccaa gggtgtcaat atatagtata    4740
aatacattaa aaaaattacc tatctacaca gtgtaatttt ccgacaaagg ggtgtcggtt    4800
gacactcctt gaatacatgt ggctctgcca ctgggtacga ttacaaagtt ctgttaccta    4860
tgtagatgag cttgtgctga acatgttgtg atttttggcag gtgtgtgcta aaggacagga    4920
```

-continued

```
ataagccaat cttattcaca atggcgagat tggatcgtgt gaagaattta accggacttg    4980
ttgagtggta tgccaagaac gcacggctaa gggagttggt taaccttgtt gtggttggtg    5040
gagatcgaag gaaagaatcc aaagatttgg aagagcaaac agaaatgaaa aagatgtatg    5100
agctaataaa gactcacaat ttaaatggcc aattcagatg gatttcttca cagatgaacc    5160
gagtgaggaa cggtgaactc taccgataca ttgctgacac tagaggagct ttcgtgcagc    5220
ctgcattcta cgaggctttc ggtttgactg ttgttgaggc catgacctgt ggtttgccta    5280
catttgcaac taatcatggc ggtccagctg agatcatcgt taacggaaaa tctggcttcc    5340
acatcgatcc atatcacggt gagcaagctg ctgatctgct agctgatttc tttgagaaat    5400
gtaagacaga accttctcat tgggaaacca tttcaacggg tggcctgaag cgcatccaag    5460
agaagtaagc aactctttct tgactctagt cattgaaatt aactttcttg actctagtca    5520
ttgaaattaa ctcgggattt gaggcgtagt tgattgatat tttatcgcgt ctctactact    5580
gatatataca ggtacacgtg gcaaatctac tcggagaggc tattgacatt ggctgctgtt    5640
tacgggttct ggaaacatgt ttctaagctt gatcgtctag aaatccgtcg atatcttgaa    5700
atgttttatg ctctcaaata ccgcaagatg gtgagttcct cttcttcctt gcccttctcc    5760
tagtgtttaa gatacaatat aattgattgc attatcttag agaatcatta atgttaaatt    5820
ttcttaattc ttgaatctgt taatgaagtt tttctcttgg tttttgttta ggctgaagct    5880
gttccattgg ctgctgagtg a                                              5901
```

<210> SEQ ID NO 17
<211> LENGTH: 825
<212> TYPE: PRT
<213> ORGANISM: Nicotiana tabacum

<400> SEQUENCE: 17

```
Met Leu Phe Met Gly Leu Lys Gln Leu Ser Glu Asp Phe Ser Pro Ala
1               5                   10                  15

Glu Ser Thr Ala Met Ala Glu Arg Val Leu Thr Arg Val His Ser Leu
            20                  25                  30

Arg Glu Arg Leu Asp Ala Thr Leu Ala Ala His Arg Asn Glu Ile Leu
        35                  40                  45

Leu Phe Leu Ser Arg Ile Glu Ser His Gly Lys Gly Ile Leu Lys Pro
    50                  55                  60

His Gln Leu Leu Ala Glu Phe Asp Ala Ile Arg Gln Asp Asp Lys Lys
65                  70                  75                  80

Lys Leu Asn Asp His Ala Phe Glu Glu Leu Lys Ser Thr Gln Glu
                85                  90                  95

Ala Ile Val Leu Pro Pro Trp Val Ala Leu Ala Ile Arg Leu Arg Pro
            100                 105                 110

Gly Val Trp Glu Tyr Val Arg Val Asn Val Asn Ala Leu Val Val Glu
        115                 120                 125

Glu Leu Thr Val Pro Glu Tyr Leu His Phe Lys Glu Glu Leu Val Asp
    130                 135                 140

Gly Thr Ser Asn Gly Asn Phe Val Leu Glu Leu Asp Phe Glu Pro Phe
145                 150                 155                 160

Thr Ala Ser Phe Pro Lys Pro Thr Leu Thr Lys Ser Ile Gly Asn Gly
                165                 170                 175

Val Glu Phe Leu Asn Arg His Leu Ser Ala Lys Met Phe His Asp Lys
            180                 185                 190
```

Glu Ser Met Thr Pro Leu Leu Glu Phe Leu Arg Val His Asn Tyr Lys
        195                 200                 205

Gly Lys Thr Met Met Leu Asn Asp Arg Ile Gln Asn Leu Thr Thr Leu
        210                 215                 220

Gln Asn Val Leu Arg Lys Ala Glu Glu Tyr Leu Ile Met Leu Pro Pro
225                 230                 235                 240

Glu Thr Pro Phe Ser Glu Phe Glu His Lys Phe Gln Glu Ile Gly Leu
                245                 250                 255

Glu Lys Gly Trp Gly Asp Thr Ala Glu Arg Val Leu Glu Met Ile Cys
                260                 265                 270

Met Leu Leu Asp Leu Leu Glu Ala Pro Asp Ser Cys Thr Leu Glu Lys
                275                 280                 285

Phe Leu Gly Arg Ile Pro Met Val Phe Asn Val Val Ile Leu Ser Pro
        290                 295                 300

His Gly Tyr Phe Ala Gln Glu Asn Val Leu Gly Tyr Pro Asp Thr Gly
305                 310                 315                 320

Gly Gln Val Val Tyr Ile Leu Asp Gln Val Pro Ala Leu Glu Arg Glu
                325                 330                 335

Met Leu Lys Arg Leu Lys Glu Gln Gly Leu Asp Ile Thr Pro Arg Ile
                340                 345                 350

Leu Ile Val Thr Arg Leu Leu Pro Asp Ala Val Gly Thr Thr Cys Gly
        355                 360                 365

Gln Arg Leu Glu Lys Val Tyr Gly Ala Glu His Ser His Ile Leu Arg
        370                 375                 380

Val Pro Phe Arg Thr Glu Lys Gly Ile Val Arg Lys Trp Ile Ser Arg
385                 390                 395                 400

Phe Glu Val Trp Pro Tyr Met Glu Thr Phe Thr Glu Asp Val Ala Lys
                405                 410                 415

Glu Leu Ala Ala Glu Leu Gln Ala Lys Pro Asp Leu Ile Ile Gly Asn
                420                 425                 430

Tyr Ser Glu Gly Asn Leu Val Ala Ser Leu Leu Ala His Lys Leu Gly
        435                 440                 445

Val Thr Gln Cys Thr Ile Ala His Ala Leu Glu Lys Thr Lys Tyr Pro
        450                 455                 460

Asp Ser Asp Ile Tyr Trp Lys Lys Phe Asp Glu Lys Tyr His Phe Ser
465                 470                 475                 480

Ser Gln Phe Thr Ala Asp Leu Ile Ala Met Asn His Thr Asp Phe Ile
                485                 490                 495

Ile Thr Ser Thr Phe Gln Glu Ile Ala Gly Ser Lys Asp Thr Val Gly
                500                 505                 510

Gln Tyr Glu Ser His Gln Ala Phe Thr Met Pro Gly Leu Tyr Arg Val
                515                 520                 525

Val His Gly Ile Asp Val Phe Asp Pro Lys Phe Asn Ile Val Ser Pro
        530                 535                 540

Gly Ala Asp Ile Asn Leu Tyr Phe Pro Tyr Ser Glu Lys Glu Lys Arg
545                 550                 555                 560

Leu Thr Ala Leu His Pro Glu Ile Glu Glu Leu Leu Tyr Ser Asp Ile
                565                 570                 575

Glu Asn Glu Glu His Leu Cys Val Leu Lys Asp Arg Asn Lys Pro Ile
                580                 585                 590

Leu Phe Thr Met Ala Arg Leu Asp Arg Val Lys Asn Leu Thr Gly Leu
        595                 600                 605

Val Glu Trp Tyr Ala Lys Asn Ala Arg Leu Arg Glu Leu Val Asn Leu

Val Val Val Gly Gly Asp Arg Arg Lys Glu Ser Lys Asp Leu Glu Glu
625                 630                 635                 640

Gln Thr Glu Met Lys Lys Met Tyr Glu Leu Ile Lys Thr His Asn Leu
            645                 650                 655

Asn Gly Gln Phe Arg Trp Ile Ser Ser Gln Met Asn Arg Val Arg Asn
            660                 665                 670

Gly Glu Leu Tyr Arg Tyr Ile Ala Asp Thr Arg Gly Ala Phe Val Gln
            675                 680                 685

Pro Ala Phe Tyr Glu Ala Phe Gly Leu Thr Val Val Glu Ala Met Thr
690                 695                 700

Cys Gly Leu Pro Thr Phe Ala Thr Asn His Gly Gly Pro Ala Glu Ile
705                 710                 715                 720

Ile Val Asn Gly Lys Ser Gly Phe His Ile Asp Pro Tyr His Gly Glu
            725                 730                 735

Gln Ala Ala Asp Leu Leu Ala Asp Phe Phe Glu Lys Cys Lys Thr Glu
            740                 745                 750

Pro Ser His Trp Glu Thr Ile Ser Thr Gly Gly Leu Lys Arg Ile Gln
            755                 760                 765

Glu Lys Tyr Thr Trp Gln Ile Tyr Ser Glu Arg Leu Leu Thr Leu Ala
            770                 775                 780

Ala Val Tyr Gly Phe Trp Lys His Val Ser Lys Leu Asp Arg Leu Glu
785                 790                 795                 800

Ile Arg Arg Tyr Leu Glu Met Phe Tyr Ala Leu Lys Tyr Arg Lys Met
            805                 810                 815

Ala Glu Ala Val Pro Leu Ala Ala Glu
            820                 825

<210> SEQ ID NO 18
<211> LENGTH: 8323
<212> TYPE: DNA
<213> ORGANISM: Nicotiana tabacum

<400> SEQUENCE: 18
atggcgaatc caaagttcac aagagtacct agcatgaggg agagagttga ggatactctc      60
tctgctcacc gtaaccagct tgttgctctc ctctccaggt atattaataa actctatata     120
cttgttattt tctttatttt tttgtcttta ctgataaatt taactgtttt cttctttaaa     180
tcttgctttc gatgcatgat ttctgttgtg ttaaattgcg taaccatttt atctaaaagt     240
ttatgctgat aaacactttt aaatttttaat atgtaaatta tattatgtct caacatcaac     300
atgtggatgg ccaaaaatat aaagcttaat tttcgttatt ttgaatgatt tttctctgcg     360
agtgttacgg tttgcgtaca cattacctaa acctcctccc tagtcccac ttgtgggaat      420 ttaatttttt ttttctttgt tttttttttgt tgttgttgtt gtctgagttc aattcctacc     480
atgttagctt ggcaaaaata agttggtaaa gcttgacccc aactagtttt agttgatcga     540
tttatttggt gatttatagt tcaataataa taattactat tagagaaagt tccagcagct     600
tttctgtttg tttttccagt tttagtgatt gatatatgtg tatatatatt ctttgtttct     660
tttaagatac gtggcgcagg ggaaggggat attgcaacct caccacttga tcgatgagtt     720
caacaacgct gtatgtgatg acactgcttg tgagaagctc aaagatggtc cctttagtga     780
agtcttgaaa gctactcagg tatattcact aatccatggg aatcaagatg atactgtata     840
tctttattat ggtgtctttc agaaatttga cgatgatgaa atgcaacttt ctctgttttg     900

| | |
|---|---|
| tcaccttatc cagactgttt ttttatttttt tatttttcat tttttaactt gaaatgctct | 960 |
| taatttcctt tgtttatcga taagaccgga tttacaatgt atgaacggag catcttaaga | 1020 |
| accttctgga atgaagatat aagatataaa acatggtgtc cgttttctcc tttgtggaat | 1080 |
| cagtgtacat atagactgtt attttggtcc cactttctgg atcttctgat cacaccttct | 1140 |
| catgcagagg cgagcttgat ggtttcaacc tttaaattct tactattgaa tccatttcac | 1200 |
| tttcgaaatt atgagttcga aatctaatat ttgttgaaat ttttgcaaat gttcacatat | 1260 |
| aagtttaagc tttgtgtcaa gaatactggg ctcaatggat tccaatagac caggctgtat | 1320 |
| ccgcctctgt ctccactctc cctgcatcca cttctttcgt gtgactaata atgcttaatg | 1380 |
| agctagaact cgttttaatg tttgaataag ttgcttatat cagagcagct tttgatgttt | 1440 |
| caatctttaa cgggttatgc agtaccagca ttctgcggct gaaaaacagg aatctgagat | 1500 |
| ttacttgtct ctggctgaat ttcttgttca ttttgctaac aagtactttg gagttaatgc | 1560 |
| ttgctctctg ttgtcaaaat aggaagccat tgtgctgcca ccatttgttg ccatagcagt | 1620 |
| tcgtccaagg ccaggtgttt gggagtatgt tcgtgttaat gtatatgatt tgagcgttga | 1680 |
| acaattgact gttcctgaat atcttcattt caaggaagaa cttgtggatg gagagtaagc | 1740 |
| tctttcttat ttcaatacga aacataaaaa tttacagaag ttgaataatt aacaaatttg | 1800 |
| ttgatttta atgtatgcca ggggtaataa tcactttgtg cttgagctgg attttgagcc | 1860 |
| atttaatgca tcagttcctc gtccatctcg atcgtcatcc attggcaatg gagtccaatt | 1920 |
| cctcaatcgt catctttcct caattatgtt tcgcagcaaa gactctctgg accccttact | 1980 |
| tgatttcctt agaggacact gtcataaagg gaatgtaagt accaaaagca gttttcccttt | 2040 |
| tgtaaatgtc tgcttgtccc tgattatcta ctaaatcttt caacacgcgc aaccattata | 2100 |
| agaaatgtac aatacttcta gttagaattt catcatcgac aaactatctg ctttacttttt | 2160 |
| tattttccc atttgatgga tgatagttta gtttatataa cagatgatat tttggttgaa | 2220 |
| gggtaccatg aacttttttca caaccactta atggatacat agttgtaata gttgacatttt | 2280 |
| tggaataata ttgtctcact tggaaatgtt taagaagtat tactacttct atttgtaaga | 2340 |
| tggattgttt atctatgcag gtcttgatgt tgaatgatcg tatacagcga atctccaggc | 2400 |
| tggagtctgc tctttctaaa gcagaggatt atctctccaa gctatcacca gatacatcct | 2460 |
| ataatgagtt cgaatacgcg tgagcttgta cacatttgtt ttgttttctt tcaagcatat | 2520 |
| gtaatttctc aagaaaaggg aaatctatag gagttgaaac attctttatg gaaccatgtg | 2580 |
| catgcagatt gcaagaaatg ggcttttgaga gaggttgggg tgatactgcc agacgtgttt | 2640 |
| tggagacgat gcatcttctt tctgacattc ttcaggctcc ggatccatca accttggaga | 2700 |
| catttcttgg tagactacct atggtgttca atgtcgtcat attatcccct catggatatt | 2760 |
| ttggccaagc aaatgtcttg ggtttgcccg acactggtgg ccaggtaata acaaggagaa | 2820 |
| tgaggtcttg tattatgtac tccctccgtt ccaatctata tgaacctatt tgactgggta | 2880 |
| tggaaagaaa tgaagacttg taaaacttgt ggttctttag aaattccaaa cattacatttt | 2940 |
| ggttttttcc ctcttcctgg aaattatact actgaatcat ctctagatgt tccagtttaa | 3000 |
| cttgagacgt aagggtaaat aacgaccat tactctgtcc tttcttgcag taggcttggt | 3060 |
| acaatgaata tagttcgcat agttgccgga agctagagct gtgttagaaa actcaggaac | 3120 |
| attaatttgg cgatgctaat cactgctaat gttactgaag catccatggt tttccttgat | 3180 |
| gttattctcc ttttggttgc ttcacaggtt gtctatatac tggatcaagt gcgtgccttg | 3240 |
| gaggccgaaa tgcttcttag aataaagcaa caaggactta acttcaagcc tagaatccctt | 3300 |

| | |
|---|---|
| gtcgtgagta catatatatt atgcaagctc ttatttggtt tgtgggattg cagttgacat | 3360 |
| caatttgctt actctgatta ctaaaggtca cacggctgat acctgatgct aaaggaacca | 3420 |
| tgtgcaacca gaggttggag aggattagtg gaactgaata ctcgcatatt ttacgtgtcc | 3480 |
| cttttaggac agagaaggga atccttcata aatggatatc taggtttgat gtatggcctt | 3540 |
| acctggagaa gttcactgag gtaacctctt tgtcccttgg aaattgcctt ttgttgctga | 3600 |
| tgtttctgct agtgtgctta aatgacggat gttaactagt cacttgctag cgtttgcaat | 3660 |
| agcaacggga aagaaagga tttttgctag tttgaagtct gcctccaaga aaaattatat | 3720 |
| taaaagttta tggctagtgg aaacatcagt cattcatgta ccttatttct atgcccaagt | 3780 |
| tgtttaagtt gaaagtaatt tggccaacta tgcaaattgg gagaacgtgt agccaactat | 3840 |
| tgtgtttgcc gacatgttga tatactttt ggtcctgatt tatatttgtt ggtttgtcat | 3900 |
| actggatgaa gcaattctca tgttttctg cttatatata ttggaagaag agatacttgt | 3960 |
| cgtttcatca ttttctcga cctctctatt accaacactt tgccaattta atgtttggaa | 4020 |
| atgtcttctt gaccaggatg tggcaagtga aatgaccgct gagctccagg gaaagccaga | 4080 |
| tctgattatt ggcaactaca gtgatggaaa tttagttgcc tccctttgg catataaaat | 4140 |
| gggtgtcaca caggtaggaa atacatgatt ctttatcttg ctagcactaa gtcttgaggt | 4200 |
| tatgtatctg caatagaaat tttacgcttt gccttcattt cttttaatt attttttccag | 4260 |
| tgtaccattg ctcatgcctt ggaaaaaaca aagtatcctg attctgacat ctactggaaa | 4320 |
| aagtttgagg agaaatatca ttttttcatgt cagtttactg ctgatctact ggcaatgaat | 4380 |
| aattcagatt tcattatcac cagtacttat caagagattg caggaacgta agtcatttta | 4440 |
| atctggtcgt ttaaatctga tatttcttcc ctagtagtct attcaatccg aatttcagtt | 4500 |
| cagtatatga tgtcatcggt tgaggaactg tgattggtaa cctatcaaa tccgtagctg | 4560 |
| ctctataatt ttatttcgta attggagaaa caattttta ttattgagct tgtagtctga | 4620 |
| gctagaattt ggttctttat ctatcaagta gcataatact acaactattt tttatgtgtg | 4680 |
| gcaatttgca atttcaattt tctatttcta taagttgcag cttttcttcc tgttctgatc | 4740 |
| atatttacat ggctgaaact caatagaaaa ctaggctagt tgatcaaaag tagttggatg | 4800 |
| ctttaaaatt agtagacgtt ttgctaaatg agtgaccaat gttattaaaa aaacgttcat | 4860 |
| gttttcaacc cttttggcat acatttgacc actgcccaag attttggata agtacatgca | 4920 |
| gtgcttataa ttataaagca ttttatccca ccttgttttt cattatgaaa attaagtaat | 4980 |
| ttacgagtat ttgtataagt tacttcataa attagaagta aatctggatt gtgtaaagtt | 5040 |
| attcgccccg tatatactga aagctacttg aacaagcaaa aaaacagaca aacgtaacat | 5100 |
| tctccatgga ttaatgagac ttgtatatat atatatatat atatgtaaag agagagagag | 5160 |
| agagatttgg cttgtaacca catgtatatt atgccatatg gatgtgacat tgatgtgact | 5220 |
| agacctaaat gttttgtttc aatgtccacg ggagttttac gtagagttaa gaggagaaga | 5280 |
| gagtgaggaa tactaatgtt tgatggtacc ccttggcttc ttgacctgga tactcagtgt | 5340 |
| tcttattcat gcctatactt tggtccttga tttcattctc ccttttctag cttgagctgc | 5400 |
| atcaaagaaa ttccactgta aaaaaataa tgctcaccat attggtgcaa catggcaaac | 5460 |
| atgtatccta tttgatgatc aatcaacttt attttctcc tgttaattga cctcagtgtg | 5520 |
| taactctcta tgtatgatag cattgtaact tgtgtcatga ttcataaata gggtactaga | 5580 |
| attggatggt tgacatagta aatggtcaat tgatgatcca caaaatatgc acctactgat | 5640 |

```
taaaatgtga tagggcaggt ttattttgt ttgtggttaa cacagtactt aacctatat    5700
ttaatacaat ttggcttatc tacaatcttt tcttcagtgt ttatgcgaat tccttattgc    5760
acaacaatat tgtctttctg agttctattc tgttgttgct tacactttta ttattccagt    5820
aacatagatg tgaagacatt agattggttg cttgcaaatt gatagccact tgtttcagga    5880
agaatactgt tggtcagtac gagagccata ctgcattcac cctcccggga ctatatcgcg    5940
tcgttcatgg cattgatgtt ttcgatccca aattcaatat agtgtctcct ggagctgaca    6000
tgacaattta tttcccatat tctgacaagg aaaaaagact aacgtctttg catggctcga    6060
ttgaaaagtt gttatttgat cctgcgcaga atgaagagca tatgtaagtg gcatccgttt    6120
gtacttaatt tttttggaat agatgacata ttatttgcat gaatatgaaa aggagggtct    6180
gatatgattt tctatagata aactaccaat gatattattt aaaaactcct ggatactgta    6240
ttaggagaag aagagaacca ggggtagatg gcattagaat cccttaaatc ttgaagagtc    6300
gtcactaacg ctcccaacac ttctgcctca gaccctcaac taaatactat tattgttgat    6360
ttctttggag aagctataag aatctctctc tccttatggt gaaaatttta cttggcttta    6420
tacttaactt ccaaggctcc ctcttataaa atgcaaaaac tgtctgtatt cactctcttg    6480
gttaacaatt gatccaatca aatgcatatg gaacatcttt ctttacgttt cttctaaagt    6540
tcgtttgagg ataaggagta gaatctgaga agatagacta gtaggtaacc ttagggacgg    6600
atgtggaaat taacatatgg gctcagcttt tctgccgagt gcagaccatg tatatgcgtt    6660
aaaaaattca ctaaacaagt aaatgtttga ttttgaaccc agtaaatcaa atgagttgtg    6720
gtagaatctc gaactcgaac cgataaagtt caaatccagg atccgctttt aggtaaactc    6780
taccttggga agtgttatat atatgtccct gattatttct ttttccgttt cctttctatt    6840
ttaatttta agttatttt tagatggttt tattttttga taagtggtaa gttgttaata    6900
ttccaaatta aatgccattg tcataactat atacatttat aaagaatgat tgatcctagt    6960
ttctcattcc taagatccaa ataaggcaat aaacaatgtc ttagtaattg gacctgcttc    7020
tggtgatcaa cgcttgatcg cgtagttagt tatagatgac tgtaaaaact ttaaccattt    7080
taatggtttt gtcaaagaac aaatatcgga catattatag agaatggact attgtacttt    7140
gcttctgatt ggtcatttta ttgtgatccg taaattggct gtgactgatg tcatatcttt    7200
gcttacagag gtaatctgaa tgataaatca aaacccataa ttttttcaat ggcaaggcta    7260
gaccatgtta agaacattac gggactagtt gagtgctatg ctaaaaatgc cacattgagg    7320
gaattggcga accttgttgt agtagctgga tacaacgatg taaagaaatc cagtgataga    7380
gaagaaataa cagaaattga gaagatgcat gctcttatta aggagcataa attggatggg    7440
caattcagat gggtatcagc ccaaacaaac cgggcacgta atggtgagct ctatcgctat    7500
atagctgacc agagaggtat atttgttcag gtatgctatt tgtattgtat tagtccaatt    7560
tcattttttg caccaaaaga aaggttgtta ttgtgacgta tatgtttgtt ttagcctgca    7620
ttttatgaag catttggact aacggtggtt gaagctatga cttgtggtct tccaacattt    7680
gcaacttgcc atggtggtcc taatgagatc attgaacccg gtgtatctgg gttccatatt    7740
gatccttatc atcccgataa agctgctgaa ctcatgtcag aattctttca acgctgcaaa    7800
caagatccta ctcactggga aaaatatct gcatctggtc tccgaaggat tcttgagagg    7860
tctgtagttg tgtacatgta tagaagatta agaatgcta ccttgatatt tatttgaatc    7920
aaaaataaca ggaacatctc ttttttgaac atcactcaag ttcttatatt aaataatttt    7980
taggtatacg tggaagattt actccgagag gctgatgact ttatctggcg tatatggttt    8040
```

```
ctggaagctt gtttcaaaac ttgagaggcg tgaaactaga cgataccttg agatgttcta    8100
cattctcaaa ttccgcgagt tggtgagtgc cttttagctc cttttcagtt ccaataaact    8160
atatatgtgg tttaagtaag tattaagcat aaacatgtcc gtgcttgggg ctgtcgaaaa    8220
tgctatggac atatcctgag ctaaggattt ttcaagaaaa ttgatgttag ctttactcta    8280
tttacaggca aaatctgtac ctctagcaat tgatgacaag tga                      8323
```

<210> SEQ ID NO 19
<211> LENGTH: 810
<212> TYPE: PRT
<213> ORGANISM: Nicotiana tabacum

<400> SEQUENCE: 19

```
Met Ala Asn Pro Lys Phe Thr Arg Val Pro Ser Met Arg Glu Arg Val
1               5                   10                  15

Glu Asp Thr Leu Ser Ala His Arg Asn Gln Leu Val Ala Leu Leu Ser
            20                  25                  30

Arg Tyr Val Ala Gln Gly Lys Gly Ile Leu Gln Pro His His Leu Ile
        35                  40                  45

Asp Glu Phe Asn Asn Ala Val Cys Asp Asp Thr Ala Cys Glu Lys Leu
    50                  55                  60

Lys Asp Gly Pro Phe Ser Glu Val Leu Lys Ala Thr Gln Glu Ala Ile
65                  70                  75                  80

Val Leu Pro Pro Phe Val Ala Ile Ala Val Arg Pro Arg Pro Gly Val
                85                  90                  95

Trp Glu Tyr Val Arg Val Asn Val Tyr Asp Leu Ser Val Glu Gln Leu
            100                 105                 110

Thr Val Pro Glu Tyr Leu His Phe Lys Glu Glu Leu Val Asp Gly Glu
        115                 120                 125

Gly Asn Asn His Phe Val Leu Glu Leu Asp Phe Glu Pro Phe Asn Ala
    130                 135                 140

Ser Val Pro Arg Pro Ser Arg Ser Ser Ser Ile Gly Asn Gly Val Gln
145                 150                 155                 160

Phe Leu Asn Arg His Leu Ser Ser Ile Met Phe Arg Ser Lys Asp Ser
                165                 170                 175

Leu Asp Pro Leu Leu Asp Phe Leu Arg Gly His Cys His Lys Gly Asn
            180                 185                 190

Val Leu Met Leu Asn Asp Arg Ile Gln Arg Ile Ser Arg Leu Glu Ser
        195                 200                 205

Ala Leu Ser Lys Ala Glu Asp Tyr Leu Ser Lys Leu Ser Pro Asp Thr
    210                 215                 220

Ser Tyr Asn Glu Phe Glu Tyr Ala Leu Gln Glu Met Gly Phe Glu Arg
225                 230                 235                 240

Gly Trp Gly Asp Thr Ala Arg Arg Val Leu Glu Thr Met His Leu Leu
                245                 250                 255

Ser Asp Ile Leu Gln Ala Pro Asp Pro Ser Thr Leu Glu Thr Phe Leu
            260                 265                 270

Gly Arg Leu Pro Met Val Phe Asn Val Val Ile Leu Ser Pro His Gly
        275                 280                 285

Tyr Phe Gly Gln Ala Asn Val Leu Gly Leu Pro Asp Thr Gly Gly Gln
    290                 295                 300

Val Val Tyr Ile Leu Asp Gln Val Arg Ala Leu Glu Ala Glu Met Leu
305                 310                 315                 320
```

-continued

```
Leu Arg Ile Lys Gln Gln Gly Leu Asn Phe Lys Pro Arg Ile Leu Val
            325                 330                 335

Val Thr Arg Leu Ile Pro Asp Ala Lys Gly Thr Met Cys Asn Gln Arg
        340                 345                 350

Leu Glu Arg Ile Ser Gly Thr Glu Tyr Ser His Ile Leu Arg Val Pro
    355                 360                 365

Phe Arg Thr Glu Lys Gly Ile Leu His Lys Trp Ile Ser Arg Phe Asp
370                 375                 380

Val Trp Pro Tyr Leu Glu Lys Phe Thr Glu Asp Val Ala Ser Glu Met
385                 390                 395                 400

Thr Ala Glu Leu Gln Gly Lys Pro Asp Leu Ile Ile Gly Asn Tyr Ser
            405                 410                 415

Asp Gly Asn Leu Val Ala Ser Leu Leu Ala Tyr Lys Met Gly Val Thr
            420                 425                 430

Gln Cys Thr Ile Ala His Ala Leu Glu Lys Thr Lys Tyr Pro Asp Ser
        435                 440                 445

Asp Ile Tyr Trp Lys Lys Phe Glu Glu Lys Tyr His Phe Ser Cys Gln
    450                 455                 460

Phe Thr Ala Asp Leu Leu Ala Met Asn Asn Ser Asp Phe Ile Ile Thr
465                 470                 475                 480

Ser Thr Tyr Gln Glu Ile Ala Gly Thr Lys Asn Thr Val Gly Gln Tyr
            485                 490                 495

Glu Ser His Thr Ala Phe Thr Leu Pro Gly Leu Tyr Arg Val Val His
            500                 505                 510

Gly Ile Asp Val Phe Asp Pro Lys Phe Asn Ile Val Ser Pro Gly Ala
        515                 520                 525

Asp Met Thr Ile Tyr Phe Pro Tyr Ser Asp Lys Glu Lys Arg Leu Thr
    530                 535                 540

Ser Leu His Gly Ser Ile Glu Lys Leu Leu Phe Asp Pro Ala Gln Asn
545                 550                 555                 560

Glu Glu His Ile Gly Asn Leu Asn Asp Lys Ser Lys Pro Ile Ile Phe
            565                 570                 575

Ser Met Ala Arg Leu Asp His Val Lys Asn Ile Thr Gly Leu Val Glu
            580                 585                 590

Cys Tyr Ala Lys Asn Ala Thr Leu Arg Glu Leu Ala Asn Leu Val Val
        595                 600                 605

Val Ala Gly Tyr Asn Asp Val Lys Lys Ser Ser Asp Arg Glu Glu Ile
    610                 615                 620

Thr Glu Ile Glu Lys Met His Ala Leu Ile Lys Glu His Lys Leu Asp
625                 630                 635                 640

Gly Gln Phe Arg Trp Val Ser Ala Gln Thr Asn Arg Ala Arg Asn Gly
            645                 650                 655

Glu Leu Tyr Arg Tyr Ile Ala Asp Gln Arg Gly Ile Phe Val Gln Pro
            660                 665                 670

Ala Phe Tyr Glu Ala Phe Gly Leu Thr Val Val Glu Ala Met Thr Cys
        675                 680                 685

Gly Leu Pro Thr Phe Ala Thr Cys His Gly Gly Pro Asn Glu Ile Ile
    690                 695                 700

Glu Pro Gly Val Ser Gly Phe His Ile Asp Pro Tyr His Pro Asp Lys
705                 710                 715                 720

Ala Ala Glu Leu Met Ser Glu Phe Phe Gln Arg Cys Lys Gln Asp Pro
            725                 730                 735

Thr His Trp Glu Lys Ile Ser Ala Ser Gly Leu Arg Arg Ile Leu Glu
```

```
                        740                 745                 750
Arg Tyr Thr Trp Lys Ile Tyr Ser Glu Arg Leu Met Thr Leu Ser Gly
            755                 760                 765

Val Tyr Gly Phe Trp Lys Leu Val Ser Lys Leu Glu Arg Arg Glu Thr
        770                 775                 780

Arg Arg Tyr Leu Glu Met Phe Tyr Ile Leu Lys Phe Arg Glu Leu Ala
785                 790                 795                 800

Lys Ser Val Pro Leu Ala Ile Asp Asp Lys
                805                 810

<210> SEQ ID NO 20
<211> LENGTH: 3604
<212> TYPE: DNA
<213> ORGANISM: Nicotiana tabacum

<400> SEQUENCE: 20
atgtttacat ggctgaaact caatatataaaa acaagggta ggtgatcaaa aatcgttgga    60
```

```
atgtttacat ggctgaaact caatataaaa acaagggta ggtgatcaaa aatcgttgga     60
tgcttaaaat cagtagacgt tttgctaaat gagcgaccaa tgttattgaa acgttcatg    120
ttttcaaccc ttttggcata catttgagca ttgcccaaga ttttggataa gtagatgcag   180
tgcttataat tttaaagcat tgtatcctgc cttgttttc  attgtcaaaa ttaattaact   240
tacaagtatt tctataagtt gcttcataaa ttagaagtaa atctggattg tgtaatgtta   300
ttcgcctcgt aaatactgaa agctgcttga acaagtgaaa aaacacagac aaacgtaaca   360
ttctccatgg attgatgaga cttgtaaaat acatatatag aaatttggct tgtaaccaca   420
tgtatattat gccatgggaa tgtgacattg atgtgactag acctaaatgt tttgtttcca   480
tgtccactgg agttttacgt atagttaaga ggagaaaaga ctgaggaata ctaatgtatg   540
atggtacccc tttgcttctt gacctggata cccagtgttc ctattcatgc ctatactttg   600
gtccttgatt tcactctccc ttttctaact tgagctgcat caaagaaatt tccactgtaa   660
aaaaataaat aatgctcacc atatctctgc aacattgcaa acatgtatcc catatgattg   720
atattggtgc gacatggcaa acatgtatcc tatttgatga tcaatcaaat ttattttttcc   780
cctgtcaaaa tgacctcagt gtgtaattcc ctatgtattt gatagcattg taactcgtgt   840
catgattcat gaatagggta ctagaattgc atggttgaca atattaact  ggtcgattga   900
tgatccacaa aacatgcact tactgactaa aatgtgatgg gacagattta ttttttgttt g   960
tgattaacac agtacttaac cctatactta atacaatttg gcctagctac aatcttttct  1020
tcagtgcaaa ttccttgtta cacgaccaat attgtctttc tgagttctat tctgttgtta  1080
cttacacttt tattattcga ataagacatt agattgcttg catgcaaatt gatagccact  1140
tgtttcagga agaatactgt tggtcagtac gagagccata ctgcattcac cctcccagga  1200
ctatatcgcg tcgttcatgg cattgatgtt ttcgatccca aattcaatat agtgtctcct  1260
ggagctgaca tgacaattta cttcccatat tctgacaagg aaaaaagact aacgtctttg  1320
catggctcga ttgagaagtt gttatttgat cctgcgcaga atgaagagca tatgtaagtg  1380
acatccattt gtacttattt taatttggaa tagatgacat acttatttgc atgaatataa  1440
actgacaacc cagagatttc ctacattaga aaaggagggt ctgatatgat tttctacaaa  1500
taaattccca gtgatattgt tcaaaaagtc ctggatactt tattatgaga gaaccaggga  1560
tagatggcac tagaatccct taatcttgag aagtcgccac ttatcgctcc caacactttc  1620
tgagaccctc aagtaactac tattattgtt tgatatcttg gagaagctat aagaatcttt  1680
ttctccttat tgtaattttt tttacgtgac tttaaactta acttccaagc tccttctgat  1740
```

```
aaaatgcaaa aactgtctgt attcactgtc ttggtttatt aacaattgat ccaatcaaat    1800
gcatatggaa catctttctt tttgtttctt caaaagttcg tttgaggata aggagtagaa    1860
tctgagaaga tagactagta ggtaacctta ggggcggatg tagaaatcaa cgtatgggtt    1920
cagctttgtt gcagaccctg tatatgcatt aaaaaaatca ctaaataagt aaataattga    1980
ttttgaaccc agtaaatcaa aatgagttgt agtagaatcc tgaactcgaa ccgataaagt    2040
tggatccact accgggtaaa ctctaccttg agaagtgttt atatatgtcc ctaattattt    2100
cttttctgtt tcctttctat tttaatttt taagttcctt tttagatggt tttattttt    2160
gacaagtggt aagttgttag tattccaaat taaatgccat tgccataact atatacattt    2220
ataaagattg attgaccta gtttctcatt cctaagatcc aaataaggca ataaacaata    2280
tgtcttagta cttgaacctg cttctggtgg tcaacacttg atcgcgtagt tagttataga    2340
tgactgtaaa aaccttaatc attttaatgg ttttgtcaaa gaacaaatat cggacatatt    2400
atagcgaatg gactattgta cttttcttct gattggtcat tttattgtga tccgtaagtt    2460
ggctgagact gatgtcatat ctttgcttac agaggtaatc tgaatgataa atcaaaaccc    2520
ataattttt caatggcaag gctagaccat gttaagaaca ttacgggact agttgagtgc    2580
tatgctaaaa atgccacatt gagggaattg gctaaccttg ttgttgtagc tggatacaac    2640
gatgtaaaga aatccagtga tagagaagaa atagcagaaa ttgagaagat gcatgctctt    2700
attaaggagc ataaattgga tggcaattc agatggatag cagcccaaac aaaccgggca    2760
cgtaatggtg agctctatcg ctatatagct gacaagagag gtatatttgt tcaggtacgc    2820
tgtttgtatt gtatttgtcc acattccttt ttttgcaccg aaagaaaggt tgttattgtg    2880
acaaatatgt ttgttttagc ctgcatttta tgaagcattt ggactcacgg tggttgaagc    2940
tatgacttgt ggtcttccaa catttgcaac ttgccatggt ggtccgaacg agatcattga    3000
acacggtgta tctgggttcc atattgatcc ttatcatccc gataaagctg ctgaactcat    3060
ggcagaattc tttcaacgct gcaaacaaga tcctactcac tgggaaaaaa tatctgcatc    3120
tggtctccga aggattcttg agaggtttgt agttgtgtac atatatagaa gattaaagat    3180
tgttcccttg atattatttg aatgaaaaat aacagtaaca tctctttttg aacatcgctc    3240
aagttcttgt gttaaataat tgttaggtat acgtggaaaa tttactccga gaggctgatg    3300
actttgtctg gtgtatatgg tttctggaag cttgtttcaa aacttgagag gcgcgaaact    3360
agacgatacc ttgagatgtt ctacattctc aaattccgcg agttggtgag tgccttttg    3420
ctcattttca gttacaatca actatatatg tggtttaaat acgtattaag cataaacatg    3480
tccgtgattg cggctgtcga aaatgctatg gacatatcct gagctaagga gttttcaaga    3540
gaattgattt ggcttactct gtttacaggc aaaatctgtt cctctggcaa ttgatgacaa    3600
gtga                                                                3604
```

<210> SEQ ID NO 21
<211> LENGTH: 335
<212> TYPE: PRT
<213> ORGANISM: Nicotiana tabacum

<400> SEQUENCE: 21

Met Phe Thr Trp Leu Lys Leu Asn Ile Lys Asn Lys Gly Arg Lys Asn
1               5                   10                  15

Thr Val Gly Gln Tyr Glu Ser His Thr Ala Phe Thr Leu Pro Gly Leu
            20                  25                  30

```
Tyr Arg Val Val His Gly Ile Asp Val Phe Asp Pro Lys Phe Asn Ile
             35                  40                  45

Val Ser Pro Gly Ala Asp Met Thr Ile Tyr Phe Pro Tyr Ser Asp Lys
 50                  55                  60

Glu Lys Arg Leu Thr Ser Leu His Gly Ser Ile Glu Lys Leu Leu Phe
 65                  70                  75                  80

Asp Pro Ala Gln Asn Glu Glu His Ile Gly Asn Leu Asn Asp Lys Ser
                 85                  90                  95

Lys Pro Ile Ile Phe Ser Met Ala Arg Leu Asp His Val Lys Asn Ile
            100                 105                 110

Thr Gly Leu Val Glu Cys Tyr Ala Lys Asn Ala Thr Leu Arg Glu Leu
        115                 120                 125

Ala Asn Leu Val Val Val Ala Gly Tyr Asn Asp Val Lys Lys Ser Ser
130                 135                 140

Asp Arg Glu Glu Ile Ala Glu Ile Glu Lys Met His Ala Leu Ile Lys
145                 150                 155                 160

Glu His Lys Leu Asp Gly Gln Phe Arg Trp Ile Ala Ala Gln Thr Asn
                165                 170                 175

Arg Ala Arg Asn Gly Glu Leu Tyr Arg Tyr Ile Ala Asp Lys Arg Gly
            180                 185                 190

Ile Phe Val Gln Pro Ala Phe Tyr Glu Ala Phe Gly Leu Thr Val Val
        195                 200                 205

Glu Ala Met Thr Cys Gly Leu Pro Thr Phe Ala Thr Cys His Gly Gly
    210                 215                 220

Pro Asn Glu Ile Ile Glu His Gly Val Ser Gly Phe His Ile Asp Pro
225                 230                 235                 240

Tyr His Pro Asp Lys Ala Ala Glu Leu Met Ala Glu Phe Phe Gln Arg
                245                 250                 255

Cys Lys Gln Asp Pro Thr His Trp Glu Lys Ile Ser Ala Ser Gly Leu
            260                 265                 270

Arg Arg Ile Leu Glu Arg Tyr Thr Trp Lys Ile Tyr Ser Glu Arg Leu
        275                 280                 285

Met Thr Leu Ser Gly Val Tyr Gly Phe Trp Lys Leu Val Ser Lys Leu
290                 295                 300

Glu Arg Arg Glu Thr Arg Arg Tyr Leu Glu Met Phe Tyr Ile Leu Lys
305                 310                 315                 320

Phe Arg Glu Leu Ala Lys Ser Val Pro Leu Ala Ile Asp Asp Lys
                325                 330                 335

<210> SEQ ID NO 22
<211> LENGTH: 4030
<212> TYPE: DNA
<213> ORGANISM: Nicotiana tabacum

<400> SEQUENCE: 22
atggcggaac gtgtgctgac tcgtgttcat agccttcgtg aacgtcttga tgctactttg      60
gctgctcatc gcaatgagat tttgctgttt ctttcaaggt atagtcttag cagattgttc     120
tttgatttag ttgttattgc cagttctaat gtatgggctt atatataaac aaagtgttga     180
agtatgcaac catataaact gacagcttaa aatgcttgag agaacacact tttatttatt     240
taattatgcc ttcagcacaa gaagtggaac ttgacgcaat ggaaccatag gtcacgggtt     300
caagtcttgg aacagcctgc aatctaaggc tgcgtgtagt agaccctagt ggtccggccc     360
ttccacatat ctcgcttagt gtaccgggcc cattgagtac gggttcggcc gaacccagtc     420
```

```
gctttggtcc aatccatata tttgtcttaa aaatatattg aatatataca aattgttaat    480
ttagtttaaa tatgtgtatc atgggttatt catgctggtt ttggctgttg caggattgaa    540
agccatggaa aagggatact gaaacctcac cagttgctgg ctgaatttga ttcaattcac    600
aaagaagaca aaaacaaact gaatgatcat gcttttgaag aagtcctgaa atccactcag    660
gtatttgtgg ttttagtgtt aggtgatgga tagcatttat tgttttacta agatcacata    720
tgtgtcagtt tgtggctagt atttaaaatc tggtgtattt tgtcatacta ggaagcaatt    780
gttttgtccc cttgggttgc gcttgccatt cgtctgaggc ctggtgtgtg ggaatacgtt    840
cgtgtgaatg tcaacgctct tgttgttgag gagcttaccg tgcctgagta tttgcaattc    900
aaggaagaac ttgttaatgg aacgtaagtt ttaggttcga atttgttgat tgttagata    960 acatgttctg aacttttga ttaaagttgt gtttttgact gatgcagctc gcacgataac   1020
tttgttcttg agttggattt tgagcccttc actgcatcat ttccaaaacc aaccctcacc   1080
aaatcaattg gaaatggagt tgaattcctt aaccgacacc tctctgccaa atgttccat   1140 gacaaggaaa gcatgacccc tcttctcgag tttcttcgag ttcaccacta caagggcaag   1200
gtaaacttgt ttttcctgtt tgtctatgaa tttagtttag ttgttttgct ccgcgaaaat   1260
ttcagtggaa actgatttat gcaaccactg agtgattaat atgttcaaac ttaccgactt   1320
ctggttttct gtgtagacaa tgatgctgaa tgacagaatt caggacttaa atactctcca   1380
aaatgtccta aggaaagctg aggaatacct cactacccttt tcccctgaaa cttcatactc   1440
ggcatttgag cacaagttcc aagaaattgg cttggagagg ggttggggtg cacactgcgga   1500 gcgtgttcta gagatgatct gcatgctcct ggatctcctc gaggctcctg actcgtgcac   1560
gcttgagaag ttccttggta gaattccaat ggttttaat gtggtcatac tttcaccca    1620 tggttatttc gcccaggaaa atgtcttggg ttaccccgac actggtggcc aggtgcactg   1680
cttatctgtg ttcggtctta ttatctcttt aaaccctact gccacaagtg ctgagatgaa   1740
cctcctttaa tttgcaggtt gtctatattt tggatcaagt tcctgctttg gagcgtgaga   1800
tgctcaagcg cataaaggag caaggacttg acatcaaacc gcgtattctt attgttcgta   1860
ttcccagtaa ttgtgtttaa acttatgatt atgcaggatt ttatctgttc taatacagca   1920
ctcttgctta aattctcagg ttactcggct gctgcctgat gcggttggta ccacttgtgg   1980
tcagaggctt gagaaagtgt ttggaacaga gcactcacac attcttaggg tccccttag   2040 gaccgagaag ggcattgttc gcaaatggat ctctcgcttt gaagtctggc catacatgga   2100
gacattcact gaggtgaagc aagctttctc tattcatttt tcaatcttcc aattggtttt   2160
ggcagcaatt ttctgcttgc tttgacttcc gctaaaactt cggattttat tgcattagga   2220
tgtggcgaaa gaaattgctg cagaattgca ggctaagcca gatcttatca ttggcaatta   2280
tagtgagggc aaccttgctg cctccttgtt ggctcacaaa ttaggtgtaa cacaggtcgg   2340
caatgtttgt gacatgtaat ttcatctttg catttccttt cgtttgcaac taaaagattt   2400
aagagttctc tctctctttt tttttccgt ctactttgcc ttatgcagtg cacgatagct   2460
catgctttgg agaaaacaaa atatcctgat tctgatatct acttgaagaa atttgatgaa   2520
aaataccatt tctcagccca gtttactgcc gatcttattg caatgaatca caccgatttc   2580
atcatcacca gcactttcca ggagatagcg ggaaggtatt tttacatcag tttcccactc   2640
tgattaaatt acaatgtatt tccctatatg attaaatact gtgtttgatc ctaaatcatt   2700
tctaaatttt ccagcaagga cactgttgga cagtacgaga gccacatggc gttcacaatg   2760
cctggactgt atagagttgt tcacggcatt gatgtgtttg accccaaatt taacattgtg   2820
```

```
tcaccaggag ctgatatgaa tctctatttc ccatactacg agaaggaaaa gagattgaca    2880
gcatatcacc ctgaaattga ggagctgctg tttagtgatg ttgagaatga cgaacacatg    2940
tatgttacta aactagcaat cctgctgcaa aattatggct aattatgtaa acaagtttgt    3000
actgaataga tttgttattc gatcaggtgt gtgctgaaga acaggaataa gcctatcata    3060
ttcactatgg ctagattgga tcgagtgaag aacttaactg gacttgtcga gctgtacgcc    3120
aagaacccac ggctaaggga gttggttaac cttgtcgtgg ttggaggaga ccgaaggaaa    3180
gaatccaaag acttggaaga acaggcagag atgaagaaga tgtacgaact tataaagact    3240
cacaatttga acggccaatt ccgatggatt tcttcccaga tgaaccgcgt gaggaatggc    3300
gaactctaca ggtacattgc cgatactagg ggagctttcg tgcagcctgc attttacgag    3360
gcttttggtt tgactgttgt tgaggccatg acctgtggtt tgcctacatt tgcaactaat    3420
cacggtggtc cagctgagat catcgttcac gggaaatctg gtttccacat tgatccatac    3480
cacggggatc aggcagctga acttctcgct gatttctttg agaaatgtaa gaaagaacct    3540
tcgcactggg aagccatttc cgagggcggc cttaagcgta tacaggagaa gtaagcaaac    3600
tgctactctt ttcattttg caaaacctac tatgatcatt attaagctca tttttgcaaa    3660
acctacttgc tgttgttatt gtttgttgct tccttttcac tgttctttga gctgaaggtc    3720
tatcagaaac agtctctcta ccttcacaag gtaggggtaa gatctgcgtg cacgttaccc    3780
tcctcaaact ctacttaatt gtgagattac actaggtttg ttgttgttga ttctttgcta    3840
attaattaaa aggtacacat ggcaaatata ctcggatcgg ttgttgacac tggctgctgt    3900
atatggattc tggaagcatg tttccaagct tgatcgtctt gaaattcgcc gttatcttga    3960
aatgttctat gctctcaaat tccgcaagct ggtgagtttc attgctttct gcactcctgc    4020
aattgtatag                                                          4030
```

<210> SEQ ID NO 23
<211> LENGTH: 808
<212> TYPE: PRT
<213> ORGANISM: Nicotiana tabacum

<400> SEQUENCE: 23

```
Met Ala Glu Arg Val Leu Thr Arg Val His Ser Leu Arg Glu Arg Leu
1               5                   10                  15

Asp Ala Thr Leu Ala Ala His Arg Asn Glu Ile Leu Leu Phe Leu Ser
                20                  25                  30

Arg Ile Glu Ser His Gly Lys Gly Ile Leu Lys Pro His Gln Leu Leu
            35                  40                  45

Ala Glu Phe Asp Ser Ile His Lys Glu Asp Lys Asn Lys Leu Asn Asp
        50                  55                  60

His Ala Phe Glu Glu Val Leu Lys Ser Thr Gln Glu Ala Ile Val Leu
65                  70                  75                  80

Ser Pro Trp Val Ala Leu Ala Ile Arg Leu Arg Pro Gly Val Trp Glu
                85                  90                  95

Tyr Val Arg Val Asn Val Asn Ala Leu Val Val Glu Glu Leu Thr Val
                100                 105                 110

Pro Glu Tyr Leu Gln Phe Lys Glu Glu Leu Val Asn Gly Thr Ser His
            115                 120                 125

Asp Asn Phe Val Leu Glu Leu Asp Phe Glu Pro Phe Thr Ala Ser Phe
        130                 135                 140

Pro Lys Pro Thr Leu Thr Lys Ser Ile Gly Asn Gly Val Glu Phe Leu
```

-continued

```
            145                 150                 155                 160
        Asn Arg His Leu Ser Ala Lys Met Phe His Asp Lys Glu Ser Met Thr
                        165                 170                 175
        Pro Leu Leu Glu Phe Leu Arg Val His His Tyr Lys Gly Lys Thr Met
                        180                 185                 190
        Met Leu Asn Asp Arg Ile Gln Asp Leu Asn Thr Leu Gln Asn Val Leu
                        195                 200                 205
        Arg Lys Ala Glu Glu Tyr Leu Thr Thr Leu Ser Pro Glu Thr Ser Tyr
                        210                 215                 220
        Ser Ala Phe Glu His Lys Phe Gln Glu Ile Gly Leu Glu Arg Gly Trp
        225                 230                 235                 240
        Gly Asp Thr Ala Glu Arg Val Leu Glu Met Ile Cys Met Leu Leu Asp
                        245                 250                 255
        Leu Leu Glu Ala Pro Asp Ser Cys Thr Leu Glu Lys Phe Leu Gly Arg
                        260                 265                 270
        Ile Pro Met Val Phe Asn Val Val Ile Leu Ser Pro His Gly Tyr Phe
                        275                 280                 285
        Ala Gln Glu Asn Val Leu Gly Tyr Pro Asp Thr Gly Gly Gln Val Val
                        290                 295                 300
        Tyr Ile Leu Asp Gln Val Pro Ala Leu Glu Arg Glu Met Leu Lys Arg
        305                 310                 315                 320
        Ile Lys Glu Gln Gly Leu Asp Ile Lys Pro Arg Ile Leu Ile Val Thr
                        325                 330                 335
        Arg Leu Leu Pro Asp Ala Val Gly Thr Thr Cys Gly Gln Arg Leu Glu
                        340                 345                 350
        Lys Val Phe Gly Thr Glu His Ser His Ile Leu Arg Val Pro Phe Arg
                        355                 360                 365
        Thr Glu Lys Gly Ile Val Arg Lys Trp Ile Ser Arg Phe Glu Val Trp
                        370                 375                 380
        Pro Tyr Met Glu Thr Phe Thr Glu Asp Val Ala Lys Glu Ile Ala Ala
        385                 390                 395                 400
        Glu Leu Gln Ala Lys Pro Asp Leu Ile Ile Gly Asn Tyr Ser Glu Gly
                        405                 410                 415
        Asn Leu Ala Ala Ser Leu Leu Ala His Lys Leu Gly Val Thr Gln Cys
                        420                 425                 430
        Thr Ile Ala His Ala Leu Glu Lys Thr Lys Tyr Pro Asp Ser Asp Ile
                        435                 440                 445
        Tyr Leu Lys Lys Phe Asp Glu Lys Tyr His Phe Ser Ala Gln Phe Thr
                        450                 455                 460
        Ala Asp Leu Ile Ala Met Asn His Thr Asp Phe Ile Ile Thr Ser Thr
        465                 470                 475                 480
        Phe Gln Glu Ile Ala Gly Ser Lys Asp Thr Val Gly Gln Tyr Glu Ser
                        485                 490                 495
        His Met Ala Phe Thr Met Pro Gly Leu Tyr Arg Val Val His Gly Ile
                        500                 505                 510
        Asp Val Phe Asp Pro Lys Phe Asn Ile Val Ser Pro Gly Ala Asp Met
                        515                 520                 525
        Asn Leu Tyr Phe Pro Tyr Tyr Glu Lys Glu Lys Arg Leu Thr Ala Tyr
                        530                 535                 540
        His Pro Glu Ile Glu Glu Leu Leu Phe Ser Asp Val Glu Asn Asp Glu
        545                 550                 555                 560
        His Met Cys Val Leu Lys Asn Arg Asn Lys Pro Ile Ile Phe Thr Met
                        565                 570                 575
```

```
Ala Arg Leu Asp Arg Val Lys Asn Leu Thr Gly Leu Val Glu Leu Tyr
            580                 585                 590

Ala Lys Asn Pro Arg Leu Arg Glu Leu Val Asn Leu Val Val Gly
            595                 600                 605

Gly Asp Arg Arg Lys Glu Ser Lys Asp Leu Glu Gln Ala Glu Met
            610                 615                 620

Lys Lys Met Tyr Glu Leu Ile Lys Thr His Asn Leu Asn Gly Gln Phe
625                 630                 635                 640

Arg Trp Ile Ser Ser Gln Met Asn Arg Val Arg Asn Gly Glu Leu Tyr
                    645                 650                 655

Arg Tyr Ile Ala Asp Thr Arg Gly Ala Phe Val Gln Pro Ala Phe Tyr
                660                 665                 670

Glu Ala Phe Gly Leu Thr Val Val Glu Ala Met Thr Cys Gly Leu Pro
            675                 680                 685

Thr Phe Ala Thr Asn His Gly Gly Pro Ala Glu Ile Ile Val His Gly
            690                 695                 700

Lys Ser Gly Phe His Ile Asp Pro Tyr His Gly Asp Gln Ala Ala Glu
705                 710                 715                 720

Leu Leu Ala Asp Phe Phe Glu Lys Cys Lys Lys Glu Pro Ser His Trp
                    725                 730                 735

Glu Ala Ile Ser Glu Gly Gly Leu Lys Arg Ile Gln Glu Lys Tyr Thr
                740                 745                 750

Trp Gln Ile Tyr Ser Asp Arg Leu Leu Thr Leu Ala Ala Val Tyr Gly
            755                 760                 765

Phe Trp Lys His Val Ser Lys Leu Asp Arg Leu Glu Ile Arg Arg Tyr
770                 775                 780

Leu Glu Met Phe Tyr Ala Leu Lys Phe Arg Lys Leu Val Ser Phe Ile
785                 790                 795                 800

Ala Phe Cys Thr Pro Ala Ile Val
                805

<210> SEQ ID NO 24
<211> LENGTH: 4054
<212> TYPE: DNA
<213> ORGANISM: Nicotiana tabacum

<400> SEQUENCE: 24
atggccgaac gtgtgctaac tcgtgttcac agccttcgcg aacgtcttga tgctactttg      60
gctgctcatc gcaatgagat tttgctgttt cttttcaaggt atagtcttag cagattgttc    120
tttgatttag ttggtgttat tgccagttc taatgtatgg actaatatat gaacaaagtg      180
cgaccatttc aactgacaac ttaaaatgtt tgagagaata cacgtttatt tacttaatta    240
tggcttgagc ataggaagtg tatcttggcg taactcgtaa agttgacctc atgtgacaag    300
gaggtcacgg tttcgagccg tggaaacagc ctcttgcaga aatgcaggta aggctgcgtg    360
caatagatcg cccttccacg gacccgcgca tagcgggaac ttagtgcacc ggttgggctg    420 tccttttttta tgtcttcagc acaaaaattt agtttaaaca tgtgtatcat ggattattca    480
tgctggtttt gccggttgca ggattgaaag ccacggaaaa gggatattga aacctcacca    540
gttgctggct gagtttgaat caattcacaa agaagacaaa acaaactga atgatcatgc      600 ttttgaagaa gtcctgaaat ctactcaggt aatttgtggt tttagtgtta ggtgatggat    660
agcatttatt gtcttactaa gatcatatat gtgtcagttt gtggctagta tttgaaaagt    720
ctggtgtggt ttgtcatact aggaagcaat tgtcttgtcc ccttgggttg cgcttgccat    780
```

```
tcgtctgcgg cctggtgtgt gggaatatgt tcgtgtgaat gtcaatgcac ttattgtcga    840
ggagctgact gtgcctgaat atttgcaatt caaggaagaa cttgttaatg gaacgtaagt    900
tttaggttcg aaaatgatgat ttgttaaata atatgttctg aacttttga ttaatgttgt     960
gttttcccct gatgcagctc gaacgataac tttgttcttg agctggattt tgagcccttc   1020
actgcatcat ttcccaaacc aaccctcacc aaatcaattg gaaatggagt tgaattcctc   1080
aaccgacacc tctctgccaa aatgttccat gacaaggaaa gcatgacccc tcttctcgag   1140
tttcttcgag ttcatcacta caagggcaag gtaaacttgt ttttcctgtt tgtctatgaa   1200
tttagtttct gaaagttgct ttgcttcgtg aattttttag tggcaactga tttatgattt   1260
tctgtgcaga caatgatgct gaatgacaga gttcaggact taaacactct ccaaaatgtc   1320
ctaaggaagg ctgaggaata tctcactacc ctttcccctg aaacttcata ctcggtattt   1380
gagcacaagt tccaagaaat tggcctagag aggggctggg gtgacaatgc tgagcgtgtt   1440
ctagagatga tctgcatgct cctggatctc ctcgaggctc cagactcatg cactcttgag   1500
aagttccttg gtagaattcc tatggttttt aatgtggtca ttctttcacc tcacggatat   1560
ttcgcccagg aaaatgtctt gggttacccc gatactggtg gccaggtgca ctgcttattt   1620
gtaacacctt acgcttttcc ctctgaaact tatttgcggc aagttctaag gtcctccttc   1680
cttaatttgc aggttgtcta tattttggat caagttccgg ccttggagcg tgagatgctc   1740
aagcgcataa aggagcaagg acttgatatc aaaccgcgta ttcttattgt tcgtatctcc   1800
aataattgcg tttaaactta tgattgtgca ggatttgatc tgttcaaatc taatgactga   1860
ttttcttttt tttttttttt tccctcaggt tactcggctg ctgcctgatg cggttggtac   1920
cacttgtggt cagcggcttg agaaagtgtt tggaacagag cattcacata ttcttagggt   1980
cccctttagg accgagaagg gcatcgttcg caaatggatc tctcgctttg aagtctggcc   2040
ttacatggag acattcactg aggtgaagca agctttctct attcattttt caatcttcca   2100
atctgttttg gcagcaattt ttcacttact aacactttgg ctttcgctaa aacttcggat   2160
tttattacat taggatgtgg caaaagaaat tgctgcagaa ctgcaggcaa agccagatct   2220
tataatcggc aactacagcg agggcaacct tgctgcctcc ttgttggctc acaagttagg   2280
tgtaactcag gtctgtaatg tttgtcacct gttatttcaa cttttgcattt cctttcattt   2340
gcaactagaa gttaagagtt ctctctcttt tatcttttcc gtctatttg ccttctgcag    2400
tgcaccatag ctcatgcgtt ggagaaaaca aaatatcctg attctgatat ctacttgaag   2460
aaatttgatg aaaaatacca tttctcagcc cagtttactg ccgatcttat tgcaatgaat   2520
cacaccgatt tcataatcac cagcactttc caggagatag cgggaaggta ttacatcaca   2580
atggatttcc gatatgatta aattagttaa tttaatccta cttcattgtg tttgatccta   2640
aaacttttct aaatttccca gcaaggacac tgttggacag tacgagagcc acatggcttt   2700
cacgatgcct ggattgtata gagttgttca cggcattgat gtgttcgatc ccaaattcaa   2760
cattgtgtca ccaggagctg atatgaatct ctatttcccc tacttcgaga aggaaaagcg   2820
attgacagca tatcaccctg aaattgagga gctgctgttt agcgatgttg agaatgacga   2880
acacatgtat gttactaaac tagcaatcct gctgcaaaat tgtggctaat tatgtaaaaa   2940
agttttact gaatagattt gtgcttctat caggtgtgtg ctgaaggaca ggaataagcc    3000
aattatattc accatggcta gattggatcg agtgaagaac ttaactggac ttgtggagtt   3060
gtacgccaag aacccacggc taagggagtt ggttaacctt gtcgtggttg gtggagaccg   3120
```

```
aaggaaggaa tccaaagatt tggaagaaca ggcagagatg aagaagatgt atgaacttat    3180
aaagacgcac aatttaaacg gccaattccg atggatttct tcccagatga accgcgtgag    3240
gaatggcgaa ctctacaggt acattgccga tactagggga gcttttgtgc agcctgcatt    3300
ttacgaggct tttggtttga ctgttgttga ggccatgacc tgtggtttgc ctacgtttgc    3360
aactaatcac ggtggtccag ctgagatcat cgttcacggg aagtctggtt ttcacattga    3420
tccataccac ggcgagcagg cagctgaact tctagctgat ttctttgaga gatgtaagaa    3480
agaaccttca cactgggaag ccatttccga gggcggcctt aagcgtatac aggagaagta    3540
agcaagctgc tactcttttc attttttgcaa aacctaccat gatcattatt aagctcattt    3600
ttgcaaaacc tacttgttat tctttgttgc ttccttttcc ctgttttttg agccgaggtt    3660
ttatcgaaaa catgctttct accttcacaa ggtaggggta aggtctgcgt ttgttattat    3720
tgttgttgtt gattctctgc gaattaatta aaggtacac atggcaaatc tactcggatc    3780
ggttgttgac actggctgct gtttatggat tctggaagca tgtttccaaa cttgatcgtc    3840
ttgaaattcg tcgttatctt gaaatgttct atgctctaaa attccgcaaa ctggtgagtt    3900
tcactgcttt ctgcactctt ccaattgtta gttgagtgca ctcatttaaa ctgtagctaa    3960
agctgttgta aatcttcagt taagcagctg ctaatgaagt ttttatcttt tgtttttggt    4020
tcaggctgaa gctgtcccgt tggctgttga gtaa                                4054
```

<210> SEQ ID NO 25
<211> LENGTH: 805
<212> TYPE: PRT
<213> ORGANISM: Nicotiana tabacum

<400> SEQUENCE: 25

```
Met Ala Glu Arg Val Leu Thr Arg Val His Ser Leu Arg Glu Arg Leu
1               5                   10                  15

Asp Ala Thr Leu Ala Ala His Arg Asn Glu Ile Leu Leu Phe Leu Ser
            20                  25                  30

Arg Ile Glu Ser His Gly Lys Gly Ile Leu Lys Pro His Gln Leu Leu
        35                  40                  45

Ala Glu Phe Glu Ser Ile His Lys Glu Asp Lys Asn Lys Leu Asn Asp
    50                  55                  60

His Ala Phe Glu Glu Val Leu Lys Ser Thr Gln Glu Ala Ile Val Leu
65                  70                  75                  80

Ser Pro Trp Val Ala Leu Ala Ile Arg Leu Arg Pro Gly Val Trp Glu
                85                  90                  95

Tyr Val Arg Val Asn Val Asn Ala Leu Ile Val Glu Glu Leu Thr Val
            100                 105                 110

Pro Glu Tyr Leu Gln Phe Lys Glu Glu Leu Val Asn Gly Thr Ser Asn
        115                 120                 125

Asp Asn Phe Val Leu Glu Leu Asp Phe Glu Pro Phe Thr Ala Ser Phe
    130                 135                 140

Pro Lys Pro Thr Leu Thr Lys Ser Ile Gly Asn Gly Val Glu Phe Leu
145                 150                 155                 160

Asn Arg His Leu Ser Ala Lys Met Phe His Asp Lys Glu Ser Met Thr
                165                 170                 175

Pro Leu Leu Glu Phe Leu Arg Val His His Tyr Lys Gly Lys Thr Met
            180                 185                 190

Met Leu Asn Asp Arg Val Gln Asp Leu Asn Thr Leu Gln Asn Val Leu
        195                 200                 205
```

```
Arg Lys Ala Glu Glu Tyr Leu Thr Thr Leu Ser Pro Glu Thr Ser Tyr
210                 215                 220

Ser Val Phe Glu His Lys Phe Gln Glu Ile Gly Leu Glu Arg Gly Trp
225                 230                 235                 240

Gly Asp Asn Ala Glu Arg Val Leu Glu Met Ile Cys Met Leu Leu Asp
            245                 250                 255

Leu Leu Glu Ala Pro Asp Ser Cys Thr Leu Glu Lys Phe Leu Gly Arg
            260                 265                 270

Ile Pro Met Val Phe Asn Val Ile Leu Ser Pro His Gly Tyr Phe
        275                 280                 285

Ala Gln Glu Asn Val Leu Gly Tyr Pro Asp Thr Gly Gly Gln Val Val
    290                 295                 300

Tyr Ile Leu Asp Gln Val Pro Ala Leu Glu Arg Glu Met Leu Lys Arg
305                 310                 315                 320

Ile Lys Glu Gln Gly Leu Asp Ile Lys Pro Arg Ile Leu Ile Val Thr
                325                 330                 335

Arg Leu Leu Pro Asp Ala Val Gly Thr Thr Cys Gly Gln Arg Leu Glu
            340                 345                 350

Lys Val Phe Gly Thr Glu His Ser His Ile Leu Arg Val Pro Phe Arg
    355                 360                 365

Thr Glu Lys Gly Ile Val Arg Lys Trp Ile Ser Arg Phe Glu Val Trp
370                 375                 380

Pro Tyr Met Glu Thr Phe Thr Glu Asp Val Ala Lys Glu Ile Ala Ala
385                 390                 395                 400

Glu Leu Gln Ala Lys Pro Asp Leu Ile Ile Gly Asn Tyr Ser Glu Gly
            405                 410                 415

Asn Leu Ala Ala Ser Leu Leu Ala His Lys Leu Gly Val Thr Gln Cys
            420                 425                 430

Thr Ile Ala His Ala Leu Glu Lys Thr Lys Tyr Pro Asp Ser Asp Ile
        435                 440                 445

Tyr Leu Lys Lys Phe Asp Glu Lys Tyr His Phe Ser Ala Gln Phe Thr
    450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
            485                 490                 495

His Met Ala Phe Thr Met Pro Gly Leu Tyr Arg Val Val His Gly Ile
            500                 505                 510

Asp Val Phe Asp Pro Lys Phe Asn Ile Val Ser Pro Gly Ala Asp Met
        515                 520                 525

Asn Leu Tyr Phe Pro Tyr Phe Glu Lys Glu Lys Arg Leu Thr Ala Tyr
    530                 535                 540

His Pro Glu Ile Glu Glu Leu Leu Phe Ser Asp Val Glu Asn Asp Glu
545                 550                 555                 560

His Met Cys Val Leu Lys Asp Arg Asn Lys Pro Ile Ile Phe Thr Met
            565                 570                 575

Ala Arg Leu Asp Arg Val Lys Asn Leu Thr Gly Leu Val Glu Leu Tyr
            580                 585                 590

Ala Lys Asn Pro Arg Leu Arg Glu Leu Val Asn Leu Val Val Val Gly
        595                 600                 605

Gly Asp Arg Arg Lys Glu Ser Lys Asp Leu Glu Glu Gln Ala Glu Met
    610                 615                 620

Lys Lys Met Tyr Glu Leu Ile Lys Thr His Asn Leu Asn Gly Gln Phe
```

```
                   625                  630                  635                  640
Arg Trp Ile Ser Ser Gln Met Asn Arg Val Arg Asn Gly Glu Leu Tyr
                            645                  650                  655
Arg Tyr Ile Ala Asp Thr Arg Gly Ala Phe Val Gln Pro Ala Phe Tyr
                        660                  665                  670
Glu Ala Phe Gly Leu Thr Val Val Glu Ala Met Thr Cys Gly Leu Pro
                    675                  680                  685
Thr Phe Ala Thr Asn His Gly Gly Pro Ala Glu Ile Ile Val His Gly
                690                  695                  700
Lys Ser Gly Phe His Ile Asp Pro Tyr His Gly Glu Gln Ala Ala Glu
705                  710                  715                  720
Leu Leu Ala Asp Phe Phe Glu Arg Cys Lys Lys Glu Pro Ser His Trp
                            725                  730                  735
Glu Ala Ile Ser Glu Gly Gly Leu Lys Arg Ile Gln Glu Lys Tyr Thr
                        740                  745                  750
Trp Gln Ile Tyr Ser Asp Arg Leu Leu Thr Leu Ala Ala Val Tyr Gly
                    755                  760                  765
Phe Trp Lys His Val Ser Lys Leu Asp Arg Leu Glu Ile Arg Arg Tyr
                770                  775                  780
Leu Glu Met Phe Tyr Ala Leu Lys Phe Arg Lys Leu Ala Glu Ala Val
785                  790                  795                  800
Pro Leu Ala Val Glu
            805

<210> SEQ ID NO 26
<211> LENGTH: 3752
<212> TYPE: DNA
<213> ORGANISM: Nicotiana tabacum

<400> SEQUENCE: 26
atggcctcaa cagttgctga tagcatgcct gatgctttga aacaaagccg gtatcatatg      60
aagagatgct cgctaggtg aacacccttc ttttatgttt tttcccctct acgtgtttat      120
gtcaaatttc catgcataat gctaactact tttcttcttt ttgacttcaa aattggatgt     180
gaaaggttca ttgcaatggg aaggaggcta atgaagttga acatttaac agaagaaata      240
gaagaaacta ttgaagacaa ggcagaaaga accaggattt tggagggttc acttggaaaa    300
attatgagtt ccacacaggt cagcaccatt taaccaactt agttgaacag aaaaaaaga    360
aaaagcaaaa gagttattgc aaggcgtaac gattttcttt gaaattttca ggaggcagct     420
gttgttccac cttatgttgc ttttgcagta aggcacaatc ctggcttctg ggattatgtc    480
aaagttaacg ctgaaactct ctctgtggaa gctatttcag ccagggaata tctcaaattc     540
aaagagatga tctttgacga agactggtaa gtggaaaatt gtatcatttt aaagagaaac    600
aattttgtaa catacaagaa tagttttgat ggttgaatgt gcaagcaggg caaggatga     660
taatgcactg gaagtagatt ttggtgcttt tgactactct aatcctcggt tagcccttt     720
ctcttctgtc ggaaatgggc tcaactttat ctcaaaagtt ctgtcttcaa agtttggtgg    780
aaagccagag gacgcccagc ctttgcttga ttacttacta gctcttaatc atcaaggaga     840
ggtatgaaaa tggactacct ttgtttctta aaggtattat ataatgatgc gcgttataaa    900
gttcctttt aaaattgaaac tttgcagaat ctaatgatca atgagaatct gaatggtgtt    960
gctaagcttc aagcagcatt gatagtagct gaagttttg tatcttccct tcccaaagac    1020
acaccttata aagactttga gcataagtaa gcttctcata tgcttccatt gtcatatgca   1080
```

```
gtataccaat gacatgctac cgaaaagttg tttatgtttg tgacttgatt atgaaaactc    1140
taggctcaaa gaatggggct ttgataaagg gtggggtcac aatgcaggaa gagtaagaga    1200
gacaatgaga ctgctttccg agataatcca agcaccagat cccataaata tggagtcctt    1260
tttcagcaag cttcctacta cattcaacat tgttatcttc tccattcatg gttactttgg    1320
ccaagcagat gtccttggtc tgcccgatac tggaggccag gtctacatat acagcaattt    1380
atctcctttt gcctcatatt gcttattagc gacacttgca tcattgaaat cagactttta    1440
cttcacaggt tgtttatatt ctggatcaag taagggcttt agaggaggaa atgttacaaa    1500
gaatcaagca gcaagggcta aacgtgaagc ccaagattct tgtggtgagt tttgcaaaaa    1560
tatgcttaga caggttttga gattgatcgg agaagggatt aagatgatca agatctttgt    1620
ttcctgcttt catgatgtaa acaggtatct cgtctcatac cagatgctcg agggacaaca    1680
tgcaatcagg agatggaacc tattcttaac tcatcccatt ctcacatcct gagaattcca    1740
ttcaggactg agaaaggagt tcttcgccaa tgggtttctc ggtttgatat ctatccttac    1800
ttggagaact atgccaaggc aagtcttcta acaaaattac cacctattca tacactttat    1860
ttactttctt gaactaatcg tttggtttgt gacgtatatc attaggatgc ttctgctaag    1920
atacttgagc tcatgaaagg taaaccagac ctcataattg gaactacac tgatggaaat     1980 ttagtggcat ctctattggc caacaaactt ggagttactc aggttccgta gctgatcata    2040
tgatcatatt ttctacattg tttcttgata attaaatgga aatcttattg gatgataaca    2100
ttttagggaa ccattgctca tgcattagag aaaactaagt atgaagattc tgatgtgaag    2160
tggaagcagt ttgatcccaa gtaccacttt tcttgccaat ttactgccga tttattggca    2220
atgaatgctg ctgattttat cattaccagc acatatcaag aaatcgctgg aaggttagca    2280
ctgactctct cagtatattt ggcaacttaa tgaatttact gcagtggcca acactaaaag    2340
ctatcattcg tccttcagcg aaactaggcc tggacaatat gaaagtcaca cagcatttac    2400
catgccgggg ctttatagag ctgtttcagg catcaatgta tttgatccaa agttcaacat    2460
tgctgctcct ggggctgaac agtctaccta tttcccttc actgagaaac agaaacgatt    2520
cagcacattt cgtcctgcta ttaacgaatt actttacagt aatgaggaaa caatgagca    2580 catgtaagtc taattgccca ttttcctaat ctaaccattg cttaaatcgt tctgttttta    2640
ccggatgtgt ggtacttatc agtaacattt ttttttggat cagtggattt cttgcagacc    2700
ggaaaaaacc aattatattt tcaatggcga gatttgatac agtgaagaac ctgtcaggct    2760
tgactgagtg gtatgggaag aataagaagt tgcggaactt ggtaaacctt gttattgttg    2820
ggggattctt cgatccatca aaatcaaaag accgggagga agcagctgaa atcaagaaga    2880
tgcatgaatt gattgagaaa taccagctca agggacaaat gagatggata gcagctcaaa    2940
ctgataaata tcgaaatagt gagctatacc gaactattgc tgacactaag ggagcttttg    3000
tccaaccggc tttatatgaa gcttttggac taaccgttat tgaagcaatg gattgtggat    3060
tgcctacgtt tgcaactaat caaggtggac ctgcagaaat cattgttgat ggggtttcag    3120
gtttccatat tgatccttac aatggggacg aatcaagcaa gaaaatagct gatttctttg    3180
agaagtgtaa ggttgattct aaatattgga acaggatatc tgagggaggt ctcaagcgca    3240
ttgaagaatg gtaacaaact agttccaagt ttaaaaaatg gaaaaaatgc ttatcatgtt    3300
atattttcgt ggttttaagt tctgcttcga tgcagttata cgtggaagat ttatgcaaac    3360
aaagtgttga atatgggatc aatctatgga tttgggagac aattcaatgt ggggcaaaag    3420
caggctaagc aaagatactt tgagatgttt tacaatcctc tcttcaggaa attggtaggt    3480
```

-continued

```
tgtatatgtt gaatacaatt tactaagatc ctcaaaatga ccaagaaata tacattgact    3540
atgctacttt tgtaatttca caggccaaaa gcgtgccgat cccacatgaa gagccattgc    3600
cacttgcaac atcagactct actcaatccc aagaattaaa actaccacta ccagttccag    3660
cagcagtagc taaagttctg ccattaacaa ggcatgcttt taacttaatt acttctctac    3720
ctagagtaac tggtaaagtg gatgtcaagt ga                                  3752

<210> SEQ ID NO 27
<211> LENGTH: 840
<212> TYPE: PRT
<213> ORGANISM: Nicotiana tabacum

<400> SEQUENCE: 27

Met Ala Ser Thr Val Ala Asp Ser Met Pro Asp Ala Leu Lys Gln Ser
1               5                   10                  15

Arg Tyr His Met Lys Arg Cys Phe Ala Arg Phe Ile Ala Met Gly Arg
            20                  25                  30

Arg Leu Met Lys Leu Lys His Leu Thr Glu Glu Ile Glu Glu Thr Ile
        35                  40                  45

Glu Asp Lys Ala Glu Arg Thr Arg Ile Leu Glu Gly Ser Leu Gly Lys
    50                  55                  60

Ile Met Ser Ser Thr Gln Glu Ala Ala Val Val Pro Pro Tyr Val Ala
65                  70                  75                  80

Phe Ala Val Arg His Asn Pro Gly Phe Trp Asp Tyr Val Lys Val Asn
                85                  90                  95

Ala Glu Thr Leu Ser Val Glu Ala Ile Ser Ala Arg Glu Tyr Leu Lys
            100                 105                 110

Phe Lys Glu Met Ile Phe Asp Glu Asp Trp Ala Lys Asp Asp Asn Ala
        115                 120                 125

Leu Glu Val Asp Phe Gly Ala Phe Asp Tyr Ser Asn Pro Arg Leu Ala
    130                 135                 140

Leu Ser Ser Ser Val Gly Asn Gly Leu Asn Phe Ile Ser Lys Val Leu
145                 150                 155                 160

Ser Ser Lys Phe Gly Gly Lys Pro Glu Asp Ala Gln Pro Leu Leu Asp
                165                 170                 175

Tyr Leu Leu Ala Leu Asn His Gln Gly Glu Asn Leu Met Ile Asn Glu
            180                 185                 190

Asn Leu Asn Gly Val Ala Lys Leu Gln Ala Ala Leu Ile Val Ala Glu
        195                 200                 205

Val Phe Val Ser Ser Phe Pro Lys Asp Thr Pro Tyr Lys Asp Phe Glu
    210                 215                 220

His Lys Leu Lys Glu Trp Gly Phe Asp Lys Gly Trp Gly His Asn Ala
225                 230                 235                 240

Gly Arg Val Arg Glu Thr Met Arg Leu Leu Ser Glu Ile Ile Gln Ala
                245                 250                 255

Pro Asp Pro Ile Asn Met Glu Ser Phe Phe Ser Lys Leu Pro Thr Thr
            260                 265                 270

Phe Asn Ile Val Ile Phe Ser Ile His Gly Tyr Phe Gly Gln Ala Asp
        275                 280                 285

Val Leu Gly Leu Pro Asp Thr Gly Gly Gln Val Val Tyr Ile Leu Asp
    290                 295                 300

Gln Val Arg Ala Leu Glu Glu Glu Met Leu Gln Arg Ile Lys Gln Gln
305                 310                 315                 320
```

```
Gly Leu Asn Val Lys Pro Lys Ile Leu Val Ser Arg Leu Ile Pro
                325                 330                 335

Asp Ala Arg Gly Thr Thr Cys Asn Gln Glu Met Glu Pro Ile Leu Asn
            340                 345                 350

Ser Ser His Ser His Ile Leu Arg Ile Pro Phe Arg Thr Glu Lys Gly
        355                 360                 365

Val Leu Arg Gln Trp Asp Ala Ser Ala Lys Ile Leu Glu Leu Met Glu
    370                 375                 380

Gly Lys Pro Asp Leu Ile Ile Gly Asn Tyr Thr Asp Gly Asn Leu Val
385                 390                 395                 400

Ala Ser Leu Leu Ala Asn Lys Leu Gly Val Thr Gln Gly Thr Ile Ala
                405                 410                 415

His Ala Leu Glu Lys Thr Lys Tyr Glu Asp Ser Asp Val Lys Trp Lys
            420                 425                 430

Gln Phe Asp Pro Lys Tyr His Phe Ser Cys Gln Phe Thr Ala Asp Leu
        435                 440                 445

Leu Ala Met Asn Ala Ala Asp Phe Ile Ile Thr Ser Thr Tyr Gln Glu
    450                 455                 460

Ile Ala Gly Ser Glu Thr Arg Pro Gly Gln Tyr Glu Ser His Thr Ala
465                 470                 475                 480

Phe Thr Met Pro Gly Leu Tyr Arg Ala Val Ser Gly Ile Asn Val Phe
                485                 490                 495

Asp Pro Lys Phe Asn Ile Ala Ala Pro Gly Ala Glu Gln Ser Thr Tyr
            500                 505                 510

Phe Pro Phe Thr Glu Lys Gln Lys Arg Phe Ser Thr Phe Arg Pro Ala
        515                 520                 525

Ile Asn Glu Leu Leu Tyr Ser Asn Glu Glu Asn Asn Glu His Ile Gly
    530                 535                 540

Phe Leu Ala Asp Arg Lys Lys Pro Ile Ile Phe Ser Met Ala Arg Phe
545                 550                 555                 560

Asp Thr Val Lys Asn Leu Ser Gly Leu Thr Glu Trp Tyr Gly Lys Asn
                565                 570                 575

Lys Lys Leu Arg Asn Leu Val Asn Leu Val Ile Val Gly Gly Phe Phe
            580                 585                 590

Asp Pro Ser Lys Ser Lys Asp Arg Glu Glu Ala Ala Glu Ile Lys Lys
        595                 600                 605

Met His Glu Leu Ile Glu Lys Tyr Gln Leu Lys Gly Gln Met Arg Trp
    610                 615                 620

Ile Ala Ala Gln Thr Asp Lys Tyr Arg Asn Ser Glu Leu Tyr Arg Thr
625                 630                 635                 640

Ile Ala Asp Thr Lys Gly Ala Phe Val Gln Pro Ala Leu Tyr Glu Ala
                645                 650                 655

Phe Gly Leu Thr Val Ile Glu Ala Met Asp Cys Gly Leu Pro Thr Phe
            660                 665                 670

Ala Thr Asn Gln Gly Gly Pro Ala Glu Ile Ile Val Asp Gly Val Ser
        675                 680                 685

Gly Phe His Ile Asp Pro Tyr Asn Gly Asp Glu Ser Ser Lys Lys Ile
    690                 695                 700

Ala Asp Phe Phe Glu Lys Cys Lys Val Asp Ser Lys Tyr Trp Asn Arg
705                 710                 715                 720

Ile Ser Glu Gly Gly Leu Lys Arg Ile Glu Glu Cys Tyr Thr Trp Lys
                725                 730                 735

Ile Tyr Ala Asn Lys Val Leu Asn Met Gly Ser Ile Tyr Gly Phe Trp
```

|  |  | 740 |  |  | 745 |  |  | 750 |  |  |  |
|---|---|---|---|---|---|---|---|---|---|---|---|
| Arg | Gln | Phe | Asn | Val | Gly | Gln | Lys | Gln | Ala | Lys | Gln |

Arg Tyr Phe Glu
    755              760              765

Met Phe Tyr Asn Pro Leu Phe Arg Lys Leu Ala Lys Ser Val Pro Ile
770                     775                     780

Pro His Glu Glu Pro Leu Pro Leu Ala Thr Ser Asp Ser Thr Gln Ser
785                     790                     795                     800

Gln Glu Leu Lys Leu Pro Leu Pro Val Pro Ala Val Ala Lys Val
            805                     810                     815

Leu Pro Leu Thr Arg His Ala Phe Asn Leu Ile Thr Ser Leu Pro Arg
            820                     825                     830

Val Thr Gly Lys Val Asp Val Lys
            835                     840

<210> SEQ ID NO 28
<211> LENGTH: 3268
<212> TYPE: DNA
<213> ORGANISM: Nicotiana tabacum

<400> SEQUENCE: 28

| atggcctcaa ctgttgctgg tagcatgcct gatgctttga acaaagccg atatcatatg | 60 |
|---|---|
| aagagatgct tcgctaggtg aacacccttc ttgttctttt tgtttttcc ctctaccatt | 120 |
| tatgtcaaat ttcaatgcat aatgctaact actttttttc ttttgactt caaaattgga | 180 |
| cgtgaaaggt tcattgcaat gggaaggagg ttgatgaagc tgaaacattt aacagaagaa | 240 |
| atagaaaaaa ctattgaaga caaggcagaa agaaccaaga ttttggaggg ttcacttgga | 300 |
| aaaattatga gttccacaca ggtcagcacc atttaaccaa cttaattgaa taggaagaaa | 360 |
| aaaaaaagca aaagagttat tgcaaggcgt aacgatttcc tttgaaattt tcaggaggca | 420 |
| gctgttgtcc caccttatgt tgcttttgca gtaaggcaca atcctggctt ctgggattat | 480 |
| gtcaaagttg acgctgaaac tctctctgtg gaagctattt cagccaggga ctatctcaaa | 540 |
| ttcaaagaga tgatctttga tgaagattgg taactggaag attgtatcat tttaaagaaa | 600 |
| caatttttta atattcaaga ttagttttga tggttgaatg tgcaagcagg gcaaaggatg | 660 |
| aaaatgcact cgaagtagat tttggtgctt ttgactactc taatcatcgg ttagcccttt | 720 |
| cctcttctgt cggaaatggg ctaaacttca tctcgaaagt tttgtcttca aagtttggtg | 780 |
| gaaaggcaga agatgcccag cctttgcttg attacttact agctcttaat catcaaggag | 840 |
| aggtatggaa atggactacc ttcctttctt aaggaattat ataatgatgt atgttataaa | 900 |
| gatccttttt aaacattgac actttgcaga atctaatgat caatgagaat ctgaatggcg | 960 |
| tctctaagct tcaagcagca ttgatagtag ctgaagtttt tgtatcttcc tttcccaaag | 1020 |
| acacacctta taaagacttt gagcataagt aagcttttca aacgcttctg ttatcatatg | 1080 |
| caatatacca agaatatgtt gccttttgaa aagttgttta tgtttatgac ttgataatga | 1140 |
| aaatactagg ctcaaagaat ggggctttga gaaagggtgg ggtcacaatg caggaagagt | 1200 |
| aagagagaca atgagactgc tttccgagat aatccaagcg ccagatccca taaatatgga | 1260 |
| gtcctttttc agcaggcttc ctactacatt aacattgtt atcttctcca ttcatggtta | 1320 |
| ctttggccaa gcagatgtcc ttggtttgcc cgatactgga ggccaggttt acatacacag | 1380 |
| caatttatct ccttttgcct catatttact tattagcgac acttgcatta ttgaaatcac | 1440 |
| atttgtattt aacaggttgt ttatattctg gatcaagtaa gagccttaga ggaggaaatg | 1500 |
| ttacaaagaa tcaagcagca agggttaaat gtgaagccca agattcttgt ggtgagttat | 1560 |

```
gcaaaaatat gcgtagccaa ggttttgaaa ttgttcagag gggattaaga tgatcgagat    1620
atttgttccc ttcttccatt gatgtgtaca ggtcactcgt ctcattccag atgctcgagg    1680
gactacatgc aatcaggaga tggaacctat acttaactcg tcccattctc acatcctgag    1740
aattccattc aggacagaga aaggagttct tcgccaatgg gtttctcggt ttgatatcta    1800
tccttacttg gagaactatg ccaaggcaag tctcctacca aaattaccac ctattcatac    1860
actttattca gttttttgag ctaatcattc tcatttgtca cgtatgtgat taggatgctt    1920
ctgctaagat acttgagctc atggaaggta aaccagacct cattattggg aactacactg    1980
atggaaattt agtggcatct ctattggcca acaaacttgg agttactcag gttctacagc    2040
tgatcattta tctgatcaga ttttctacat tgttttcttg ataattaaac ggaaatctta    2100
tgagattgta acatttagg gaaccattgc tcatgcatta gagaaaacca gtatgaaga    2160 ttctgatgtc aagtggaagc agtttgattc caagtaccac ttttcttgcc aattcactgc    2220
cgatttattg gcaatgaatg ctgctgattt tatcattacc agcacatatc aagaaatcgc    2280
aggaaggtta gcactgactc tctcagtata tttggcaact taatgaatgt actgcttgtg    2340
gccaacacta aaagctatta ctcgtccttc agcgaaacta ggcctggaca atatgaaagt    2400
cacacagcat ttaccatgcc ggggctttat agagctgttt caggcatcaa tgtatttgat    2460
ccaaagttca acattgctgc tcctgggggct gaacagtctg cctatttccc cttcactgag    2520
aaacagaaac gattcagcgc gtttcgtcct gctattgagg aactacttta cagtaatgag    2580
caaaacaacg agcacatgta agtctaattg ccccatttc ctaatctaac cattgcttaa    2640
atgttctgtt tttacttgat atgtggtact tatcagtgat attttttatt ggaacagtgg    2700
atttcttgca gaccgtaaaa aaccaattat attttcaatg gcaagatttg atacggtgaa    2760
gaacttgtca ggcttgactg agtggtatgg gaagaataag aagttgcgga acttggttaa    2820
cctcgttatc gttgggggat tcttcgatcc atcaaaatca aaagaccggg aggaagcagc    2880
tgaaatcaag aagatgcatg aattgattga aaaatacaag ctcaagggac aaatgagatg    2940
gatagcagct caaactgata aatatcaaaa cagtgagcta tatcgaacta ttgctgacac    3000
taaaggagct ttcgtccaac cggctttata tgaagctttt ggactaactg ttattgaagc    3060
aatgaattgt ggactgccta catttgctac taatcaaggc ggacctgcag aaatcattgt    3120
tgatggggtt tcaggcttcc atattgatcc ttacaatggg gatgaatcga gcaagaaaat    3180
agctgatttc tttgagaagt gtaaggttga ttctaaatat tggaacaaga tatgtggagg    3240
aggtctcaag cgcattgaag aatggtaa                                       3268
```

<210> SEQ ID NO 29
<211> LENGTH: 732
<212> TYPE: PRT
<213> ORGANISM: Nicotiana tabacum

<400> SEQUENCE: 29

Met Ala Ser Thr Val Ala Gly Ser Met Pro Asp Ala Leu Lys Gln Ser
1               5                   10                  15

Arg Tyr His Met Lys Arg Cys Phe Ala Arg Phe Ile Ala Met Gly Arg
            20                  25                  30

Arg Leu Met Lys Leu Lys His Leu Thr Glu Glu Ile Glu Lys Thr Ile
        35                  40                  45

Glu Asp Lys Ala Glu Arg Thr Lys Ser Ile Leu Glu Gly Ser Leu Gly Lys
    50                  55                  60

```
Ile Met Ser Ser Thr Gln Glu Ala Ala Val Val Pro Pro Tyr Val Ala
 65                  70                  75                  80

Phe Ala Val Arg His Asn Pro Gly Phe Trp Asp Tyr Val Lys Val Asp
                 85                  90                  95

Ala Glu Thr Leu Ser Val Glu Ala Ile Ser Ala Arg Asp Tyr Leu Lys
            100                 105                 110

Phe Lys Glu Met Ile Phe Asp Glu Asp Trp Ala Lys Asp Glu Asn Ala
        115                 120                 125

Leu Glu Val Asp Phe Gly Ala Phe Asp Tyr Ser Asn His Arg Leu Ala
    130                 135                 140

Leu Ser Ser Ser Val Gly Asn Gly Leu Asn Phe Ile Ser Lys Val Leu
145                 150                 155                 160

Ser Ser Lys Phe Gly Gly Lys Ala Glu Asp Ala Gln Pro Leu Leu Asp
            165                 170                 175

Tyr Leu Leu Ala Leu Asn His Gln Gly Glu Asn Leu Met Ile Asn Glu
        180                 185                 190

Asn Leu Asn Gly Val Ser Lys Leu Gln Ala Ala Leu Ile Val Ala Glu
    195                 200                 205

Val Phe Val Ser Ser Phe Pro Lys Asp Thr Pro Tyr Lys Asp Phe Glu
210                 215                 220

His Lys Leu Lys Glu Trp Gly Phe Glu Lys Gly Trp Gly His Asn Ala
225                 230                 235                 240

Gly Arg Val Arg Glu Thr Met Arg Leu Leu Ser Glu Ile Ile Gln Ala
            245                 250                 255

Pro Asp Pro Ile Asn Met Glu Ser Phe Phe Ser Arg Leu Pro Thr Thr
        260                 265                 270

Phe Asn Ile Val Ile Phe Ser Ile His Gly Tyr Phe Gly Gln Ala Asp
    275                 280                 285

Val Leu Gly Leu Pro Asp Thr Gly Gly Gln Val Val Tyr Ile Leu Asp
    290                 295                 300

Gln Val Arg Ala Leu Glu Glu Met Leu Gln Arg Ile Lys Gln Gln
305                 310                 315                 320

Gly Leu Asn Val Lys Pro Lys Ile Leu Val Val Thr Arg Leu Ile Pro
            325                 330                 335

Asp Ala Arg Gly Thr Thr Cys Asn Gln Glu Met Glu Pro Ile Leu Asn
        340                 345                 350

Ser Ser His Ser His Ile Leu Arg Ile Pro Phe Arg Thr Glu Lys Gly
    355                 360                 365

Val Leu Arg Gln Trp Asp Ala Ser Ala Lys Ile Leu Glu Leu Met Glu
    370                 375                 380

Gly Lys Pro Asp Leu Ile Ile Gly Asn Tyr Thr Asp Gly Asn Leu Val
385                 390                 395                 400

Ala Ser Leu Leu Ala Asn Lys Leu Gly Val Thr Gln Gly Thr Ile Ala
            405                 410                 415

His Ala Leu Glu Lys Thr Lys Tyr Glu Asp Ser Asp Val Lys Trp Lys
        420                 425                 430

Gln Phe Asp Ser Lys Tyr His Phe Ser Cys Gln Phe Thr Ala Asp Leu
    435                 440                 445

Leu Ala Met Asn Ala Ala Asp Phe Ile Ile Thr Ser Thr Tyr Gln Glu
    450                 455                 460

Ile Ala Gly Ser Glu Thr Arg Pro Gly Gln Tyr Glu Ser His Thr Ala
465                 470                 475                 480

Phe Thr Met Pro Gly Leu Tyr Arg Ala Val Ser Gly Ile Asn Val Phe
```

|     |     |     | 485 |     |     |     | 490 |     |     |     | 495 |     |
| --- | --- | --- | --- | --- | --- | --- | --- | --- | --- | --- | --- | --- |
| Asp | Pro | Lys | Phe | Asn | Ile | Ala | Ala | Pro | Gly | Ala | Glu | Gln | Ser | Ala | Tyr |
|     |     |     | 500 |     |     |     | 505 |     |     |     | 510 |     |

Asp Pro Lys Phe Asn Ile Ala Ala Pro Gly Ala Glu Gln Ser Ala Tyr
                500                 505                 510

Phe Pro Phe Thr Glu Lys Gln Lys Arg Phe Ser Ala Phe Arg Pro Ala
                515                 520                 525

Ile Glu Glu Leu Leu Tyr Ser Asn Glu Gln Asn Asn Glu His Ile Gly
                530                 535                 540

Phe Leu Ala Asp Arg Lys Lys Pro Ile Ile Phe Ser Met Ala Arg Phe
545                 550                 555                 560

Asp Thr Val Lys Asn Leu Ser Gly Leu Thr Glu Trp Tyr Gly Lys Asn
                565                 570                 575

Lys Lys Leu Arg Asn Leu Val Asn Leu Val Ile Val Gly Gly Phe Phe
                580                 585                 590

Asp Pro Ser Lys Ser Lys Asp Arg Glu Glu Ala Ala Glu Ile Lys Lys
                595                 600                 605

Met His Glu Leu Ile Glu Lys Tyr Lys Leu Lys Gly Gln Met Arg Trp
610                 615                 620

Ile Ala Ala Gln Thr Asp Lys Tyr Gln Asn Ser Glu Leu Tyr Arg Thr
625                 630                 635                 640

Ile Ala Asp Thr Lys Gly Ala Phe Val Gln Pro Ala Leu Tyr Glu Ala
                645                 650                 655

Phe Gly Leu Thr Val Ile Glu Ala Met Asn Cys Gly Leu Pro Thr Phe
                660                 665                 670

Ala Thr Asn Gln Gly Gly Pro Ala Glu Ile Ile Val Asp Gly Val Ser
                675                 680                 685

Gly Phe His Ile Asp Pro Tyr Asn Gly Asp Glu Ser Ser Lys Lys Ile
                690                 695                 700

Ala Asp Phe Phe Glu Lys Cys Lys Val Asp Ser Lys Tyr Trp Asn Lys
705                 710                 715                 720

Ile Cys Gly Gly Gly Leu Lys Arg Ile Glu Glu Trp
                725                 730

<210> SEQ ID NO 30
<211> LENGTH: 3937
<212> TYPE: DNA
<213> ORGANISM: Nicotiana tabacum

<400> SEQUENCE: 30

| atggctactg caccagccct aaatagatca gagtccatag ctgatagcat gccagaggcc | 60 |
| ttaaggcaaa gccggtacca catgaagaaa tgttttgcca agtacataga gcaaggaaag | 120 |
| aggatgatga aacttcataa cttgatggat gagttggaga agtaattga tgatcctgct | 180 |
| gaaaggaacc atgttttgga aggcttactt ggctacatat tatgcactac aatggtatag | 240 |
| ctagattcat atgtacttat gatgccctta tattgtttcc tgatgtatta ctcttaaaac | 300 |
| cttctttgat caaatttaca ggaggctgca gttgttcctc cctacattgc ctttgccacg | 360 |
| agacagaatc ctggattctg gaatatgtg aaagtgaatg ctaatgatct ttctgttgag | 420 |
| ggtattacag ctacagaata cttgaaattc aaggaaatga tagttgatga atgctggtat | 480 |
| agtatacgtt gcagcttatc ataccttttg tggttttata acttcaatca gaaaactcat | 540 |
| cagagttacc tttgtgtgaa catgaaatgc agggcaaaag atgaatatgc actggaaatt | 600 |
| gattttggag cagtagactt ctcaacgcct cgactgaccc tatcctcttc aattggcaat | 660 |
| ggtctcagtt atgtttccaa gtttctaact tcaaagctaa atgctacctc cgcgagtgca | 720 |

```
cagtgtctgg ttgactactt gctcactttg aatcatcaag gagatgtacg tcaacaaaaa    780
tcaaactcca taagtaaact tgtcaactct aagaagaaaa aataggaaaa gaagattcac    840
gtaacaaatt ttctttatgt tcaactgcag aaactgatga tcaatgagac actcagcact    900
gtctcaaagc ttcaggctgc actggttgta gcagaagcat ctatttcctc tttaccaaca    960
gatacaccat atgagagctt tgagctaagg tgatttgttt tttcctctac ttccctccac   1020
ttgtgccatg ctacgtagta ctaagtaact tcaattcttg taaagattca aacagtgggg   1080
ttttgagaaa ggatggggtg atacagctga aagggtcagc gacaccatga gaacactgtc   1140
tgaggtgctt caggcaccag atccattgaa cattcagaag ttctttggaa gggttccaac   1200
tgttttcaat attgtattgt tctctgtcca tggatacttt ggccaagcag atgttcttgg   1260
cttgccagac actggtggtc aggtaagcat ttaatagctt ttacatttaa cttctatgca   1320
ttgacaataa aataatttttt aacagtttga ccacttctgc tcttgttcaa caggtagttt   1380 atgtttttgga tcaagttgta gcttttgaag aagaaatgct acaaagaatt aaacagcagg   1440
ggctcaatat taagcctcaa attcttgtgg tgagttccta gacaatcgac gtgactatgc   1500
aattatgtag aggctgttta gaaaagttaa tatcatatgt tgattgcaca gttaacccga   1560
ctgattccgg atgcaaaagg aacaaagtgc aaccaggaac tagaaccaat caagaataca   1620
aaacattcac acatcctcag agttccattt aggacagaaa aaggagtgct taatcaatgg   1680
gtttcacgat ttgatatcta tccatatctg gagagatata ctcaggtatg tatttttata   1740
tcaaccttgc tcatcaaaga tgtgttgttt cctcaattcc attttttcccc ttggcaaaag   1800 gatgctgctg acaaaatcgt cgagctaatg gaaggcaaac ctgatctaat cattggtaac   1860
tacactgatg ggaatctagt ggcttcacta atggctagaa aacttgggat aactctggta   1920
acttttctta atcatatttg atgttgcttc ttctccaagt tagttcttaa tctccactga   1980
cctagaccat ctttgcaaca gggaactatt gctcatgctt tggagaagac aaaatatgaa   2040
gactctgaca taaaattgaa ggaactcgat ccgaagtacc acttctcttg ccaattcaca   2100
gctgatttga ttgcaatgaa ttcagcagat ttcattatca ctagcacata ccaagaaata   2160
gctggaaggt aagaattaga gctaataagt aatgcattca tatgtatttc agcatcgctc   2220
tttcaccatc atcgaataca caccactact cagtaaatgt atttgctcaa aagtttgcaa   2280
cttaatggat ctcattcttg aatgcttcaa catatgcagc aaagataaac caggacagta   2340
tgagagccat agtgcattta cccttccagg gctttacaga gttgcttcag gtatcaatgt   2400
ctttgatcca aaaatttaata ttgctgcacc tggggcagac cagtcggtgt atttcccttta   2460 cacagaaaag cagaagcgtt tgactgcttt ccgccctgcc attgaggaac tgcttttttag   2520 taaagtggac aatgacgagc acgtgtaagt ctaagtgtta aacttcagct tagtgcctag   2580
aacatcccac tgctctatgt attgatgttt cacttgtttc aaacagtgga tatttagaag   2640
acagaaagaa acctatcctg tttaccatgg caaggctgga cacagtgaag aacacatctg   2700
gactaacaga atggtatggc aagaacaaga ggctcagaag cttagttaac cttgttgtgg   2760
ttggtggttc ctttgatcct acaaaatcca aggatagggga agaagcagct gaaataaaaa   2820
agatgcacat gctgatagag aaataccagc ttaagggtca gattagatgg atagcagctc   2880
agactgacag atacagaaat agtgaactct accgcacaat agcagattcc aaaggagctt   2940
ttgtgcagcc tgcattgtat gaagcatttg gtctaacagt cattgaggca atgaactgtg   3000
gattaccaac ctttgctacc aaccaaggtg gccctgctga gattattgtt gatgggtct     3060 caggctttca tattgatcca aataatgggg atgaatcaag caacaaaatt gccaactttt   3120
```

-continued

```
tccaaaaatg cagggaggat cctgagtatt ggaacaggat ttcagtccag ggtctaaacc    3180
gtatatatga atggtaactc acagataagc cattcaaatt gcaaagaggc acatatcttg    3240
cagaaaattt cttaatcctt aaatcctaat tttttgcagt tacacatgga agatctatgc    3300
aaacaaggta ttgaatatgg ggtccatcta tacttttttgg aggacattgt acagagatca    3360
gaaacaagca aagcaaagat acatcgagac tttctacaat cttgagttta ggaacttggt    3420
atagtgctgc atgacattga cagtatacca caaacatctt tatgagatga attacttta    3480 ataaaattgt ttttaacctt tgcttcctta atggcactta ttgcaggtaa aaaatgtgcc    3540
tatcagaaag gacgaaacac cacaaggacc aaggagagg gagaaagtta agccacagat    3600
atcacaaagg catgctctaa agcttttgcc tacagttttt caagagaccc tagtatattc    3660
tagtactaaa ttagaattat acagcatgca gcttttgctg ttcacctttc taaatcacca    3720
gttgtgtcaa tcaagttgac aaaatcaata aattgggatt ttccctttcc tatgcttgat    3780
tgttattact cctactttgt ttatggtagt cttccttcat tgttttctcc tgtacttctt    3840
ttactacaac tgtactgaca tactaattat ttctgtgtac caggcgctca caatcaaggt    3900
tgcagaagta agattagata aaattgctac tgcatga                            3937
```

<210> SEQ ID NO 31
<211> LENGTH: 860
<212> TYPE: PRT
<213> ORGANISM: Nicotiana tabacum

<400> SEQUENCE: 31

```
Met Ala Thr Ala Pro Ala Leu Asn Arg Ser Glu Ser Ile Ala Asp Ser
1               5                   10                  15

Met Pro Glu Ala Leu Arg Gln Ser Arg Tyr His Met Lys Lys Cys Phe
            20                  25                  30

Ala Lys Tyr Ile Glu Gln Gly Lys Arg Met Met Lys Leu His Asn Leu
        35                  40                  45

Met Asp Glu Leu Glu Lys Val Ile Asp Pro Ala Glu Arg Asn His
    50                  55                  60

Val Leu Glu Gly Leu Leu Gly Tyr Ile Leu Cys Thr Thr Met Glu Ala
65                  70                  75                  80

Ala Val Pro Pro Tyr Ile Ala Phe Ala Thr Arg Gln Asn Pro Gly
                85                  90                  95

Phe Trp Glu Tyr Val Lys Val Asn Ala Asn Asp Leu Ser Val Glu Gly
            100                 105                 110

Ile Thr Ala Thr Glu Tyr Leu Lys Phe Lys Glu Met Ile Val Asp Glu
        115                 120                 125

Cys Trp Ala Lys Asp Glu Tyr Ala Leu Glu Ile Asp Phe Gly Ala Val
    130                 135                 140

Asp Phe Ser Thr Pro Arg Leu Thr Leu Ser Ser Ile Gly Asn Gly
145                 150                 155                 160

Leu Ser Tyr Val Ser Lys Phe Leu Thr Ser Lys Leu Asn Ala Thr Ser
                165                 170                 175

Ala Ser Ala Gln Cys Leu Val Asp Tyr Leu Leu Thr Leu Asn His Gln
            180                 185                 190

Gly Asp Lys Leu Met Ile Asn Glu Thr Leu Ser Thr Val Ser Lys Leu
        195                 200                 205

Gln Ala Ala Leu Val Val Ala Glu Ala Ser Ile Ser Ser Leu Pro Thr
    210                 215                 220
```

-continued

Asp Thr Pro Tyr Glu Ser Phe Glu Leu Arg Phe Lys Gln Trp Gly Phe
225                 230                 235                 240

Glu Lys Gly Trp Gly Asp Thr Ala Glu Arg Val Ser Asp Thr Met Arg
            245                 250                 255

Thr Leu Ser Glu Val Leu Gln Ala Pro Asp Pro Leu Asn Ile Gln Lys
        260                 265                 270

Phe Phe Gly Arg Val Pro Thr Val Phe Asn Ile Val Leu Phe Ser Val
    275                 280                 285

His Gly Tyr Phe Gly Gln Ala Asp Val Leu Gly Leu Pro Asp Thr Gly
290                 295                 300

Gly Gln Val Val Tyr Val Leu Asp Gln Val Val Ala Phe Glu Glu Glu
305                 310                 315                 320

Met Leu Gln Arg Ile Lys Gln Gln Gly Leu Asn Ile Lys Pro Gln Ile
            325                 330                 335

Leu Val Leu Thr Arg Leu Ile Pro Asp Ala Lys Gly Thr Lys Cys Asn
            340                 345                 350

Gln Glu Leu Glu Pro Ile Lys Asn Thr Lys His Ser His Ile Leu Arg
        355                 360                 365

Val Pro Phe Arg Thr Glu Lys Gly Val Leu Asn Gln Trp Val Ser Arg
370                 375                 380

Phe Asp Ile Tyr Pro Tyr Leu Glu Arg Tyr Thr Gln Asp Ala Ala Asp
385                 390                 395                 400

Lys Ile Val Glu Leu Met Glu Gly Lys Pro Asp Leu Ile Ile Gly Asn
                405                 410                 415

Tyr Thr Asp Gly Asn Leu Val Ala Ser Leu Met Ala Arg Lys Leu Gly
            420                 425                 430

Ile Thr Leu Gly Thr Ile Ala His Ala Leu Glu Lys Thr Lys Tyr Glu
            435                 440                 445

Asp Ser Asp Ile Lys Leu Lys Glu Leu Asp Pro Lys Tyr His Phe Ser
450                 455                 460

Cys Gln Phe Thr Ala Asp Leu Ile Ala Met Asn Ser Ala Asp Phe Ile
465                 470                 475                 480

Ile Thr Ser Thr Tyr Gln Glu Ile Ala Gly Ser Lys Asp Lys Pro Gly
            485                 490                 495

Gln Tyr Glu Ser His Ser Ala Phe Thr Leu Pro Gly Leu Tyr Arg Val
        500                 505                 510

Ala Ser Gly Ile Asn Val Phe Asp Pro Lys Phe Asn Ile Ala Ala Pro
            515                 520                 525

Gly Ala Asp Gln Ser Val Tyr Phe Pro Tyr Thr Glu Lys Gln Lys Arg
530                 535                 540

Leu Thr Ala Phe Arg Pro Ala Ile Glu Glu Leu Leu Phe Ser Lys Val
545                 550                 555                 560

Asp Asn Asp Glu His Val Gly Tyr Leu Glu Asp Arg Lys Lys Pro Ile
            565                 570                 575

Leu Phe Thr Met Ala Arg Leu Asp Thr Val Lys Asn Thr Ser Gly Leu
            580                 585                 590

Thr Glu Trp Tyr Gly Lys Asn Lys Arg Leu Arg Ser Leu Val Asn Leu
        595                 600                 605

Val Val Val Gly Gly Ser Phe Asp Pro Thr Lys Ser Lys Asp Arg Glu
            610                 615                 620

Glu Ala Ala Glu Ile Lys Lys Met His Met Leu Ile Glu Lys Tyr Gln
625                 630                 635                 640

Leu Lys Gly Gln Ile Arg Trp Ile Ala Ala Gln Thr Asp Arg Tyr Arg

```
                       645                 650                 655
Asn Ser Glu Leu Tyr Arg Thr Ile Ala Asp Ser Lys Gly Ala Phe Val
                660                 665                 670

Gln Pro Ala Leu Tyr Glu Ala Phe Gly Leu Thr Val Ile Glu Ala Met
                675                 680                 685

Asn Cys Gly Leu Pro Thr Phe Ala Thr Asn Gln Gly Gly Pro Ala Glu
                690                 695                 700

Ile Ile Val Asp Gly Val Ser Gly Phe His Ile Asp Pro Asn Asn Gly
705                 710                 715                 720

Asp Glu Ser Ser Asn Lys Ile Ala Asn Phe Phe Gln Lys Cys Arg Glu
                725                 730                 735

Asp Pro Glu Tyr Trp Asn Arg Ile Ser Val Gln Gly Leu Asn Arg Ile
                740                 745                 750

Tyr Glu Cys Tyr Thr Trp Lys Ile Tyr Ala Asn Lys Val Leu Asn Met
                755                 760                 765

Gly Ser Ile Tyr Thr Phe Trp Arg Thr Leu Tyr Arg Asp Gln Lys Gln
                770                 775                 780

Ala Lys Gln Arg Tyr Ile Glu Thr Phe Tyr Asn Leu Glu Phe Arg Asn
785                 790                 795                 800

Leu Val Lys Asn Val Pro Ile Arg Lys Asp Glu Thr Pro Gln Gly Pro
                805                 810                 815

Lys Glu Arg Glu Lys Val Lys Pro Gln Ile Ser Gln Arg His Ala Leu
                820                 825                 830

Lys Leu Leu Pro Thr Val Phe Gln Gly Thr Leu Ala Leu Thr Ile Lys
                835                 840                 845

Val Ala Glu Val Arg Leu Asp Lys Ile Ala Thr Ala
                850                 855                 860

<210> SEQ ID NO 32
<211> LENGTH: 3905
<212> TYPE: DNA
<213> ORGANISM: Nicotiana tabacum

<400> SEQUENCE: 32
atggctactg caccagccct gaaaagatca gagtccatag ctgatagcat gccagaggcc    60
ttaaggcaaa gccggtacca catgaagaaa tgttttgcca agtacataga gcaaggcaag   120
aggatgatga aacttcataa cttgatggat gaattggaga agtaattga tgatcctgct    180 gaaaggaacc atgttttgga aggcttactt ggctacatat tatgtactac aatggtatag   240
ctagattcat atgtacttat gatgtcctta tattgtttcc ggaggcatta ttcttaaatc   300
cttctttgat caaatttgta ggaggctgca gttgttcctc cctatattgc cttcgccacg   360
agacagaatc ctggattctg gaatatgtg aaagtcaatg ctaatgatct ttctgttgag   420
ggtattacag ctacagatta cttgaaattc aaggaaatga tagttgatga agctggtat    480 agaatacttt gcagcttatc ataccttttg tggttttata atttcaatca gaaaactcat   540
cagagttacc tttgtgtgaa catgacatgc agggcaaaag atgaatatgc actggaaatt   600
gattttggag cagtagactt ctcaacgcct cgactgaccc tatcctcttc aattggaaat   660
ggtctcagtt atgtttccaa gtttctaact tcaaagctaa atgctacctc agcgagtgca   720
cagtgtctgg ttgactactt gctcactttg aatcaccaag agatgtacg tcaacaaaaa   780 tcaaactcca taagtaaact tgtcaactct aagaagtaaa ataggaaaa gaagattcat   840 gtaacaaatt ttctttatgt tcaactgtag aaactgatga tcaatgagac actcggcact   900
```

```
gtctcaaagc ttcaggctgc actggttgta gcagaagcat ctatttcctc cttaccaaca    960
gatacaccat accagagctt tgagctaagg tgatttgttt tttcctctac ttccttccac   1020
ttttggtgtg ctacatagta ctaagtaact tcaattcttg taaagattca aacagtgggg   1080
ttttgagaaa ggatggggtg atacagctga aagggtccgc gacaccatga gaacactttc   1140
tgaggtactt caggcgccag atccattgaa cattgagaag ttctttggga gggttccaac   1200
tgttttcaat attgtattgt tctctgttca tggatacttt ggccaagcaa atgttcttgg   1260
cttgccagac acaggtggtc aggtaagcat ctaatagctt ttacatttaa cttctatgca   1320
ttgacaataa ataacttct acactaccaa ataattttg aaagtttgac cacttcggct     1380
cttgttcaac aggtggttta tgttttggat caagttgtag cttttgaaga agaaatgctc   1440
caaagaatta aacagcaggg gctcaatatt aagcctcaaa ttcttgtggt gagctcctag   1500
acaatgacgt gactatgcaa ttaagtagag gctgtttaga aaagttaata tcatatgttg   1560
attgcacagt taacccgact gattccggac gccaaaggaa caaagtgcaa ccaggaacta   1620
gaaccaatca agaatacaaa acattcacac atccctcagag ttccatttag gacagaaaaa  1680
ggagtgctta atcaatgggt ttcacgattt gatatctatc catatctgga gagatatact   1740
caggtgtgta tttttatatc aaccctgctc atcaaagatg tgttgtttcc tcaattccat   1800
ttttcgcctt gacaaaagga cgctgctgac aaaatcatcg agctaatgga aggcaaacct   1860
gatctaatca ttggtaacta cactgatggg aatctagtgg cttctctaat ggctagaaag   1920
cttgggataa ctctggtaac ttttcttatc atatttgatg ttgtttcttc tccaagttgg   1980
ttcttaatgt caactaaccc agaccatctt tgtaacaggg aactattgct catgctctgg   2040
agaagacaaa atatgaagac tctgacatca aattgaagga actcgatccg aagtaccact   2100
tttcttgcca attcacagct gatttgattg caatgaattc agcagatttc attatcacaa   2160
gcacatatca agaaatagcc ggaaggtaag aattggaact acggaagcag agagctaata   2220
agtagtgcac tcatatattt cagcatcgct cttcgcata atcgaataca caccactact    2280
cagtaaatgt acttgctcaa aagtttacaa gtttatggat cttattcttg aatgcttcaa   2340
catatgcagc aaagataggc caggacagta tgagagccat agtgcattta cccttccagg   2400
gctttacaga gttgcttcag gcatcaatgt ctttgatcct aaatttaata ttgctgcacc   2460
tggggcagac caatcggtgt atttccctta cacagaaaag cagacgcgtt tgactgcttt   2520
ccgccctgcc attgaggaac tgcttttag taaagtggac aatgacgagc acatgtaagt    2580
cttagtgtta aacttcagct ttcagcttag tgcctagaac attccactgg ctctatgtat   2640
taatgtttca cttgtttcaa acacagtgga tatttagaag acagaaagaa acctatcctg   2700
tttaccatgg caaggctgga cacagtgaag aacacatctg gactaacaga atggtatggc   2760
aagaacaaga ggctcagaag cttagttaac cttgttgtgg ttggtggttc ctttgatcct   2820
acaaaatcca aggatagaga agaagcagct gaaataaaaa agatgcacat gctgatagag   2880
aaataccagc ttaagggtca gatcagatgg atagcagctc agactgacag atatagaaac   2940
agtgaactct accgcacaat agcagattcc aaaggagctt tgtgcagcc tgcattatat     3000 gaagcatttg gtctaacagt cattgaggca atgaactgtg gattaccaac ctttgctacc   3060
aaccaaggtg gccctgctga gattattgtt gatgggtctc caggctttca tattgatcca   3120
aataatgggg atgaatcaag caacaaagtt gccaactttt tccaaaaatg cagggaggat   3180
cctgagtatt ggaacaggat ttcagtccag ggtctaaacc gtatatatga atggtaactc   3240
acagataagc cattcaaatt gcaaagaggc acatatcttg ctgaaaattt cttaatccct   3300
```

```
taatcctaaa attttgcagt tacacatgga agatctatgc aaacaaggta ttgaatatgg    3360
ggtccatcta tactttttgg aggacattgt acagagatca gaaacaagca aagcaaagat    3420
acatcgagac tttctacaat cttgagttta ggaacttggt atagtgctgc atgacattga    3480
cagtatacca caaacatctt tatgagatga attactttta ataaaattgt ttttaacctt    3540
tgcctcctta atgacactta ttgcaggtaa aaaatgtgcc tatcagacag gacgaaacac    3600
cacaaggacc aaaggagagg agggagaaag ttaagccaca gatatcacaa aggcatgctc    3660
taaagctttt gcctatagtt tttcaggaga ccctagtata ttctagtact aaattagaat    3720
tatacagcat gcagcttgct tctgctgttc acctttctaa atcaccagtt atgtcaatca    3780
agttgacaaa atcaataaat tcggcttttc cctttcctat gcttgattgt tattactcct    3840
acttcgttta tggtagtctt ccttcattgt tttctcctgt acttctttta ctacaactgt    3900
actga                                                                 3905
```

<210> SEQ ID NO 33
<211> LENGTH: 913
<212> TYPE: PRT
<213> ORGANISM: Nicotiana tabacum

<400> SEQUENCE: 33

```
Met Ala Thr Ala Pro Ala Leu Lys Arg Ser Glu Ser Ile Ala Asp Ser
1               5                   10                  15

Met Pro Glu Ala Leu Arg Gln Ser Arg Tyr His Met Lys Lys Cys Phe
            20                  25                  30

Ala Lys Tyr Ile Glu Gln Gly Lys Arg Met Met Lys Leu His Asn Leu
        35                  40                  45

Met Asp Glu Leu Glu Lys Val Ile Asp Pro Ala Glu Arg Asn His
    50                  55                  60

Val Leu Glu Gly Leu Leu Gly Tyr Ile Leu Cys Thr Thr Met Glu Ala
65                  70                  75                  80

Ala Val Val Pro Pro Tyr Ile Ala Phe Ala Thr Arg Gln Asn Pro Gly
                85                  90                  95

Phe Trp Glu Tyr Val Lys Val Asn Ala Asn Asp Leu Ser Val Glu Gly
            100                 105                 110

Ile Thr Ala Thr Asp Tyr Leu Lys Phe Lys Glu Met Ile Val Asp Glu
        115                 120                 125

Ser Trp Ala Lys Asp Glu Tyr Ala Leu Glu Ile Asp Phe Gly Ala Val
    130                 135                 140

Asp Phe Ser Thr Pro Arg Leu Thr Leu Ser Ser Ile Gly Asn Gly
145                 150                 155                 160

Leu Ser Tyr Val Ser Lys Phe Leu Thr Ser Lys Leu Asn Ala Thr Ser
                165                 170                 175

Ala Ser Ala Gln Cys Leu Val Asp Tyr Leu Leu Thr Leu Asn His Gln
            180                 185                 190

Gly Asp Lys Leu Met Ile Asn Glu Thr Leu Gly Thr Val Ser Lys Leu
        195                 200                 205

Gln Ala Ala Leu Val Val Ala Glu Ala Ser Ile Ser Ser Leu Pro Thr
    210                 215                 220

Asp Thr Pro Tyr Gln Ser Phe Glu Leu Arg Phe Lys Gln Trp Gly Phe
225                 230                 235                 240

Glu Lys Gly Trp Gly Asp Thr Ala Glu Arg Val Arg Asp Thr Met Arg
                245                 250                 255
```

-continued

```
Thr Leu Ser Glu Val Leu Gln Ala Pro Asp Pro Leu Asn Ile Glu Lys
                260                 265                 270

Phe Phe Gly Arg Val Pro Thr Val Phe Asn Ile Val Leu Phe Ser Val
            275                 280                 285

His Gly Tyr Phe Gly Gln Ala Asn Val Leu Gly Leu Pro Asp Thr Gly
        290                 295                 300

Gly Gln Val Val Tyr Val Leu Asp Gln Val Val Ala Phe Glu Glu Glu
305                 310                 315                 320

Met Leu Gln Arg Ile Lys Gln Gln Gly Leu Asn Ile Lys Pro Gln Ile
                325                 330                 335

Leu Val Leu Thr Arg Leu Ile Pro Asp Ala Lys Gly Thr Lys Cys Asn
            340                 345                 350

Gln Glu Leu Glu Pro Ile Lys Asn Thr Lys His Ser His Ile Leu Arg
        355                 360                 365

Val Pro Phe Arg Thr Glu Lys Gly Val Leu Asn Gln Trp Val Ser Arg
    370                 375                 380

Phe Asp Ile Tyr Pro Tyr Leu Glu Arg Tyr Thr Gln Asp Ala Ala Asp
385                 390                 395                 400

Lys Ile Ile Glu Leu Met Glu Gly Lys Pro Asp Leu Ile Ile Gly Asn
                405                 410                 415

Tyr Thr Asp Gly Asn Leu Val Ala Ser Leu Met Ala Arg Lys Leu Gly
            420                 425                 430

Ile Thr Leu Gly Thr Ile Ala His Ala Leu Glu Lys Thr Lys Tyr Glu
        435                 440                 445

Asp Ser Asp Ile Lys Leu Lys Glu Leu Asp Pro Lys Tyr His Phe Ser
    450                 455                 460

Cys Gln Phe Thr Ala Asp Leu Ile Ala Met Asn Ser Ala Asp Phe Ile
465                 470                 475                 480

Ile Thr Ser Thr Tyr Gln Glu Ile Ala Gly Ser Lys Asp Arg Pro Gly
                485                 490                 495

Gln Tyr Glu Ser His Ser Ala Phe Thr Leu Pro Gly Leu Tyr Arg Val
            500                 505                 510

Ala Ser Gly Ile Asn Val Phe Asp Pro Lys Phe Asn Ile Ala Ala Pro
        515                 520                 525

Gly Ala Asp Gln Ser Val Tyr Phe Pro Tyr Thr Glu Lys Gln Thr Arg
    530                 535                 540

Leu Thr Ala Phe Arg Pro Ala Ile Glu Glu Leu Leu Phe Ser Lys Val
545                 550                 555                 560

Asp Asn Asp Glu His Ile Gly Tyr Leu Glu Asp Arg Lys Lys Pro Ile
                565                 570                 575

Leu Phe Thr Met Ala Arg Leu Asp Thr Val Lys Asn Thr Ser Gly Leu
            580                 585                 590

Thr Glu Trp Tyr Gly Lys Asn Lys Arg Leu Arg Ser Leu Val Asn Leu
        595                 600                 605

Val Val Val Gly Gly Ser Phe Asp Pro Thr Lys Ser Lys Asp Arg Glu
    610                 615                 620

Glu Ala Ala Glu Ile Lys Lys Met His Met Leu Ile Glu Lys Tyr Gln
625                 630                 635                 640

Leu Lys Gly Gln Ile Arg Trp Ile Ala Ala Gln Thr Asp Arg Tyr Arg
                645                 650                 655

Asn Ser Glu Leu Tyr Arg Thr Ile Ala Asp Ser Lys Gly Ala Phe Val
            660                 665                 670

Gln Pro Ala Leu Tyr Glu Ala Phe Gly Leu Thr Val Ile Glu Ala Met
```

-continued

```
                675                 680                 685
Asn Cys Gly Leu Pro Thr Phe Ala Thr Asn Gln Gly Gly Pro Ala Glu
        690                 695                 700
Ile Ile Val Asp Gly Val Ser Gly Phe His Ile Asp Pro Asn Asn Gly
705                 710                 715                 720
Asp Glu Ser Ser Asn Lys Val Ala Asn Phe Phe Gln Lys Cys Arg Glu
                725                 730                 735
Asp Pro Glu Tyr Trp Asn Arg Ile Ser Val Gln Gly Leu Asn Arg Ile
            740                 745                 750
Tyr Glu Cys Tyr Thr Trp Lys Ile Tyr Ala Asn Lys Val Leu Asn Met
        755                 760                 765
Gly Ser Ile Tyr Thr Phe Trp Arg Thr Leu Tyr Arg Asp Gln Lys Gln
        770                 775                 780
Ala Lys Gln Arg Tyr Ile Glu Thr Phe Tyr Asn Leu Glu Phe Arg Asn
785                 790                 795                 800
Leu Val Lys Asn Val Pro Ile Arg Gln Asp Glu Thr Pro Gln Gly Pro
                805                 810                 815
Lys Glu Arg Arg Glu Lys Val Lys Pro Gln Ile Ser Gln Arg His Ala
                820                 825                 830
Leu Lys Leu Leu Pro Ile Val Phe Gln Glu Thr Leu Val Tyr Ser Ser
        835                 840                 845
Thr Lys Leu Glu Leu Tyr Ser Met Gln Leu Ala Ser Ala Val His Leu
        850                 855                 860
Ser Lys Ser Pro Val Met Ser Ile Lys Leu Thr Lys Ser Ile Asn Ser
865                 870                 875                 880
Ala Phe Pro Phe Pro Met Leu Asp Cys Tyr Tyr Ser Tyr Phe Val Tyr
                885                 890                 895
Gly Ser Leu Pro Ser Leu Phe Ser Pro Val Leu Leu Leu Leu Gln Leu
            900                 905                 910
Tyr
```

MODULATING REDUCING SUGAR CONTENT IN A PLANT (INV)

CROSS-REFERENCE TO RELATED APPLICATIONS

This application is a U.S. National Stage Application of International Application No. PCT/EP2020/077048 filed Sep. 28, 2020, which was published in English on Apr. 8, 2021, as International Publication No. WO 2021/063860 A1. International Application No. PCT/EP2020/077048 claims priority to European Application No. 19200865.4 filed Oct. 1, 2019.

FIELD OF THE INVENTION

The present invention relates to plant cells and the like with modulated expression or activity of invertase (INV).

BACKGROUND

To manufacture tobacco products, different types of tobaccos are mixed at various ratios to create blends with certain flavour characteristics. Flue-cured tobacco (for example, Virginia) is the most widely grown tobacco and is characterised by a high ratio of sugar to nitrogen but it has a limited flavour profile. Other tobacco types—such as air-cured (for example, Burley, Maryland and Galpao) or fire-cured (for example, Dark) tobacco types—offer alternative flavour profiles. These different flavour profiles are important in the production of blended tobacco products.

The flavour characteristics are the result of particular flavour compounds or the precursors for these compounds that are present at certain levels in tobacco plants. By way of example, altered content of sugars in cured tobacco can result in a different flavour and aroma perception of the tobacco. In aerosol and smoke, glucose and to a lesser extent fructose may generate Amadori compounds via the Maillard reaction. This can result in bready, nutty or popcorn-like flavours.

However, since the varieties of tobacco for commercial production are limited, this means that the opportunities to develop tobacco products with different flavour and aroma profiles are also limited. This equally applies to the manufacture of reconstituted tobacco material that is used in heated tobacco sticks in reduced risk products.

There remains a need in the art to improve the opportunities to create tobacco that offers new flavours and sensory experiences for consumers, whilst still retaining commercially acceptable yields and traits. The present invention seeks to address this and other needs.

SUMMARY OF THE INVENTION

Polynucleotide and polypeptide sequences of INV from *Nicotiana tabacum* are disclosed herein. Whilst many different genes are believed to encode probable INVs in plants based on structural identity, the point at which these genes become active in their function as INVs in plants is not typically known. In particular, very little is known about INV gene expression in tobacco, especially during curing. The present inventors have now identified certain NtINV polynucleotides in plants that are functionally expressed during curing. Surprisingly, it is observed that modulating the expression of these certain NtINV genes or the activity of the protein encoded thereby can change the pool of reducing sugars and sucrose generated during leaf curing. It is unexpected that changes to certain INV genes can lead to changes in the levels of reducing sugars and sucrose generated during leaf curing. Advantageously, this now provides the opportunity to create tobacco blends with new flavour and aroma characteristics. This can also result in a different flavour or sensory perception of the aerosol or smoke generated upon heating the tobacco blend. Likewise, liquid extracts obtained from the tobacco can have a different flavour or sensory perception. Modifying the reducing sugar and sucrose balance may also impact the release of acrylamide in aerosol and smoke.

Several INV genomic polynucleotide sequences from *Nicotiana tabacum* are described herein, namely NtINV3-S (SEQ ID NO: 1), NtINV3-T (SEQ ID NO: 3), NtINV4-S (SEQ ID NO: 5), and NtINV4-T (SEQ ID NO: 7). Several INV polypeptide sequences from *Nicotiana tabacum* are also described herein, namely NtINV3-S (SEQ ID NO: 2), NtINV3-T (SEQ ID NO: 4), NtINV4-S (SEQ ID NO: 6), and NtINV4-T (SEQ ID NO: 8). NtINV4-S and NtINV4-T, in particular, are shown to play a role in sugar metabolism during curing. During tobacco curing, flue-cured tobacco (for example, Virginia) usually contains at least eight times more reducing sugars than air-cured tobacco (for example, Burley) which is principally due to its genetic predisposition to accumulate high levels of starch. After leaf harvest and during the senescence process (yellowing phase) a large part of starch is converted first into sucrose and then into reducing sugars likely involving INV.

NtINV4-S and NtINV4-T polypeptide sequences are very similar, sharing 96% identity. The situation is similar for NtINV3-S and NtINV3-T polypeptide sequences which are also very similar and share 96% identity. Notably, the pair NtINV4-S and NtINV4-T and the pair NtINV3-S and NtINV3-T share low identity of only about 60% suggesting a different function or regulation. Surprisingly, only NtINV4-S and NtINV4-T are over-expressed during curing, whereas NtINV3-S and NtINV3-T are not over-expressed during curing. In certain embodiments, the expression or activity of NtINV3-S and NtINV3-T is not modulated. NtINV3-S and NtINV3-T are likely involved in other metabolic pathways and changes in their expression could result in a phenotype that may be detrimental agronomically (for example, slow growth). Knowing which INV genes are over-expressed during curing advantageously allows for the selection of plants with changes in only the relevant genes and reduces potential negative effects on other metabolic processes.

Modifications to the expression or activity of one or more INVs can be combined together with modifications to the expression or activity of one or more sucrose synthases (SUSs) to further modulate the levels of sugars in cured leaves. Accordingly, a combination of modifications to INV and SUS is disclosed. For example, reducing the expression or activity of one or more INVs as described herein may increase or decrease glucose or fructose levels or a combination thereof and increase sucrose levels in cured leaf. By way of further example, increasing the expression or activity of one or more INVs as described herein may increase glucose or fructose levels or a combination thereof and decrease sucrose levels in cured leaf. By way of further example, reducing the expression or activity of one or more INVs and one or more SUSs as described herein may further decrease glucose or fructose levels or a combination thereof in cured leaf as compared to reducing the expression or activity of one or more INVs alone. By way of further example, increasing the expression or activity of one or more INVs and one or more SUSs as described herein may further increase glucose or fructose levels or a combination thereof in cured leaf as compared to increasing the expression or activity of one or more INVs alone.

NtSUS1-S (SEQ ID NO: 10), NtSUS1-T (SEQ ID NO: 12), NtSUS2-S (SEQ ID NO: 14), NtSUS2-T (SEQ ID NO: 16), NtSUS3-S (SEQ ID NO: 18), NtSUS3-T (SEQ ID NO: 20), NtSUS4-S (SEQ ID NO: 22), NtSUS4-T (SEQ ID NO: 24), NtSUS5-S (SEQ ID NO: 26), NtSUS5-T (SEQ ID NO: 28), NtSUS6-S (SEQ ID NO: 30) and NtSUS6-T (SEQ ID NO: 32) are disclosed. The corresponding deduced polypeptide sequences for NtSUS1-S (SEQ ID NO: 11), NtSUS1-T (SEQ ID NO: 13), NtSUS2-S (SEQ ID NO: 15), NtSUS2-T (SEQ ID NO: 17), NtSUS3-S (SEQ ID NO: 19), NtSUS3-T (SEQ ID NO: 21), NtSUS4-S (SEQ ID NO: 23), NtSUS4-T (SEQ ID NO: 25), NtSUS5-S (SEQ ID NO: 27), NtSUS5-T (SEQ ID NO: 29), NtSUS6-S (SEQ ID NO: 31) and NtSUS6-T (SEQ ID NO: 33) are also disclosed. NtSUS2-S, NtSUS2-T, NtSUS3-S, NtSUS3-T, NtSUS4-S and NtSUS4-T may play a role in sugar metabolism during curing. NtSUS2-S, NtSUS3-S, NtSUS3-T and NtSUS4-S, in particular, may play a role in sugar metabolism during curing.

In one aspect, there is provided a plant cell comprising: (i) a polynucleotide comprising, consisting or consisting essentially of a sequence having at least 81% sequence identity to SEQ ID NO: 5 (NtINV4-S) or at least 62% sequence identity to SEQ ID NO: 7 (NtINV4-T); (ii) a polypeptide encoded by the polynucleotide set forth in (i); (iii) a polypeptide comprising, consisting or consisting essentially of a sequence having at least 84% or at least 85% sequence identity to SEQ ID NO: 6 (NtINV4-S) or at least 85% sequence identity to SEQ ID NO: 8 (NtINV4-T); or (iv) a construct, vector or expression vector comprising the isolated polynucleotide set forth in (i), wherein said plant cell comprises at least one modification which modulates (a) the expression or activity of the polynucleotide or (b) the expression or activity of the polynucleotide the polypeptide, as compared to a control plant cell in which the expression or activity of the polynucleotide or polypeptide has not been modified.

Suitably, the modulated expression or modulated activity modulates the level of one or more reducing sugars in cured leaf of a plant comprising the plant cell as compared to the level of the one or more reducing sugars in cured leaf of a control plant containing the control plant cell, suitably wherein the reducing sugar is glucose or fructose or a combination thereof.

Suitably, the modulated expression or modulated activity also modulates the level of sucrose in cured leaf of a plant comprising the plant cell.

Suitably, a cured leaf has reduced levels of glucose of at least about 63% as compared to a control cured leaf.

Suitably, a cured leaf has reduced levels of fructose of at least about 43% as compared to a control cured leaf. Suitably, a cured leaf has reduced levels of glucose and fructose of at least about 63% and at least about 43%, respectively, as compared to a control cured leaf.

Suitably, the cured leaf is from a mid-position leaf on a plant.

Suitably, there is negligible impact on the phenotype of a plant comprising the plant cell. For example, the phenotype of the plant may be unchanged.

Suitably, there is no variation in total free amino acids as compared to a control plant comprising a control plant cell.

Suitably, the at least one modification is at least one modification in the plant cell's genome, or at least one modification in the construct, vector or expression vector, or at least one transgenic modification.

Suitably, the at least one modification is a genetic mutation in the polynucleotide.

Suitably, the plant is *Nicotiana tabacum*.

Suitably, the plant cell further comprises at least one modification in a NtSUS polynucleotide or polypeptide encoded thereby, more suitably, wherein the NtSUS polynucleotide or polypeptide encoded thereby is selected from the group consisting of NtSUS2-T, NtSUS3-S, NtSUS3-T, NtSUS4-S, NtSUS4-T or a combination of two or more thereof, more suitably, wherein the NtSUS polynucleotide or polypeptide encoded thereby is selected from the group consisting of NtSUS2-S, NtSUS3-S, NtSUS3-T and NtSUS4-S or a combination of two or more thereof.

Suitably, the plant cell comprises at least one mutation in the NtINV4 polynucleotide(s) or the NtINV4 polypeptide(s) and at least one mutation in the NtSUS polynucleotide(s) or polypeptide(s) encoded thereby.

In a further aspect, there is provided a plant or part thereof comprising the plant cell described herein.

Plant material, cured plant material, or homogenized plant material, derived or obtained from the plant or part is disclosed in a further aspect, suitably, wherein the plant material is selected from the group consisting of biomass, seed, stem, flowers, or leaves or a combination of two or more thereof. The cured plant material can be selected from the group consisting of flue-cured plant material, sun-cured plant material or air-cured plant material or a combination of two or more thereof.

In a further aspect, there is provided a tobacco product comprising the plant cell, the part of the plant or the plant material.

In a further aspect, there is provided a method for producing the plant described herein, comprising the steps of: (a) providing a plant cell comprising at least one modification as described herein; and (b) propagating the plant cell into a plant.

Suitably, in step (a) the at least one modification is introduced by genome editing, suitably, wherein the genome editing is selected from CRISPR-mediated genome editing, zinc finger nuclease-mediated mutagenesis, chemical or radiation mutagenesis, homologous recombination, oligonucleotide-directed mutagenesis and meganuclease-mediated mutagenesis.

Suitably, in step (a) the at least one modification is introduced using an interference polynucleotide or by introducing at least one mutation or a combination thereof.

In a further aspect, there is disclosed a method for producing cured plant material with an altered amount of reducing sugars as compared to control plant material, comprising the steps of: (a) providing a plant or part thereof or the plant material as described herein; (b) harvesting the plant material therefrom; and (c) curing the plant material.

In a further aspect, there is provided a method of producing a liquid tobacco extract, the method comprising the steps of: (a) preparing tobacco starting material from a plant or part thereof containing a plant cell comprising at least one modification which modulates the expression or activity of NtINV as described herein; (b) heating the tobacco starting material at a suitable extraction temperature; (c) collecting the volatile compounds released from the tobacco starting material during heating; and (d) combining the collected volatile compounds released from the tobacco starting material and forming a liquid tobacco extract.

In a further aspect, there is disclosed a method of producing a liquid tobacco extract, the method comprising the steps of: (a) preparing a first tobacco starting material from a plant or part thereof containing a plant cell in which the expression or activity of NtINV is modified as described herein; (b) preparing a second tobacco starting material from a plant or part thereof containing a plant cell in which the expression or activity of NtSUS is modified as described herein; (c) heating the first tobacco starting material at a first extraction temperature; (d) heating the second tobacco starting material at a second extraction temperature; (e) collecting the volatile compounds released from the first tobacco starting materials and second tobacco starting materials during heating; and (f) combining the collected volatile compounds released from the first and second tobacco starting materials and forming a liquid tobacco extract from the combined volatile compounds.

In a further aspect, there is disclosed a liquid tobacco extract produced, obtained or obtainable by the method of producing a liquid tobacco extract, as described herein.

In a further aspect, there is disclosed a plant cell comprising: (i) a polynucleotide comprising, consisting or consisting essentially of a sequence having at least 60% sequence identity to SEQ ID NO: 1, SEQ ID NO: 3 SEQ ID NO: 5 and SEQ ID NO: 7; a polynucleotide comprising, consisting or consisting essentially of a sequence having at least 50% sequence identity to SEQ ID NO: 2, SEQ ID NO: 4, SEQ ID NO: 6, SEQ ID NO: 8; (ii) a polypeptide encoded by the polynucleotide set forth in (i); (iii) a polypeptide comprising, consisting or consisting essentially of a sequence having at least 80% sequence identity to SEQ ID NO: 2 or SEQ ID NO: 4, 80% and sequence identity to SEQ ID NO: 6 or SEQ ID NO: 8; (iv) a construct, vector or expression vector comprising the isolated polynucleotide set forth in (i), wherein said plant cell comprises at least one modification which modulates the expression or activity of the polynucleotide or the polypeptide as compared to a control plant cell in which the expression or activity of the polynucleotide or polypeptide has not been modified.

Some Advantages

Advantageously, modifying the sugar-amino acid balance in tobacco may impact the release of flavour compounds and acrylamide (a carcinogenic compound resulting from the interaction of glucose (fructose) with asparagine) upon heating in aerosol and smoke.

Advantageously, reconstituted tobacco material of heated tobacco sticks requires reducing sugars for proper cast leaf preparation. The present disclosure may impact the content and the balance of the sugars thereby affecting cast leaf preparation.

Advantageously, non-genetically modified plants can be created which may be more acceptable to consumers.

Advantageously, the present disclosure is not restricted to the use of EMS mutant plants.

The disclosure may be applied to various plant varieties or crops. Usually, senescing leaves (source leaves) produce sucrose as a source of carbon and asparagine as assimilated nitrogen resources for sink leaves and seeds. Therefore sucrose and asparagine has to be transported first from parenchymal (photosynthetic) senescing leaf cells to the phloem and then to upper sink tissues. Manipulating NtINV or the polypeptide encoded thereby can impact the level of reducing sugars—such as glucose and fructose—with low impact on free amino acids. This approach may allow the development of novel tobacco varieties with lower glucose and fructose and more sucrose content.

Advantageously, the present disclosure can be combined together with modulating the expression of other genes—such as NtSUS or the polypeptide encoded thereby, as described herein.

DETAILED DESCRIPTION

Figure 1:
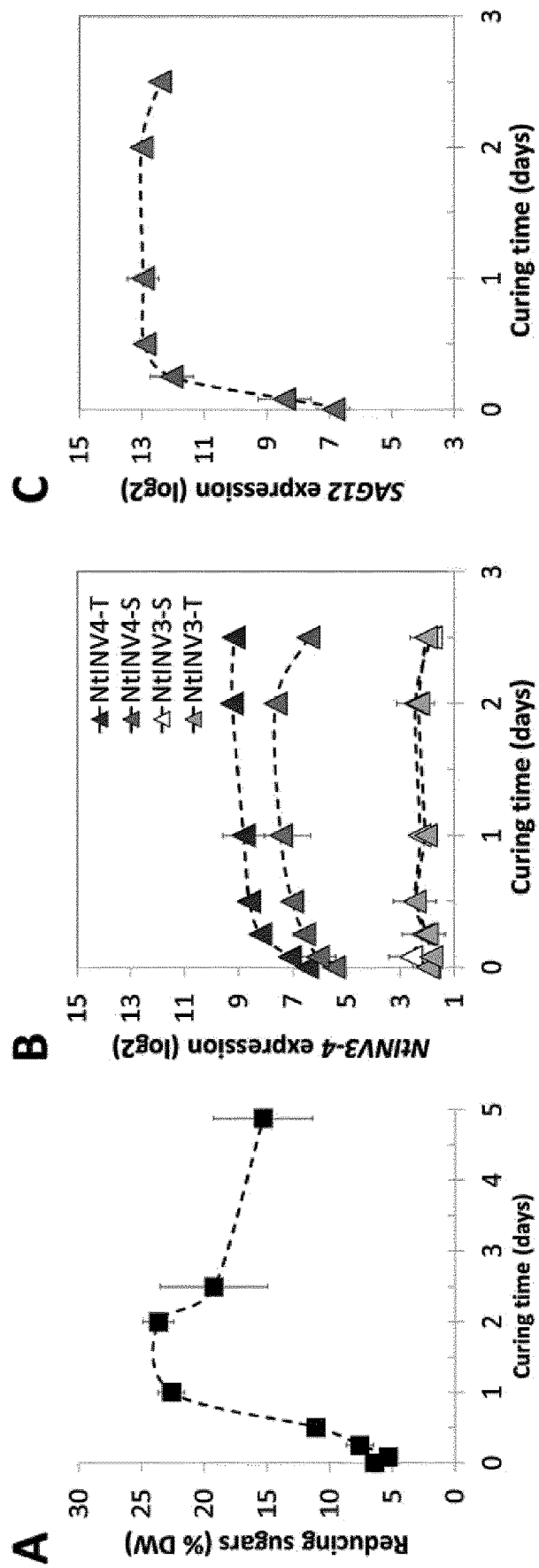
FIG. 1 is a series of graphs showing: (A) evolution of reducing sugars (glucose and fructose) during a Virginia flue-curing time course; (B) expression (Tobarray-Affymetrix) of NtINV3-S, NtINV3-T, NtINV4-S and NtINV4-T during a Virginia flue-curing time course; and (C) expression of the senescence associated gene SAG12 during a Virginia flue-curing time course.

Section headings as used in this disclosure are for organisation purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. The materials, methods, and examples disclosed herein are illustrative only and not intended to be limiting.

The terms "comprise(s)," "include(s)," "having," "has," "can," "contain(s)," and variants thereof are intended to be open-ended transitional phrases, terms, or words that do not preclude the possibility of additional acts or structures.

The singular forms "a," "and" and "the" include plural references unless the context clearly dictates otherwise.

The present disclosure contemplates other embodiments "comprising," "consisting of" and "consisting essentially of" the embodiments or elements presented herein, whether explicitly set forth or not.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used throughout the specification and the claims, the following terms have the following meanings:

"Coding sequence" or "polynucleotide encoding" means the nucleotides (RNA or DNA molecule) that comprise a polynucleotide which encodes a polypeptide. The coding sequence can further include initiation and termination signals operably linked to regulatory elements including a promoter and polyadenylation signal capable of directing expression in the cells of an individual or mammal to which the polynucleotide is administered. The coding sequence may be codon optimized.

"Complement" or "complementary" can mean Watson-Crick (for example, A-T/U and C-G) or Hoogsteen base pairing between nucleotides or nucleotide analogues. "Complementarity" refers to a property shared between two polynucleotides, such that when they are aligned antiparallel to each other, the nucleotide bases at each position will be complementary.

"Construct" refers to a double-stranded, recombinant polynucleotide fragment comprising one or more polynucleotides. The construct comprises a "template strand" base-paired with a complementary "sense or coding strand." A given construct can be inserted into a vector in two possible orientations, either in the same (or sense) orientation or in the reverse (or anti-sense) orientation with respect to the orientation of a promoter positioned within a vector—such as an expression vector.

The term "control" in the context of a control plant or control plant cells means a plant or plant cells in which the expression, function or activity of one or more genes or polypeptides has not been modified (for example, increased or decreased) and so it can provide a comparison with a plant in which the expression, function or activity of the same one or more genes or polypeptides has been modified. A "control plant" is a plant that is substantially equivalent to a test plant or modified plant in all parameters with the exception of the test parameters. For example, when referring to a plant into which a polynucleotide has been introduced, a control plant is an equivalent plant into which no such polynucleotide has been introduced. A control plant can be an equivalent plant into which a control polynucleotide has been introduced. In such instances, the control polynucleotide is one that is expected to result in little or no phenotypic effect on the plant. The control plant may comprise an empty vector. The control plant may correspond to a wild-type plant. The control plant may be a null segregant wherein the T1 segregant no longer possesses the transgene.

The term "decrease" or "decreased", refers to a reduction of from about 10% to about 99%, or a reduction of at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or, or at least 150%, or at least 200% more of a quantity or a function—such as polypeptide function, transcriptional function, or polypeptide expression. The term "decreased," or the phrase "a decreased amount" can refer to a quantity or a function that is less than what would be found in a plant or a product from the same variety of plant processed in the same manner, which has not been modified. Thus, in some contexts, a wild-type plant of the same variety that has been processed in the same manner is used as a control by which to measure whether a reduction in quantity is obtained.

"Donor DNA" or "donor template" refers to a double-stranded DNA fragment or molecule that includes at least a portion of the gene of interest. The donor DNA may encode a functional polypeptide.

"Endogenous gene or polypeptide" refers to a gene or polypeptide that originates from the genome of an organism and has not undergone a change, such as a loss, gain, or exchange of genetic material. An endogenous gene undergoes normal gene transmission and gene expression. An endogenous polypeptide undergoes normal expression.

"Enhancer sequences" refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms including increasing transcriptional efficiency, stabilization of mature mRNA and translational enhancement.

"Expression" refers to the production of a functional product. For example, expression of a polynucleotide fragment may refer to transcription of the polynucleotide fragment (for example, transcription resulting in mRNA or functional RNA) or translation of mRNA into a precursor or mature polypeptide, or a combination thereof.

"Overexpression" refers to the production of a gene product in transgenic organisms that exceeds levels of production in a null segregating (or non-transgenic) organism from the same experiment.

"Functional" describes a polypeptide that has biological function or activity. A "functional gene" refers to a gene transcribed to mRNA, which is translated to a functional or active polypeptide.

"Genetic construct" refers to DNA or RNA molecules that comprise a polynucleotide that encodes a polypeptide. The coding sequence can include initiation and termination signals operably linked to regulatory elements including a promoter and polyadenylation signal capable of directing expression.

"Genome editing" generally refers to the process by which genomic nucleic acid in a cell is altered. This can be by removing, inserting or replacing one or more nucleotides in the genomic nucleic acid, for example. Endonucleases can be used to create specific breaks or nicks at defined locations in the genome and are further described herein.

The terms "homology" or "similarity" refer to the degree of sequence similarity between two polypeptides or between two polynucleotide molecules compared by sequence alignment. The degree of homology between two discrete polynucleotides being compared is a function of the number of identical, or matching, nucleotides at comparable positions. Homology or similarity can be determined across the full length of a subject sequence.

"Identical" or "identity" in the context of two or more polynucleotides or polypeptides means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be determined manually or by using a computer sequence algorithm such as ClustalW, ClustalX, BLAST, FASTA or Smith-Waterman. Suitable parameters for ClustalW maybe as follows: For polynucleotide alignments: Gap Open Penalty=15.0, Gap Extension Penalty=6.66, and Matrix=Identity. For polypeptide alignments: Gap Open Penalty=10. o, Gap Extension Penalty=0.2, and Matrix=Gonnet. For DNA and Protein alignments: ENDGAP=−1, and GAPDIST=4.

The term "increase" or "increased" refers to an increase of from about 10% to about 99%, or an increase of at least 10%, at least 20%, at least 25%, at least 30%, at least 40%, at least 50%, at least 60%, at least 70%, at least 75%, at least 80%, at least 90%, at least 95%, at least 98%, at least 99%, at least 100%, at least 150%, or at least 200% or more or more of a quantity or a function or an activity, such as but not limited to one or more of polypeptide function or activity, transcriptional function or activity and polypeptide expression. The term "increased," or the phrase "an increased amount" can refer to a quantity or a function or an activity in a plant or a product generated from the plant that is more than what would be found in a plant or a product from the same variety of plant processed in the same manner, which has not been modified. Thus, in some contexts, a wild-type plant of the same variety that has been processed in the same manner is used as a control by which to measure whether an increase in quantity is obtained.

The term "inhibit" or "inhibited" refers to a reduction of from about 98% to about 100%, or a reduction of at least 98%, at least 99%, but particularly of 100%, of a quantity or a function or an activity, such as but not limited to one or more of polypeptide function or activity, transcriptional function or activity and polypeptide expression.

The term "introduced" means providing a polynucleotide (for example, a construct) or polypeptide into a cell. Introduced includes reference to the incorporation of a polynucleotide into a eukaryotic cell where the polynucleotide may be incorporated into the genome of the cell, and includes reference to the transient provision of a polynucleotide or polypeptide to the cell. Introduced includes reference to stable or transient transformation methods, as well as sexually crossing. Thus, "introduced" in the context of inserting a polynucleotide (for example, a recombinant construct/expression construct) into a cell, means "transfection" or "transformation" or "transduction" and includes reference to the incorporation of a polynucleotide into a eukaryotic cell where the polynucleotide may be incorporated into the genome of the cell (for example, chromosome, plasmid, plastid or mitochondrial DNA), converted into an autonomous replicon, or transiently expressed (for example, transfected mRNA).

The terms "isolated" or "purified" refer to material that is substantially or essentially free from components that normally accompany it as found in its native state. Purity and homogeneity are typically determined using analytical chemistry techniques such as polyacrylamide gel electrophoresis or high performance liquid chromatography. A polypeptide that is the predominant species present in a preparation is substantially purified. In particular, an isolated polynucleotide is separated from open reading frames that flank the desired gene and encode polypeptides other than the desired polypeptide. The term "purified" denotes that a polynucleotide or polypeptide gives rise to essentially one band in an electrophoretic gel. Particularly, it means that the polynucleotide or polypeptide is at least 85% pure, more preferably at least 95% pure, and most preferably at least 99% pure. Isolated polynucleotides may be purified from a host cell in which they naturally occur. Conventional polynucleotide purification methods known to skilled artisans may be used to obtain isolated polynucleotides. The term also embraces recombinant polynucleotides and chemically synthesized polynucleotides.

"Liquid tobacco extract" describes the direct product of an extraction process carried out on a tobacco starting material. The extraction process for producing the liquid tobacco extract can comprise heating the tobacco starting material under specific heating conditions and collecting the volatile compounds generated. The liquid tobacco extract can contain a mixture of compounds that have derived from the tobacco starting material and have been removed during the extraction process, typically in combination with a liquid carrier or solvent.

"Modulate" or "modulating" refers to causing or facilitating a qualitative or quantitative change, alteration, or modification in a process, pathway, function or activity of interest. Without limitation, such a change, alteration, or modification may be an increase or decrease in the relative process, pathway, function or activity of interest. For example, gene expression or polypeptide expression or polypeptide function or activity can be modulated. Typically, the relative change, alteration, or modification will be determined by comparison to a control.

The term 'non-naturally occurring' describes an entity—such as a polynucleotide, a genetic mutation, a polypeptide, a plant, a plant cell and plant material—that is not formed by nature or that does not exist in nature. Such non-naturally occurring entities or artificial entities may be made, synthesized, initiated, modified, intervened, or manipulated by methods described herein or that are known in the art. Such non-naturally occurring entities or artificial entities may be made, synthesized, initiated, modified, intervened, or manipulated by man. Thus, by way of example, a non-naturally occurring plant, a non-naturally occurring plant cell or non-naturally occurring plant material may be made using traditional plant breeding techniques—such as backcrossing—or by genetic manipulation technologies—such as antisense RNA, interfering RNA, meganuclease and the like. By way of further example, a non-naturally occurring plant, a non-naturally occurring plant cell or non-naturally occurring plant material may be made by introgression of or by transferring one or more genetic mutations (for example one or more polymorphisms) from a first plant or plant cell into a second plant or plant cell (which may itself be naturally occurring), such that the resulting plant, plant cell or plant material or the progeny thereof comprises a genetic constitution (for example, a genome, a chromosome or a segment thereof) that is not formed by nature or that does not exist in nature. The resulting plant, plant cell or plant material is thus artificial or non-naturally occurring. Accordingly, an artificial or non-naturally occurring plant or plant cell may be made by modifying a genetic sequence in a first naturally occurring plant or plant cell, even if the resulting genetic sequence occurs naturally in a second plant or plant cell that comprises a different genetic background from the first plant or plant cell. In certain embodiments, a mutation is not a naturally occurring mutation that exists naturally in a polynucleotide or a polypeptide—such as a gene or a polypeptide. Differences in genetic background can be detected by phenotypic differences or by molecular biology techniques known in the art—such as polynucleotide sequencing, presence or absence of genetic markers (for example, microsatellite RNA markers).

"Oligonucleotide" or "polynucleotide" means at least two nucleotides covalently linked together. The depiction of a single strand also defines the sequence of the complementary strand. Thus, a polynucleotide also encompasses the complementary strand of a depicted single strand.

Many variants of a polynucleotide may be used for the same purpose as a given polynucleotide.

Thus, a polynucleotide also encompasses substantially identical polynucleotides and complements thereof. A single strand provides a probe that may hybridize to a given sequence under stringent hybridization conditions. Thus, a polynucleotide also encompasses a probe that hybridizes under stringent hybridization conditions. Polynucleotides may be single stranded or double stranded, or may contain portions of both double stranded and single stranded sequence. The polynucleotide may be DNA, both genomic and cDNA, RNA, or a hybrid, where the polynucleotide may contain combinations of deoxyribo- and ribo-nucleotides, and combinations of bases including uracil, adenine, thymine, cytosine, guanine, inosine, xanthine hypoxanthine, isocytosine and isoguanine. Polynucleotides may be obtained by chemical synthesis methods or by recombinant methods.

The specificity of single-stranded DNA to hybridize complementary fragments is determined by the "stringency" of the reaction conditions (Sambrook et al., Molecular Cloning and Laboratory Manual, Second Ed., Cold Spring Harbor (1989)). To hybridize under "stringent conditions" describes hybridization protocols in which polynucleotides at least 60% homologous to each other remain hybridized. Generally, stringent conditions are selected to be about 5° C. lower than the thermal melting point (Tm) for the specific sequence at a defined ionic strength and pH.

The Tm is the temperature (under defined ionic strength, pH, and polynucleotide concentration) at which 50% of the probes complementary to the given sequence hybridize to the given sequence at equilibrium. Since the given sequences are generally present at excess, at Tm, 50% of the probes are occupied at equilibrium.

Stringent conditions typically comprise: (1) low ionic strength and high temperature washes, for example 15 mM sodium chloride, 1.5 mM sodium citrate, 0.1% sodium dodecyl sulfate, at 50° C.; (2) a denaturing agent during hybridization, for example, 50% (v/v) formamide, 0.1% bovine serum albumin, 0.1% Ficoll, 0.1% polyvinylpyrrolidone, 50 mM sodium phosphate buffer (750 mM sodium chloride, 75 mM sodium citrate; pH 6.5), at 42° C.; or (3) 50% formamide. Washes typically also comprise 5×SSC (0.75 M NaCl, 75 mM sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with a wash at 42° C. in 0.2×SSC (sodium chloride/sodium citrate) and 50% formamide at 55° C., followed by a high-stringency wash consisting of 0.1×SSC containing EDTA at 55° C. Suitably, the conditions are such that sequences at least about 65%, 70%, 75%, 85%, 90%, 95%, 98%, or 99% homologous to each other typically remain hybridized to each other.

"Moderately stringent conditions" use washing solutions and hybridization conditions that are less stringent, such that a polynucleotide will hybridize to the entire, fragments, derivatives, or analogs of the polynucleotide. One example comprises hybridization in 6×SSC, 5×Denhardt's solution, 0.5% SDS and 100 µg/mL denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions have been described (see Ausubel et al., Current Protocols in Molecular Biology, Volumes 1-3, John Wiley & Sons, Inc., Hoboken, N.J. (1993); Kriegler, Gene Transfer and Expression: A Laboratory Manual, Stockton Press, New York, N.Y. (1990); Perbal, A Practical Guide to Molecular Cloning, 2nd edition, John Wiley & Sons, New York, N.Y. (1988)). "Low stringent conditions" use washing solutions and hybridization conditions that are less stringent than those for moderate stringency, such that a polynucleotide will hybridize to the entire, fragments, derivatives, or analogs of the polynucleotide. A non-limiting example of low stringency hybridization conditions includes hybridization in 35% formamide, 5×SSC, 50 mM Tris HCl (pH 7.5), 5 mM EDTA, 0.02% PVP, 0.02% Ficoll, 0.2% BSA, 100 µg/mL denatured salmon sperm DNA, 10% (wt/vol) dextran sulfate at 40° C., followed by one or more washes in 2×SSC, 25 mM Tris HCl (pH 7.4), 5 mM EDTA, and 0.1% SDS at 50° C. Other conditions of low stringency, such as those for cross-species hybridizations, are well-described (see Ausubel et al., 1993; Kriegler, 1990).

"Operably linked" means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function. "Operably linked" refers to the association of polynucleotide fragments in a single fragment so that the function of one is regulated by the other. For example, a promoter is operably linked with a polynucleotide fragment when it is capable of regulating the transcription of that polynucleotide fragment.

The term "plant" refers to any plant at any stage of its life cycle or development, and its progenies. In one embodiment, the plant is a tobacco plant, which refers to a plant belonging to the genus *Nicotiana*. The term includes reference to whole plants, plant organs, plant tissues, plant propagules, plant seeds, plant cells and progeny of same. Plant cells include, without limitation, cells from seeds, suspension cultures, embryos, meristematic regions, callus tissue, leaves, roots, shoots, gametophytes, sporophytes, pollen, and microspores. Suitable species, cultivars, hybrids and varieties of tobacco plant are described herein.

"Plant material" includes leaf, root, sepal, root tip, petal, flower, shoot, stem, seed and stalk. Plant material can be viable or non-viable plant material.

"Polynucleotide", "polynucleotide sequence" or "polynucleotide fragment" are used interchangeably herein and refer to a polymer of RNA or DNA that is single- or double-stranded, optionally containing synthetic, non-natural or altered nucleotide bases. The polynucleotides of the present disclosure are set forth in the accompanying sequence listing.

"Polypeptide" or "polypeptide sequence" refer to a polymer of amino acids in which one or more amino acid residues is an artificial chemical analogue of a corresponding naturally occurring amino acid, as well as to naturally occurring polymers of amino acids. The terms are also inclusive of modifications including, but not limited to, glycosylation, lipid attachment, sulfation, gamma-carboxylation of glutamic acid residues, hydroxylation and ADPribosylation. The polypeptides of the present disclosure are set forth in the accompanying sequence listing.

"Promoter" means a synthetic or naturally-derived molecule which is capable of conferring, activating or enhancing expression of a polynucleotide in a cell. The term refers to a polynucleotide element/sequence, typically positioned upstream and operably-linked to a double-stranded polynucleotide fragment. Promoters can be derived entirely from regions proximate to a native gene of interest, or can be composed of different elements derived from different native promoters or synthetic polynucleotide segments. A promoter may comprise one or more specific transcriptional regulatory sequences to further enhance expression, or to alter spatial expression or to alter temporal expression. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents.

"Tissue-specific promoter" and "tissue-preferred promoter" as used interchangeably herein refer to a promoter that is expressed predominantly but not necessarily exclusively in one tissue or organ, but that may also be expressed in one specific cell. A "developmentally regulated promoter" refers to a promoter whose function is determined by developmental events. A "constitutive promoter" refers to a promoter that causes a gene to be expressed in most cell types at most times. An "inducible promoter" selectively express an operably linked DNA sequence in response to the presence of an endogenous or exogenous stimulus, for example by chemical compounds (chemical inducers) or in response to environmental, hormonal, chemical or developmental signals or a combination of two or more thereof. Examples of inducible or regulated promoters include promoters regulated by light, heat, stress, flooding or drought, pathogens, phytohormones, wounding, or chemicals such as ethanol, jasmonate, salicylic acid, or safeners.

"Recombinant" refers to an artificial combination of two otherwise separated segments of sequence—such as by chemical synthesis or by the manipulation of isolated segments of polynucleotides by genetic engineering techniques. The term also includes reference to a cell or vector, that has been modified by the introduction of a heterologous polynucleotide or a cell derived from a cell so modified, but does not encompass the alteration of the cell or vector by naturally occurring events (for example, spontaneous mutation, natural transformation or transduction or transposition) such as those occurring without deliberate human intervention.

"Recombinant construct" refers to a combination of polynucleotides that are not normally found together in nature. Accordingly, a recombinant construct may comprise regulatory sequences and coding sequences that are derived from different sources, or regulatory sequences and coding sequences derived from the same source, but arranged in a manner different than that normally found in nature. The recombinant construct can be a recombinant DNA construct.

"Regulatory sequences" and "regulatory elements" as used interchangeably herein refer to polynucleotide sequences located upstream (5' non-coding sequences), within, or downstream (3' non-coding sequences) of a coding sequence, and which influence the transcription, RNA processing or stability, or translation of the associated coding sequence. Regulatory sequences include promoters, translation leader sequences, introns, and polyadenylation recognition sequences. The terms "regulatory sequence" and "regulatory element" are used interchangeably herein.

The term "tobacco" is used in a collective sense to refer to tobacco crops (for example, a plurality of tobacco plants grown in the field and not hydroponically grown tobacco), tobacco plants and parts thereof, including but not limited to, roots, stems, leaves, flowers, and seeds prepared or obtained, as described herein. It is understood that "tobacco" includes *Nicotiana tabacum* plants and products thereof.

The term "tobacco products" refers to consumer tobacco products, including but not limited to, smoking materials (for example, cigarettes, cigars, and pipe tobacco), snuff, chewing tobacco, gum, and lozenges, as well as components, materials and ingredients for manufacture of consumer tobacco products. Suitably, these tobacco products are manufactured from tobacco leaves and stems harvested from tobacco and cut, dried, cured, or fermented according to conventional techniques in tobacco preparation.

"Transcription terminator", "termination sequences", or "terminator" refers to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Transgenic" refers to any cell, cell line, callus, tissue, plant part or plant, the genome of which has been altered by the presence of a heterologous polynucleotide, such as a recombinant construct, including those initial transgenic events as well as those created by sexual crosses or asexual propagation from the initial transgenic event. The term does not encompass the alteration of the genome (chromosomal or extra-chromosomal) by conventional plant breeding methods or by naturally occurring events—such as random cross-fertilization, non-recombinant viral infection, non-recombinant bacterial transformation, non-recombinant transposition, or spontaneous mutation.

"Transgenic plant" refers to a plant which comprises within its genome one or more heterologous polynucleotides, that is, a plant that contains recombinant genetic material not normally found therein and which has been introduced into the plant in question (or into progenitors of the plant) by human manipulation. For example, the heterologous polynucleotide can be stably integrated within the genome such that the polynucleotide is passed on to successive generations. The heterologous polynucleotide can be integrated into the genome alone or as part of a recombinant construct. The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant or tree and parts of the plant or tree, for instance grains, seeds, flowers, leaves, roots, fruit, pollen, stems and the like. Each heterologous polynucleotide may confer a different trait to the transgenic plant.

"Transgene" refers to a gene or genetic material containing a gene sequence that has been isolated from one organism and is introduced into a different organism. This non-native segment of DNA may retain the ability to produce RNA or polypeptide in the transgenic organism, or it may alter the normal function of the transgenic organism's genetic code.

"Variant" with respect to a polynucleotide means: (i) a portion or fragment of a polynucleotide; (ii) the complement of a polynucleotide or portion thereof; (iii) a polynucleotide that is substantially identical to a polynucleotide of interest or the complement thereof; or (iv) a polynucleotide that hybridizes under stringent conditions to the polynucleotide of interest, complement thereof, or a polynucleotide substantially identical thereto.

"Variant" with respect to a peptide or polypeptide means a peptide or polypeptide that differs in sequence by the insertion, deletion, or conservative substitution of amino acids, but retain at least one biological function or activity. Variant may also mean a polypeptide that retains at least one biological function or activity. A conservative substitution of an amino acid, that is, replacing an amino acid with a different amino acid of similar properties (for example, hydrophilicity, degree and distribution of charged regions) is recognized in the art as typically involving a minor change.

The term "variety" refers to a population of plants that share constant characteristics which separate them from other plants of the same species. While possessing one or more distinctive traits, a variety is further characterized by a very small overall variation between individuals within that variety. A variety is often sold commercially.

"Vector" refers to a polynucleotide vehicle that comprises a combination of polynucleotide components for enabling the transport of polynucleotides, polynucleotide constructs and polynucleotide conjugates and the like. A vector may be a viral vector, bacteriophage, bacterial artificial chromosome or yeast artificial chromosome. A vector may be a DNA or RNA vector.

Suitable vectors include episomes capable of extra-chromosomal replication such as circular, double-stranded nucleotide plasmids; linearized double-stranded nucleotide plasmids; and other vectors of any origin. An "expression vector" is a polynucleotide vehicle that comprises a combination of polynucleotide components for enabling the expression of polynucleotide(s), polynucleotide constructs and polynucleotide conjugates and the like. Suitable expression vectors include episomes capable of extra-chromosomal replication such as circular, double-stranded nucleotide plasmids; linearized double-stranded nucleotide plasmids; and other functionally equivalent expression vectors of any origin. An expression vector comprises at least a promoter positioned upstream and operably-linked to a polynucleotide, polynucleotide constructs or polynucleotide conjugate, as defined below.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and polypeptide and polynucleotide chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. Polynucleotides

An isolated polynucleotide is disclosed comprising, consisting or consisting essentially of a sequence having at least 60% sequence identity to any of the sequences described herein, including any of polynucleotides shown in the sequence listing. Suitably, the isolated polynucleotide comprises, consists or consists essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity thereto.

Suitably, the polynucleotide(s) described herein encode an active polypeptide that has at least about 50%, 60%, 70%, 80%, 90%, 95%, 96%, 97%, 98%, 99%, 100% or more of the function or activity of the polypeptide(s) shown in the sequence listing.

In another embodiment, there is provided an isolated NtINV polynucleotide comprising, consisting or consisting essentially of a polynucleotide having at least 60% sequence identity to SEQ ID NO: 1, SEQ ID NO: 3, SEQ ID NO: 5, SEQ ID NO: 7 or SEQ ID NO: 9.

In another embodiment, there is provided an isolated NtSUS polynucleotide comprising, consisting or consisting essentially of a polynucleotide having at least 60% sequence identity to SEQ ID NO: 10, SEQ ID NO: 12, SEQ ID NO: 14, SEQ ID NO: 16, SEQ ID NO: 18, SEQ ID NO: 20, SEQ ID NO: 22 or SEQ ID NO: 24; SEQ ID NO: 26, SEQ ID NO: 28, SEQ ID NO: 30 or SEQ ID NO: 32.

Suitably, the isolated polynucleotide comprises, consists or consist essentially of a sequence having at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 1, SEQ ID NO: 3, SEQ ID NO: 5, SEQ ID NO: 7 or SEQ ID NO: 9.

Suitably, the isolated polynucleotide comprises, consists or consist essentially of a sequence having at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 10, SEQ ID NO: 12, SEQ ID NO: 14, SEQ ID NO: 16, SEQ ID NO: 18, SEQ ID NO: 20, SEQ ID NO: 22 or SEQ ID NO: 24; SEQ ID NO: 26, SEQ ID NO: 28, SEQ ID NO: 30 or SEQ ID NO: 32.

Suitably, the isolated polynucleotide comprises, consists or consist essentially of a sequence having at least about 80%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 1, SEQ ID NO: 3, SEQ ID NO: 5, SEQ ID NO: 7 or SEQ ID NO: 9.

Suitably, the isolated polynucleotide comprises, consists or consist essentially of a sequence having at least about 80%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 10, SEQ ID NO: 12, SEQ ID NO: 14, SEQ ID NO: 16, SEQ ID NO: 18, SEQ ID NO: 20, SEQ ID NO: 22 or SEQ ID NO: 24; SEQ ID NO: 26, SEQ ID NO: 28, SEQ ID NO: 30 or SEQ ID NO: 32.

Suitably, the isolated polynucleotide comprises, consists or consist essentially of a sequence having at least about 95%, 96%, 97%, 98%, 99%, 99.1%, 99.2%, 99.3%, 99.4%, 99.5%, 99.6%, 99.7%, 99.8%, 99.9% or 100% sequence identity to SEQ ID NO: 1, SEQ ID NO: 3, SEQ ID NO: 5, SEQ ID NO: 7 or SEQ ID NO: 9.

Suitably, the isolated polynucleotide comprises, consists or consist essentially of a sequence having at least about 95%, 96%, 97%, 98%, 99%, 99.1%, 99.2%, 99.3%, 99.4%, 99.5%, 99.6%, 99.7%, 99.8%, 99.9% or 100% sequence identity to SEQ ID NO: 10, SEQ ID NO: 12, SEQ ID NO: 14, SEQ ID NO: 16, SEQ ID NO: 18, SEQ ID NO: 20, SEQ ID NO: 22 or SEQ ID NO: 24; SEQ ID NO: 26, SEQ ID NO: 28, SEQ ID NO: 30 or SEQ ID NO: 32.

In another embodiment, there is provided polynucleotides comprising, consisting or consisting essentially of polynucleotides with substantial homology (that is, sequence similarity) or substantial identity to SEQ ID NO: 1, SEQ ID NO: 3, SEQ ID NO: 5, SEQ ID NO: 7 or SEQ ID NO: 9.

In another embodiment, there is provided polynucleotides comprising, consisting or consisting essentially of polynucleotides with substantial homology (that is, sequence similarity) or substantial identity to SEQ ID NO: 10, SEQ ID NO: 12, SEQ ID NO: 14, SEQ ID NO: 16, SEQ ID NO: 18, SEQ ID NO: 20, SEQ ID NO: 22 or SEQ ID NO: 24; SEQ ID NO: 26, SEQ ID NO: 28, SEQ ID NO: 30 or SEQ ID NO: 32.

In another embodiment, there is provided fragments of SEQ ID NO: 1, SEQ ID NO: 3, SEQ ID NO: 5, SEQ ID NO: 7 or SEQ ID NO: 9 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO: 1, SEQ ID NO: 3, SEQ ID NO: 5, SEQ ID NO: 7 or SEQ ID NO: 9.

In another embodiment, there is provided fragments of SEQ ID NO: 10, SEQ ID NO: 12, SEQ ID NO: 14, SEQ ID NO: 16, SEQ ID NO: 18, SEQ ID NO: 20, SEQ ID NO: 22 or SEQ ID NO: 24; SEQ ID NO: 26, SEQ ID NO: 28, SEQ ID NO: 30 or SEQ ID NO: 32 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO: 10, SEQ ID NO: 12, SEQ ID NO: 14, SEQ ID NO: 16, SEQ ID NO: 18, SEQ ID NO: 20, SEQ ID NO: 22 or SEQ ID NO: 24; SEQ ID NO: 26, SEQ ID NO: 28, SEQ ID NO: 30 or SEQ ID NO: 32.

In another embodiment, there is provided polynucleotides comprising a sufficient or substantial degree of identity or similarity to SEQ ID NO: 1, SEQ ID NO: 3, SEQ ID NO: 5, SEQ ID NO: 7 or SEQ ID NO: 9 that encode a polypeptide that functions as an INV.

In another embodiment, there is provided polynucleotides comprising a sufficient or substantial degree of identity or similarity to SEQ ID NO: 10, SEQ ID NO: 12, SEQ ID NO: 14, SEQ ID NO: 16, SEQ ID NO: 18, SEQ ID NO: 20, SEQ ID NO: 22 or SEQ ID NO: 24; SEQ ID NO: 26, SEQ ID NO: 28, SEQ ID NO: 30 or SEQ ID NO: 32 that encode a polypeptide that functions as an SUS.

In another embodiment, there is provided a polymer of polynucleotides which comprises, consists or consists essentially of a polynucleotide designated herein as SEQ ID NO: 1, SEQ ID NO: 3, SEQ ID NO: 5, SEQ ID NO: 7 or SEQ ID NO: 9.

In another embodiment, there is provided a polymer of polynucleotides which comprises, consists or consists essentially of a polynucleotide designated herein as SEQ ID NO: 10, SEQ ID NO: 12, SEQ ID NO: 14, SEQ ID NO: 16, SEQ ID NO: 18, SEQ ID NO: 20, SEQ ID NO: 22 or SEQ ID NO: 24; SEQ ID NO: 26, SEQ ID NO: 28, SEQ ID NO: 30 or SEQ ID NO: 32.

Suitably, the polynucleotides described herein encode members of the INV family or the SUS family that have INV activity or SUS activity, respectively.

A polynucleotide can include a polymer of nucleotides, which may be unmodified or modified deoxyribonucleic acid (DNA) or ribonucleic acid (RNA). Accordingly, a polynucleotide can be, without limitation, a genomic DNA, complementary DNA (cDNA), mRNA, or antisense RNA or a fragment(s) thereof. Moreover, a polynucleotide can be single-stranded or double-stranded DNA, DNA that is a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide nucleic acid. Generally, polynucleotides can be assembled from isolated or cloned fragments of cDNA, genomic DNA, oligonucleotides, or individual nucleotides, or a combination of the foregoing. Although the polynucleotides described herein are shown as DNA sequences, they include their corresponding RNA sequences, and their complementary (for example, completely complementary) DNA or RNA sequences, including the reverse complements thereof.

Fragments of a polynucleotide may range from at least about 25 nucleotides, about 50 nucleotides, about 75 nucleotides, about 100 nucleotides about 150 nucleotides, about 200 nucleotides, about 250 nucleotides, about 300 nucleotides, about 400 nucleotides, about 500 nucleotides, about 600 nucleotides, about 700 nucleotides, about 800 nucleotides, about 900 nucleotides, about 1000 nucleotides, about 1100 nucleotides, about 1200 nucleotides, about 1300 nucleotides or about 1400 nucleotides and up to the full-length polynucleotide encoding the polypeptides described herein.

A polynucleotide will generally contain phosphodiester bonds, although in some cases, polynucleotide analogues are included that may have alternate backbones, comprising, for example, phosphoramidate, phosphorothioate, phosphorodithioate, or O-methylphophoroamidite linkages; and peptide polynucleotide backbones and linkages. Other analogue polynucleotides include those with positive backbones; non-ionic backbones, and non-ribose backbones. Modifications of the ribose-phosphate backbone may be done for a variety of reasons, for example, to increase the stability and half-life of such molecules in physiological environments or as probes on a biochip. Mixtures of naturally occurring polynucleotides and analogues can be made; alternatively, mixtures of different polynucleotide analogues, and mixtures of naturally occurring polynucleotides and analogues may be made.

A variety of polynucleotide analogues are known, including, for example, phosphoramidate, phosphorothioate, phosphorodithioate, O-methylphophoroamidite linkages and peptide polynucleotide backbones and linkages. Other analogue polynucleotides include those with positive backbones, non-ionic backbones and non-ribose backbones. Polynucleotides containing one or more carbocyclic sugars are also included.

Other analogues include peptide polynucleotides which are peptide polynucleotide analogues. Among the uses of the disclosed polynucleotides, and fragments thereof, is the use of fragments as probes in hybridisation assays or primers for use in amplification assays. Such fragments generally comprise at least about 10, 11, 12, 13, 14, 15, 16, 17, 18, 19 or 20 or more contiguous nucleotides of a DNA sequence. In other embodiments, a DNA fragment comprises at least about 10, 15, 20, 30, 40, 50 or 60 or more contiguous nucleotides of a DNA sequence.

Thus, in one aspect, there is also provided a method for detecting a polynucleotide comprising the use of the probes or primers or both.

The basic parameters affecting the choice of hybridization conditions and guidance for devising suitable conditions are described by Sambrook, J., E. F. Fritsch, and T. Maniatis (1989, Molecular Cloning: A Laboratory Manual, Cold Spring Harbor Laboratory Press, Cold Spring Harbor, N.Y.). Using knowledge of the genetic code in combination with the polypeptide sequences described herein, sets of degenerate oligonucleotides can be prepared. Such oligonucleotides are useful as primers, for example, in polymerase chain reactions (PCR), whereby DNA fragments are isolated and amplified.

At least one modification (for example, mutation) can be included in one or more of NtINV3-S, NtINV3-T, NtINV4-S, and NtINV4-T.

At least one modification (for example, mutation) can be included in one or more of NtINV4-S, and NtINV4-T.

At least one modification (for example, mutation) can be included in one or more of NtINV3-S, NtINV3-T, NtINV4-S, and NtINV4-T. Optionally, at least one or more further modifications (for example, mutations) can be included in one or more of NtSUS1-S, NtSUS1-T, NtSUS2-S, NtSUS2-T, NtSUS3-S, NtSUS3-T, NtSUS4-S, NtSUS4-T, NtSUS5-S, NtSUS5-T, NtSUS6-S and NtSUS6-T, suitably, in one or more of NtSUS2-S, NtSUS2-T, NtSUS3-S, NtSUS3-T, NtSUS4-S and NtSUS4-T.

At least one modification (for example, mutation) can be included in one or more of NtINV3-S, NtINV3-T, NtINV4-S, and NtINV4-T and at least one modification (for example, mutation) can be included in one or more of NtSUS2-S, NtSUS2-T, NtSUS3-S, NtSUS3-T, NtSUS4-S and NtSUS4-T whereas no modification(s) (for example, mutation(s)) are included in one or more of NtSUS1-S, NtSUS1-T, NtSUS5-S, NtSUS5-T, NtSUS6-S and NtSUS6-T.

At least one modification (for example, mutation) can be included in one or more of NtINV3-S, NtINV3-T, NtINV4-S, and NtINV4-T and at least one modification (for example, mutation) can be included in one or more of NtSUS2-S, NtSUS3-S, NtSUS3-T and NtSUS4-S whereas no modification(s) (for example, mutation(s)) are included in one or more of NtSUS1-S, NtSUS1-T, NtSUS2-T, NtSUS4-T, NtSUS5-S, NtSUS5-T, NtSUS6-S and NtSUS6-T.

At least one modification (for example, mutation) can be included in one or more of NtINV4-S and NtINV4-T and at least one modification (for example, mutation) can be included in one or more of NtSUS2-S, NtSUS2-T, NtSUS3-S, NtSUS3-T, NtSUS4-S and NtSUS4-T whereas no modification(s) (for example, mutation(s)) are included in one or more of NtSUS1-S, NtSUS1-T, NtSUS5-S, NtSUS5-T, NtSUS6-S and NtSUS6-T.

At least one modification (for example, mutation) can be included in one or more of NtINV4-S and NtINV4-T and at least one modification (for example, mutation) can be included in one or more of NtSUS2-S, NtSUS3-S, NtSUS3-T and NtSUS4-S whereas no modification(s) (for example, mutation(s)) are included in one or more of NtSUS1-S, NtSUS1-T, NtSUS2-T, NtSUS4-T, NtSUS5-S, NtSUS5-T, NtSUS6-S and NtSUS6-T.

3. Polypeptide

There is also provided an isolated polypeptide comprising, consisting or consisting essentially of a polypeptide having at least 60% sequence identity to any of the polypeptide described herein, including any of the polypeptides shown in the sequence listing. Suitably, the isolated polypeptide comprises, consists or consists essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity thereto.

There is also provided a NtINV polypeptide comprising, consisting or consisting essentially of a sequence having at least 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 2, SEQ ID NO: 4, SEQ ID NO: 6, or SEQ ID NO: 8.

There is also provided a polypeptide comprising, consisting or consisting essentially of a sequence having at least 80%, 81%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 2, SEQ ID NO: 4, SEQ ID NO: 6, or SEQ ID NO: 8.

There is also provided a polypeptide comprising, consisting or consisting essentially of a sequence having at least 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 2, SEQ ID NO: 4, SEQ ID NO: 6, or SEQ ID NO: 8.

There is also provided a polypeptide encoded by SEQ ID NO: 2, SEQ ID NO: 4, SEQ ID NO: 6, or SEQ ID NO: 8.

The polypeptide can include sequences comprising a sufficient or substantial degree of identity or similarity to SEQ ID NO: 2, SEQ ID NO: 4, SEQ ID NO: 6, or SEQ ID NO: 8 to function as an INV.

There is also provided a NtSUS polypeptide comprising, consisting or consisting essentially of a sequence having at least 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29 or SEQ ID NO: 31; or SEQ ID NO: 33.

There is also provided a polypeptide comprising, consisting or consisting essentially of a sequence having at least 80%, 81%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29 or SEQ ID NO: 31; or SEQ ID NO: 33.

There is also provided a polypeptide comprising, consisting or consisting essentially of a sequence having at least 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29 or SEQ ID NO: 31; or SEQ ID NO: 33.

There is also provided a polypeptide encoded by SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29 or SEQ ID NO: 31; or SEQ ID NO: 33.

The polypeptide can include sequences comprising a sufficient or substantial degree of identity or similarity to SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29 or SEQ ID NO: 31; or SEQ ID NO: 33 to function as a SUS.

The fragments of the polypeptide(s) typically retain some or all of the function or activity of the full length sequence—such as INV or SUS activity. Fragments of a polypeptide may range from at least about 25 amino acids, about 50 amino acids, about 75 amino acids, about 100 amino acids about 150 amino acids, about 200 amino acids, about 250 amino acids, about 300 amino acids, about 400 amino acids, about 500 amino acids, and up to the full-length polypeptide described herein.

The polypeptides also include mutants produced by introducing any type of alterations (for example, insertions, deletions, or substitutions of amino acids; changes in glycosylation states; changes that affect refolding or isomerization, three-dimensional structures, or self-association states), which can be deliberately engineered or isolated naturally provided that they still have some or all of their function or activity. Suitably, this function or activity is modulated.

A deletion refers to removal of one or more amino acids from a polypeptide. An insertion refers to one or more amino acid residues being introduced into a predetermined site in a polypeptide.

Insertions may comprise intra-sequence insertions of single or multiple amino acids. A substitution refers to the replacement of amino acids of the polypeptide with other amino acids having similar properties (such as similar hydrophobicity, hydrophilicity, antigenicity, propensity to form or break a-helical structures or β-sheet structures). Amino acid substitutions are typically of single residues, but may be clustered depending upon functional constraints placed upon the polypeptide and may range from about 1 to about 10 amino acids. The amino acid substitutions are preferably conservative amino acid substitutions as described below. Amino acid substitutions, deletions or insertions can be made using peptide synthetic techniques— such as solid phase peptide synthesis or by recombinant DNA manipulation. Methods for the manipulation of DNA sequences to produce substitution, insertion or deletion variants of a polypeptide are well known in the art. The variant may have alterations which produce a silent change and result in a functionally equivalent polypeptide. Deliberate amino acid substitutions may be made on the basis of similarity in polarity, charge, solubility, hydrophobicity, hydrophilicity and the amphipathic nature of the residues as long as the secondary binding of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine. Conservative substitutions may be made, for example according to the Table below.

Amino acids in the same block in the second column and preferably in the same line in the third column may be substituted for each other:

| ALIPHATIC | Non-polar | Gly Ala Pro |
| | | Ile Leu Val |
| | Polar - uncharged | Cys Ser Thr Met |
| | | Asn Gly |
| | Polar - charged | Asp Glu |
| | | Lys Arg |
| AROMATIC | | His Phe TrpTyr |

The polypeptide may be a mature polypeptide or an immature polypeptide or a polypeptide derived from an immature polypeptide. Polypeptides may be in linear form or cyclized using known methods. Polypeptides typically comprise at least 10, at least 20, at least 30, or at least 40 contiguous amino acids.

At least one modification (for example, mutation) can be included in one or more of NtINV3-S, NtINV3-T, NtINV4-S, and NtINV4-T.

At least one modification (for example, mutation) can be included in one or more of NtINV4-S, and NtINV4-T.

At least one modification (for example, mutation) can be included in one or more of NtINV3-S, NtINV3-T, NtINV4-S, and NtINV4-T. Optionally, at least one or more further modifications (for example, mutations) can be included in one or more of NtSUS1-S, NtSUS1-T, NtSUS2-S, NtSUS2-T, NtSUS3-S, NtSUS3-T, NtSUS4-S, NtSUS4-T, NtSUS5-S, NtSUS5-T, NtSUS6-S and NtSUS6-T, suitably, in one or more of NtSUS2-S, NtSUS2-T, NtSUS3-S, NtSUS3-T, NtSUS4-S and NtSUS4-T.

At least one modification (for example, mutation) can be included in one or more of NtINV3-S, NtINV3-T, NtINV4-S, and NtINV4-T and at least one modification (for example, mutation) can be included in one or more of NtSUS2-S, NtSUS2-T, NtSUS3-S, NtSUS3-T, NtSUS4-S and NtSUS4-T whereas no modification(s) (for example, mutation(s)) are included in one or more of NtSUS1-S, NtSUS1-T, NtSUS5-S, NtSUS5-T, NtSUS6-S and NtSUS6-T.

At least one modification (for example, mutation) can be included in one or more of NtINV3-S, NtINV3-T, NtINV4-S, and NtINV4-T and at least one modification (for example, mutation) can be included in one or more of NtSUS2-S, NtSUS3-S, NtSUS3-T and NtSUS4-S whereas no modification(s) (for example, mutation(s)) are included in one or more of NtSUS1-S, NtSUS1-T, NtSUS2-T, NtSUS4-T, NtSUS5-S, NtSUS5-T, NtSUS6-S and NtSUS6-T.

At least one modification (for example, mutation) can be included in one or more of NtINV4-S and NtINV4-T and at least one modification (for example, mutation) can be included in one or more of NtSUS2-S, NtSUS2-T, NtSUS3-S, NtSUS3-T, NtSUS4-S and NtSUS4-T whereas no modification(s) (for example, mutation(s)) are included in one or more of NtSUS1-S, NtSUS1-T, NtSUS5-S, NtSUS5-T, NtSUS6-S and NtSUS6-T.

At least one modification (for example, mutation) can be included in one or more of NtINV4-S and NtINV4-T and at least one modification (for example, mutation) can be included in one or more of NtSUS2-S, NtSUS3-S, NtSUS3-T and NtSUS4-S whereas no modification(s) (for example, mutation(s)) are included in one or more of NtSUS1-S, NtSUS1-T, NtSUS2-T, NtSUS4-T, NtSUS5-S, NtSUS5-T, NtSUS6-S and NtSUS6-T.

4. Modifying Plants a. Transformation

Recombinant constructs can be used to transform plants or plant cells in order to modulate polypeptide expression, function or activity. A recombinant polynucleotide construct can comprise a polynucleotide encoding one or more polynucleotides as described herein, operably linked to a regulatory region suitable for expressing the polypeptide. Thus, a polynucleotide can comprise a coding sequence that encodes the polypeptide as described herein. Plants or plant cells in which polypeptide expression, function or activity are modulated can include mutant, non-naturally occurring, transgenic, man-made or genetically engineered plants or plant cells.

Suitably, the transgenic plant or plant cell comprises a genome that has been altered by the stable integration of recombinant DNA. Recombinant DNA includes DNA which has been genetically engineered and constructed outside of a cell and includes DNA containing naturally occurring DNA or cDNA or synthetic DNA. A transgenic plant can include a plant regenerated from an originally-transformed plant cell and progeny transgenic plants from later generations or crosses of a transformed plant. Suitably, the transgenic modification alters the expression or function or activity of the polynucleotide or the polypeptide described herein as compared to a control plant.

The polypeptide encoded by a recombinant polynucleotide can be a native polypeptide, or can be heterologous to the cell. In some cases, the recombinant construct contains a polynucleotide that modulates expression, operably linked to a regulatory region. Examples of suitable regulatory regions are described herein.

Vectors containing recombinant polynucleotide constructs such as those described herein are also provided. Suitable vector backbones include, for example, those routinely used in the art such as plasmids, viruses, artificial chromosomes, bacterial artificial chromosomes, yeast artificial chromosomes, or bacteriophage artificial chromosomes. Suitable expression vectors include, without limitation, plasmids and viral vectors derived from, for example, bacteriophage, baculoviruses, and retroviruses. Numerous vectors and expression systems are commercially available.

The vectors can include, for example, origins of replication, scaffold attachment regions or markers. A marker gene can confer a selectable phenotype on a plant cell. For example, a marker can confer biocide resistance, such as resistance to an antibiotic (for example, kanamycin, G418, bleomycin, or hygromycin), or an herbicide (for example, glyphosate, chlorsulfuron or phosphinothricin). In addition, an expression vector can include a tag sequence designed to facilitate manipulation or detection (for example, purification or localization) of the expressed polypeptide. Tag sequences, such as luciferase, beta-glucuronidase, green fluorescent polypeptide, glutathione S-transferase, polyhistidine, c-myc or hemagglutinin sequences typically are expressed as a fusion with the encoded polypeptide. Such tags can be inserted anywhere within the polypeptide, including at either the carboxyl or amino terminus.

A plant or plant cell can be transformed by having the recombinant polynucleotide integrated into its genome to become stably transformed. The plant or plant cell described herein can be stably transformed. Stably transformed cells typically retain the introduced polynucleotide with each cell division. A plant or plant cell can be transiently transformed such that the recombinant polynucleotide is not integrated into its genome. Transiently transformed cells typically lose all or some portion of the introduced recombinant polynucleotide with each cell division such that the introduced recombinant polynucleotide cannot be detected in daughter cells after a sufficient number of cell divisions.

A number of methods are available in the art for transforming a plant cell including biolistics, gene gun techniques, Agrobacterium-mediated transformation, viral vector-mediated transformation, freeze-thaw method, microparticle bombardment, direct DNA uptake, sonication, microinjection, plant virus-mediated transfer, and electroporation.

If a cell or cultured tissue is used as the recipient tissue for transformation, plants can be regenerated from transformed cultures if desired, by techniques known to those skilled in the art.

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a polynucleotide can be modulated in a similar manner. Some suitable regulatory regions initiate transcription only, or predominantly, in certain cell types. Methods for identifying and characterizing regulatory regions in plant genomic DNA are known in the art.

Exemplary promoters include tissue-specific promoters recognized by tissue-specific factors present in different tissues or cell types (for example, root-specific promoters, shoot-specific promoters, xylem-specific promoters), or present during different developmental stages, or present in response to different environmental conditions. Suitable promoters include constitutive promoters that can be activated in most cell types without requiring specific inducers. Examples of promoters that can be used to controlpolypeptide expression include the cauliflower mosaic virus 35S (CaMV/35S), SSU, OCS, lib4, usp, STLS1, B33, nos or ubiquitin- or phaseolin-promoters. Persons skilled in the art are capable of generating multiple variations of recombinant promoters.

Tissue-specific promoters are transcriptional control elements that are only active in particular cells or tissues at specific times during plant development, such as in vegetative tissues or reproductive tissues. Examples of tissue-specific promoters under developmental control include promoters that can initiate transcription only (or primarily only) in certain tissues, such as vegetative tissues, for example, roots or leaves, or reproductive tissues, such as fruit, ovules, seeds, pollen, pistols, flowers, or any embryonic tissue. Reproductive tissue-specific promoters may be, for example, anther-specific, ovule-specific, embryo-specific, endosperm-specific, integument-specific, seed and seed coat-specific, pollen-specific, petal-specific, sepal-specific, or combinations thereof.

Exemplary leaf-specific promoters include pyruvate, orthophosphate dikinase (PPDK) promoter from C4 plant (maize), cab-m1Ca+2 promoter from maize, the *Arabidopsis thaliana* myb-related gene promoter (Atmyb5), the ribulose biphosphate carboxylase (RBCS) promoters (for example, the tomato RBCS 1, RBCS2 and RBCS3A genes expressed in leaves and light-grown seedlings, RBCS1 and RBCS2 expressed in developing tomato fruits or ribulose bisphosphate carboxylase promoter expressed almost exclusively in mesophyll cells in leaf blades and leaf sheaths at high levels).

Exemplary senescence-specific promoters include a tomato promoter active during fruit ripening, senescence and abscission of leaves, a maize promoter of gene encoding a cysteine protease, the promoter of 82E4 and the promoter of SAG genes. Exemplary anther-specific promoters can be used. Exemplary root-preferred promoters known to persons skilled in the art may be selected. Exemplary seed-preferred promoters include both seed-specific promoters (those promoters active during seed development such as promoters of seed storage polypeptides) and seed-germinating promoters (those promoters active during seed germination).

Examples of inducible promoters include promoters responsive to pathogen attack, anaerobic conditions, elevated temperature, light, drought, cold temperature, or high salt concentration.

Pathogen-inducible promoters include those from pathogenesis-related polypeptides (PR polypeptides), which are induced following infection by a pathogen (for example, PR polypeptides, SAR polypeptides, beta-1,3-glucanase, chitinase).

In addition to plant promoters, other suitable promoters may be derived from bacterial origin for example, the octopine synthase promoter, the nopaline synthase promoter and other promoters derived from Ti plasmids, or may be derived from viral promoters (for example, 35S and 19S RNA promoters of cauliflower mosaic virus (CaMV), constitutive promoters of tobacco mosaic virus, cauliflower mosaic virus (CaMV) 19S and 35S promoters, or figwort mosaic virus 35S promoter).

b. Mutation

A plant or plant cell comprising at least one mutation in one or more polynucleotides or polypeptides as described herein is disclosed, wherein said mutation results in modulated function or activity of NtINV or the polypeptide(s) encoded thereby or modulated function or activity of NtINV and NtSUS or the polypeptides encoded thereby. Combinations of such mutations are discussed herein.

There is provided a method for modulating the level of a NtINV polypeptide or a NtINV polypeptide and a NtSUS polypeptide in a (cured) plant or in (cured) plant material said method comprising introducing into the genome of said plant one or more mutations that modulate expression of at least one NtINV gene or at least one NtINV gene and at least one NtSUS gene, wherein said at least one gene is selected from any of the sequences according to the present disclosure.

There is also provided a method for identifying a plant with modulated levels of reducing sugars, said method comprising screening a polynucleotide sample from a plant of interest for the presence of one or more mutations in the sequences according to the present disclosure—such as NtINV or NtINV and NtSUS or a combination thereof, and optionally correlating the identified mutation(s) with mutation(s) that are known to modulate levels of reducing sugars.

There is also disclosed a plant or plant cell that is heterozygous or homozygous for one or more mutations in a NtINV gene or a NtINV gene and a NtSUS gene according to the present disclosure, wherein said mutation results in modulated expression of the gene or function or activity of the NtINV polypeptide or the NtINV and NtSUS polypeptides encoded thereby.

A number of approaches can be used to combine mutations in one plant including sexual crossing. A plant having one or more favourable heterozygous or homozygous mutations in a gene according to the present disclosure that modulates expression of the gene or the function or activity of the polypeptide encoded thereby can be crossed with a plant having one or more favourable heterozygous or homozygous mutations in one or more other genes that modulate expression thereof or the function or activity of the polypeptide encoded thereby. In one embodiment, crosses are made in order to introduce one or more favourable heterozygous or homozygous mutations within gene according to the present disclosure within the same plant.

The function or activity of one or more polypeptides of the present disclosure in a plant is increased or decreased if the function or activity is lower or higher than the function or activity of the same polypeptide(s) in a plant that has not been modified to inhibit the function or activity of that polypeptide and which has been cultured, harvested and cured using the same protocols.

In some embodiments, the mutation(s) is introduced into a plant or plant cell using a mutagenesis approach, and the introduced mutation is identified or selected using methods known to those of skill in the art—such as Southern blot analysis, DNA sequencing, PCR analysis, or phenotypic analysis. Mutations that impact gene expression or that interfere with the function of the encoded polypeptide can be determined using methods that are well known in the art. Insertional mutations in gene exons usually result in null-mutants. Mutations in conserved residues can be particularly effective in inhibiting the metabolic function of the encoded polypeptide. It will be appreciated, for example, that a mutation in one or more of the highly conserved regions would likely alter polypeptide function, while a mutation outside of those highly conserved regions would likely have little to no effect on polypeptide function. In addition, a mutation in a single nucleotide can create a stop codon, which would result in a truncated polypeptide and, depending on the extent of truncation, loss of function.

Methods for obtaining mutant polynucleotides and polypeptides are also disclosed. Any plant of interest, including a plant cell or plant material can be genetically modified by various methods known to induce mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and other equivalent methods.

Mutations in the polynucleotides and polypeptides described herein can include man-made mutations or synthetic mutations or genetically engineered mutations. Mutations in the polynucleotides and polypeptides described herein can be mutations that are obtained or obtainable via a process which includes an in vitro or an in vivo manipulation step. Mutations in the polynucleotides and polypeptides described herein can be mutations that are obtained or obtainable via a process which includes intervention by man. The function or activity of the mutant polypeptide variant may be higher, lower or about the same as the unmutated polypeptide.

Methods that introduce a mutation randomly in a polynucleotide can include chemical mutagenesis and radiation mutagenesis. Chemical mutagenesis involves the use of exogenously added chemicals—such as mutagenic, teratogenic, or carcinogenic organic compounds—to induce mutations. Mutagens that create primarily point mutations and short deletions, insertions, missense mutations, simple sequence repeats, transversions ortransitions, including chemical mutagens or radiation, may be used to create the mutations. Mutagens include ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)aminopropylamino]acridine dihydrochloride and formaldehyde.

Spontaneous mutations in the locus that may not have been directly caused by the mutagen are also contemplated provided that they result in the desired phenotype. Suitable mutagenic agents can also include, for example, ionising radiation—such as X-rays, gamma rays, fast neutron irradiation and UV radiation. The dosage of the mutagenic chemical or radiation is determined experimentally for each type of plant tissue such that a mutation frequency is obtained that is below a threshold level characterized by lethality or reproductive sterility. Any method of plant polynucleotide preparation known to those of skill in the art may be used to prepare the plant polynucleotide for mutation screening.

The mutation process may include one or more plant crossing steps.

After mutation, screening can be performed to identify mutations that create premature stop codons or otherwise non-functional genes. After mutation, screening can be performed to identify mutations that create functional genes that are capable of being expressed at increased or decreased levels. Screening of mutants can be carried out by sequencing, or by the use of one or more probes or primers specific to the gene or polypeptide. Specific mutations in polynucleotides can also be created that can result in modulated gene expression, modulated stability of mRNA, or modulated stability of polypeptide. Such plants are referred to herein as "non-naturally occurring" or "mutant" plants. Typically, the mutant or non-naturally occurring plants will include at least a portion of foreign or synthetic or man-made nucleotide (for example, DNA or RNA) that was not present in the plant before it was manipulated. The foreign nucleotide may be a single nucleotide, two or more nucleotides, two or more contiguous nucleotides or two or more non-contiguous nucleotides—such as at least 10, 20, 30, 40, 50,100, 200, 300, 400, 500, 600, 700, 800, 900, 1000, 1100, 1200, 1300, 1400 or 1500 or more contiguous or non-contiguous nucleotides.

c. Transgenics and Genome Editing

Sequence-specific polynucleotides that can interfere with the transcription of one or more endogenous gene(s); sequence-specific polynucleotides that can interfere with the translation of RNA transcripts (for example, double-stranded RNAs, siRNAs, ribozymes); sequence-specific polypeptides that can interfere with the stability of one or more polypeptides; sequence-specific polynucleotides that can interfere with the enzymatic function of one or more polypeptides or the binding function of one or more polypeptides with respect to substrates or regulatory polypeptides; antibodies that exhibit specificity for one or more polypeptides; small molecule compounds that can interfere with the stability of one or more polypeptides or the enzymatic function of one or more polypeptides or the binding function of one or more polypeptides; zinc finger polypeptides that bind one or more polynucleotides; and meganucleases that have function towards one or more polynucleotides can be used to modulate the expression or function or activity of one or more of the polynucleotides or polypeptides described herein.

Genome editing technologies are well known in the art and are discussed further below.

d. Zinc Finger Nucleases

Zinc finger polypeptides can be used to modulate the expression or function or activity of the one or more NtINV or NtINV and NtSUS polynucleotides described herein. The use of zinc finger nucleases is described in *Nature Rev. Genet.* (2010) 11 (9): 636-646).

e. Meganucleases

Meganucleases, such as I-CreI, can be used to modulate the expression or function or activity of one or more of the NtINV or NtINV and NtSUS polynucleotides described herein. The use of meganucleases is described in Curr Gene Ther. (2011) February; 11(1):11-27 and Int J Mol Sci. (2019) 20(16), 4045.

f. TALENs

Transcription activator-like effector nucleases (TALENs) can be used to modulate the expression or function or activity of one or more of the NtINV or NtINV and NtSUS polynucleotides described herein. The use of TALENs is described in *Nature Rev. Mol. Cell Biol.* (2013) 14: 49-55 and *Int J Mol Sci*. (2019) 20(16), 4045.

g. CRISPR

The CRISPR system can be used to modulate the expression or function or activity of one or more of the NtINV or NtINV and NtSUS polynucleotides described herein and is a preferred method. This technology is described in, for example, *Plant Methods* (2016) 12:8; *Front Plant Sci.* (2016) 7: 506; *Biotechnology Advances* (2015) 33, 1, p 41-52; *Acta Pharmaceutica Sinica B* (2017) 7, 3, p 292-302; *Curr. Op. in Plant Biol*. (2017) 36, 1-8 and *Int J Mol Sci* (2019) 20(16), 4045. As is well known in the art, the CRISPR editing system generally includes two components: a CRISPR-associated endonuclease (Cas) (for example, Cas9) and a guide RNA (gRNA). Cas forms a double stranded DNA break at a site in the genome that is defined by the sequence of a gRNA molecule bound to Cas. The location at which Cas breaks the DNA is defined by the unique sequence of the gRNA that is bound to it. gRNA is a specifically designed RNA sequence that recognizes the target DNA region of interest and directs the Cas nuclease there for editing. It has two sections: (i) a tracr RNA, which serves as a binding scaffold for the Cas nuclease; and (ii) crispr RNA (crRNA), a 17-20 nucleotide sequence complementary to the target DNA. The exact region of the DNA to be targeted will depend on the specific application. For example, to activate or repress a target polynucleotide, gRNAs can be targeted to the promoter driving expression of the target polynucleotide. Methods for designing gRNAs are well known in the art, including Chop Chop Harvard.

The application of Cas9-based genome editing in *Arabidopsis* and tobacco is described in, for example, *Methods Enzymol*. (2014) 546:459-72 and *Plant Physiol Biochem*. (2018) 131:37-46. CRISPR technology has been widely implemented in plants (see, for example, WO2015/189693).

In addition to Cas9, other RNA-guided nucleases for use in the CRISPR system have been described, including, CasI, CasIB, Cas2, Cas3, Cas4, Cas5, Cas6, Cas7, Cas8, CasIO, Cpfl, Csyl, Csy2, Csy3, Csel, Cse2, Cscl, Csc2, Csa5, Csn2, Csm2, Csm3, Csm4, Csm5, Csm6, Cmrl, Cmr3, Cmr4, Cmr5, Cmr6, Csbl, Csb2, Csb3, Csx17, Csx14, CsxlO, Csx16, CsaX, Csx3, Csxl, Csx15, Csfl, Csf2, Csf3 and Csf4. In certain embodiments, the use of Cas9 is preferred.

The present disclosure further provides a CRISPR based genome editing system comprising an RNA-guided nuclease and a gRNA, where the CRISPR based genome editing system modulates the activity of one or more of the polynucleotides described herein. The present disclosure also provides a method of cleaving one or more polynucleotides in a plant cell, comprising introducing a gRNA and an RNA-guided nuclease into the plant cell, wherein the gRNA acts in association with the RNA-guided nuclease to create a strand break in one or more of the polynucleotides described herein. A CRISPR construct is also disclosed comprising: (i) a polynucleotide encoding a CRISPR-associated endonuclease; and (ii) a gRNA including a polynucleotide sequence (typically of about 17-20 nucleotides) complementary to the DNA of the polynucleotide as described herein that is to be targeted.

h. Antisense Modification

Antisense technology is another well-known method that can be used to modulate the expression or activity of one or more NtINV polypeptides or one or more NtINV and NtSUS polypeptides. See, for example, Gene (1988) 10; 72(1-2): 45-50.

i. Mobile Genetic Elements

Alternatively, genes can be targeted for inactivation by introducing transposons (for example, IS elements) into the genomes of plants of interest. See, for example, *Cytology and Genetics* (2006) 40(4):68-81.

j. Ribozymes

Alternatively, NtINV or NtINV and NtSUS polynucleotides can be targeted for inactivation by introducing ribozymes derived from a number of small circular RNAs that are capable of self-cleavage and replication in plants. See, for example, FEMS Microbiology Reviews (1999) 23, 3, 257-275.

5. Plants

The mutant or non-naturally occurring plants or plant cells can have any combination of one or more modifications (for example, mutations) in one or more of NtINV or NtINV and NtSUS one or one or more of NtINV or NtINV and NtSUS which result in modulated expression or function or activity of those polynucleotides or their polynucleotide products. For example, the mutant or non-naturally occurring plants or plant cells may have a single modification in a single NtINV or a single NtINV and a single NtSUS polynucleotide or polypeptide; multiple modifications in a single NtINV or a single NtINV and a single NtSUS polynucleotide or polypeptide; a single modification in two or more or three or more or four or more NtINV or NtINV and a NtSUS polynucleotide or polypeptide; or multiple modifications in two or more or three or more or four or more NtINV or NtINV and NtSUS polynucleotides or polypeptides. By way of further example, the mutant or non-naturally occurring plants or plant cells may have one or more modifications in a specific portion of NtINV or NtINV and NtSUS polynucleotide(s) or polypeptide(s)—such as in a region of NtINV or NtINV and NtSUS that encodes an active site of the NtINV or NtSUS polypeptide or a portion thereof. By way of further example, the mutant or non-naturally occurring plants or plant cells may have one or more modifications in a region outside of one or more NtINV or NtINV and NtSUS polynucleotide(s) or polypeptide(s)—such as in a region upstream or downstream of the NtINV or NtINV and NtSUS polynucleotide(s) it regulates provided that they modulate the function or expression of the NtINV or NtINV and NtSUS p(s).

Upstream elements can include promoters, enhancers or transcription factors. Some elements—such as enhancers—can be positioned upstream or downstream of the gene it regulates. The element(s) need not be located near to the gene that it regulates since some elements have been found located several hundred thousand base pairs upstream or downstream of the gene that it regulates. The mutant or non-naturally occurring plants or plant cells may have one or more modifications located within the first 100 nucleotides of the gene(s), within the first 200 nucleotides of the gene(s), within the first 300 nucleotides of the gene(s), within the first 400 nucleotides of the gene(s), within the first 500 nucleotides of the gene(s), within the first 600 nucleotides of the gene(s), within the first 700 nucleotides of the gene(s), within the first 800 nucleotides of the gene(s), within the first 900 nucleotides of the gene(s), within the first 1000 nucleotides of the gene(s), within the first 1100 nucleotides of the gene(s), within the first 1200 nucleotides of the gene(s), within the first 1300 nucleotides of the gene(s), within the first 1400 nucleotides of the gene(s) or within the first 1500 nucleotides of the gene(s). The mutant or non-naturally occurring plants or plant cells may have one or more modifications located within the first, second, third, fourth, fifth, sixth, seventh, eighth, ninth, tenth, eleventh, twelfth, thirteenth, fourteenth or fifteenth set of 100 nucleotides of the gene(s) or combinations thereof. Mutant or non-naturally occurring plants or plant cells (for example, mutant, non-naturally occurring or transgenic plants or plant cells and the like, as described herein) comprising the mutant polypeptide variants are disclosed.

In one embodiment, seeds from plants are mutagenised and then grown into first generation mutant plants. The first generation plants are then allowed to self-pollinate and seeds from the first generation plant are grown into second generation plants, which are then screened for mutations in their loci. Though the mutagenized plant material can be screened for mutations, an advantage of screening the second generation plants is that all somatic mutations correspond to germline mutations. One of skill in the art would understand that a variety of plant materials, including but not limited to, seeds, pollen, plant tissue or plant cells, may be mutagenised in order to create the mutant plants. However, the type of plant material mutagenised may affect when the plant polynucleotide is screened for mutations. For example, when pollen is subjected to mutagenesis prior to pollination of a non-mutagenized plant the seeds resulting from that pollination are grown into first generation plants. Every cell of the first generation plants will contain mutations created in the pollen; thus these first generation plants may then be screened for mutations instead of waiting until the second generation.

6. Preparation of Modified Plants, Screening, and Crossing

Prepared NtINV or NtINV and NtSUS polynucleotides from individual plants, plant cells, or plant material can optionally be pooled in order to expedite screening for mutations in the population of plants originating from the mutagenized plant tissue, cells or material. One or more subsequent generations of plants, plant cells or plant material can be screened. The size of the optionally pooled group is dependent upon the sensitivity of the screening method used.

After the samples are optionally pooled, they can be subjected to polynucleotide-specific amplification techniques, such as PCR. Any one or more primers or probes specific to the gene or the sequences immediately adjacent to the gene may be utilized to amplify the sequences within the optionally pooled sample. Suitably, the one or more primers or probes are designed to amplify the regions of the locus where useful mutations are most likely to arise. Most preferably, the primer is designed to detect mutations within regions of the polynucleotide. Additionally, it is preferable for the primer(s) and probe(s) to avoid known polymorphic sites in order to ease screening for point mutations. To facilitate detection of amplification products, the one or more primers or probes may be labelled using any conventional labelling method. Primer(s) or probe(s) can be designed based upon the sequences described herein using methods that are well understood in the art.

To facilitate detection of amplification products, the primer(s) or probe(s) may be labelled using any conventional labelling method. These can be designed based upon the sequences described herein using methods that are well understood in the art.

Polymorphisms may be identified by means known in the art and some have been described in the literature.

In some embodiments, a plant may be regenerated or grown from the plant, plant tissue or plant cell. Any suitable methods for regenerating or growing a plant from a plant cell or plant tissue may be used, such as, without limitation, tissue culture or regeneration from protoplasts.

Suitably, plants may be regenerated by growing transformed plant cells on callus induction media, shoot induction media or root induction media. See, for example, McCormick et al., Plant Cell Reports 5:81-84 (1986). These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. Thus, "transformed seeds" refers to seeds that contain the nucleotide construct stably integrated into the plant genome.

Accordingly, in a further aspect there is provided a method of preparing a mutant plant. The method involves providing at least one cell of a plant comprising a NtINV or NtINV and NtSUS gene encoding a functional polynucleotide described herein (or any combination thereof as described herein). Next, the at least one cell of the plant is treated under conditions effective to modulate the function of the polynucleotide(s). The at least one mutant plant cell is then propagated into a mutant plant, where the mutant plant has modulated levels of NtINV or NtINV and NtSUS polypeptide(s) described herein (or any combination thereof as described herein) as compared to that of a control plant. In one embodiment of this method of making a mutant plant, the treating step involves subjecting the at least one cell to a chemical mutagenising agent as described above and under conditions effective to yield at least one mutant plant cell.

In another embodiment of this method, the treating step involves subjecting the at least one cell to a radiation source under conditions effective to yield at least one mutant plant cell. The term "mutant plant" includes mutant plants in which the genotype is modified as compared to a control plant, suitably by means other than genetic engineering or genetic modification.

In certain embodiments, the mutant plant, mutant plant cell or mutant plant material may comprise one or more mutations that have occurred naturally in another plant, plant cell or plant material and confer a desired trait. This mutation can be incorporated (for example, introgressed) into another plant, plant cell or plant material (for example, a plant, plant cell or plant material with a different genetic background to the plant from which the mutation was derived) to confer the trait thereto. Thus by way of example, a mutation that occurred naturally in a first plant may be introduced into a second plant—such as a second plant with a different genetic background to the first plant. The skilled person is therefore able to search for and identify a plant carrying naturally in its genome one or more mutant alleles of the genes described herein which confer a desired trait. The mutant allele(s) that occurs naturally can be transferred to the second plant by various methods including breeding, backcrossing and introgression to produce a lines, varieties or hybrids that have one or more mutations in the genes described herein. The same technique can also be applied to the introgression of one or more non-naturally occurring mutation(s) from a first plant into a second plant. Plants showing a desired trait may be screened out of a pool of mutant plants. Suitably, the selection is carried out utilising the knowledge of the polynucleotide as described herein. Consequently, it is possible to screen for a genetic trait as compared to a control. Such a screening approach may involve the application of conventional amplification or hybridization techniques as discussed herein. Thus, a further aspect of the present disclosure relates to a method for identifying a mutant plant comprising the steps of: (a) providing a sample comprising one or more NtINV or NtINV and NtSUS polynucleotide(s) from a plant; and (b) determining the sequence of the polynucleotide(s), wherein a difference in the sequence of the polynucleotide(s) as compared to the polynucleotide(s) of a control plant is indicative that said plant is a mutant plant. In another aspect there is provided a method for identifying a mutant plant which accumulates increased or decreased levels of reducing sugar(s) as compared to a control plant comprising the steps of: (a) providing a sample from a plant to be screened; (b) determining if said sample comprises one or more mutations in one or more NtINV or NtINV and NtSUS polynucleotides described herein; and (c) determining the level of at least one reducing sugar of said plant—suitably glucose or fructose or a combination thereof. Suitably the level of the at least one reducing sugar is determined in cured leaves. In another aspect there is provided a method for preparing a mutant plant which has increased or decreased levels of at least one reducing sugar—suitably glucose or fructose or a combination thereof—as compared to a control plant comprising the steps of: (a) providing a sample from a first plant; (b) determining if said sample comprises one or more mutations in one or more NtINV or NtINV and NtSUS polynucleotides described herein that result in modulated levels of the at least one reducing sugar; and (c) transferring the one or more mutations into a second plant. Suitably the level of the at least one reducing sugar is determined in cured leaves. The mutation(s) can be transferred into the second plant using various methods that are known in the art—such as by genetic engineering, genetic manipulation, introgression, plant breeding, backcrossing and the like. In one embodiment, the first plant is a naturally occurring plant. In one embodiment, the second plant has a different genetic background to the first plant. In another aspect there is provided a method for preparing a mutant plant which has increased or decreased levels of at least one reducing sugar—suitably glucose or fructose or a combination thereof—as compared to a control plant comprising the steps of: (a) providing a sample from a first plant; (b) determining if said sample comprises one or more mutations in one or more of the NtINV or NtINV and NtSUS polynucleotides described herein that results in modulated levels of the at least one reducing sugar; and (c) introgressing the one or more mutations from the first plant into a second plant. Suitably the level of the at least one reducing sugar is determined in cured leaves. In one embodiment, the step of introgressing comprises plant breeding, optionally including backcrossing and the like. In one embodiment, the first plant is a naturally occurring plant. In one embodiment, the second plant has a different genetic background to the first plant. In one embodiment, the first plant is not a cultivar or an elite cultivar. In one embodiment, the second plant is a cultivar or an elite cultivar.

A further aspect relates to a mutant plant (including a cultivar or elite cultivar mutant plant) obtained or obtainable by the methods described herein. In certain embodiments, the mutant plant may have one or more mutations localised only to a specific region of the plant—such as within the sequence of the one or more NtINV or NtINV and NtSUS polynucleotide(s) described herein. According to this embodiment, the remaining genomic sequence of the mutant plant will be the same or substantially the same as the plant prior to the mutagenesis.

In certain embodiments, the mutant plants may have one or more mutations localised in more than one genomic region of the plant—such as within the sequence of one or more of the NtINV or NtINV and NtSUS polynucleotides described herein and in one or more further regions of the genome. According to this embodiment, the remaining genomic sequence of the mutant plant will not be the same or will not be substantially the same as the plant prior to the mutagenesis.

In certain embodiments, the mutant plants may not have one or more mutations in one or more, two or more, three or more, four or more or five or more exons of the NtINV or NtINV and NtSUS polynucleotide(s) described herein; or may not have one or more mutations in one or more, two or more, three or more, four or more or five or more introns of the NtINV or NtINV and NtSUS polynucleotide(s) described herein; or may not have one or more mutations in a promoter of the NtINV or NtINV and NtSUS polynucleotide(s) described herein; or may not have one or more mutations in the 3' untranslated region of the NtINV or NtINV and NtSUS polynucleotide(s) described herein; or may not have one or more mutations in the 5' untranslated region of the NtINV or NtINV and NtSUS polynucleotide(s) described herein; or may not have one or more mutations in the coding region of the NtINV or NtINV and NtSUS polynucleotide(s) described herein; or may not have one or more mutations in the non-coding region of the NtINV or NtINV and NtSUS polynucleotide(s) described herein; or any combination of two or more, three or more, four or more, five or more; or six or more thereof parts thereof.

In a further aspect there is provided a method of identifying a plant, a plant cell or plant material comprising a mutation in a gene encoding a NtINV or NtINV and NtSUS polynucleotide described herein comprising: (a) subjecting a plant, a plant cell or plant material to mutagenesis; (b) obtaining a sample from said plant, plant cell or plant material or descendants thereof; and (c) determining the polynucleotide sequence of the NtINV or NtINV and NtSUS gene(s) or a variant or a fragment thereof, wherein a difference in said sequence is indicative of one or more mutations therein. This method also allows the selection of plants having mutation(s) that occur(s) in genomic regions that affect the expression of the NtINV or NtINV and NtSUS gene in a plant cell, such as a transcription initiation site, a start codon, a region of an intron, a boundary of an exon-intron, a terminator, or a stop codon.

7. Plant Families, Species, Varieties, Seeds, and Tissue Culture

Plants suitable for use in the present disclosure include monocotyledonous and dicotyledonous plants and plant cell systems and can include members of the genera *Camellia, Cannabis* or *Nicotiana*. Suitable species of *Camellia* and *Cannabis* include *Camellia sinensis* (tea), *Cannabis sativa, Cannabis indica* and *Cannabis ruderalis*.

Various embodiments are directed to mutant tobacco, non-naturally occurring tobacco or transgenic tobacco plants or tobacco plant cells and can be applied to any species of the genus *Nicotiana*, including *N. rustica* and *N. tabacum* (for example, LA B21, LN KY171, TI 1406, Basma, Galpao, Perique, Beinhart 1000-1, and *Petico*). Other species include *N. acaulis, N. acuminata, N. africana, N. alata, N. ameghinoi, N. amplexicaulis, N. arentsii, N. attenuata, N. azambujae, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosulata* subsp. *ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and *N. x sanderae*. In one embodiment, the plant is *N. tabacum*.

The use of tobacco cultivars and elite tobacco cultivars is also contemplated herein. The transgenic, non-naturally occurring or mutant plant may therefore be a tobacco variety or elite tobacco cultivar that comprises one or more transgenes, or one or more genetic mutations or a combination thereof. The genetic mutation(s) (for example, one or more polymorphisms) can be mutations that do not exist naturally in the individual tobacco variety or tobacco cultivar (for example, elite tobacco cultivar) or can be genetic mutation(s) that do occur naturally provided that the mutation does not occur naturally in the individual tobacco variety or tobacco cultivar (for example, elite tobacco cultivar).

Particularly useful *Nicotiana tabacum* varieties include Burley type, dark type, flue-cured type, and Oriental type tobaccos. Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KY14xL8 LC, Little Crittenden, McNair 373, McNair 944, msKY 14xL8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B13P, Xanthi (Mitchell-Mor), Bel-W3, 79-615, Samsun Holmes NN, KTRDC number 2 Hybrid 49, Burley 21, KY8959, KY9, MD 609, PG01, PG04, P01, P02, P03, RG11, RG 8, VA509, AS44, Banket Al, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpso Comum, HB04P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

Embodiments are also directed to compositions and methods for producing mutant plants, non-naturally occurring plants, hybrid plants, or transgenic plants that have been modified to modulate the expression or function of one or more NtINV or NtINV and NtSUS polynucleotide(s) described herein (or any combination thereof as described herein).

Advantageously, the mutant plants, non-naturally occurring plants, hybrid plants, or transgenic plants that are obtained may be similar or substantially the same in overall appearance to control plants. Various phenotypic characteristics such as degree of maturity, number of leaves per plant, stalk height, leaf insertion angle, leaf size (width and length), internode distance, and lamina-midrib ratio can be assessed by field observations.

One aspect relates to a seed of a mutant plant, a non-naturally occurring plant, a hybrid plant or a transgenic plant described herein. Preferably, the seed is a tobacco seed. A further aspect relates to pollen or an ovule of a mutant plant, a non-naturally occurring plant, a hybrid plant or a transgenic plant that is described herein. In addition, there is provided a mutant plant, a non-naturally occurring plant, a hybrid plant or a transgenic plant as described herein which further comprises a polynucleotide conferring male sterility.

Also provided is a tissue culture of regenerable cells of the mutant plant, non-naturally occurring plant, hybrid plant, or transgenic plant or a part thereof as described herein, which culture regenerates plants capable of expressing all the morphological and physiological characteristics of the parent. The regenerable cells include cells from leaves, pollen, embryos, cotyledons, hypocotyls, roots, root tips, anthers, flowers and a part thereof, ovules, shoots, stems, stalks, pith and capsules or callus or protoplasts derived therefrom.

The plant material that is described herein can be cured tobacco material—such as cured tobacco material from Virginia type or Oriental type. Cured tobacco material can be flue cured or sun-cured or air cured tobacco material.

The CORESTA recommendation for tobacco curing is described in: CORESTA Guide N°17, April 2016, Sustainability in Leaf Tobacco Production.

8. Modulating Sugar Content

The mutant, transgenic or non-naturally occurring plants or parts thereof of the present disclosure exhibit modulated levels of at least one reducing sugar—such as glucose or fructose or a combination thereof—in the plant material, for example, in cured leaves. In certain embodiments, when levels of glucose or fructose or a combination thereof are decreased, sucrose levels may increase.

Suitably, the modulated levels of at least one reducing sugar are observed in at least cured leaves, suitably fully cured leaves. Suitably, the cured leaves are taken from mid-position leaves of a plant. Suitably, there is no or negligible on phenotype—such as visual plant fitness as compared to a control plant. Suitably, there is no or negligible variation of total free amino acids as compared to a control plant. Acrylamide levels in smoke obtained from heating the cured leaves or a product derived therefrom may be modulated in certain embodiments.

A further aspect, relates to a mutant, non-naturally occurring or transgenic plant or cell as described herein that has decreased levels of at least one reducing sugar of at least 5% therein as compared to a control plant in which the expression or the function of said NtINV or NtINV and NtSUS polypeptide(s) has not been modulated.

In certain embodiments, the levels of glucose or fructose or a combination thereof are reduced by about 30% or more—such as about 40%, or about 50%, or about 60% or about 70% or about 80% or about 90% or more as compared to a control plant.

In certain embodiments, the levels of glucose or fructose or a combination thereof are reduced by about 40% or more—such as about 50%, or about 60% or about 70% or about 80% or about 90% or more as compared to a control plant.

In certain embodiments, the level of glucose is reduced by at least 60% or more or at least 63% or more and the level of fructose is reduced by at least about 40% or more or at least 63% or more as compared to a control plant.

In certain embodiments, the level of glucose is reduced by at least 60% or more or at least 63% or more and the level of fructose is reduced by at least about 40% or more or at least 63% or more and the level of sucrose is increased by at least 2 times, at least 3 times or at least 4 times as compared to a control plant.

In certain embodiments, the levels of glucose and fructose are increased as compared to a control plant.

In certain embodiments, the level of glucose is increased, the level of fructose is increased and the level of sucrose is decreased as compared to a control plant.

The increase can be an increase of about 25%, 50%, 100%, 250% or 500% or more as compared to a control plant. The decrease can be a decrease of about 25%, 50% or 75% or more as compared to a control plant.

A still further aspect, relates to cured plant material—such as cured leaf or cured tobacco—derived or derivable from the mutant, non-naturally occurring or transgenic plant or cell, wherein expression of one or more of the NtINV or NtINV and NtSUS polynucleotides described herein or the function of the NtINV or NtINV and NtSUS polypeptide encoded thereby is modulated and wherein the level of glucose, fructose and optionally sucrose is modulated as discussed above as compared to a control plant.

Embodiments are also directed to compositions and methods for producing mutant, non-naturally occurring or transgenic plants or plant cells that have been modified to modulate the expression or function of the one or more of the NtINV or NtINV and NtSUS polynucleotides or NtINV or NtINV and NtSUS polypeptides described herein which can result in plants or plant components (for example, leaves—such as cured leaves) or plant cells with modulated glucose, fructose and optionally sucrose content.

In one embodiment, the phenotype of the mutant, non-naturally occurring or transgenic plant is substantially the same as the control plant. In one embodiment, the leaf weight of the mutant, non-naturally occurring or transgenic plant is substantially the same as the control plant. In one embodiment, the leaf number of the mutant, non-naturally occurring or transgenic plant is substantially the same as the control plant. In one embodiment, the leaf weight and the leaf number of the mutant, non-naturally occurring or transgenic plant is substantially the same as the control plant. In one embodiment, the stalk height of the mutant, non-naturally occurring or transgenic plants is substantially the same as the control plants at, for example, one, two or three or more months after field transplant or 10, 20, 30 or 36 or more days after topping. For example, the stalk height of the mutant, non-naturally occurring or transgenic plants is not less than the stalk height of the control plants. In another embodiment, the chlorophyll content of the mutant, non-naturally occurring or transgenic plants is substantially the same as the control plants. In another embodiment, the stalk height of the mutant, non-naturally occurring or transgenic plants is substantially the same as the control plants and the chlorophyll content of the mutant, non-naturally occurring or transgenic plants is substantially the same as the control plants. In other embodiments, the size or form or number or colouration of the leaves of the mutant, non-naturally occurring or transgenic plants is substantially the same as the control plants.

In another aspect, there is provided a method for modulating the amount of at least one reducing sugar in at least a part of a plant (for example, the leaves—such as cured leaves—or in tobacco), comprising the steps of: (i) modulating the expression or function of an one or more of the NtINV or NtINV and NtSUS polypeptides described herein (or any combination thereof as described herein), suitably, wherein the NtINV or NtINV and NtSUS polypeptide(s) is encoded by the corresponding NtINV or NtINV and NtSUS polynucleotides described herein; (ii) measuring the level of the at least one reducing sugar (for example, glucose and fructose) and optionally at least one non-reducing sugar—such as sucrose—in at least a part (for example, the leaves—such as cured leaves—or tobacco or in smoke) of the mutant, non-naturally occurring or transgenic plant obtained in step (i); and (iii) identifying a mutant, non-naturally occurring or transgenic plant in which the level of the at least one reducing sugar and optionally, at least one non-reducing sugar therein has been modulated in comparison to a control plant.

In another aspect, there is provided a method for modulating the amount of at least one reducing sugar in at least a part of cured plant material—such as cured leaf—comprising the steps of: (i) modulating the expression or function of an one or more of the NtINV or NtINV and NtSUS polypeptides (or any combination thereof as described herein), suitably, wherein the NtINV or NtINV and NtSUS polypeptide(s) is encoded by the corresponding NtINV or NtINV and NtSUS polynucleotides described herein; (ii) harvesting plant material—such as one or more of the leaves—and curing for a period of time; (iii) measuring the level of the at least one reducing sugar (for example, glucose and fructose) and optionally at least one non-reducing sugar—such as sucrose—in at least a part of the cured plant material obtained in step (ii) or during step (ii); and (iv) identifying cured plant material in which the level of the at least one reducing sugar and optionally the at least one non-reducing sugar therein has been modulated in comparison to a control plant.

An increase in expression as compared to the control may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200%, 300%, 500%, 1000% or more, which includes an increase in transcriptional function or NtINV or NtINV and NtSUS polynucleotide expression or NtINV or NtINV and NtSUS polypeptide expression or a combination thereof.

An increase in function or activity as compared to a control may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200%, 300%, 500%, 1000% or more, which includes an increase in transcriptional function or NtINV or NtINV and NtSUS polynucleotide expression or NtINV or NtINV and NtSUS polypeptide expression or a combination thereof.

A reduction in expression as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%, which includes a reduction in transcriptional function or NtINV or NtINV and NtSUS polynucleotide expression or NtINV or NtINV and NtSUS polypeptide expression or a combination thereof.

A reduction in function or activity as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%, which includes a reduction in transcriptional function or NtINV or NtINV and NtSUS polynucleotide expression or NtINV or NtINV and NtSUS polypeptide expression or a combination thereof.

Polynucleotides and recombinant constructs described herein can be used to modulate the expression or function or activity of the NtINV or NtINV and NtSUS polynucleotides or NtINV or NtINV and NtSUS polypeptides described herein in a plant species of interest, suitably tobacco.

A number of polynucleotide based methods can be used to increase gene expression in plants and plant cells. By way of example, a construct, vector or expression vector that is compatible with the plant to be transformed can be prepared which comprises the gene of interest together with an upstream promoter that is capable of overexpressing the gene in the plant or plant cell.

Exemplary promoters are described herein. Following transformation and when grown under suitable conditions, the promoter can drive expression in order to modulate the levels of NtINV or NtINV and NtSUS in the plant, or in a specific tissue thereof. In one exemplary embodiment, a vector carrying one or more NtINV or NtINV and NtSUS polynucleotides described herein (or any combination thereof as described herein) is generated to overexpress the gene in a plant or plant cell. The vector carries a suitable promoter—such as the cauliflower mosaic virus CaMV 35S promoter—upstream of the transgene driving its constitutive expression in all tissues of the plant. The vector also carries an antibiotic resistance gene in order to confer selection of the transformed calli and cell lines.

The expression of sequences from promoters can be enhanced by including expression control sequences, which are well known in the art. Signals associated with senescence and signals which are active during the curing procedure are specifically indicated.

Various embodiments are therefore directed to methods for modulating the expression level of one or more NtINV or NtINV and NtSUS polynucleotides described herein (or any combination thereof as described herein) by integrating multiple copies of the NtINV or NtINV and NtSUS polynucleotide into a plant genome, comprising: transforming a plant cell host with an expression vector that comprises a promoter operably-linked to one or more NtINV or NtINV and NtSUS polynucleotides described herein. The polypeptide encoded by a recombinant polynucleotide can be a native polypeptide, or can be heterologous to the cell.

In one embodiment, the plant for use in the present disclosure is a plant that is flue-cured as such plants have a high reducing sugar content (greater than about 14% dry weight when field grown at the end of curing). Mutant, transgenic or non-naturally occurring plants or parts thereof that are flue-cured can have a reducing sugar content that is less than about 14% dry weight when field grown at the end of curing—such as less than about 10% dry weight when field grown at the end of curing, or less than about 5% dry weight when field grown at the end of curing, or less than about 1% dry weight when field grown at the end of curing.

In one embodiment, the plant of use in the present disclosure is a plant that is sun-cured as such plants have a reducing sugar content (greater than about 6.8% dry weight when field grown at the end of curing). Mutant, transgenic or non-naturally occurring plants or parts thereof that are sun-cured can have a reducing sugar content that is less than about 5% dry weight when field grown at the end of curing—such as less than about 2.5% dry weight when field grown at the end of curing, or less than about 1% dry weight when field grown at the end of curing.

In one embodiment, the plant of use in the present disclosure is a plant that is air-cured. Such plants have a reducing sugar content of greater than about 1.7% dry weight when field grown at the end of curing. Mutant, transgenic or non-naturally occurring plants or parts thereof that are sun-cured can have a reducing sugar content that is less than about 1.5% dry weight when field grown at the end of curing—such as less than about 1% dry weight when field grown at the end of curing, or less than about 0.5% dry weight when field grown at the end of curing.

In certain embodiments, the use of plants that are flue-cured or sun-cured is preferred.

9. Breeding

A plant carrying a mutant allele of one or more NtINV or NtINV and NtSUS polynucleotides described herein (or any combination thereof as described herein) can be used in a plant breeding program to create useful lines, varieties and hybrids. In particular, the mutant allele can be introgressed into the commercially important varieties described above. Thus, methods for breeding plants are provided, that comprise crossing a mutant plant, a non-naturally occurring plant or a transgenic plant as described herein with a plant comprising a different genetic identity. The method may further comprise crossing the progeny plant with another plant, and optionally repeating the crossing until a progeny with the desirable genetic traits or genetic background is obtained. One purpose served by such breeding methods is to introduce a desirable genetic trait into other varieties, breeding lines, hybrids or cultivars, particularly those that are of commercial interest. Another purpose is to facilitate stacking of genetic modifications of different genes in a single plant variety, lines, hybrids or cultivars. Intraspecific as well as interspecific matings are contemplated. The progeny plants that arise from such crosses, also referred to as breeding lines, are examples of non-naturally occurring plants of the disclosure.

In one embodiment, a method is provided for producing a non-naturally occurring plant comprising: (a) crossing a mutant or transgenic plant with a second plant to yield progeny tobacco seed; (b) growing the progeny tobacco seed, under plant growth conditions, to yield the non-naturally occurring plant. The method may further comprises: (c) crossing the previous generation of non-naturally occurring plant with itself or another plant to yield progeny tobacco seed; (d) growing the progeny tobacco seed of step (c) under plant growth conditions, to yield additional non-naturally occurring plants; and (e) repeating the crossing and growing steps of (c) and (d) multiple times to generate further generations of non-naturally occurring plants. The method may optionally comprises prior to step (a), a step of providing a parent plant which comprises a genetic identity that is characterized and that is not identical to the mutant or transgenic plant. In some embodiments, depending on the breeding program, the crossing and growing steps are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to generate generations of non-naturally occurring plants. Backcrossing is an example of such a method wherein a progeny is crossed with one of its parents or another plant genetically similar to its parent, in order to obtain a progeny plant in the next generation that has a genetic identity which is closer to that of one of the parents. Techniques for plant breeding, particularly plant breeding, are well known and can be used in the methods of the disclosure. The disclosure further provides non-naturally occurring plants produced by these methods. Certain embodiments exclude the step of selecting a plant.

In some embodiments of the methods described herein, lines resulting from breeding and screening for variant genes are evaluated in the field using standard field procedures. Control genotypes including the original unmutagenized parent are included and entries are arranged in the field in a randomized complete block design or other appropriate field design. For tobacco, standard agronomic practices are used, for example, the tobacco is harvested, weighed, and sampled for chemical and other common testing before and during curing. Statistical analyses of the data are performed to confirm the similarity of the selected lines to the parental line.

Cytogenetic analyses of the selected plants are optionally performed to confirm the chromosome complement and chromosome pairing relationships.

DNA fingerprinting, single nucleotide polymorphism, microsatellite markers, or similar technologies may be used in a marker-assisted selection (MAS) breeding program to transfer or breed mutant alleles of a gene into other tobaccos, as described herein. For example, a breeder can create segregating populations from hybridizations of a genotype containing a mutant allele with an agronomically desirable genotype. Plants in the F2 or backcross generations can be screened using a marker developed from a genomic sequence or a fragment thereof, using one of the techniques listed herein. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

According to the disclosure, in a breeding program, successful crosses yield F1 plants that are fertile. Selected F1 plants can be crossed with one of the parents, and the first backcross generation plants are self-pollinated to produce a population that is again screened for variant gene expression (for example, the null version of the gene). The process of backcrossing, self-pollination, and screening is repeated, for example, at least 4 times until the final screening produces a plant that is fertile and reasonably similar to the recurrent parent. This plant, if desired, is self-pollinated and the progeny are subsequently screened again to confirm that the plant exhibits variant gene expression. In some embodiments, a plant population in the F2 generation is screened for variant gene expression, for example, a plant is identified that fails to express a polypeptide due to the absence of the gene according to standard methods, for example, by using a PCR method with primers based upon the polynucleotide sequence information for the polynucleotide(s) described herein (or any combination thereof as described herein).

Hybrid tobacco varieties can be produced by preventing self-pollination of female parent plants (that is, seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis or pollen formation, or self-incompatibility. Female parent plants containing CMS are particularly useful. In embodiments in which the female parent plants are CMS, pollen is harvested from male fertile plants and applied manually to the stigmas of CMS female parent plants, and the resulting F1 seed is harvested.

Varieties and lines described herein can be used to form single-cross tobacco F1 hybrids. In such embodiments, the plants of the parent varieties can be grown as substantially homogeneous adjoining populations to facilitate natural cross-pollination from the male parent plants to the female parent plants. The F1 seed formed on the female parent plants is selectively harvested by conventional means. One also can grow the two parent plant varieties in bulk and harvest a blend of F1 hybrid seed formed on the female parent and seed formed upon the male parent as the result of self-pollination. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed.

A population of mutant, non-naturally occurring or transgenic plants can be screened or selected for those members of the population that have a desired trait or phenotype. For example, a population of progeny of a single transformation event can be screened for those plants having a desired level of expression or function of the polypeptide(s) encoded thereby.

Physical and biochemical methods can be used to identify expression or activity levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme function of polypeptides and polynucleotides; and polypeptide gel electrophoresis, Western blots, immunoprecipitation, and enzyme-linked immunoassays to detect polypeptides. Other techniques such as in situ hybridization, enzyme staining, and immunostaining and enzyme assays also can be used to detect the presence or expression, function or activity of NtINV or NtINV and NtSUS polypeptides or polynucleotides.

Mutant, non-naturally occurring or transgenic plant cells and plants are described herein comprising one or more recombinant polynucleotides, one or more polynucleotide constructs, one or more double-stranded RNAs, one or more conjugates or one or more vectors/expression vectors.

10. Modification of Other Genes

Without limitation, the plants and parts thereof described herein can be modified either before or after the expression, function or activity of the one or more NtINV or NtINV and NtSUS polynucleotides or NtINV or NtINV and NtSUS polypeptides according to the present disclosure have been modulated.

One or more of the following further genetic modifications can be present in the mutant, non-naturally occurring or transgenic plants and parts thereof.

One or more genes that are involved in the conversion of nitrogenous metabolic intermediates can be modified resulting in lower levels of at least one tobacco-specific nitrosamine (TSNA).

Non-limiting examples of such genes include those encoding nicotine demethylase—such as CYP82E4, CYP82E5 and CYP82E10 as described in WO2006/091194, WO2008/070274, WO2009/064771 and WO2011/088180—and nitrate reductase, as described in WO2016/046288.

One or more genes that are involved in heavy metal uptake or heavy metal transport can be modified resulting in lower heavy metal content. Non-limiting examples include genes in the family of multidrug resistance associated polypeptides, the family of cation diffusion facilitators (CDF), the family of Zrt-Irt-like polypeptides (ZIP), the family of cation exchangers (CAX), the family of copper transporters (COPT), the family of heavy-metal ATPases (for example, HMAs, as described in WO2009/074325 and WO2017/129739), the family of homologs of natural resistance-associated macrophage polypeptides (NRAMP), and other members of the family of ATP-binding cassette (ABC) transporters (for example, MRPs), as described in WO2012/028309, which participate in transport of heavy metals—such as cadmium.

Other exemplary modifications can result in plants with modulated expression or function of isopropylmalate synthase which results in a change in sucrose ester composition which can be used to alter favour profile (see WO2013/029799).

Other exemplary modifications can result in plants with modulated expression or function of threonine synthase in which levels of methional can be modulated (see WO2013/029800).

Other exemplary modifications can result in plants with modulated expression or function of one or more of neoxanthin synthase, lycopene beta cyclase and 9-cis-epoxycarotenoid dioxygenase to modulate beta-damascenone content to alter flavour profile (see WO2013/064499).

Other exemplary modifications can result in plants with modulated expression or function of members of the CLC family of chloride channels to modulate nitrate levels therein (see WO2014/096283 and WO2015/197727).

Other exemplary modifications can result in plants with modulated expression or function of one or more asparagine synthetases to modulate levels of asparagine in leaf and modulated levels of acrylamide in aerosol produced upon heating or combusting the leaf (see WO2017/129739).

Other exemplary modifications can result in plants with modulated protease activity during curing (see WO2016/009006).

Other exemplary modifications can result in plants having reduced nitrate levels by altering the gene expression of nitrate reductase (for example, Nia2) or the activity of the protein encoded thereby (see WO2016/046288).

Other exemplary modifications can result in plants having modified alkaloid levels by altering the gene expression of putative ABC-2 transporters NtABCGI-T and NtABCGI-S or the activity of the protein encoded thereby (see WO2019/086609) Other exemplary modifications can result in plants having modulated time to flowering by altering the gene expression of genes encoding Terminal Flower 1 (TFL1) or the activity of the protein encoded thereby (see WO2018/114641). Other exemplary modifications can result in plants with modulated expression or function of one or more asparagine synthetases to modulate levels of asparagine in leaf and modulated levels of acrylamide in aerosol produced upon heating or combusting the leaf (see WO2017/042162).

Examples of other modifications include modulating herbicide tolerance, for example, glyphosate is an active ingredient of many broad spectrum herbicides. Glyphosate resistant transgenic plants have been developed by transferring the aroA gene (a glyphosate EPSP synthetase from *Salmonella typhimurium* and *E. coli*). Sulphonylurea resistant plants have been produced by transforming the mutant ALS (acetolactate synthetase) gene from *Arabidopsis*. OB polypeptide of photosystem II from mutant *Amaranthus hybridus* has been transferred in to plants to produce atrazine resistant transgenic plants; and bromoxynil resistant transgenic plants have been produced by incorporating the bxn gene from the bacterium *Klebsiella pneumoniae*.

Another exemplary modification results in plants that are resistant to insects. *Bacillus thuringiensis* (Bt) toxins can provide an effective way of delaying the emergence of Bt-resistant pests, as recently illustrated in broccoli where pyramided cry1Ac and cry1C Bt genes controlled diamondback moths resistant to either single polypeptide and significantly delayed the evolution of resistant insects.

Another exemplary modification results in plants that are resistant to diseases caused by pathogens (for example, viruses, bacteria, fungi). Plants expressing the Xa21 gene (resistance to bacterial blight) with plants expressing both a Bt fusion gene and a chitinase gene (resistance to yellow stem borer and tolerance to sheath) have been engineered.

Another exemplary modification results in altered reproductive capability, such as male sterility.

Another exemplary modification results in plants that are tolerant to abiotic stress (for example, drought, temperature, salinity), and tolerant transgenic plants have been produced by transferring acyl glycerol phosphate enzyme from *Arabidopsis*; genes coding mannitol dehydrogenase and sorbitol dehydrogenase which are involved in synthesis of mannitol and sorbitol improve drought resistance.

Another exemplary modification results in plants in which the activity of one or more nicotine N-demethylases is modulated such that the levels of nornicotine and metabolites of nornicotine—that are formed during curing can be modulated (see WO2015169927).

Other exemplary modifications can result in plants with improved storage polypeptides and oils, plants with enhanced photosynthetic efficiency, plants with prolonged shelf life, plants with enhanced carbohydrate content, and plants resistant to fungi. Transgenic plants in which the expression of S-adenosyl-L-methionine (SAM) or cystathionine gamma-synthase (CGS), or a combination thereof, has been modulated are also contemplated.

One or more genes that are involved in the nicotine synthesis pathway can be modified resulting in plants or parts of plants that when cured, produce modulated levels of nicotine. The nicotine synthesis genes can be selected from the group consisting of: A622, BBLa, BBLb, JRE5L1, JRE5L2, MATE1, MATE 2, MPO1, MPO2, MYC2a, MYC2b, NBB1, nic1, nic2, NUP1, NUP2, PMT1, PMT2, PMT3, PMT4 and QPT or a combination of one or more thereof.

One or more genes that are involved in controlling the amount of one or more alkaloids can be modified resulting in plants or parts of plants that produce modulated levels of alkaloid. Alkaloid level controlling genes can be selected from the group consisting of; BBLa, BBLb, JRE5L1, JRE5L2, MATE1, MATE 2, MYC2a, MYC2b, nic1, nic2, NUP1 and NUP2 or a combination of two or more thereof.

One or more such traits may be introgressed into the mutant, non-naturally occurring or transgenic plants from another cultivar or may be directly transformed into it.

Various embodiments provide mutant plants, non-naturally occurring plants or transgenic plants, as well as biomass in which the expression level of one or more polynucleotides according to the present disclosure are modulated to thereby modulate the level of polypeptide(s) encoded thereby.

11. Consumable Products

Parts of the plants described herein, particularly the leaf lamina and midrib of such plants, can be incorporated into or used in making various consumable products including but not limited to aerosol forming materials, aerosol forming devices, smoking articles, smokable articles, smokeless products, medicinal or cosmetic products, intravenous preparations, tablets, powders, and tobacco products. Examples of aerosol forming materials include tobacco compositions, tobaccos, tobacco extract, cut tobacco, cut filler, cured tobacco, expanded tobacco, homogenized tobacco, reconstituted tobacco, and pipe tobaccos. Smoking articles and smokable articles are types of aerosol forming devices. Examples of smoking articles or smokable articles include cigarettes, cigarillos, and cigars. Examples of smokeless products comprise chewing tobaccos, and snuffs. In certain aerosol forming devices, rather than combustion, a tobacco composition or another aerosol forming material is heated by one or more electrical heating elements to produce an aerosol. In another type of heated aerosol forming device, an aerosol is produced by the transfer of heat from a combustible fuel element or heat source to a physically separate aerosol forming material, which may be located within, around or downstream of the heat source. Smokeless tobacco products and various tobacco-containing aerosol forming materials may contain tobacco in any form, including as dried particles, shreds, granules, powders, or a slurry, deposited on, mixed in, surrounded by, or otherwise combined with other ingredients in any format, such as flakes, films, tabs, foams, or beads. The term 'smoke' is used to describe a type of aerosol that is produced by smoking articles, such as cigarettes, or by combusting an aerosol forming material.

In one embodiment, there is also provided cured plant material from the mutant, transgenic and non-naturally occurring plants described herein. Processes of curing green tobacco leaves are known by those having skills in the art and include without limitation air-curing, fire-curing, flue-curing and sun-curing as described herein.

In another embodiment, there is described tobacco products including tobacco-containing aerosol forming materials comprising plant material—such as leaves, preferably cured leaves—from the mutant tobacco plants, transgenic tobacco plants or non-naturally occurring tobacco plants described herein. The tobacco products described herein can be a blended tobacco product which may further comprise unmodified tobacco.

12. Products and Methods for Crop Management and Agriculture

The mutant, non-naturally occurring or transgenic plants may have other uses in, for example, agriculture.

The disclosure also provides methods for producing seeds comprising cultivating the mutant plant, non-naturally occurring plant, or transgenic plant described herein, and collecting seeds from the cultivated plants. Seeds from plants described herein can be conditioned and bagged in packaging material by means known in the art to form an article of manufacture. Packaging material such as paper and cloth are well known in the art. A package of seed can have a label, for example, a tag or label secured to the packaging material, a label printed on the package that describes the nature of the seeds therein.

Compositions, methods and kits for genotyping plants for identification, selection, or breeding can comprise a means of detecting the presence of a NtINV or NtINV and NtSUS polynucleotide(s) in a sample of polynucleotide. Accordingly, a composition is described comprising one or more primers for specifically amplifying at least a portion of one or more of the NtINV or NtINV and NtSUS polynucleotides and optionally one or more probes and optionally one or more reagents for conducting the amplification or detection.

Accordingly, gene specific oligonucleotide primers or probes comprising about 10 or more contiguous polynucleotides corresponding to the NtINV or NtINV and NtSUS polynucleotide(s) described herein are disclosed. Said primers or probes may comprise or consist of about 15, 20, 25, 30, 40, 45 or 50 more contiguous polynucleotides that hybridise (for example, specifically hybridise) to the NtINV or NtINV and NtSUS polynucleotide(s) described herein. In some embodiments, the primers or probes may comprise or consist of about 10 to 50 contiguous nucleotides, about 10 to 40 contiguous nucleotides, about 10 to 30 contiguous nucleotides or about 15 to 30 contiguous nucleotides that may be used in sequence-dependent methods of gene identification (for example, Southern hybridization) or isolation (for example, in situ hybridization of bacterial colonies or bacteriophage plaques) or gene detection (for example, as one or more amplification primers in amplification or detection). The one or more specific primers or probes can be designed and used to amplify or detect a part or all of the polynucleotide(s). By way of specific example, two primers may be used in a PCR protocol to amplify a polynucleotide fragment. The PCR may also be performed using one primer that is derived from a polynucleotide sequence and a second primer that hybridises to the sequence upstream or downstream of the polynucleotide sequence—such as a promoter sequence, the 3' end of the mRNA precursor or a sequence derived from a vector. Examples of thermal and isothermal techniques useful for in vitro amplification of polynucleotides are well known in the art. The sample may be or may be derived from a plant, a plant cell or plant material or a tobacco product made or derived from the plant, the plant cell or the plant material as described herein.

In a further aspect, there is also provided a method of detecting a NtINV or NtINV and NtSUS polynucleotide(s) described herein (or any combination thereof as described herein) in a sample comprising the step of: (a) providing a sample comprising, or suspected of comprising, a polynucleotide; (b) contacting said sample with one or more primers or one or more probes for specifically detecting at least a portion of the NtINV or NtINV and NtSUS polynucleotide(s); and (c) detecting the presence of an amplification product, wherein the presence of an amplification product is indicative of the presence of the NtINV or NtINV and NtSUS polynucleotide(s) in the sample. In a further aspect, there is also provided the use of one or more primers or probes for specifically detecting at least a portion of the NtINV or NtINV and NtSUS polynucleotide(s). Kits for detecting at least a portion of the NtINV or NtINV and NtSUS polynucleotide(s) are also provided which comprise one or more primers or probes for specifically detecting at least a portion of the NtINV or NtINV and NtSUS polynucleotide(s). The kit may comprise reagents for polynucleotide amplification—such as PCR—or reagents for probe hybridization-detection technology—such as Southern Blots, Northern Blots, in-situ hybridization, or microarray. The kit may comprise reagents for antibody binding-detection technology such as Western Blots, ELISAs, SELDI mass spectrometry or test strips. The kit may comprise reagents for DNA sequencing. The kit may comprise reagents and instructions for using the kit.

In some embodiments, a kit may comprise instructions for one or more of the methods described. The kits described may be useful for genetic identity determination, phylogenetic studies, genotyping, haplotyping, pedigree analysis or plant breeding particularly with co-dominant scoring.

The present disclosure also provides a method of genotyping a plant, a plant cell or plant material comprising a NtINV or NtINV and NtSUS polynucleotide as described herein.

Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. The specific method of genotyping may employ any number of molecular marker analytic techniques including amplification fragment length polymorphisms (AFLPs). AFLPs are the product of allelic differences between amplification fragments caused by polynucleotide variability. Thus, the present disclosure further provides a means to follow segregation of one or more genes or polynucleotides as well as chromosomal sequences genetically linked to these genes or polynucleotides using such techniques as AFLP analysis.

13. Tobacco Extracts

There is also disclosed herein methods of producing a liquid tobacco extract and a liquid tobacco extract produced by the method(s).

A specific extraction temperature is selected for the tobacco starting material, preferably based on at least the reducing sugar content and optionally the nicotine content of the tobacco starting material(s). The extraction temperature(s) is typically selected from within the range of about 100 degrees Celsius to about 160 degrees Celsius. The duration of the heating step may optionally be controlled to provide a degree of control over the composition of the extract derived from the tobacco starting material(s). Suitably, the tobacco starting material(s) is heated at the extraction temperature for at least about 90 minutes, more suitably at least about 120 minutes. The heating step is typically carried out in an inert atmosphere. Suitably, a flow of an inert gas—such as nitrogen—is passed through the starting tobacco material during the heating step. The volatile tobacco compounds are released into the flow of inert gas during the heating step such that the inert gas acts as a carrier for the volatile components. The flow of inert gas can be at a flow rate of at least about 25 litres per minute, more suitably at least about 30 litres per minute. A relatively high flow rate of inert gas may advantageously improve the efficiency of extraction from the tobacco starting material. Optionally, the heating step may be carried out under vacuum. Suitable heating methods for carrying out the heating of the tobacco starting material are known to the skilled person and include: dry distillation, hydrodistillation, vacuum distillation, flash distillation and thin film hydrodistillation.

Where the volatile compounds are collected by absorption in a liquid solvent the step of forming the liquid tobacco extract can comprise drying the solution of the volatile compounds in the liquid solvent in order to concentrate the solution. Drying may be carried out using any suitable means, including but not limited to desiccation, molecular sieves, freeze drying, phase separation, distillation, membrane permeation, controlled crystallisation of water and filtering, reverse hygroscopicity, ultracentrifugation, liquid chromatography, reverse osmosis or chemical drying.

The liquid tobacco extract is particularly suitable for producing a composition or formulation or gel composition, for use in an aerosol-generating system. An aerosol-generating system comprising the composition or formulation or gel composition is disclosed. In such an aerosol-generating system, the composition or formulation or gel is typically heated within an aerosol-generating device—such as a device comprising a heater element that interacts with the composition or formulation or gel incorporating the liquid tobacco extract to produce an aerosol.

During use, volatile compounds are released by heat transfer and entrained in air drawn through the aerosol generating device. As the released compounds cool they condense to form an aerosol that is inhaled by the consumer.

The invention is further described in the Examples below, which are provided to describe the invention in further detail. These examples, which set forth a preferred mode presently contemplated for carrying out the invention, are intended to illustrate and not to limit the invention.

EXAMPLES

Example 1—Materials & Methods

DNA Extraction and Plant Genotyping

Leaf samples are extracted using the BioSprint 96 (Qiagen, Hilden, Germany) together with the BioSprint 96 DNA plant kit (Qiagen, Hilden, Germany). DNA samples are used in a TaqMan reaction in order to determine the plant genotype. Taqman is carried out using the ABI PRISM 7900HT Sequence Detection System (Applied Biosystems, Life Technologies, Foster City, Calif., USA) and TaqMan Fast Advanced Master Mix (Applied Biosystems, Foster City, Calif., USA).

Measuring Free Amino Acid Content

Amino acid content can be measured using various methods that are known in the art. One such method is Method MP 1471 rev 5 2011, Resana, Italy: Chelab Silliker S.r.I, Mérieux NutriSciences Company. For amino acid determination in cured plant leaves, after mid-rib removal, cured lamina are dried at 40° C. for 2-3 days, if required. Tobacco material is then ground in fine powder (~100 uM) before the analysis of amino acid content. Another method for measuring amino acid content in plant material is described in UNI EN ISO 13903:2005. The measurement of free amino acid content can be performed according to UNI EN ISO 13903:2005.

Measuring Reducing Sugar Content

Reducing sugar content can be measured using a segmented-flow colorimetric method developed for analysis of tobacco samples as adapted by Skalar Instrument Co (West Chester, Pa.) and described in Tobacco Science 20: 139-144 (1976). The measurement of reducing sugar content is also described in Coresta Recommended Method 38, CRM38, CRM and ISO 15154: 2003. For reducing sugar determination in cured leaves, after mid-rib removal, cured lamina are dried at 40° C. for 2-3 days, if required. Tobacco material is then ground in fine powder (~100 uM) before the analyses of reducing sugars. The measurement of reducing sugar content is performed according to ISO 15154: 2003.

Example 2—Analysis of the Expression of NtINV4-S and NtINV4-T in Plant Tissues Table 1 shows that NtINV4-S and NtINV4-T are expressed in whole plant tissues, particularly in petal, and also in immature flower, sepal, bottom leaf, middle leaf and upper leaf to a lesser extent in Virginia tobacco plants grown in the field. In contrast, NtINV3-S and NtINV3-T have very low expression in the tissues that are investigated, with the only tangible expression, although very low, occurring in immature flower in Virginia tobacco plants grown in the field

Example 3—Evolution of Reducing Sugars (Glucose and Fructose) During Virginia Flue-Curing Time Course During Virginia (flue-cured) tobacco curing, reducing sugars, mainly glucose and fructose strongly increase in yellowing leaf, reaching a maximum level after one or two days (see FIG. 1A). Interestingly, NtINV4-S and NtINV4-T expression increases by a factor ~2 (in log 2) to reach a plateau after 1 or 2 days (see FIG. 1A). NtINV4-T is expressed to a greater extent during curing than NtINV4-S (see FIG. 1B and Table 2). Both copies of NtINV3 are not significantly expressed in cured leaf (see FIG. 2B) or green leaf (see Table 1). As a control, SAG12, a general marker of senescence in plants is fully expressed after one day of curing (see FIG. 1C).

Example 4—Evolution of Reducing Sugars (Glucose and Fructose) During Air-Curing Time Course in Dark Tobacco To determine whether the induction of NtINV4-S and NtINV4-T is not specific to Virginia tobacco, expression data in a dark tobacco is studied. In this case, leaves are air-cured. During the first 120 hours, samples are collected after 24, 48, 96 and 120 hours, frozen, lyophilized and submitted to metabolomic analyses. As observed in Virginia tobacco leaf, glucose and fructose (reducing sugars) increase by a factor of 4-6 from 0 hours to 120 hours curing (end of yellowing phase) (see FIG. 2). In the fully cured leaves (~10 days after curing start), glucose and fructose levels decrease in the leaf matrix as in flue-cured tobacco (compare FIGS. 1 and 2), but to a larger extent. Sucrose remained almost stable during the first 120 hours curing, thereby suggesting that the supply of sucrose molecules during leaf yellowing is maintained in dark tobacco. At the end of curing, sucrose is fully hydrolyzed and thus likely metabolized completely (see FIG. 2C).

In the same samples, frozen leaf material is used to isolate RNA to analyse expression of NtINV3-S, NtINV3-T, NtINV4-S and NtINV4-T. As observed in flue-cured tobacco, NtINV3 genes are neither expressed in harvested leaf nor up-regulated during air-curing of dark tobacco. On the other hand, NtINV4-S and NtINV4-T are up-regulated by a factor >10 to reach a maximum after 5 curing days (120 hours, see Table 2). As observed in flue-cured tobacco, SAG12 is more rapidly up-regulated and then decreased after 5 curing days (120 hours).

Example 5—Silencing of NtINV4 in Flue-Cured Tobacco

Figure 3:
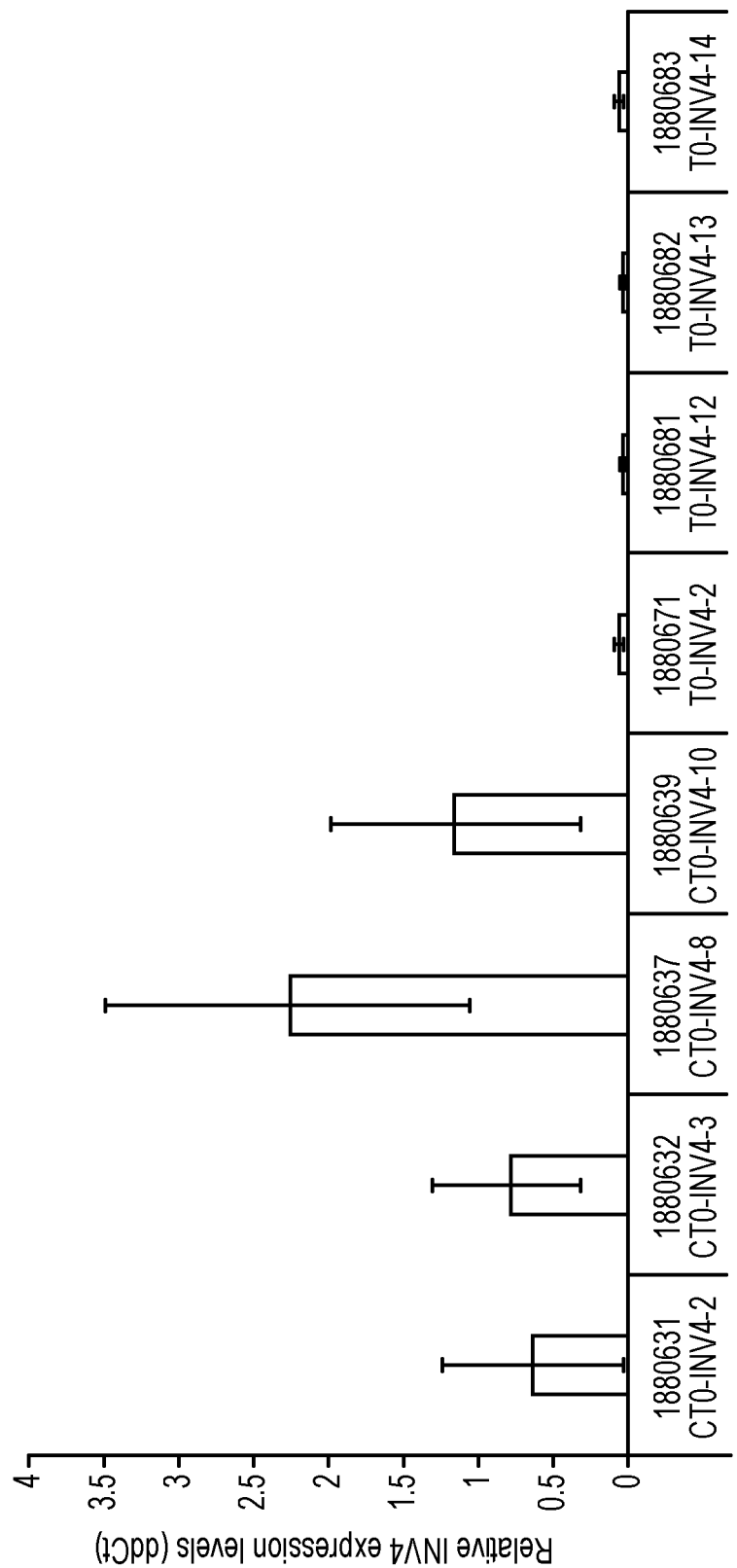
FIG. 3 is a graph showing the results of silencing NtINV4-S and NtINV4-T using a GATEWAY vector and measurements of the expression of NtINV4-S and NtINV4-T in Virginia tobacco leaf after 48 h curing (qPCR). T0-INV4 is the generated transgenic line and CT0-INV4 is the corresponding control lines.

The silencing of NtINV4 in flue-cured tobacco is investigated to determine if these genes contribute to decrease reducing sugars level in cured tobacco leaves. A specific DNA fragment (SEQ ID NO: 9) within the coding sequence of both NtINV4-S and NtINV4-T is cloned with the strong constitutive *Mirabilis* Mosaic Virus (MMV) promoter in a GATEWAY vector. The NtINV4 gene fragment is flanked between MMV and the 3' nos terminator sequence of the nopaline synthase gene of *Agrobacterium tumefaciens*. The tobacco line K326 is transformed using standard *Agrobacterium*-mediated transformation protocols. Results are shown in FIG. 3 in respect of INV4 expression levels for four controls and four transgenic 35S:INV4-RNAi lines. To enable the selection of low reducing sugar content plants, independent T0 plant leaves and respective control lines are analyzed after 48 h curing to determine the impact on reducing sugar content. The best T0 lines displaying the lowest level of NtINV4 expression compared to the control lines are selected by qPCR. Seeds are harvested from these best T0 lines. Manipulating NtINV4 genes (for example, with either a constitutive promoter or a specific senescence promotor—such as SAG12 or E4) may change the chemistry of tobacco cured leaves. Similarly knocking-out NtINV4 genes using a genome editing strategy—such as CRISPR or mutant selection may change amino acid leaf chemistry of the main varieties of commercial tobacco.

Figure 4:
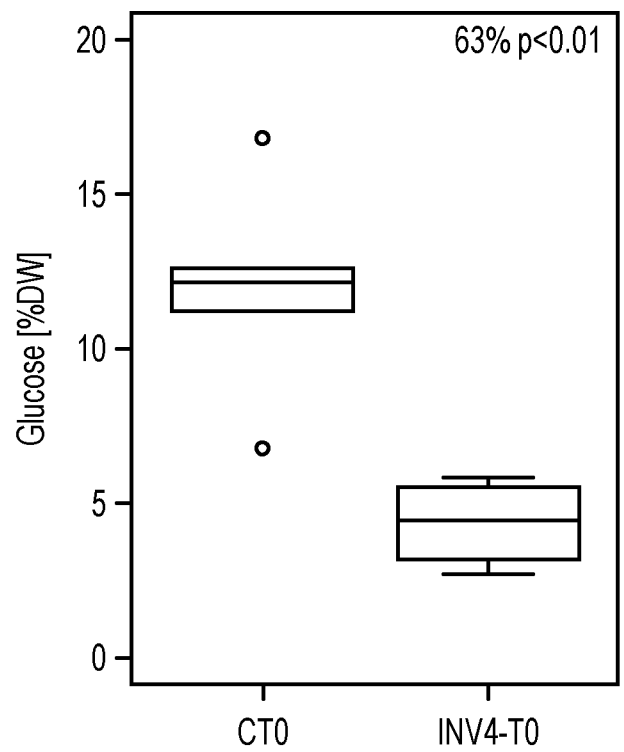
FIG. 4 is a series of graphs showing: (A) glucose; (B) fructose; and (C) sucrose content in silenced 35S:INV4-RNAi (INV4-T0) cured leaves and control (CT0) cured leaves (CT0, n=4; and T0, n=4). Box plots are presented as well as T-test statistical analyses.
Figure 4:
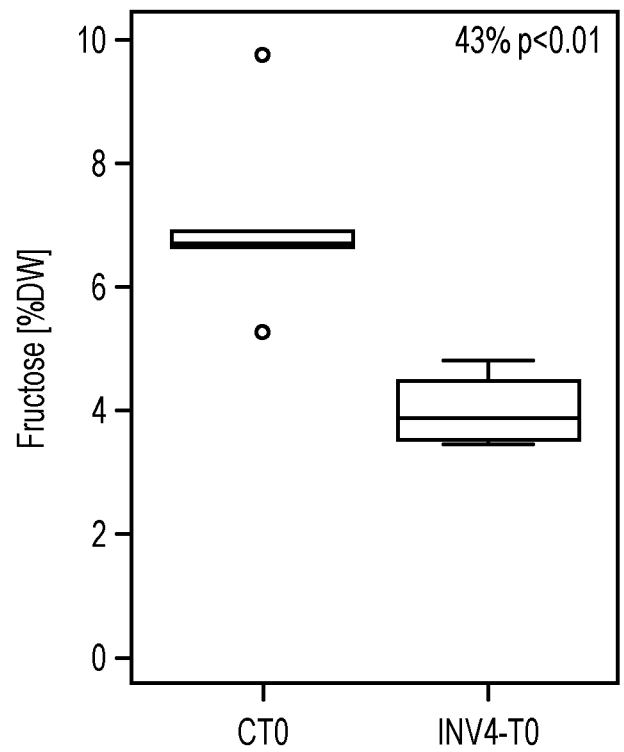
Figure 4:
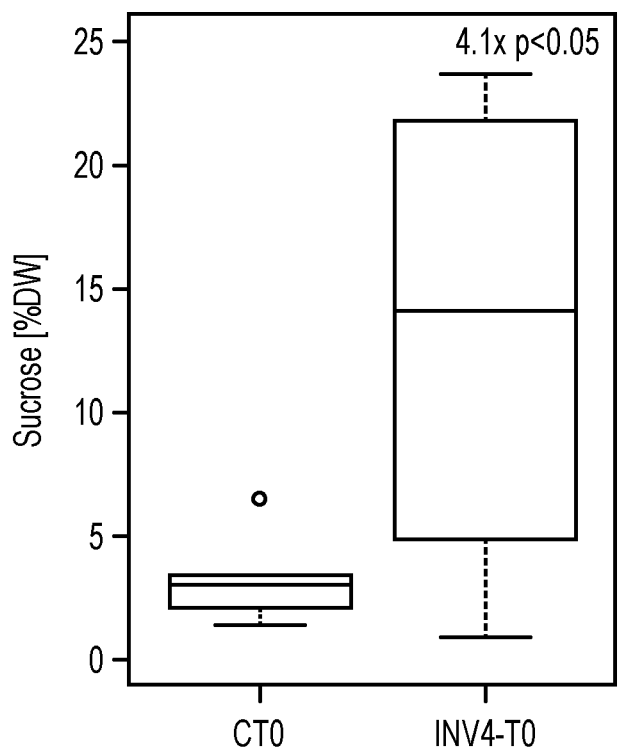
Figure 5:
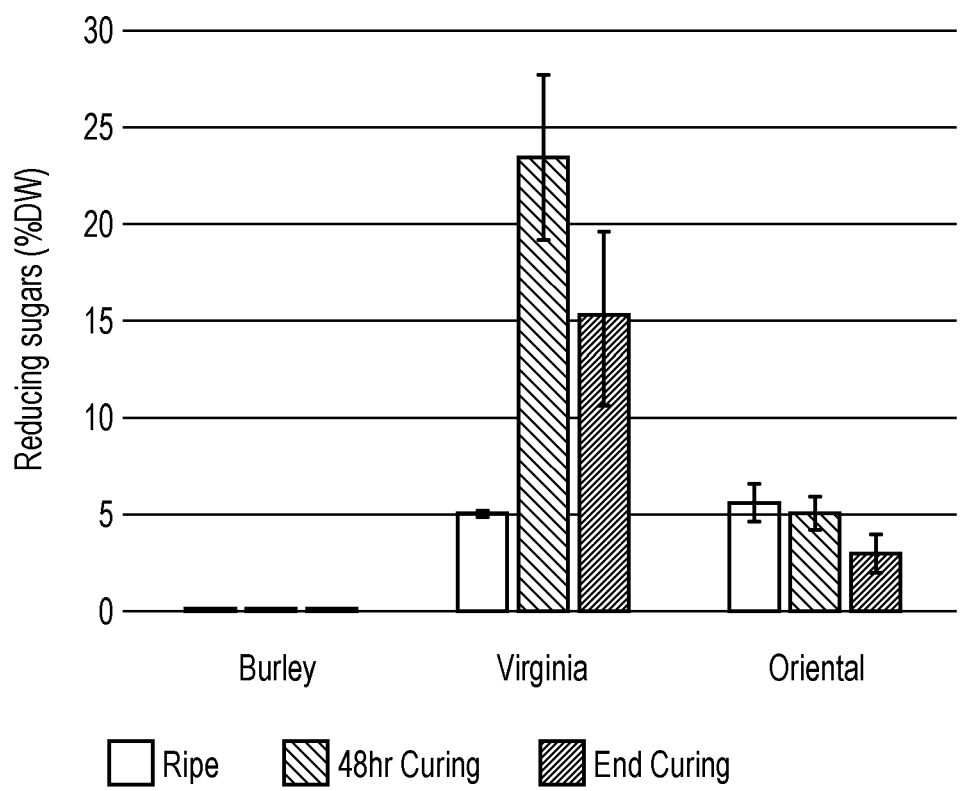
FIG. 5 is a bar graph showing the content per variety of reducing sugars after harvest (ripe), after two days of curing (48 hours curing) and at the end of curing in Burley, Virginia and Oriental tobacco.

Example 6—Analysis of Glucose, Fructose and Sucrose in Fully Cured Leaves of Four Controls and Four Transgenic 35S:INV4-RNAi Lines The five mid-position leaves of the four controls and four transgenic 35S:INV4-RNAi lines described in FIG. 3 are collected at maturation and subjected to flue-curing. The sugars (glucose, fructose and sucrose) are analyzed in fully cured leaves. The data presented in FIG. 4 shows a strong and significant reduction of glucose and fructose in the anti-INV4 plants. The level of glucose and fructose is reduced by about 63% and about 43% respectively.

Interestingly, sucrose is significantly 4.1 times higher in 35S:INV4-RNAi lines, thereby suggesting that part of the sucrose pool accumulating during leaf curing is not hydrolyzed by INV4 genes in the silenced lines. No impact on visual plant fitness and variation of total free amino acids between control and 35S:INV4-RNAi lines is observed.

Knocking-out or down regulating the expression of NtINV4-S and NtINV4-T may contribute to reduce the content of reducing sugars in cured leaves. To even further decrease the amount of reducing sugars, a combination of knocking-out or downregulating NtSUS and NtINV can be considered. To increase the pool of reducing sugars in cured leaves, overexpression of NtINV4-S or NtINV4-T, or a combination thereof, using a senescence induced promoter like SAG12 or E4 might be considered (the use of a constitutive promoter may change plant metabolism under vegetative stage).

Example 7—Identification of SUS Genes after Curing in Burley, Virginia and Oriental Tobacco Leaf To identify key functions contributing to sucrose metabolism during early curing time of Burley, Virginia and Oriental tobacco leaf, an overrepresentation analysis for the function of genes up-regulated in cured leaves after 48 hours curing, as compared to the ripe leaves at harvest (log 2 fold change >2, adjusted p-value <0.05) is performed in Burley, Virginia and Oriental tobacco.

Genes involved in the production of reducing sugars and that are active after 48 hours curing independently of the curing types and tobacco varieties are identified. Tobacco genes involved in the production of reducing sugars are identified.

The key genes directly involved in the production of reducing sugars during early curing in leaves belong to the gene family of SUS. SUS is likely a key enzyme to drive the accumulation of reducing sugars in cured detached leaves.

The tobacco genome is found to have 12 NtSUS gene products distributed in 6 families with one S and one T copy from each ancestor: NtSUS1-S (SEQ ID NO: 10), NtSUS1-T (SEQ ID NO: 12), NtSUS2-S (SEQ ID NO: 14), NtSUS2-T (SEQ ID NO: 16), NtSUS3-S (SEQ ID NO: 18), NtSUS3-T (SEQ ID NO: 20), NtSUS4-S (SEQ ID NO: 22), NtSUS4-T (SEQ ID NO: 24), NtSUS5-S (SEQ ID NO: 26), NtSUS5-T (SEQ ID NO: 28), NtSUS6-S (SEQ ID NO: 30) and NtSUS6-T (SEQ ID NO: 32).

SUS transcripts are from the genomic sequences NtSUS2-S (SEQ ID NO: 14), NtSUS3-S(SEQ ID NO: 18), NtSUS3-T (SEQ ID NO: 20) and NtSUS4-S (SEQ ID NO: 22). These genes are up-regulated during leaf curing (senescence), as shown in Table 3. This confirms that S copies are particularly involved in the chemical modification of early cured leaves and in this particular case the increase of glucose and fructose.

Although low amounts of reducing sugar levels are found in cured leaves of Burley, compared to Virginia and Oriental, NtSUS genes are nevertheless activated in Burley (see Table 3), likely as a constitutive response to also ensure available carbon source for amino acid synthesis during the early curing phase.

In both Burley (BU) and Virginia (FC), NtSUS1-S and NtSUS1-T, which are not expressed during early curing (see Table 3), are particularly expressed in root and stem, indicating a possible specific function in these tissues to deliver carbohydrates for cell wall synthesis or supply carbon resources under anoxia (see Table 4). On the other hand, NtSUS3-S, NtSUS3-T, NtSUS4-S, which are induced during early leaf curing, are also expressed in all organs, whereas NtSUS2-S and NtSUS2-T are mainly expressed in immature flowers and petals.

NtSUS5-S, NtSUS5-T, NtSUS6-S and NtSUS6-T are expressed at low levels in all the analysed plant tissues (see Table 4).

To increase the pool of reducing sugars in cured leaves, overexpression of NtSUS2-S, NtSUS3-S, NtSUS3-T or NtSUS4-S, or a combination thereof using a senescence induced promoter like SAG12 or E4 might be considered (the use of a constitutive promoter may strongly change plant metabolism). On the other hand, knocking-out NtSUS2-S, NtSUS3-S, NtSUS3-T and/or NtSUS4-S may contribute to reduce the content of reducing sugars in cured leaves.

Example 8—Silencing of NtSUS Expression in Virginia Tobacco Leaf

The silencing of NtSUS in Burley tobacco is investigated to determine if these genes contribute to decreasing reducing sugar content in cured Virginia tobacco leaves. A specific DNA fragment within the coding sequence of both NtSUS is cloned with the strong constitutive Mirabilis Mosaic Virus (MMV) promoter in a GATEWAY vector. The NtSUS gene fragment is flanked between MMV and the 3' nos terminator sequence of the nopaline synthase gene of Agrobacterium tumefaciens.

To enable the selection of low reducing sugar content plants, independent T0 plant leaves and respective control lines are analyzed after 60 h curing to determine the impact on reducing sugar content. The best T0 lines displaying the lowest level of reducing sugar are selected. Seeds are harvested from these best T0 lines. T1 progeny are assayed by qPCR to determine the efficiency of the NtSUS silencing events in relation to decreasing reducing sugar content.

Manipulating NtSUS genes (for example, with either a constitutive promotor or a specific senescence promotor—such as SAG12 or E4) may change the chemistry of tobacco cured leaves. Similarly knocking-out NtSUS genes using a genome editing strategy—such as CRISPR or mutant selection may change amino acid leaf chemistry of the main varieties of commercial tobacco.

Example 9—Producing a Liquid Tobacco Extract from a NtINV4 Modified Tobacco Plant and a NtSUS Modified Tobacco Plant Each Having Modulated Reducing Sugar Content A tobacco starting material is prepared from cured leaves of a NtINV4 modified tobacco plant or a NtSUS modified tobacco plant according to the present disclosure. The tobacco material is cut to form tobacco shreds having dimensions of about 2.5 millimetres by about 2.5 millimetres and the tobacco shreds are loaded into an extraction chamber, without compression. The tobacco starting material is heated within the extraction chamber. During heating, a flow of nitrogen is passed through the extraction chamber at a flow rate of about 40 litres per minute.

For each tobacco starting material, the volatile compounds released during the heating step are collected by absorption into a liquid solvent formed of propylene glycol, at minus 10 degrees Celsius and with agitation of 750 rpm. The solution of propylene glycol with the collected volatile compounds is dried in a desiccation process to reduce the moisture level of the solution to approximately 15 percent. Concentrated solutions of collected volatiles from the tobacco starting materials are collected.

A combined liquid tobacco extract can be prepared. For each of the tobacco starting materials processed as described above, the first tobacco starting material is heated at a temperature and for a period time that is different to the second tobacco starting material. For each tobacco starting material, the volatile compounds released during the heating step are collected and dried. The resultant concentrated solutions of collected volatiles from the first and second tobacco starting materials can be combined at a defined ratio to produce a liquid tobacco extract.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

TABLE 1

Expression of NtINV3 and NtINV4 genes in root, stem, mid-leaf, immature flower, sepal, and petal of Virginia plants grown in the field (RNAseq, FPKM)

|  | NtINV3-S | NtINV3-T | NtINV4-S | NtINV4-T |
|---|---|---|---|---|
| Immature Flower | 2.7 | 1.01 | 31.15 | 25.84 |
| Petal | 0.03 | 0.07 | 70.51 | 51.48 |
| Sepal | 0.03 | 0.01 | 20.35 | 13.57 |
| Bottom Leaf | 0 | 0 | 21.84 | 16.95 |
| Middle Leaf | 0.01 | 0 | 27.52 | 11.86 |
| Upper Leaf | 0 | 0 | 28.54 | 17.71 |
| Root | 0.16 | 0.14 | 4.11 | 2.35 |
| Stem | 0 | 0.01 | 4.57 | 13.29 |

TABLE 2

Figure 2A:
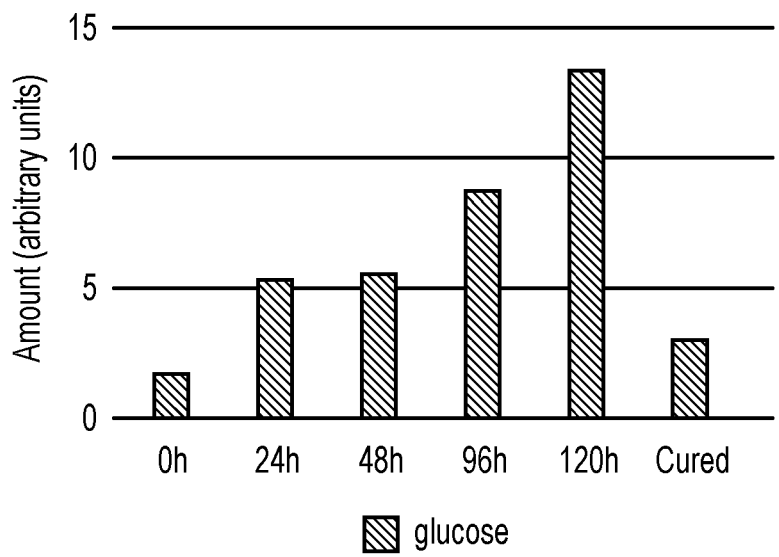
FIG. 2 is a series of graphs showing: (A) evolution of glucose; (B) evolution of fructose; (C) evolution of sucrose during an air-curing time course of a dark tobacco. Data were generated from metabolomic analyses by Metabolon (no available units).
Figure 2B:
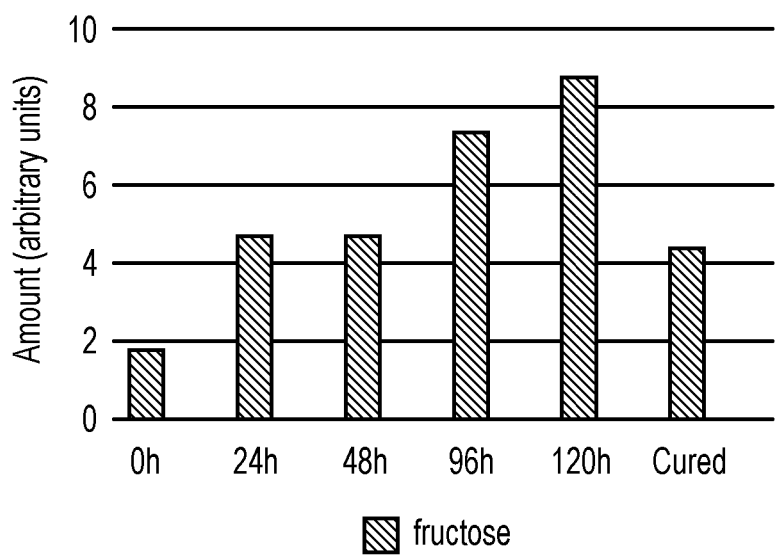
Figure 2C:
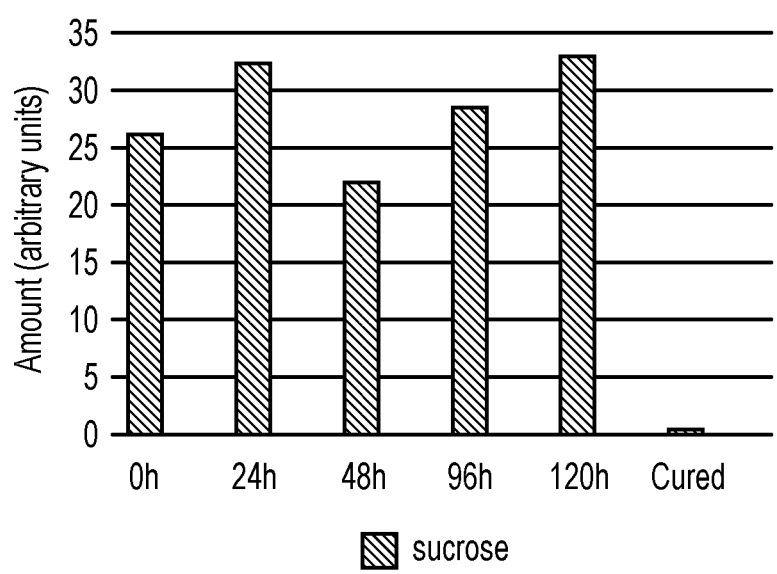

Expression of NtINV3-S, NtINV3-T, NtINV4-S and NtINV4-T during the air-curing time-course of the dark tobacco presented in FIG. 2

|       | NtINV3-S | NtINV3-T | NtINV4-S | NtINV4-T | SAG12   |
|-------|----------|----------|----------|----------|---------|
| 0 h   | 0        | 0        | 12.62    | 22.41    | 13.32   |
| 24 h  | 0.04     | 0        | 11.04    | 37.54    | 235.93  |
| 48 h  | 0        | 0        | 44.15    | 150.72   | 365.38  |
| 96 h  | 0        | 0        | 86.13    | 331.67   | 1445.87 |
| 120 h | 0        | 0        | 152.18   | 335.32   | 102.06  |

TABLE 3

Expression of NtSUS genes during early curing in Burley (BU), Virginia (FC) and Oriental (OR)

|         | BU    |      |            | FC    |      |            | OR    |      |            |
|---------|-------|------|------------|-------|------|------------|-------|------|------------|
|         | Green | Ripe | 48 h curing| Green | Ripe | 48 h curing| Green | Ripe | 48 h curing|
| NtSUS1-S| 3.4   | 0.2  | 0.0        | 10.4  | 0.0  | 0.4        | 3.4   | 0.1  | 0.5        |
| NtSUS1-T| 4.1   | 0.2  | 0.0        | 11.4  | 0.1  | 0.2        | 3.4   | 0.2  | 0.6        |
| NtSUS2-S| 0.2   | 0.3  | 28.5       | 0.3   | 0.1  | 1.7        | 0.6   | 2.3  | 17.8       |
| NtSUS2-T| 4.0   | 1.7  | 5.0        | 2.6   | 0.3  | 0.5        | 2.7   | 2.8  | 3.7        |
| NtSUS3-S| 23.4  | 65.6 | 130.4      | 14.2  | 57.8 | 82.3       | 18.7  | 42.0 | 163.9      |
| NtSUS3-T| 8.5   | 12.2 | 76.5       | 2.4   | 3.2  | 41.2       | 6.1   | 10.7 | 126.7      |
| NtSUS4-S| 11.6  | 4.9  | 22.8       | 15.5  | 3.6  | 22.9       | 19.0  | 18.9 | 105.4      |
| NtSUS4-T| 3.2   | 2.7  | 8.1        | 2.7   | 3.1  | 1.9        | 38.0  | 56.2 | 37.9       |
| NtSUS5-S| 0.6   | 0.2  | 0.1        | 5.1   | 0.1  | 0.5        | 1.4   | 0.3  | 0.8        |
| NtSUS5-T| 0.5   | 0.5  | 0.3        | 3.6   | 0.4  | 0.6        | 1.1   | 0.8  | 1.6        |
| NtSUS6-S| 7.8   | 9.5  | 8.2        | 7.6   | 7.7  | 5.4        | 7.8   | 8.2  | 8.3        |
| NtSUS6-T| 3.1   | 4.2  | 4.7        | 1.6   | 4.3  | 3.2        | 3.7   | 4.9  | 5.0        |

TABLE 4

Expression of NtSUS genes in root, stem, mid-leaf, immature flower (imflower), sepal, and petal of Burley (BU) and Virginia (FC) plants grown in the field

|         | BU    |      |          |          |       |       | FC    |       |          |          |       |       |
|---------|-------|------|----------|----------|-------|-------|-------|-------|----------|----------|-------|-------|
|         | root  | stem | mid-leaf | imflower | sepal | petal | root  | stem  | mid-leaf | imflower | sepal | petal |
| NtSUS1-S| 206.4 | 294.0| 0.9      | 8.2      | 1.6   | 6.4   | 95.7  | 129.1 | 0.7      | 31.7     | 1.1   | 0.7   |
| NtSUS1-T| 170.0 | 348.6| 1.0      | 14.4     | 2.5   | 9.0   | 70.9  | 137.6 | 1.1      | 36.9     | 1.7   | 1.7   |
| NtSUS2-S| 26.4  | 17.0 | 0.4      | 86.1     | 12.9  | 97.9  | 27.3  | 13.5  | 0.4      | 197.3    | 7.7   | 150.3 |
| NtSUS2-T| 61.5  | 55.1 | 2.2      | 96.9     | 37.3  | 172.7 | 4.2   | 12.7  | 0.4      | 122.6    | 12.4  | 111.4 |
| NtSUS3-S| 7.7   | 23.0 | 31.8     | 10.3     | 22.5  | 32.4  | 81.0  | 98.7  | 40.4     | 14.6     | 67.5  | 34.6  |
| NtSUS3-T| 6.7   | 6.4  | 5.0      | 8.8      | 7.9   | 13.7  | 13.9  | 20.2  | 2.8      | 4.7      | 6.8   | 17.7  |
| NtSUS4-S| 26.5  | 40.0 | 8.5      | 19.4     | 14.7  | 23.4  | 30.6  | 43.4  | 6.6      | 31.4     | 10.3  | 34.1  |
| NtSUS4-T| 40.7  | 29.3 | 6.4      | 3.2      | 6.0   | 4.1   | 52.6  | 47.7  | 4.8      | 5.4      | 12.6  | 20.4  |
| NtSUS5-S| 2.6   | 6.5  | 0.5      | 5.6      | 1.4   | 1.1   | 2.2   | 2.2   | 0.3      | 4.4      | 0.5   | 0.4   |
| NtSUS5-T| 2.6   | 5.9  | 0.6      | 5.3      | 1.0   | 1.9   | 2.6   | 2.3   | 1.2      | 3.4      | 0.8   | 1.8   |
| NtSUS6-S| 8.3   | 7.8  | 7.8      | 8.9      | 6.8   | 7.1   | 9.4   | 8.5   | 6.6      | 9.5      | 7.3   | 8.6   |
| NtSUS6-T| 2.7   | 2.4  | 4.1      | 3.0      | 3.1   | 4.9   | 4.0   | 3.4   | 3.6      | 4.2      | 3.2   | 5.2   |

SEQUENCE LISTING

SEQ ID NO 1: Polynucleotide sequence of NtINV3-S atggcggaaacaaacaatagcgttccttacacccaattaccggcggaggacaataacacctccgttaattctccggccggatgccggctacgaccca aaagagtgtcgtttatagtattaacagggctggtggcagctttgttacttttttgtggcagtgaaatatgggaaaaacgaggcggaggatgtgaatcc agggccagtaccaccacaagaaaccgtgtgcaatatgcttggttctaatctaatgccgctgaccagcatgaagacggtggcgcgtggggtggcagaa ggtgtctccgccaagtcacgcggtcgtttcttgggattacggccgtttccatggaccaaacaaatgttggcttggcaaagaacatccttccactttc aacctaagaagaattggatgaatggttagtaattcttttctcttatgttattaattttcataaatcaactttattattattattatacaataaatc aacattgcttattgatgaattttaacataaacccgccttatgcttgacgagattaactagaactatatatacaatgaatgattatctccattccatt acataaccatgaattatgtttcttaattaattaaagatttgacatgacattatatttcgtttatagtttaagaaaagctttgtattgatgtaaaaga -continued

SEQUENCE LISTING

```
aaccattacagcttcgaatatgggatacctttgtctttttcttttcctaagatggatctttgattgcaagaacagagtttgaattactcaggaaactt atttgcttatttattatttttttgaggtgaacattaatgatttattcttatttggcatgtgttggattatttggcttggattgcgctgatcacggaaa ttgcctgattcttttcgtcagatcctaatggtaaagtccatatatttctacttgttattgttgttgttcttcttattattatattattattgaaaat tatcgacataatcgggacctcaaaacatactagtcgtagcagttttttaagtagacagattgtcaatatgatgaagacagttgttttcagacaattgc atgtgaattttctaggagcaaacacaaattcctagaatggtaagcaacttccaccctgtctgttccaattataacctcgctacttttgatccactta atcttattcaaccaacagtggatcacttatttaattatatgtgacctagtttattgagacatttttacattaagcccttttcgtatttacacttcaat atgcatcatacaaaaaaaatgtacttcaaagttatacgttatattaatttctaactccaattttttaaaaaaaaatatattttaggtcccttattct acaaaggatggtaccatttgttctatcaatacaatccagaggctgcagtatggggaaatattgtatgggacatgcagtttcaagagacttaattca ctggcaacaccttccagttgctatggttgcggatcaatggtacgacattaatggtgtatggaccggatccgaaccattttacccgatggtaaactc gtcatgttgtatactgggtcaaccaacgagtcagtacaggttcaaaatttagcgtacccggctgacccatcggatcctctcctaataaaatgggtca agtatgagggcaacccggttcttgtaccaccaccccggaattgctgctaaggatttccgtgaccccaccactgcatggaccacaccacaaggcaaatg gcggattactattggttcaaaagttaataaaaactggaatttcattggtctatgacactattgattttaagaattttgagttgctggatggggtgctc catggtgtatcgggtacgggtatgtgggaatgtgtggattttttacccggtttcgaaagttgttgaaaatgggcttgacacttcagataatgggcctg cagtaaaacatgtgttaaagtccagtcttgatgatgatagaaatgattattatgcacttggaacttatgatgctgtggctggaaaatgggttcctga taatcccactattgatgttggtattggattaagatatgattatggaaattttatgcatcaaaaacattttatgaccaagagaaaagagaagagtc ctttgggcttggattactgaaagtgatagtgaagctgctgatatttgcaaaggttgggcatcacttcaggtacaattcaattgtgtcaagctagcgc ttgcacatagatttagttgaaacctaaaaatgagtatttgaaattccgtagaaaaataattttttgaaagttgaagttgtgtttgaatatgcatttt atttgaaaaaaaaacagttctaattttatgagaaagaaaaattcacctaaaaactgccctaaaccagattttaggaacttgaaaaaaaaataaact ttttcaaaaactgattatattctatgaacaaacaatattatcaaaaatctatttttttttgccaaaatctatggccaaacaggagctaatttcctt tatttttttttttcaaacttcatgtcatatttgaattttggtctcatttaacactttggtaacgtgtgatgtaacacagcccattccaaggactataa aatatgacaagaagacaggaagcaatataattacttggccagtggcagaggttgagaatttgagatttaacagcaaggaattcgacaaggtggaggt caagccaggaaatgttgttccactagaagttggcactgccactcaggtttgttcattaaatttagcttatatacactgactgcctaaaagaatttt ttgacattattagtgtattttaagctattatagcacgtaacatgctaatgctcgaataagtttaacttactataacttgaattgttgatgattacag ttggacataatggctgagtttgaagtagaccctaaggtcttggagaaattagaaggaagtaatgctacatatgagtgcagaagcagcggtggatctg ctgaacgtggtgccttaggaccatttggtttattggttttaacagataagggattgtccgagcaaactccaatttacttctacattgctaaagacgc tgctggaaatttcaecacattcttctgcaatgatcttaccaggttctaatttctcctctcttgcattttcatctcatcaatgaagttttagcccttc accccctcccccaaaaccaaactaataaattggagaaaaccctttattggttcagtgcttaatagcagtacggaattcaggattttaagtcagtggg ttctgcgatctatatatataataatattttctgcacatacatatagtccgagctagacatagtgagttccgttgaacctgttgcatttagtctg agtccgccactgcttaagcacatccttctcataacaaccgagctttccaaaaacttaagtatttctcatgtccatactttttattcatgtttgaaaat gaagtcacattttgttttataaccgaaaaatcccgagggcaagtggccagtacatggttcgaagctcaatggacactggcaccgccccctttatcgtg ctccacttaaatactaagattttgtccgtggcagggtttcaaccaatcacgtacgtttaactcatatattaggaatagcttttaccactagaccaaa actcggggacaatgtatgaagccggatatttgttgcaattctttttaaattaaaatggggacaagatccgagacaaatcttgaaaatgcattacgaa gtattgttaagtaagtatgaaaatggtgattctcatcttttttacttcctttttttaggtcatctgaagcaacagatgttcgcaaactaatctacgaa gcacagttccagtcctccaaggagagaagctttctctaagaacactggtaatatccccttttttctttcttaatttcttaatccaaattcttaattag
```

-continued

SEQUENCE LISTING

```
tgcttgttttcctttgtgcgtataattaagtttactaagtatcaattaatggggtattttttgtcaatgtaataggtggatcattcaatagtagaaag ttttgcacaaaatggaaggacagcaataacatcaaggttatatccaacaaaggcaatatatgaagatgctaagctctacttgtttaacaatgctaca gatgttaccattactgcctcggtcaagatttggcaaatacattctgcaaatatacaatctagttaa
```

SEQ ID NO 2: Polypeptide sequence of NtINV3-S
```
MAETNNSVPYTQLPAEDNNTSVNSPAGCRLRPKRVSFIVLTGLVAALLLFVAVKYGKNEAEDVNPGPVPPQETVCNMLGSNLMPLTSMKTVARGVAE GVSAKSRGRFLGLRPFPWTKQMLAWQRTSFHFQPKKNWMNDPNGPLFYKGWYHLFYQYNPEAAVWGNIVWGHAVSRDLIHWQHLPVAMVADQWYDIN GVWTGSATILPDGKLVMLYTGSTNESVQVQNLAYPADPSDPLLIKWVKYEGNPVLVPPPGIAAKDFRDPTTAWTTPQGKWRITIGSKVNKTGISLVY DTIDFKNFELLDGVLHGVSGTGMWECVDFYPVSKVVENGLDTSDNGPAVKHVLKSSLDDDRNDYYALGTYDAVAGKWVPDNPTIDVGIGLRYDYGNF YASKTFYDQEKKRRVLWAWITESDSEAADICKGWASLQPIPRTIKYDKKTGSNIITWPVAEVENLRFNSKEFDKVEVKPGNVVPLEVGTATQLDIMA EFEVDPKVLEKLEGSNATYECRSSGGSAERGALGPFGLLVLTDKGLSEQTPIYFYIAKDAAGNFTTFFCNDLTRSSEATDVRKLIYGSTVPVLQGEK

LSLRTLVDHSIVESFAQNGRTAITSRLYPTKAIYEDAKLYLFNNATDVTITASVKIWQIHSANIQSS
```

SEQ ID NO 3: Polynucleotide sequence of NtINV3-T
```
atggcggaaacaaacaataagcgttccttacacccaattaccggcggaggacaataacacctccagtaattctccggccaaatgccggcgacgaccca aaagagtgtcgttcatagtattaacagggctggtggcagctttgttacttttttgtggcagtgaaatatgggaataacgaggcggaggatgtaaatcc agggccagtaccaccacaagaaaccgtgtgtaacatgcttggttctaatctaatgccgctgaccaccatgaggacggtggcgcgtggggtggcagaa ggtgtctccgccaagtcacgcggtcgtttcttgggattacggccgtttccatggaccaaacaaatgttggcttggcaaagaacatccttccactttc aacctaagaagaattggatgaatggttagtaattcttttctcttatgttattttcataaatcagctttgttttattaaacaataaatcaacagct tattgataattttaaacataaaaccgccttatgcttgacgagattaactagaactttatgtacaatgaatggttatctccattccattacatgccca tgaattttatgtgtcttaatttaaagatttgacaggacattacattacgtttatagtttaagaaaagcttggtattgatataaaaaaaaccattaca gcttcgaatatgggataccttgtcttttctttgcctaagatggatctttgattgcaagaacagagtttgaattactcaggaaaaatatgaaatcgt tttggaacttatttgcttgttattatttttgaggtgaacattaatgatttattcttatttggcatgtgttggattctttggctttggactgcgtt gctcacggaaattacctgattctgttcgtcagatcctaatggtaagtccatattttctgccggtattattattattattattgttattgttattatt attattattattattaatttattttgatatattggaaaccatcgacaaaacggggacctcaaaacatactagtcggggtagtttgtaagtagacaga ttgacaatatgatgaagacagttgtctttagacaattgcatgtgaattttgtaggagcaaacacaaattcctagaatggtatacaacttcaatcctg tctgtccaattataacctcgctacttttgatccactacacctttttcgatcaacaggggatcacttatttaattatacggaaccctttatataacaa tcatatttgttcccgtattttttaggttttatattgagtggttgttatgcaaatattacaggatttgacgtttaaatattttttggttgttataga taaaaattatctataaataaataatcattcctttttcatgttacatataaaaaataaggaaattatttaaatttaaaatctcacaagctatgcata tttcactaattaaatattaaagaaagttaatacattattaataaattcataactaaaaatataaagatttaaactctaaggcagacattttaaggct accaaaaaataattttttttcaagattgatggaagtggaacaactttgtaattgtagcttgtttcgtagatttcattctcttactagcgatataaca cttgaattggcaaagatccgtgtctaaattttcagcaaaaaggtatccaatagttttccttgaatacaatctaagagtttaaccgttaaattttct atccaagtatttttttaaatttatccaataaaaaagatatcatgtgcaaatctataaatcttatattttatgcaagatagaaactttatttatttta gaattattattagcaatcttaaagattttatatggctgttatagaggggtaattttacaaaaagcgttctgctataaatatggttgttgctgttata ggtaaaaagttgttataaaattgtttatgaaagtcactttactttattttttaactgaaaagtcactatactttgcacattgtaactcaaaagtcaa tcaacacttttagggcgttattaaacattattttttcatatttcttttcagcccaacctttaaaaaataaaaaaaaatatttaaatcatgactcgac ggttccatgacctgacccatttttctcttatttatgttataaaaaacataaatattacttttgttgtagtgtattatattggttctcaatatagttata ctaaatgtatacattggtttaagcaaagtattaaatagagaataaggaattaatcttaacaaactagaggagttagatttgaaactgaaacaagaa attagtagcgttgaagtgaaaaaaaataaaaaggaggaagaaaaaataaaaaaagtatttatgcttgaaattttgactgagaaatattaatataaga gtaaattaaaagacaatatccttgatgttttagaacaagaacgcgcattttagtaaagataatgttactagacgaccatttttagtcgaactaattt aatactttgcttaaatcaatatgttgaaaatcaagacaattaacagtaaagtaatatttacgttttttttgtaacaaaaataagagagtgggtcgagt
```

SEQUENCE LISTING

```
taaagagcgggttgagtcacggtttaaatgggtatttttttattgtttaaatgattgagttaaaaaaaatatgaaaaaaaaatttaatatggccta
aatgtattgagtgacttttgagttacaatgtgtaaagtatgatgactttccttttacaaaacaaagtaaagtgactttcataaacaattttcattag
ttcaatgacttctgagaaatggactccttaaaaaattgattctgaagaaaacttggttttttacggtgaatgactgttatatatgaatgttgttatcg
aaaggtctgactgtatgtgacctagtttattgagacgtttttacattaaagcccttttcgtatttacacttcaatatgcatcatacaaaaaatatgtg
cttcataattatacattacattcatttctaactccacttttacaaaaaatattttaggtccattattctacaaaggatggtaccatttgttctatca
atacaatccagaggctgcagtatggggaaatattgtatggggccatgcagtttcaagagacttaattcactggcaacaccttccagttgctatggtt
gcggatcaatggtacgacattaacggtgtatggaccggatccgcaaccattttacccgatggtaaactcgtcatgttatataccgggtcaaccaacg
agtcagtacaggttcaaaatctagcgtacccggctgacccatcggatcctctcctaagaaaatgggtcaaatatgagggcaacccggtacttgtacc
accaccccggaattgctactaaagattttcgtgaccccaccactgcatggaccacaccacaaggcaaatggaggattactattggttcaaaggttaat
aaaactggaatttcattggtctatgacactattgattttaagaaatttgagttgttggatggggtgctccatggtgtaccgggtacgggtatgtggg
aatgtgtggactttacccggtttcgaaagttgttgaaaatgggcttgacacatcagataatgggcctgcagtaaaacatgtgttaaagtccagtct
agatgatgatagaaatgattattatgcacttggaacttatgatgcagtggctggtaaatggattcctgataatcccacaattgatgttggtattgga
ttaagatatgattatggaaattttttacgcatcaaaaacattttatgaccaagaaaaaagagaagagtcctttgggcttggattactgaaggtgata
gtgaagctgctgatatttgcaaaggttgggcatcacttcaggtacaattcaattgtgtcgaagacaatttagctagtgttgggatatagatttggtt
gaaacttaaaaaaaaaatattttaaaattatggacatgtattttatttgaaaaaaattaaaattctgtgagtggaagaaaaccttttacccaaaaac
taccctaaaccagattttgggaatgtaaaaaaagaatcagatcatattctatgaacaaacaatattatcaaaagttttttaaaaacaattttcaaa
atctatggtcaatttcctcttttattttacttcattttgtcatatttgaattttggtctcatttaacacttggtaacgtgtgatgtaaaacagccta
ttccaaggactataaaatatgacaagaagacaggaagcaacataattacttggccagtggcggaggttgagaatttgagattaaacagtaaggaatt
cgacaaggtggaggtaaaaccagggtcagttttttccactagaagttggcactgccactcaggtttgttgattgaatttaactatacacgtgtaaaag
aatttctttacgttatcggtctattttaaactattatagcacgtaacatgctaatattcgataagtttaacttactataatttgaattgttgatgat
tatagttggacataatggctgagtttgaaatagaccctaaggtcttggagagattagaaggaaataatgctacatatgagtgcagaagcagtggggg
atctgctgaacgtggtgccttaggaccatttggtttattggttttaacagataagggcttgtccgagcaaactccaatttacttctacattgcaaaa
gacgctgctggaaatttcaccacattcttctgcaatgatcttaccaggttctaatttctcctctcttgcattttcatctcatcaatgaagttttagc
ccctccccccaccaaaaccaaactaagaaattggagaaaaacctttattggttcactgcttaatagcagtacggaattcaggattttgagtcatta
ggttctgctctatatatatatatataataatattttttctacacatatatatagttcgagctaaacataatgagttccgtcgaacctgttgcatctag
tctgaatccgccactgcttttaacacatctttctcataataaccactatttccaagagcttaagtatttctcatgtccatacttctatccacgtttaa
aaatgaagtcagattttgttttatatccgagaaatcccgagggcaagtggccagtacatggttcgaagctcaatggacactggcaccgccctttatc
gtgctctacttaaatattaagattttgtctgttgcagggttttaaccaaggacgtacgtttaacccatatataacgagtagcttttaccactagacc
aaaactcggggcaatatatgaagccagatatttgttgcaattctcttaattaaattaaaatggtgacaagatccgagacaaatcttggaagtgcat
tacgtagtattttaagtaagtatgataatggtgattctcatcttttttacttccttttttttaggtcatctgaagcaacagatgttcgcaaactaat
ctacggaagcacagttccagtcctccaaggagagaagctttctctaagaacactggtaattttcattttcttcttttttttaattgcttattcaaaa
ttcttgattatattgcgtacacttaagtttaccaaatataaattaatggggtatttttgtgaatgtaataggtggatcattcaatagtagaaagttt
tgcacaaagtggaaggacagcaataacgtcaagggtatatccaacaaaggcaatatgaagatgctaagctctacttatttaacaatgctacagat
gttagcattactgcctcactcaagatttggcaaatgaattctgcaaatatacaatctagttaa
```

SEQ ID NO 4: Polypeptide sequence of NtINV3-T
MAETNNSVPYTQLPAEDNNTSSNSPAKCRRRPKRVSFIVLTGLVAALLLFVAVKYGNNEAEDVNPGPVPPQETVCNMLGSNLMPLTTMRTVARGVAE
GVSAKSRGRFLGLRPFPWTKQMLAWQRTSFHFQPKKNWMNGPLFYKGWYHLFYQYNPEAAVWGNIVWGHAVSRDLIHWQHLPVAMVADQWYDINGVW
TGSATILPDGKLVMLYTGSTNESVQVQNLAYPADPSDPLLRKWVKYEGNPVLVPPPGIATKDFRDPTTAWTTPQGKWRITIGSKVNKTGISLVYDTI
DFKKFELLDGVLHGVPGTGMWECVDFYPVSKVVENGLDTSDNGPAVKHVLKSSLDDDRNDYYALGTYDAVAGKWIPDNPTIDVGIGLRYDYGNFYAS KTFYDQEKKRRVLWAWITEGDSEAADICKGWASLQPIPRTIKYDKKTGSNIITWPVAEVENLRLNSKEFDKVEVKPGSVFPLEVGTATQLDIMAEFE
IDPKVLERLEGNNATYECRSSGGSAERGALGPFGLLVLTDKGLSEQTPIYFYIAKDAAGNFTTFFCNDLTRSSEATDVRKLIYGSTVPVLQGEKLSL
RTLVDHSIVESFAQSGRTAITSRVYPTKAIYEDAKLYLFNNATDVSTASLKIWQMNSANIQSS SEQ ID NO 5: Polynucleotide sequence of NtINV4-S
atggccacccaccattcccattatgacccggaaaactccacgacccattacactgtcctaccggatcaacccgaatccgccggcgccgggcgccgga
agtctcttaaagttgtctccggcattttgctctcctctttcttttttgctttcttttagtctttgtgatcctcaaccagtcttcagatttatcacaaga
aaactcccgctcgtcggagactttgacgccggcgttgtcacgaggtgtatctcaggagtttccgagaagactttcaaggatgtttccggtagaagc
ctttcgtactacccgtggactaatgctatgcttacttggcaaaggactgcttaccattttcaacctcaaaagaattggatgaacggtaaattttttg
gcttatctttctcttattaattcttttaataaaacatgaattttaagatacttatactggcttttttcttattgattcttatggctattttgttgggg
tatcctatggattctgattggatgatatgctgcagatcctaatggtgagtttacttattaccataattacttttattatttattattcccaaacca
tgattagtgcatccggctattggttaaagattcacaaaaccaataaaatagtaatcttgtcatagtttccataataatctacacgtacgctattgtt
taatgacaagaaatttgacgctcagcatagttaattctctcatatttgtattgtttactttatagcctttgagctaattaattctgggtttctttga
actaaacctttataagttacaatcacacatagatgagttggcacattattcaggctaataatgaaagaaattggattacttgactaatatggcaaat
gcggccaatttaatttggattaacacgatatatgtgtggtaataatgcttttgtgcaacatctctcatacaaggacacatgattaggtgattttgta
ccaagtctcgggaccaatcacaatatatgggtcacaccttatatattattgtaagagttgggacccaccaaggatttgtctgtcttccaactagcc
acttgtcttttctcttttttatattttaaatgaaatggtgtgggtttttattttgggtcgatctaaccgcttctgcctattatcaatttagcc
ttgtgattgtgagaatagaagagagaaatagaggataataataataaggataagaattaagaacgtaccttcttattgtcgaaattatttgagaaga
ctattcattgttctgattagtgtccatcgatgtcccttcctcctttttctatcttggagaggtttcctcttctttgttttacttttccttttcta
aatatgcattccaaaatcttaacactactcgaacgtccattcttggaaagtctctttgaaagtttagggcaacatcattcggacaacttaattagca
ttcactattaaaaattaatagaacagaaaagttcatgtatttttttaggagagtaagaggcggattcagaatttaaatcttatgtgtttagttttt
aaaatttttaggattgataactgaacatggcgagaaacatgaacatgtgacataaattccgtgtttcaacactaaacaggtccattataccacaaag
gatggtaccatctttttatcaatacaatcctgattcagctgtttggggaaatatcacatggggccatgcaatatccacggacttgatccactggct
ttacttgcctttcgccatggttccgatcaatggtacgatatcaacggtgtctggaccgggtccgcgaccatcttcccgacggtcagatcatgatgc
tatacaccggtgataccaatgattacgtgcaggtgcaaaatcttgcataccctgctaacttatcggatcctctcctcatcgactgggtcaagtacca
ggacaatccggtcatggttcccccacccggcattggtgtcaaggacttcagagacccgacaactgcttggaccggaccccaaaacgggcagtggctg
ctaaccatcgggtccaagattggtaaaacgggtattgcacttgtttatgatacgtccaacttcacaaactttaagctattggatggagttttgcatg
cggttccgggtacgggtatgtgggagtgtgtggacttttaccccggtatcaaccgttgaggcaaacggggtggacacatcatataacgggccaggtat
aagcatgtgttaaaagcaagtttagatgacgataagcatgattactatgctattgggacatatgacccggtaaagaacaaatggactcctgataacc
cggaattggatgtgggtatcgggttgagactggactacgggaaatactatgcgtcaaagacattttatgacccgaaagaacaaagaagaatattgtg
gggatggattggagaaactgacagtgaagctgctgatctgctgaagggatgggcatctgtacaggtatggactcttttaagtacactacctcagcat
ccgaagagcattacacttttatttttgttttacattagaccacatgaatgggtgttttggcataactggtaaagttgttgccatgtgaccctgaggt
cacgggttcgagccgtagaaatagcctcttgcagtaatgtaataaactcttagtgcatagggttgcctttttattagaccacacacatgttcaagt
tatgtcatgttagtcgtgtcaattttttgtgaaatcaatttactgcacctcaatcttgaattagttgagactagctataggaacctttgtattgag
aggacttatcataatttgatcattttttgcactaactgtcacactatgatattcactttctttatccagtttagtagtgtgccaatacaccttaagca
cgtgacaagaatttattagcagggtcatctcgatttatgtaggagtacagaattgaattgaatcttttcttctagtaaattctcaattgcaacttg
acaatgaagttttcagatgcaaaaagatgaaatatctctaataatttccttttccaataacagagtattccaaggactctgctttatgacaagga
gacaaggacacatgtacttcagtggccagttaaagaaattgagagcttaagaattggtgatcctctagtgaaacaggtcaatcttcaaccaggctca
attgagcttgtccatgttgactcagccgcacaggtttgctttctcatccttcgaaattgaaaacgtttcacttatatgtgcttgatgtacagtccta
aaacttgtatgcgcaatggtgcagtggatgtagaagcctcatttgaagtggacaaagcagcactcgcgggaacaattgaagcagatgtggtttcaa

SEQUENCE LISTING

```
ctgcagtactagtggaggtgctgctaaaagaggcatttttgggaccatttggtgtcgttgtaattgctgatcaaacgctttctgagctaaccccagtt
tacttctacattgccaaaggaactggtggccgagctgaaacctacttctgcgctgatgaaactaggtttgcttctactatgtttatcttgtatactc
tatcttaatagtccttgtcaaagtatagaggaataacatagcggcgtgatctgatgcagatcctcagaggctcctggagttgctaaacaagtgtatg
gtagttcagtaccagtgttagatggtgaacaacactcaatgagattattggtaagtgataatccctttattctgactttcttcaaatcaagaataat
atcaagcttattagttcttccagtcatcttacttaatttgtggaaatgctccaaagtagtcaatttggtaactattcaagataatgtggttcagaat
aatttgtgttatgaatgtatttgacagttgggatgatctgtttttttagtaaaatttcttaaaaacttaattcaggtggaccactcaattgtggaaag
ctttgctcaaggaggaagaacagtcataacatcgcgaatttacccaacaaaagcaatcaatggagcagcacgactgttcgttttcaacaatgccacc
ggggctagtgtgactgcctccctcaagatttggtcactcaaatcagctgatattcgatcctccccttggaccagttgtaa
```

SEQ ID NO 6: Polypeptide sequence of NtINV4-S
```
MATHHSHYDPENSTTHYTVLPDQPESAGAGRRKSLKVVSGILLSSFFLLSLVFVILNQSSDLSQENSRSSETLTPALSRGVSQGVSEKTFKDVSGRS
LSYYPWTNAMLTWQRTAYHFQPQKNWMNDPNGPLYHKGWYHLFYQYNPDSAVWGNITWGHAISTDLIHWLYLPFAMVPDQWYDINGVWTGSATILPD
GQIMMLYTGDTNDYVQVQNLAYPANLSDPLLIDWVKYQDNPVMVPPPGIGVKDFRDPTTAWTGPQNGQWLLTIGSKIGKTGIALVYDTSNFTNFKLL
DGVLHAVPGTGMWECVDFYPVSTVEANGLDTSYNGPGIKHVLKASLDDDKHDYYAIGTYDPVKNKWTPDNPELDVGIGLRLDYGKYYASKTFYDPKE
QRRILWGWIGETDSEAADLLKGWASVQSIPRTLLYDKETRTHVLQWPVKEIESLRIGDPLVKQVNLQPGSIELVHVDSAAQLDVEASFEVDKAALAG
TIEADVGFNCSTSGGAAKRGILGPFGVVVIADQTLSELTPVYFYIAKGTGGRAETYFCADETRSSEAPGVAKQVYGSSVPVLDGEQHSMRLLVDHSI
VESFAQGGRTVITSRIYPTKAINGAARFVFNNATGASVTASLKIWSLKSADIRSFPLDQL
```

SEQ ID NO 7: Polynucleotide sequence of NtINV4-T
```
atgatgttatacaccggtgataccaatgattacgtgcaggtgcaaaatcttgcgtaccccgccaacttatcggatcccctcctcatcgactgggtca
agtaccggggcaacccggtcatggttccaccaccggcattggtgtcaaggactttagagacccaacgactgcttggaccggaccacaaaacggca
gtggctgcttaccatcgggtccaagattggtaaaacgggtattgcaattgtttatggtacttccaacttcacaaactttaagctattggatggagtt
ttgcatgcggttccgggtacgggtatgtgggagtgtgtggacttttacccggtatcaaccgatgaggcaaacgggttggacacatcatataacgggc
caggtataaagcatgtgttaaaagcaagtttagatgacgataagcatgattactatgctattgggacatatgaccggtaaagaacaaatggactcct
gataacccgcaattggatgtgggtatcggttgagactggactacggaaatactatgcgtcaaagacattttatgacccgaaggaacaaagaagaa
tattgtggggatggattggggaaactgacagtgaagctgctgatctgctgaagggatgggcatctgtacaggtatggacacttttcaagtacactac
ctcagcttccgaagagcattacacatttatttttgtattacattagggtgccttggcgtaactctggtaaagtaagttctgaattgcaacgtgaaaa
tggaggttttttagatgcaaagagatgatatatccctaatagttttcctgttttaataacagagtattccaaggactgtgctttatgataaggagact
aggacacatgttcttcagtggccagttaaagaaattgagagcttaagaattggtgatcctctagtgaaacgggtcaatcttcaaccaggctcaattg
agctagtccatgttgactcagccgcacaggttgcttttctcatccttggaaattgaaaacgtttcacttatatgtgcttaatgtgcagtcctaaaact
tgtatgtgcaatggtgcagttggatgtagaagcctcatttgaagtggacaaagcagcactcgagggaacaattgaagcagatgttggtttcaactgc
agtactagtggaggtgctgctaaaagaggcatttttgggaccatttggtgtcgttgtaattgctgatcaaacgctttctgagctaactccagtttact
tctacattgccaaaggacctgatggccgagctgaaacctacttctgctgatgaaactaggtttgcttctactatgtttatcttgtatactctatc
ttaatagtccttgtcaaagtatagatgaataacatagcggcgtgatctgatgcagatcctcagaggctcctggagttgctaaacaagtgtatggtag
ttcagtaccagtgttagatgatgaacaacactcaatgagattattggtaagtgataatcccgttattctgaccttcgtcaaatcagaataatatcaa
gcttattagttcttccagtcatcttattaaatttatggaaatgctccaaagtagtcaatttggtaactattcaagataatgtggttcagaataatttt
gtgttatgaatgtatttgacagttgggatgatctgtgttttgagtaaaatttcttaaaaactgaactcaggtggaccactcaattgtggagagctttt
gctcaaggaggaagaacagtcataacatcgcgaatttacccaacaaaggcaatcaatggagcagcacgactgttcgttttcaacaatgccacgaggg
caaggtgactgcctccctgaagatttggtcactcgaatcagctgatattcgatcctccccttggaccagttgtaa
```

SEQ ID NO 8: Polypeptide sequence of NtINV4-T
```
MATHHSHYDPENSTTHYTVLPDQPESAGSGHRKSLKVVSGILLSSFFLLSLVFVIVNQSSDLSQKNSHSSETLTPALSRGVSQGVSEKTFRDVSGGS
LSYYPWTNAMLTWQRTAYHFQPQKNWMNGPLYHKGWYHLFYQYNPDSAIWGNITWGHAISTDLIHWLYLPFALVPDQWYDINGVWTGSATFLPDGQI
```

| SEQUENCE LISTING |
| --- |
| MMLYTGDTNDYVQVQNLAYPANLSDPLLIDWVKYRGNPVMVPPPGIGVKDFRDPTTAWTGPQNGQWLLTIGSKIGKTGIAIVYGTSNFTNFKLLDGV |
| LHAVPGTGMWECVDFYPVSTDEANGLDTSYNGPGIKHVLKASLDDDKHDYYAIGTYDPVKNKWTPDNPQLDVGIGLRLDYGKYYASKTFYDPKEQRR |
| ILWGWIGETDSEAADLLKGWASVQSIPRTVLYDKETRTHVLQWPVKEIESLRIGDPLVKRVNLQPGSIELVHVDSAAQLDVEASFEVDKAALEGTIE |
| ADVGFNCSTSGGAAKRGILGPFGVVVIADQTLSELTPVYFYIAKGPDGRAETYFCADETRSSEAPGVAKQVYGSSVPVLDDEQHSMRLLVDHSIVES |
| FAQGGRTVITSRIYPTKAINGAARLFVFNNATRSVTASLKIWSLESADIRSFPLDQ |
| SEQ ID NO 9: Nucleotide sequence used for silencing NtINV4-T and NtINV4-S |
| ggtttcaactgcagtactagtggaggtgctgctaaaagaggcattttgggacctttggtgtcgttgtaattgctgatcaaacgctttctgagctaac |
| SEQ ID NO: 10: Polynucleotide sequence of NtSUS1-S |
| atggcagctagtggtcttagcattaagaaaagtttggaggaatccattttggctcatccagatgaaattttggctctcaagtcaaggtacattacta |
| catataatgatattaagaactagaggcttatccaaggttttgttacattttttgaaattataagtttagaacctaatagtacttggtagcacttgttt |
| ccttattatctagctgttgttactgcttgttgctactgctttctgttcatctttccttgagcccggtctatcggaaacaacctctctattctcaaag |
| tataaggtttgcgtacatactacctccccagactctacttgtggaatttactgttttgttgtgttgttgtaatctaatatttattagaattttact |
| gattttttcacatatatatatctatgtccctgtcgaaaattctatagctcatgttagctaaatacattagtaccattgttttttaattgttttggttt |
| tggcacaggattgaaactgaagggaaaggggtaatgaaaccacttgatctcttgaaccatttggtttctgttactagtaagacaaatggagtaaata |
| ttgtacctagtgcacttgtggaagttctcagttgcagccaagaagctgtgattgtaccaccaaaactagcactagctgtacgtccgaggcccggtgt |
| atgggagtacttgtcactgaatcttaagacaaagaaagtggctgaattaagcattcctgaataccttcaattgaaagagaacactgttgatgaaagg |
| taaagtattagtctgcgatttcgctttgtgaaattgaagttttttgttttgattcataatgttttgtgtatcaattatgttaccagtggaaacatatt |
| ggagttggattttgagccatttacaacagttacaecaccaaaaacacttttctgactctattggcaatggtttggagtttcttaatcgccacattgct |
| tcgaaaatgtttcatgataaggagatttccagatgcctccttgacttcctcagaaaccataactacaaaggaaaggtaataaaaaaaagtgtttctt |
| taaacaagttgtatgattatgtgtatatttctaagtatgttaacttgaaaacagtcattgatggtgaaagaaagcattcaaagcctagagagtttcc |
| aacttgttctgaaaaaagcagaggaacatttgtgcacattgaatccagaaactccatactccaattttgaatcaaagtttgaagagattggcttgga |
| agagggtggggaaacaccgctgaacgcgtgcaagacactatcagtcatcttttgcatctccttgaggctcctaacgcgtcttctttggaaaatttc |
| cttggtagaatcccattggttttcaatgttgtgattctaactccacatggttattttgctcaagataatgtcttgggctatcctgacactggtggcc |
| aggtttgtgtccaatattttgcattcttgatcaagttctttataccatttgaaccaacaatcttnaacattcttttttttggttgtgaaatgttgaat |
| aggttgtttacattcttgatcaagttccagctatggagcgtgagatgcttcatcgtatgaagcttcaaggactcgatgatatcatccctcgcatcct |
| tgttgtaagtggccttaattttcctagtttcatttacacctctaaatgaaattgatcttttttgttgttttatatcaggtaacaaggctgctgcctg |
| atgcagtaggaaccacctgtggcgagcggatggagaaagtatatggggcagaacattctcatataattcgtgttccatttagaactgagaagggaat |
| gttgcgcaaatggatctcacgattcgaagtctggccatacatggaaactttcactgaggttggaacataaaaacaaataaaatccattggaatgttc |
| cttctgcaattgaaaatgtcttgctaactgaagacccattttttaaattgatcatcaggatgttgcagaagaacttgtcaaagaattgcaagctaaac |
| cagacttgatcattggaaactacagtgagggaaatcttgctgcctcttttgcttgcgaagaaatttggggctactcagtgtactattgctcatgcctt |
| ggaaaaaactaagtatccaaactctgaccttaattggaagaagtttgatgacaagtatcatttctcaagtcagttcactgctgatctctttgccatg |
| aatcacactgatttcatcatccagcactttccaagaaattgctggaaggtaaaagcaaatgcacaccatcatagtatttcatattttaccccttg |
| tttatactatttccattcaccgaccccgacttgtttaggattgagccatagttgttgttgttgtttgtttatactatttccatttgccgaccacaac |
| ttgtttaggactgaggtatagttgttgttgttggtttgttcatattattttcattcgctaaccctaacttgtttgggactgaggcatagtagtagta |
| gtagttgttgctattagtttatactatttccatttgccaaccccaacttgtttggtactgagacatagttgttgttgttgtttgtttatactat |
| ttccatttgccgaccccaacttgtttaggactgaggtatagttgttgttgttggtttgttcatattattttcattcgctaaccccaacttgtttggg |
| actgaggcatagtagtagtagtagtagttgttgctattagtttatactatttccatttgccaaccccaacttgtttggtactgagacatagttgttg |
| ttgttgtttgtttatactatttcaattgtcgaccccaatttgtttgggaccaaggcatggttgttgttgttgtttgttttactgtttccat |
| tgatattggaacatttgttatttgcagcaaaaacactgtaggacagtatgagagtcatactgcttttaccatgcctggattgtaccgagtagtccat |

-continued

SEQUENCE LISTING

```
ggaatcgattcgtttgatccaaagttcaacattgtctccctggggctgatatgtcaatctacttcccttacactgagaaggagaaaaggctaacca acttccacccggaaattgaagaactcctctacagtcctgttgagaataaggaccacttgttagtctccttaatttgcttttatttcatcccatttat gatcgcttttatcccaacagatcgattaatcatttgttatcaacataaacagatgtgtgttgaaggaccggaacaagccaattctctttaccatggc aaggctagatcgcgtgaagaatctaacagggctcgtggaatggtatgctaagaatgcaaggctgagggagcttgttaaccttgtggttgtaggcgga gacagaaggaaagaatccaaagatttagaagagcaagcagagatgaagaagatgtatgatcttatcgaaacctataacctgaacggccaattcaggt ggatttcttcccaaatgaatcgtgtgaggaacggagaactctatcgttacattgcagacacgaggggtgctttcgttcaaccagcattctacgaggc ttttggtttgacagttgtagagtctatgacttgtggtttgccaacttttgctacttgtaatggtggaccatttgagattatagtgaatgaaaatct ggtttccatattgatcctaatcaaggtgacaaggctgctgatatgttggtaaatttctttgaaaaatctaaagaagatccaagttattgggatgcta tttccaagggaggtctgcaacgtattcttgaaaagtaagcttttgcatttgattagcacaagtgcacaaccaagatttaacttttgaacaaactaaa actaaccctttttgtattttcttttgctaggtatacatggcaaatttattcacagaaagtgatcacactatctgggatttatggattctggaagta tgcaaccaagaatgataaagttgctagtgcaaagaagcgctatcttgagatgttttatgaacttggatttaagaaatcagtaagtgtcaattttaaa ggggaaccttggatcaacggttaagttgtctttgtgcaacctataggtcaggggtttgagccgtagaagtagccactaatatttacattagggtaga ctgtgtacatatcacaccccttggggtacggccctttcctggatcctgtatgaacgcgggatgccttgtgcaccgggctgtattttttttttagtg tcacttctgtattttgtttgagcttgtttataaagtttggaaatctgctgctaatttgtatatttgttggttgtgtatttcaggctgagaaagttcc attggctattgatgaatag
```

SEQ ID NO: 11: Polypeptide sequence of NtSUS1-S
```
MAASGLSIKKSLEESILAHPDEILALKSRIETEGKGVMKPLDLLNHLVSVTSKTNGVNIVPSALVEVLSCSQEAVIVPPKLALAVRPRPGVWEYLSL
NLKTKKVAELSIPEYLQLKENTVDESGNILELDFEPFTTVTPPKTLSDSIGNGLEFLNRHIASKMFHDKEISRCLLDFLRNHNYKGKSLMVKESIQS
LESFQLVLKKAEEHLCTLNPETPYSNFESKFEEIGLERGWGNTAERVQDTISHLLHLLEAPNASSLENFLGRIPLVFNVVILTPHGYFAQDNVLGYP
DTGGQVVYILDQVPAMEREMLHRMKLQGLDDIIPRILVVTRLLPDAVGTTCGERMEKVYGAEHSHIIRVPFRTEKGMLRKWISRFEVWPYMETFTED
VAEELVKELQAKPDLIIGNYSEGNLAASLLAKKFGATQCTIAHALEKTKYPNSDLNWKKFDDKYHFSSQFTADLFAMNHTDFIITSTFQEIAGSKNT
VGQYESHTAFTMPGLYRVVHGIDSFDPKFNIVSPGADMSIYFPYTEKEKRLTNFHPEIEELLYSPVENKDHLCVLKDRNKPILFTMARLDRVKNLTG
LVEWYAKNARLRELVNLVVVGGDRRKESKDLEEQAEMKKMYDLIETYNLNGQFRWISSQMNRVRNGELYRYIADTRGAFVQPAFYEAFGLTVVESMT
CGLPTFATCNGGPFEIIVNGKSGFHIDPNQGDKAADMLVNFFEKSKEDPSYWDAISKGGLQRILEKYTWQIYSQKVITLSGIYGFWKYATKNDKVAS
AKKRYLEMFYELGFKKSAEKVPLAIDE
```

SEQ ID NO: 12: Polynucleotide sequence of NtSUS1-T
```
atggcaggcagtggtcttagcattaaggaaagtttggaggaatccatttggctctcaagtcaaggtacattactg cataatgatattaagacctagaagcggatccaagatttttgttacattttgaaattataagtttagaatctaatatttgttatcgcttgtttcctta ttatcttgctgttgttactgcctgttgctactagtttctgttcatccttccttgagctgagtttctatcggaaacaacctctctactctcaaagtag gaataagttatgcgtacacactaccctccccagactccacttgtgtaatttactgagtttgttgttgttgttgtaatctaatacttgttagaat tttactgattttcacatatatctatgacccatgtcgaaaatactatagctcatgtgctaaatacattagtaccattgttttgtaattgttttgg ttttggaacaggattgaaactgaagggaaaggggtaatgaaaccagttgatctcttgaaccatttggtttctgttactagtaaaacaaatggagtaa atgttgtacctagtgcacttgtggaagttctcagttgcagccaagaagctgtgattgtaccaccaaaactagcactagctgtacgtccgaggcccgg tgtatgggagtacttgtcactgaatcttaagacaaagaaagtggctgaattgagcattcctgagtaccttcaattgaaagagaatactgttgatgaa aggtaaagtaatagtctgcgatttcgctttgtgaaattgaagttttttgtttgattcttaatgttttgtgtatcaattatgttaccagtggaaacat cttggagttggattttgagccatttacaactgttacaacaccaaaaacactttctgactctattggcaatggtttggagtttcttaatcgccacatt gcttcgaaaatgtttcttgataaggagattgccaagtgcctccttgactttctcagaaaccataactacaaaggaaaggtagtaaaaaaagtgtttc tttaaacaagttgtatgattatgtgtgtatttctaaatatgtcaattttgaaaacagtcattgatggtgaaagaaagcattcaaagcctggagagttt ccaacttgttctgaaaaaagcagaggaatatttgcacacactgaatccagaaactccatactccaaatttgaatccaagtttgaagagattggcttg
```

SEQUENCE LISTING

```
gaaagagggtggggaaacaccgctgaacgcgtgcaagacaccattagtcatcttttgcatctccttgaggctcctaacgcgtcttccttggaaaatt tccttggtagaatcccattggttttcaatgttgtgattctcaccccacatggttattttgctcaagataatgtcttgggctatcctgacactggtgg ccaggtttgtgtccgatataacatatcaagaaattttgcattcttgatcatgttctttataccatttgaaccaacattcttttttttggttgtgaaat gttgaataggttgtttacattcttgatcaagttccagctatggagcgtgagatgcttcatcgtatgaagcttcaaggactcgacgatatcatccctc gcatccttgttgtaagtgcccttaattttcctggtttggtttacctctaaatgaaattgattttctggctttctaacttttttggattgatcttttt gttgttttatatcaggtaactaggctgctgcctgatgctgtaggaaccacttgtggcgagtggatggagaaagtatatggggcagaacattctcata taattcgtgttccatttagaactgagaaggaatgttgcgcaaatggatctcacgattcgaagtctggccatacatggaaactttcactgaggttgg aacataaaaacaaataaaaatcattggaatgttcttctgcatttgaaaatgtcttgctaactaaagactcatttttaaattaatcatcaggatgttg cagaagaacttgtcaaagaattgcaagctaaaccagacttgataattggaaactacagtgagggaaatcttgctgcctcattgcttgctaagaaatt tggggctactcagtgtactattgctcatgccttggaaaaaactaagtatccaaactctgaccttaattggaagaagtttgatgacaagtatcatttc tcaagtcagttcactgctgatcttttgccatgaatcacactgatttcattatcaccagcactttccaagaaattgctggaaggtaaaagcaaatgc acaccatcatagtatttcatattttttaccctagtttatactatttccatttgtcaactccaacttgtttgggattgaaccatagttgttgtttgttt atactatttccattcgccgaccccaacttatttgggactgagacataattgttgttattattgtttgtttgtttatactatttccattctcagaccc caacttctttgggactgagccgtagattgttgttgttgttgttgttgtttgtttatgctatttccgttcaccgaccccaacttatttgggactg aggtgtagaagtagtcgttgttgtttgtttatacgacttccaattgatattcgaatgttttattttttgcagcaagaacactgtaggacagtatgag agtcatactgcttttaccatgcctggattgtatcgagtagtccatggaatcaattcgtttgatccaaagttcaacattgtctcccctggggctgata tgtcaatctacttcccttacactgagaaggagaaaagactaaccaacttccacccggaaattgaagaactcctctacagtcctgttgagaataagga ccacttgttagtcttctttatttcattcatttttctacacctttttttttcaacagattgattgattggttcttatcaacgtaaacgatgtgtgttg aaggaccagaacaagccaattctctttaccatggcaaggctagatcgcgtgaagaatctaacagggctcgtggaatggtatgcaaagaatgcaaggc taagggagctcgttaaccttgtggttgtaggcggagacagaaggaaagaatccaaagatttagaagagcaagcagagatgaagaagatgtatgatct tatcgaaacatacaacctgaatggccaattcaggtggattcttcccaaatgaatcgtgtgaggaacggagaactttatcgatacattgcagacacg agggggtgcttcgttcaaccagcattttatgaggcatttggttgacagttgttgagtctatgacttgtggtttgccaacttttgctacttgtaatg gtggaccatttgagattatagtgaatggaaaatctggtttccatattgatcctaatcaaggtgacaaggctgctgatatgttggttaatttcttcga aaaatctaagaagatccaagttattgggatactatttccaagggtggtctgcagcgtattcttgaaaagtaagcttttgcatttgattagcacaag tgtacaaccaagatttaacttatgaacaaactaaaactaacccttttttatttcttttgctaggtatacatggcaaatttattcacagaaagtga tcacattatctgggatttatggattctggaaatatgcaaccaagaatgacaaagttgctagtgcgaagaagcgctatcttgaaatgttttatgaatt tgggtttaagaaatcagtaagtgtcacttctgtattttgtttgagcttgtttgtaaagtttggcaatcttctgctaatttgtactatatttgttgac ttgtgcatttcaggctgagaaagttccattggctattgatgaatag
```

SEQ ID NO: 13: Polypeptide sequence of NtSUS1-T

MAGSGLSIKESLEESILAHPDEILALKSRIETEGKGVMKPVDLLNHLVSVTSKTNGVNVVPSALVEVLSCSQEAVIVPPKLALAVRPRPGVWEYLSL

NLKTKKVAELSIPEYLQLKENTVDESGNILELDFEPFTTVTTPKTLSDSIGNGLEFLNRHIASKMFLDKEIAKCLLDFLRNHNYKGKSLMVKESIQS

LESFQLVLKKAEEYLHTLNPETPYSKFESKFEEIGLERGWGNTAERVQDTISHLLHLLEAPNASSLENFLGRIPLVFNVVILTPHGYFAQDNVLGYP

DTGGQVVYILDQVPAMEREMLHRMKLQGLDDIIPRILVVTRLLPDAVGTTCGEWMEKVYGAEHSHIIRVPFRTEKGMLRKWISRFEVWPYMETFTED

VAEELVKELQAKPDLIIGNYSEGNLAASLLAKKFGATQCTIAHALEKTKYPNSDLNWKKFDDKYHFSSQFTADLFAMNHTDFIITSTFQEIAGSKNT

VGQYESHTAFTMPGLYRVVHGINSFDPKFNIVSPGADMSIYFPYTEKEKRLTNFHPEIEELLYSPVENKDHLCVLKDQNKPILFTMARLDRVKNLTG

LVEWYAKNARLRELVNLVVVGGDRRKESKDLEEQAEMKKMYDLIETYNLNGQFRWISSQMNRVRNGELYRYIADTRGAFVQPAFYEAFGLTVVESMT

CGLPTFATCNGGPFEIIVNGKSGFHIDPNQGDKAADMLVNFFEKSKEDPSYWDTISKGGLQRILEKYTWQIYSQKVITLSGIYGFWKYATKNDKVAS

AKKRYLEMFYEFGFKKSAEKVPLAIDE

-continued

SEQUENCE LISTING

SEQ ID NO: 14: Polynucleotide sequence of NtSUS2-S
atggctgaacgtgctctgactcgtgttcacagccttcgtgaacgtcttgatgccactttggctgcacatcgcaatgagatattgctgtttctttcaa
ggtattgcctaagtagtgttcttgtttcctacaaaagattcagttggtgttcaaaaaacgatatgtgatttgatttatctgcctaagtcttggtagt
cataattatccggtacctgtgctggtgcgagttagctggttcggaaactactcttatgaaaacgagagatttagttggtgttgtctgcaattctgta
gtatggactattaagcagatagatcatgtttgatatcgaaaaggaatgtatatgtgatgttacttgaactggttttggttattacaggattgaaagc
catggaaaagggatcttgaaacctcaccagctattggctgagttcgatgcaattcgccaagatgacaaaaagaagctgaatgatcatgcatttgaag
aactcctgaaatctactcaggtaattttgattttggctaaatgtgttaccaagctgaatgatcatgcatttgagtttgtgtccgactactacaatga
tatgttataccaggaagcgattgttctgccaccttgggttgcacttgccattcgtttgaggcctggtgtgtgggaatatgtccgtgtgaatgttaat
gctctagtcgttgaggagctgaccgtccctgagtatttgcattttaaggaagaacttgttgatggaacgtaagttttagtctcttatttgatactat
gttagagaataggcagtggattcaatttatcagtgttgttttttacctaatgcagctccaatggaaaatttcgttctcgagttggattttgagcccttt
cactgcatcctttcctaaaccgaccctcaccaaatctattgggaatggagttgaattcctcaataggcacctttctgcgaaaatgttccatgacaag
gaaagcatgaccccgcttcttgaatttcttcgggttcacaattataagggcaaggtaactttgttattcccattcatatatatgttcagtttgtgct
tatcatgcgcccaatgatgtatgaatatgtactaaaggatagatgtacgatttcgtttgcagacaatgatgctgaatgacagaatacagaatttaac
cactctgcaaaatgtcctaaggaaggcagaggaataccttattatgcttcccctgaaactccattttccgaattcgaacacaagttccaagaaatt
ggattggagaagggatggggcgacactgcggagcgcgtgctagagatgatatgcatgcttcttgatctacttgaggctcccgactcctgtactcttg
agaagttcctagggagaattcctatggtgttcaacgtggttatccttccccccatggatatttcgcccaggaaaatgtcttgggttatcccgacac
tggtggccaggtgcattactttagtctttgtccgtgagtctatgttgctcagatcctctacaatgccactgtacccgtgtaggatactccaaatata
atgcattttggaggatctgtcaccggtgcaatggcattttggaggtcggagcaacaaacaactgctagtatgcttctaaagcttgcttccataaat
gctaaggtccttcacccgtaatgtgcaggttgtctacatattagatcaagttccagccttggagcgtgaaatgcttaaacgcctaaaggagcaagga
cttgatataacaccgcgtattcttattgttagtatttcttgtacttgtaattgctgcggattacacaaaattttctctttattggcaacttatcttg
atattattcccaggttactcgtctgctgcctgatgcagttggaacaacttgtggtcagcggcttgagaaggtgtatggagccgagcactcacatatt
cttagggtccccctttaggaccgagaagggcattgttcgcaaatggatatctcgctttgaagtgtggccatacatggagactttcactgaggtgacac
taagcttccttgtatttgtctatcttctaattggtattaggaacaatttgctaattattaacgctttggcttttcgtacatcaggatgttgcaaaag
aacttgctgcagaactgcaggccaagccagatttgataattggcaactatagcgagggaaatcttgtggcttcattgctggctcacaagttaggcgt
aacgcaggtctgtgttattttttcacctcttataaatctgattgtatttccattagtctggaactaaaagtactaaaattttcttttcttcgctgtgt
tatttgccttctgcagtgcaccattgcccatgcattggagaaaacaaagtatcctgattctgacatctactggaaaaaatttgacgaaaaataccat
ttctcgtcccagtttaccgctgatcttattgcaatgaatcacaccgatttatcatcaccagcactttccaggagatagcaggaaggtataacatca
attgctaattcggttgcagtaacattttgttcgatttcttccccttatgcttaacctaataccctaatgaattttccagcaaggacactgtcggaca
gtacgagagtcaccaggcattcacaatgcctggattgtacagagtcgttcacggcattgatgtgttcgatcccaaattcaacattgtctcacctgga
gctgatataaacctgtatttcccatattccgagaaggaaaagagattgacagcacttcacccagaaattgaggagcttctgtacagtgatgttgaga
acgaggaacatctgtaagtttctaacttactcgtaccgtcagtggcagagccagaattttcattaaaatggggtcaaaatataaagacataaattca
caaagaagccaaggggtgtcaatatgtagtataaatatattaaaaaaattacctagctacacaatgtaattttccgacaagggggtatcggttgcac
ttcttgaatacatgtggctctgccactgggtacagttacaaagtcctgttacctatgtagatgagcttgtgctgaacatgttgtgattttggtaggt
gtgtgctaaaggacaggaataagccaatcttattcacaatggcgagattggatcgtgtgaagaacttaaccggacttgttgagtggtacgccaagaa
cgcacggctaagggagttggttaacctttgttgtcgttggtggagaccgaaggaaggaatccaaagatttggaagagcaagcagagatgaagaagatg
tatgagctaataaagactcacaacttaaatggccaattcagatggatttcttcacagatgaaccgagtaaggaacggcgaactctaccgatacattg
ccgacactaggggagctttcgtgcagcctgcattctatgaggctttcggtttgactgttgttgaggccatgacctgtggtttgcctacatttgcaac
taatcatggcggtccagctgagatcatcgttaacggaaaatccggcttccatatcgatccatatcacggtgagcaagctgctgatctgctagctgat
ttctttgagaaatgtaagacggaaccttctcattgggaaactatttcaaccggtggcctgaagcgcatccaagagaagtaagcaactctttcttgac

```
tctagtcattcaaattaacttgggatttgaggcatagttgattgataatttatcgcgtctctactactatatacaggtacacgtggcaaatctactc ggagagattattgacgttggctgctgtttacggtttctggaaacatgtttctaagcttgatcgtctagaaatccgtcgatatctagaaatgttttat gctctcaaataccggaagatggtgagttcttctgcttcctgctcttctcatagtgtttaatatacacttgattgattgcattcacttagactaagtt gctcggacacgggtgtggatgtccgacacgagtgcggatctagagttcagatccttcaagatgtaaattataagattcggggatatggatcctagta cggatacgggtgcgagaatccggctaaaaataattttaaaaaaaattatctctaaattatgagatattatgtggaatacttacgtataacttgtaaa gtgtagatttttttttaattctcaagttgtagattagtaaatgattgatttcctagataagtatgctattttcttcaaatttactcttctgatttcga aaaatcaaattgtatctcgtctcgaattttccgtccgttatggtcaaagtacccaaaatcgtttgaccaaatcggtacggatcccatacccacaccc acactagtgtcgtattgacacgggtgccgcacctaaactgctatgtcggagcaacttagcacttagagaatcattgatgttaaattttcttaattct tgaatctgctaatgaagattttatcttggttttttgtttaggctgaagctgttccattggctgctgaatga SEQ ID NO: 15: Polypeptide sequence of NtSUS2-S
MAERALTRVHSLRERLDATLAAHRNEILLFLSRIESHGKGILKPHQLLAEFDAIRQDDKKKLNDHAFEELLKSTQEAIVLPPWVALAIRLRPGVWEY VRVNVNALVVEELTVPEYLHFKEELVDGTSNGNFVLELDFEPFTASFPKPTLTKSIGNGVEFLNRHLSAKMFHDKESMTPLLEFLRVHNYKGKTMML NDRIQNLTTLQNVLRKAEEYLIMLPPETPFSEFEHKFQEIGLEKGWGDTAERVLEMICMLLDLLEAPDSCTLEKFLGRIPMVFNVVILSPHGYFAQE NVLGYPDTGGQVVYILDQVPALEREMLKRLKEQGLDITPRILIVTRLLPDAVGTTCGQRLEKVYGAEHSHILRVPFRTEKGIVRKWISRFEVWPYME TFTEDVAKELAAELQAKPDLIIGNYSEGNLVASLLAHKLGVTQCTIAHALEKTKYPDSDIYWKKFDEKYHFSSQFTADLIAMNHTDFIITSTFQEIA GSKDTVGQYESHQAFTMPGLYRVVHGIDVFDPKFNIVSPGADINLYFPYSEKEKRLTALHPEIEELLYSDVENEEHLCVLKDRNKPILFTMARLDRV KNLTGLVEWYAKNARLRELVNLVVVGGDRRKESKDLEEQAEMKKMYELIKTHNLNGQFRWISSQMNRVRNGELYRYIADTRGAFVQPAFYEAFGLTV VEAMTCGLPTFATNHGGPAEIIVNGKSGFHIDPYHGEQAADLLADFFEKCKTEPSHWETISTGGLKRIQEKYTWQIYSERLLTLAAVYGFWKHVSKL

DRLEIRRYLEMFYALKYRKMAEAVPLAAE

SEQ ID NO: 16: Polynucleotide sequence of NtSUS2-T
atgcttttatgggagtaaatttatggccggtcattcaactttgtgttcattacgcaaaagtcattttttcttggtgtttattacgcaagtcattttt tcttttttttttgttacgtaaaaatcattcaactatgtgtttattatctaaaattcaatttttttttcctttgttacacaaaaatcatttttactt tactctatttatcacaaaagtcaccttggccagattttataataggcttttatcttttgttacacaaaaattattttactttactctatttatcaca aaagtcaccttggccagattttataataggcttttatcttttgttacacaaaaattattttactttactctatttatcacaaaagtcaccttggcca gattttacaatacttttaccttaaaagactattatgcccttgacattataaatcctctcatttatataataccttctatatgatacactatataata tatttttacctaggtattttacttataattaaaataatattaaattattttatttatcattttataatatattcatacatttaattttttcatggc aaatcactttgtttaatcatatttaaacatgaacaaattttaaatatcaaaaaaataaaaaaataaaaaaaatattttatttgaaataataacaaaca gatttgtttaacaaatgatagttttttttttatagtcaataaaattttttaaaaaaattcaaagatatttgttttttaatattaatattttttaaagctttt atctgttaatattatttatttgaaagtattaatctgatgtgtcattgtgttaaatgtgagtattttatttattggattaatgagtatggcttggctg ataaaaagctttgattttataatttttcattaaaaatatttttattaagctagtacctgacaaatttaatatcttgaaaattaacgttaagaaaaatt aaatataaaaatatattataaaaataataaatataataataatatcaagttattttaattataaataaaatacatggttaaaaatatattatatagcatat aatatagaaggtattacataaatgagatgatttaaagggcataatagacttttcaggtgaatgatttgtaaaatatggttaaagtgattattgtgat aattagagcatagtaaaataattttttatgtaacaaaagaaaaaaaaaatgactttgggtaatgaacataaatttgaataacttttacgtaacaaaa gaataaaataaattttggataataaacataaaattgaatgaccacctataaaatttattatttttttgggctcttcttgatttgattttttagttta gcctttgcagtaatcttggttgtcacgcgtagcgttgtgctttcgccacataagtatttagtagacttaattaatgtcattatatcggttggtgtgg ttttaattacttaactgtactattatattaggtggaaggtttgaaaatttatagtagtaacattctagatcattgaaaatattggtgtttcagtgac ttttagtatgtcattttcattttctaagtggttgtactaatatagtatattaaaattttgattggttgagaaacaatctctctcacctacacggta cgggtaaggtatgcgtatacgcttatcctccctacactccatttgtgggactattgttgttattttggataagctgaggtatccatcttctactaac tgcactagtttatttttttttgctgtttacagttgaaacaattgtctgaggatttctcacctgctgaatcaactgcaatggctgaacgtgtgctgact
```

SEQUENCE LISTING

```
cgtgttcacagccttcgtgaacgtcttgatgctactttggctgctcatcgcaatgagatattactgtttctttcaaggtatagccaaagatagtatt
cttgttaactaaaaagattcagttggtgttcaaaaaacgatacgtttatctgcctaagtcttggtagtcagaattatccggtacctatgctggtgt
gagttagctggctaggaaaccactcttatgaaaacaagagatttagttagagttgtctgtaattctgtagtatggactatgtatgtgatgctatttg
aactggttttggttattataggattgaaagccatggaaaagggatcttgaaaccgcatcagctattggctgagtttgatgcaattcgccaagatgac
aaaagaaactgaatgatcatgcatttgaagaactcctgaagtccactcaggtaatatggttttggctatatttgtcgccaacgccaagctcatatt
tttatattattttgagcttgtgtctgaatacgacgatgatatgttatactaggaagcaattgttctgccaccttgggttgcacttgcgattcgtttg
aggcctggtgtgtgggaatatgtccgtgtgaatgtcaatgcgctagtcgttgaggagctgactgtccctgagtatttgcatttcaaggaagaacttg
tcgatggaacgtaagtgttagtcttcaatttgatgctatgttagagaataggctgtggaatttattgatcaatgctgtgctttgtcctgatacagct
ccaatgaaatttcgttctcgagttggattttgagcccttcaccgcatcctttcctaaaccaaccctcaccaaatctatcggaaatggagttgaatt
cctcaataggcacctctctgcgaaaatgttccatgacaaggaaagcatgaccccgcttcttgaatttcttcgggttcacaattataagggcaaggtg
acttgctatttccatttatctataggttcggtttgtgcttatcatgcgcccaatgacatatgaatatgcgctaaaggatagatatatgatttccttt
gcagacaatgatgctgaacgacagaatacagaatttaaccacactgcaaaatgtcctaaggaaggcagaggaatacctcattatgcttcccctgaa
actccatttccgaattcgaacacaagttccaagaaattggattggagaagggatggggcgacactgcagagcgcgtgctggagatgatatgcatgc
ttcttgatctcctcgaggctcccgattcctgtactcttgagaagttcttggggagaattcctatggtgttcaatgtggttatcctttcccccacgg
atatttcgcccaggaaaatgtcttgggttatcccgacactggtggccaggtgcattactttaatctttatccgtgagtctatgtttgttcgaatcct
ctagaaatgtcactgtacctatgtaggatactccaaatataatgcattttggggggatctgttatgggtgcgatggcattttggaggtcggagcaa
caaacaattgctatgtattcttctaaagcttgctttcataaatgctaaggtccttcacccttaatgtgcaggttgtctatatattagatcaagttcc
agccttggagcgtgaaatgcttaagcgcctaaaggagcaaggacttgatatcacaccgcgtattcttattgttagtatttcctgtacttgtaattac
tgcggattacacaaaatttccttttatcttcttaacaacttatcttgatggtattcccaggttactcgtctgctacctgatgcagttggaacgact
tgtggtcagcggcttgagaaggtgtatggagccgagcactcacatattctgagggtccccttaggactgagaagggcattgttcgtaaatggatct
ctcgctttgaagtgtggccatatatggagactttcactgaggtgacactaaaacttccttatatttgtctatcttctaattggtattaggaataatt
tgttaattgttaactctttgtcttttcgtacatcaggatgtcgcaaaagaacttgctgcagaattgcaggccaagccagatttgataataggcaact
atagcgagggaaatcttgtggcttcattgctcgctcataagttaggcgtaacacaggtctgtgttgtttttcactctcttaaagatctgattgcatt
tccattagtctggaactagaagtactaaaaagttcttttcttcactgtgttatttgccgtcggcagtgcaccatagctcatgcattggagaaaacaa
agtatcctgattctgacatctactggaaaaaattcgatgaaaaataccatttctcgtcccagtttaccgctgatcttattgcaatgaatcacaccga
ttttatcatcaccagcacttttccaggagatagcaggaaggtataacatcaatttgctacttcgactgcaacagcattgtgttccctttctttccct
tatgcttaacctaataccgtcatgaattttccagcaaggacactgtcggacagtacgagagtcatcaggcattcacaatgcccggattgtacagagt
tgttcacggcattgatgtgttcgaccccaaattcaacattgtctcacctggagctgacataaacctctatttcccatattccgagaaggaaaagaga
ctgacagcacttcaccctgaaatcgaggagctgctgtacagtgacattgagaacgaggaacatctgtaagtttctaccttactcgtacagtcagtgg
cggagccagaattttcactaaaataaggtcaaaatataaagacataaatccacaaagaagccaagggtgtcaatatatagtataaatacattaaaaa
aattacctatctacacagtgtaattttccgacaaaggggtgtcggttgacactccttgaatacatgtggctctgccactgggtacagttacaaagtt
ctgttacctatgtgatgagcttgtgctgaacatgttgtgattttggcaggtgtgtgctaaaggacaggaataagccaatcttattcacaatggcga
gattggatcgtgtgaagaatttaaccggacttgttgagtggtatgccaagaacgcacggctaagggagttggttaaccttgttgtggttggtggaga
tcgaaggaaagaatccaaagatttggaagagcaaacagaaatgaaaaagatgtatgagctaataaagactcacaatttaaatggccaattcagatgg
atttcttcacagatgaaccgagtgaggaacggtgaactctaccgatacattgctgacactagaggagctttcgtgcagcctgcattctacgaggctt
tcggtttgactgttgttgaggccatgacctgtggtttgcctacatttgcaactaatcatggcggtccagctgagatcatcgttaacggaaaatctgg
cttccacatcgatccatatcacggtgagcaagctgctgatctgctagctgatttctttgagaaatgtaagacagaaccttctcattgggaaaccatt
tcaacgggtggcctgaagcgcatccaagaagaagtaagcaactcttcttgactctagtcattgaaattaactttcttgactctagtcattgaaatta
actcgggatttgaggcgtagttgattgatattttatcgcgtctctactactgatatatacaggtacacgtggcaaatctactcggagaggctattga
```

-continued

SEQUENCE LISTING cattggctgctgtttacgggttctggaaacatgtttctaagcttgatcgtctagaaatccgtcgatatcttgaaatgttttatgctctcaaataccg caagatggtgagttcctcttcttccttgcccttctcctagtgtttaagatacaatataattgattgcattatcttagagaatcattaatgttaaatt ttcttaattcttgaatctgttaatgaagttttctcttggttttgtttaggctgaagctgttccattggctgctgagtga SEQ ID NO: 17: Polypeptide sequence of NtSUS2-T
MLFMGLKQLSEDFSPAESTAMAERVLTRVHSLRERLDATLAAHRNEILLFLSRIESHGKGILKPHQLLAEFDAIRQDDKKKLNDHAFEELLKSTQEA IVLPPWVALAIRLRPGVWEYVRVNVNALVVEELTVPEYLHFKEELVDGTSNGNFVLELDFEPFTASFPKPTLTKSIGNGVEFLNRHLSAKMFHDKES MTPLLEFLRVHNYKGKTMMLNDRIQNLTTLONVLRKAEEYLIMLPPETPFSEFEHKFQEIGLEKGWGDTAERVLEMICMLLDLLEAPDSCTLEKFLG RIPMVFNVVILSPHGYFAQENVLGYPDTGGQVVYILDQVPALEREMLKRLKEQGLDITPRILIVTRLLPDAVGTTCGQRLEKVYGAEHSILRVPFR TEKGIVRKWISRFEVWPYMETFTEDVAKELAAELQAKPDLIIGNYSEGNLVASLLAHKLGVTQCTIAHALEKTKYPDSDIYWKKFDEKYHFSSQFTA DLIAMNHTDFIITSTFQEIAGSKDTVGQYESHQAFTMPGLYRVVHGIDVFDPKFNIVSPGADINLYFPYSEKEKRLTALHPEIEELLYSDIENEEHL CVLKDRNKPILFTMARLDRVKNLTGLVEWYAKNARLRELVNLVVVGGDRRKESKDLEEQTEMKKMYELIKTHNLNGQFRWISSQMNRVRNGELYRYI ADTRGAFVQPAFYEAFGLTVVEAMTCGLPTFATNHGGPAEIIVNGKSGFHIDPYHGEQAADLLADFFEKCKTEPSHWETISTGGLKRIQEKYTWQIY

SERLLTLAAVYGFWKHVSKLDRLEIRRYLEMFYALKYRKMAEAVPLAAE

SEQ ID NO: 18: Polynucleotide sequence of NtSUS3-S
atggcgaatccaaagttcacaagagtacctagcatgagggagagagttgaggatactctctctgctcaccgtaaccagcttgttgctctcctctcca ggtatattaataaactctatatacttgttattttctttattttttgtcttactgataaatttaactgttttcttcttaaatcttgctttcgatg catgatttctgttgtgttaaattgcgtaaccatttatctaaaagtttatgctgataaacacttttaaattttaatatgtaaattatattatgtctc aacatcaacatgtggatggccaaaaatataaagcttaattttcgttattttgaatgattttctctgcgagtgttacggtttgcgtacacattacct aaacctcctccctagtccccacttgtgggaatttaattttttttcttgttttttttgttgttgttgttgtctgagttcaattcctaccatgtt agcttggcaaaaataagttggtaaagcttgacccccaactagttttagttgatcgattatttggtgatttatagttcaataataataattactatta gagaaagttccagcagcttttctgtttgttttccagttttagtgattgatatatgtgtatatatattctttgtttcttttaagatacgtggcgcag gggaaggggatattgcaacctcaccacttgatcgatgagttcaacaacgctgtatgtgatgacactgcttgtgagaagctcaaagatggtcccttta gtgaagtcttgaaagctactcaggtatattcactaatccatgggaatcaagatgatactgtatatctttattatggtgtcttcagaaatttgacga tgatgaaatgcaacttttctctgtttgtcaccttatccagactgttttttatttttattttcatttttttaacttgaaatgctcttaatttcctt tgtttatcgataagaccggatttacaatgtatgaacggagcatcttaagaaccttctggaatgaagatataagatataaaacatggtgtccgttttc tcctttgtggaatcagtgtacatatagactgttattttggtcccactttctggatcttctgatcacaccttctcatgcagaggcgagcttgatggtt tcaacctttaaattcttactattgaatccatttcactttcgaaattatgagttcgaaatctaatatttgttgaaattttttgcaaatgttcacatata agtttaagctttgtgtcaagaatactgggctcaatggattccaatagaccaggctgtatccgcctctgtctccactctccctgcatccacttctttc gtgtgactaataatgcttaatgagctagaactcgttttaatgtttgaataagttgcttatatcagagcagcttttgatgtttcaatcttttaacgggt tatgcagtaccagcattctgcggctgaaaaacaggaatctgagatttacttgtctctggctgaatttcttgttcattttgctaacaagtactttgga gttaatgcttgctctctgttgtcaaaataggaagccattgtgctgccaccatttgttgccatagcagttcgtccaaggccaggtgtttgggagtatg ttcgtgttaatgtatatgatttgagcgttgaacaattgactgttcctgaatatcttcatttcaaggaagaacttgtggatggagagtaagctctttc ttatttcaatacgaaacataaaaatttacagaagttgaataattaacaaatttgttgattttttaatgtatgccagggtaataatcactttgtgctt gagctggattttgagccatttaatgcatcagttcctcgtccatctcgatcgtcatccattggcaatggagtccaattcctcaatcgtcatctttcct caattatgtttcgcagcaaagactctctggacccccttacttgatttccttagaggacactgtcataaagggaatgtaagtaccaaaagcagttttcc ctttgtaaatgtctgcttgtccctgattatctactaaatcttttcaacacgcgcaaccattataagaaatgtacaatacttctagttagaatttcatc atcgacaaactatctgcttttacttttttattttttcccatttgatggatgatagtttagtttatataacagatgatattttggttgaagggtaccatga acttttttcacaaccacttaatggatacatagttgtaatagttgacattttggaataatattgtctcacttggaaatgtttaagaagtattactactt ctatttgtaagatggattgtttatctatgcaggtcttgatgttgaatgatcgtatacagcgaatctccaggctggagtctgctctttctaaagcaga

```
ggattatctctccaagctatcaccagatacatcctataatgagttcgaatacgcgtgagcttgtacacatttgttttgttttctttcaagcatatgt
aatttctcaagaaaagggaaatctataggagttgaaacattctttatggaaccatgtgcatgcagattgcaagaaatgggctttgagagaggttggg
gtgatactgccagacgtgttttggagacgatgcatcttctttctgacattcttcaggctccggatccatcaaccttggagacatttcttggtagact
acctatggtgttcaatgtcgtcatattatcccctcatggatattttggccaagcaaatgtcttgggtttgcccgacactggtggccaggtaataaca
aggagaatgaggtcttgtattatgtactcctccgttccaatctatatgaacctatttgactgggtatggaaagaaatgaagacttgtaaaacttgt
ggttctttagaaattccaaacattacatttggttttttcctcttcctggaaattataetactgaatcatctctagatgttccagtttaacttgaga
cgtaagggtaaataacggaccattactctgtcctttcttgcagtaggcttggtacaatgaatatagttcgcatagttgccggaagctagagctgtgt
tagaaaactcaggaacattaatttggcgatgctaatcactgctaatgttactgaagcatccatggttttccttgatgttattctccttttggttgct
tcacaggttgtctatatactggatcaagtgcgtgccttggaggccgaaatgcttcttagaataaagcaacaaggacttaacttcaagcctagaatcc
ttgtcgtgagtacatatatattatgcaagctcttatttggtttgtgggattgcagttgacatcaatttgcttactctgattactaaaggtcacacgg
ctgatacctgatgctaaaggaaccatgtgcaaccagaggttggagaggattagtggaactgaatactcgcatattttacgtgtccttttaggacag
agaagggaatccttcataaatggatatctaggtttgatgtatggccttacctggagaagttcactgaggtaacctctttgtcccttggaaattgcct
tttgttgctgatgtttctgctagtgtgcttaaatgacggatgttaactagtcacttgctagcgtttgcaatagcaacgggaaagaaaggattttg
ctagtttgaagtctgcctccaagaaaaattatattaaaagtttatggctagtggaaacatcagtcattcatgtaccttatttctatgcccaagttgt
ttaagttgaaagtaatttggccaactatgcaaattgggagaacgtgtagccaactattgtgtttgccgacatgttgatatacttttggtcctgatt
tatatttgttggtttgtcatactggatgaagcaattctcatgtttttctgcttatatatattggaagaagagatacttgtcgtttcatcatttttct
cgacctctctattaccaacactttgccaatttaatgtttggaaatgtcttcttgaccaggatgtggcaagtgaaatgaccgctgagctccagggaaa
gccagatctgattattggcaactacagtgatggaaatttagttgcctcccttttggcatataaaatgggtgtcacacaggtaggaaatacatgattc
tttatcttgctagcactaagtcttgaggttatgtatctgcaatagaaattttacgctttgccttcatttcttttaattattttttccagtgtaccat
tgctcatgccttggaaaaaacaaagtatcctgattctgacatctactggaaaaagtttgaggagaaatatcattttcatgtcagtttactgctgat
ctactggcaatgaataattcagatttcattatcaccagtacttatcaagagattgcaggaacgtaagtcattttaatctggtcgtttaaatctgata
tttcttccctagtagtctattcaatccgaatttcagttcagtatatgatgtcatcggttgaggaactgtgattggtaaccttatcaaatccgtagct
gctctataattttatttcgtaattggagagaaacaattttttattattgagcttgtagtctgagctagaatttggttctttatctatcaagtagcataa
tactacaactatttttttatgtgtggcaatttgcaatttcaattttctatttctataagttgcagcttttcttcctgttctgatcatatttacatggc
tgaaactcaatagaaaactaggctagttgatcaaaagtagttggatgctttaaaattagtagacgttttgctaaatgagtgaccaatgttattaaaa
aaacgttcatgttttcaacccttttggcatacatttgaccactgcccaagattttggataagtacatgcagtgcttataattataaagcatttatc
ccaccttgttttttcattatgaaaattaagtaatttacgagtatttgtataagttacttcataaattagaagtaaatctggattgtgtaaagttattc
gccccgtatatactgaaagctacttgaacaagcaaaaaaacagacaaacgtaacattctccatggattaatgagacttgtatatatatatatata
tatgtaaagagagagagagagatttggcttgtaaccacatgtatattatgccatatggatgtgacattgatgtgactagacctaaatgttttgtt
tcaatgtccacgggagttttacgtagagttaagaggagaagagagtgaggaatactaatgtttgatggtaccccttggcttcttgacctggatactc
agtgttcttattcatgcctatactttggtccttgatttcattctcccttttctagcttgagctgcatcaaagaaattccactgtaaaaaaataatg
ctcaccatattggtgcaacatggcaaacatgtatcctatttgatgatcaatcaactttatttttctcctgttaattgacctcagtgtgtaactctct
atgtatgatagcattgtaacttgtgtcatgattcataaatagggtactagaattggatggttgacatagtaaatggtcaattgatgatccacaaaat
atgcacctactgattaaaatgtgatagggcaggtttattttttgtttgtggttaacacagtacttaaccctatatttaatacaatttggcttatctac
aatcttttcttcagtgtttatgcgaattccttattgcacaacaatattgtctttctgagttctattctgttgttgcttacacttttattattccagt
aacatagatgtgaagacattagattggttgcttgcaaattgatagccacttgtttcaggaagaatactgttggtcagtacgagagccatactgcatt
cacccctcccgggactatatcgcgtcgttcatggcattgatgttttcgatcccaaattcaatatagtgtctcctggagctgacatgacaatttattc
ccatattctgacaaggaaaaagactaacgtcttgcatggctcgattgaaaagttgttatttgatcctgcgcagaatgaagagcatatgtaagtgg
catccgtttgtacttaattttttttggaatagatgacatattatttgcatgaatatgaaaaggagggtctgatatgattttctatagataaactacca
```

-continued

SEQUENCE LISTING atgatattatttaaaaactcctggatactgtattaggagaagaagagaaccaggggtagatggcattagaatcccttaaatcttgaagagtcgtcac
taacgctcccaacacttctgcctcagaccctcaactaaatactattattgttgatttctttggagaagctataagaatctctctctccttatggtga
aaattttacttggctttatacttaacttccaaggctccctcttataaaatgcaaaaactgtctgtattcactctcttggttaacaattgatccaatc
aaatgcatatggaacatctttctttacgtttcttctaaagttcgtttgaggataaggagtagaatctgagaagatagactagtaggtaaccttaggg
acggatgtggaaattaacatatgggctcagcttttctgccgagtgcagaccatgtatatgcgttaaaaaattcactaaacaagtaaatgtttgattt
tgaacccagtaaatcaaatgagttgtggtagaatctcgaactcgaaccgataaagttcaaatccaggatccgcttttaggtaaactctaccttggga
agtgttatatatatgtccctgattatttctttttccgtttccttttctattttaattttaaagttatttttagatggttttattttttgataagtgg
taagttgttaatattccaaattaaatgccattgtcataactatatacatttataaagaatgattgatcctagtttctcattcctaagatccaataa
ggcaataaacaatgtcttagtaattggacctgcttctggtgatcaacgcttgatcgcgtagttagttatagatgactgtaaaaactttaaccatttt
aatggttttgtcaaagaacaaatatcggacatattatagagaatggactattgtactttgcttctgattggtcattttattgtgatccgtaaattgg
ctgtgactgatgtcatatctttgcttacagaggtaatctgaatgataaatcaaaacccataatttttcaatggcaaggctagaccatgttaagaac
attacgggactagttgagtgctatgctaaaaatgccacattgagggaattggcgaaccttgttgtagtagctggatacaacgatgtaaagaaatcca
gtgatagagaagaaataacagaaattgaagaagatgcatgctcttattaaggagcataaattggatgggcaattcagatgggatcagcccaaacaaa
ccgggcacgtaatggtgagctctatcgctatatagctgaccagagaggtatatttgttcaggtatgctatttgtattgtattagtccaatttcattt
tttgcaccaaaagaaaggttgttattgtgacgtatatgtttgttttagcctgcattttatgaagcatttggactaacggtggttgaagctatgactt
gtggtcttccaacatttgcaacttgccatggtggtcctaatgagatcattgaacccggtgtatctgggttccatattgatccttatcatcccgataa
agctgctgaactcatgtcagaattctttcaacgctgcaaacaagatcctactcactgggaaaaaatatctgcatctggtctccgaaggattcttgag
aggtctgtagttgtgtacatgtatagaagattaaagaatgctaccttgatatttatttgaatcaaaaataacaggaacatctcttttttgaacatca
ctcaagttcttatattaaataattttttaggtatacgtggaagatttactccgagaggctgatgactttatctggcgtatatggtttctggaagcttg
tttcaaaacttgagaggcgtgaaactagacgataccttgagatgttctacattctcaaattccgcgagttggtgagtgccttttagctccttttcag
ttccaataaactatatatgtggtttaagtaagtattaagcataaacatgtccgtgcttggggctgtcgaaaatgctatggacatatcctgagctaag
gattttcaagaaaattgatgttagctttactctatttacaggcaaaatctgtacctctagcaattgatgacaagtga SEQ ID NO: 19: Polypeptide sequence of NtSUS3-S
MANPKFTRVPSMRERVEDTLSAHRNQLVALLSRYVAQGKGILQPHHLIDEFNNAVCDDTACEKLKDGPFSEVLKATQEAIVLPPFVAIAVRPRPGVW
EYVRVNVYDLSVEQLTVPEYLHFKEELVDGEGNNHFVLELDFEPFNASVPRPSRSSSIGNGVQFLNRHLSSIMFRSKDSLDPLLDFLRGHCHKGNVL
MLNDRIQRISRLESALSKAEDYLSKLSPDTSYNEFEYALQEMGFERGWGDTARRVLETMHLLSDILQAPDPSTLETFLGRLPMVFNVVILSPHGYFG
QANVLGLPDTGGQVVYILDQVRALEAEMLLRIKQQGLNFKPRILVVTRLIPDAKGTMCNQRLERISGTEYSHILRVPFRTEKGILHKWISRFDVWPY
LEKFTEDVASEMTAELQGKPDLIIGNYSDGNLVASLLAYKMGVTQCTIAHALEKTKYPDSDIYWKKFEEKYHFSCQFTADLLAMNNSDFIITSTYQE
IAGTKNTVGQYESHTAFTLPGLYRVVHGIDVFDPKFNIVSPGADMTIYFPYSDKEKRLTSLHGSIEKLLFDPAQNEEHIGNLNDKSKPIIFSMARLD
HVKNITGLVECYAKNATLRELANLVVVAGYNDVKKSSDREEITEIEKMHALIKEHKLDGQFRWVSAQTNRARNGELYRYIADQRGIFVQPAFYEAFG
LTVVEAMTCGLPTFATCHGGPNEIIEPGVSGFHIDPYHPDKAAELMSEFFQRCKQDPTHWEKISASGLRRILERYTWKIYSERLMTLSGVYGFWKLV
SKLERRETRRYLEMFYILKFRELAKSVPLAIDDK SEQ ID NO: 20: Polynucleotide sequence of NtSUS3-T
atgtttacatggctgaaactcaatataaaaaacaagggtaggtgatcaaaaatcgttggatgcttaaaatcagtagacgttttgctaaatgagcgac
caatgttattgaaaacgttcatgttttcaacccttttggcatacatttgagcattgcccaagattttggataagtagatgcagtgcttataattta
aagcattgtatcctgccttgttttcattgtcaaaattaattaacttacaagtatttctataagttgcttcataaattagaagtaaatctggattgt
gtaatgttattcgcctcgtaaatactgaaagctgcttgaacaagtgaaaaaacacagacaaacgtaacattctccatggattgatgagacttgtaaa
atacatatatagaaatttggcttgtaaccacatgtatattatgccatatggatgtgacattgatgtgactagacctaaatgttttgtttccatgtcc
actgagttttacgtatagttaagaggagaaaagactgaggaatactaatgtatgatggtacccctttgcttcttgacctggatacccagtgttcct

```
attcatgcctatactttggtccttgatttcactctcccttttctaacttgagctgcatcaaagaaatttccactgtaaaaaataaataatgctcac catatctctgcaacattgcaaacatgtatcccatatgattgatattggtgcgacatggcaaacatgtatcctatttgatgatcaatcaaatttattt ttcccctgtcaaaatgacctcagtgtgtaattccctatgtatttgatagcattgtaactcgtgtcatgattcatgaatagggtactagaattgcatg gttgacaaatattaactggtcgattgatgatccacaaaacatgcacttactgactaaaatgtgatgggacagatttattttgtttgtgattaacac agtacttaaccctatacttaatacaatttggcctagctacaatcttttcttcagtgcaaattccttgttacacgaccaatattgtcttctgagttc tattctgttgttacttacacttttattattcgaataagacattagattgcttgcatgcaaattgatagccacttgtttcaggaagaatactgttggt cagtacgagagccatactgcattcaccctcccaggactatatcgcgtcgttcatggcattgatgttttcgatcccaaattcaatatagtgtctcctg gagctgacatgacaatttacttcccatattctgacaaggaaaaaagactaacgtctttgcatggctcgattgagaagttgttatttgatcctgcgca gaatgaagagcatatgtaagtgacatccatttgtacttattttaatttggaatagatgacatacttatttgcatgaatataaactgacaacccagag atttcctacattagaaaaggagggtctgatatgattttctacaaataaattcccagtgatattgttcaaaaagtcctggatactttattatgagaga accagggatagatggcactagaatcccttaatcttgagaagtcgccacttatcgctcccaacactttctgagaccctcaagtaactactattattgt ttgatatcttggagaagctataagaatcttttctccttattgtaatttttttacgtgactttaaacttaacttccaagctccttctgataaaatg caaaaactgtctgtattcactgtcttggtttattaacaattgatccaatcaaatgcatatggaacatctttcttttgtttcttcaaaagttcgttt gaggataaggagtagaatctgagaagatagactagtaggtaaccttaggggcggatgtagaaatcaacgtatgggttcagctttgttgcagaccctg tatatgcattaaaaaaatcactaaataagtaaataattgattttgaacccagtaaatcaaaatgagttgtagtagaatcctgaactcgaaccgataa agttggatccactaccgggtaaactctaccttgagaagtgtttatatatgtcccctaattatttcttttctgtttcctttctattttaattttttaag ttccttttagatggttttattttttgacaagtggtaagttgttagtattccaaattaaatgccattgccataactatacatttataaagattga ttgaccctagtttctcattcctaagatccaaataaggcaataaacaatatgtcttagtacttgaacctgcttctggtggtcaacacttgatcgcgta gttagttatagatgactgtaaaaaccttaatcattttaatggttttgtcaaagaacaaatatcggacatattatagcgaatggactattgtactttt cttctgattggtcattttattgtgatccgtaagttggctgagactgatgtcatatctttgcttacagaggtaatctgaatgataaatcaaaacccat aattttttcaatggcaaggctagaccatgttaagaacattacgggactagttgagtgctatgctaaaaatgccacattgagggaattggctaacctt gttgttgtagctggatacaacgatgtaaagaaatccagtgatagagaagaaatagcagaaattgagaagatgcatgctcttattaaggagcataaat tggatgggcaattcagatggatagcagcccaaacaaaccgggcacgtaatggtgagctctatcgctatatagctgacaagagaggtatatttgttca ggtacgctgtttgtattgtatttgtccacattcctttttttgcaccgaaagaaaggttgttattgtgacaaatatgtttgttttagcctgcattta tgaagcatttggactcacggtggttgaagctatgacttgtggtcttccaacatttgcaacttgccatggtggtccgaacgagatcattgaacacggt gtatctgggttccatattgatccttatcatcccgataaagctgctgaactcatggcagaattctttcaacgctgcaaacaagatcctactcactggg aaaaaatatctgcatctggtctccgaaggattcttgagagggtttgtagttgtgtacatatatagaagattaaagattgttcccttgatatttga atgaaaaataacagtaacatctctttttgaacatcgctcaagttcttgtgttaaataattgttaggtatacgtggaaaatttactccgagaggctga tgactttgtctggtgtatatggtttctggaagcttgtttcaaaacttgagaggcgcgaaactagacgataccttgagatgttetacattctcaaatt ccgcgagttggtgagtgccttttttgctcattttcagttacaatcaactatatatgtggtttaaatacgtattaagcataaacatgtccgtgattgcg gctgtcgaaaatgctatggacatatcctgagctaaggagttttcaagagaattgatttggcttactctgtttacaggcaaaatctgttcctctggca attgatgacaagtga
```

SEQ ID NO: 21: Polypeptide sequence of NtSUS3-T
MFTWLKLNIKNKGRKNTVGQYESHTAFTLPGLYRVVHGIDVFDPKFNIVSPGADMTIYFPYSDKEKRLTSLHGSIEKLLFDPAQNEEHIGNLNDKSK PIIFSMARLDHVKNITGLVECYAKNATLRELANLVVAGYNDVKKSSDREEIAEIEKMHALIKEHKLDGQFRWIAAQTNRARNGELYRYIADKRGIF VQPAFYEAFGLTVVEAMTCGLPTFATCHGGPNEIIEHGVSGFHIDPYHPDKAAELMAEFFQRCKQDPTHWEKISASGLRRILERYTWKIYSERLMTL

SGVYGFWKLVSKLERRETRRYLEMFYILKFRELAKSVPLAIDDK

SEQ ID NO: 22: Polynucleotide sequence of NtSUS4-S
atggcggaacgtgtgctgactcgtgttcatagccttcgtgaacgtcttgatgctactttggctgctcatcgcaatgagatttgctgtttctttcaa ggtatagtcttagcagattgttctttgatttagttgttattgccagttctaatgtatgggcttatatataaacaaagtgttgaagtatgcaaccata

```
taaactgacagcttaaaatgcttgagagaacacacttttatttatttaattatgccttcagcacaagaagtggaacttgacgcaatggaaccatagg tcacgggttcaagtcttggaacagcctgcaatctaaggctgcgtgtagtagaccctagtggtccggcccttccacatatctcgcttagtgtaccggg cccattgagtacgggttcggccgaacccagtcgctttggtccaatccatatatttgtcttaaaaatatattgaatatatacaaattgttaatttagt ttaaatatgtgtatcatgggttattcatgctggttttggctgttgcaggattgaaagccatggaaagggatactgaaacctccagttgctggct gaatttgattcaattcacaaagaagacaaaaacaaactgaatgatcatgcttttgaagaagtcctgaaatccactcaggtatttgtggttttagtgt taggtgatggatagcatttattgttttactaagatcacatatgtgtcagtttgtggctagtatttaaaatctggtgtattttgtcatactaggaagc aattgttttgtccccttgggttgcgcttgccattcgtctgaggcctggtgtgtgggaatacgttcgtgtgaatgtcaacgctcttgttgttgaggag cttaccgtgcctgagtatttgcaattcaaggaagaacttgttaatggaacgtaagttttaggttcgaatttgttgatttgttagataacatgttctg aacttttgattaaagttgtgttttgactgatgcagctcgcacgataaactttgttcttgagttggattttgagcccttcactgcatcatttccaaa accaaccctcaccaaatcaattggaaatggagttgaattccttaaccgacacctctctgccaaaatgttccatgacaaggaaagcatgacccctctt ctcgagtttcttcgagttcaecaetacaagggcaaggtaaacttgtttttcctgtttgtctatgaatttagtttagttgttttgetccgcgaaaatt tcagtggaaactgatttatgcaaccactgagtgattaatatgttcaaacttaccgacttctggttttctgtgtagacaatgatgctgaatgacagaa ttcaggacttaaatactctccaaaatgtcctaaggaaagctgaggaatacetcactaccctttccctgaaacttcatactcggcatttgagcacaa gttccaagaaattggcttggagaggggttggggtgacactgcggagcgtgttctagagatgatctgcatgctcctggatctcctcgaggctcctgac tcgtgcacgcttgagaagttccttggtagaattccaatggttttttaatgtggtcatactttcacccatggttatttcgcccaggaaaatgtcttgg gttaccccgacactggtggccaggtgcactgcttatctgtgttcggtcttattatctctttaaaccctactgccacaagtgctgagatgaacctcct ttaatttgcaggttgtctatattttggatcaagttcctgctttggagcgtgagatgctcaagcgcataaaggagcaaggacttgacatcaaaccgcg tattcttattgttcgtattcccagtaattgtgtttaaacttatgattatgcaggattttatctgttctaatacagcactcttgcttaaattctcagg ttactcggctgctgcctgatgcggttggtaccacttgtggtcagaggcttgagaaagtgtttggaacagagcactcacacattcttagggtcccctt taggaccgagaagggcattgttcgcaaatggatctctcgctttgaagtctggccatacatggagacattcactgaggtgaagcaagctttctctatt cattttcaatcttccaattggttttggcagcaattttctgcttgctttgacttccgctaaaacttcggattttattgcattaggatgtggcgaaag aaattgctgcagaattgcaggctaagccagatcttatcattggcaattatagtgagggcaaccttgctgcctccttgttggctcacaaattaggtgt aacacaggtcggcaatgtttgtgacatgtaatttcatctttgcatttccttcgtttgcaactaaaagatttaagagttctctctctcttttttttt tccgtctactttgccttatgcagtgcacgatagctcatgctttggagaaaacaaaatatcctgattctgatatctacttgaagaaatttgatgaaaa ataccatttctcagcccagtttactgccgatcttattgcaatgaatcacaccgatttcatcatcaccagcactttccaggagatagcgggaaggtat ttttacatcagtttcccactctgattaaattacaatgtatttccctatatgattaaatactgtgtttgatcctaaatcatttctaaattttccagca aggacactgttggacagtacgagagccacatggcgttcacaatgcctggactgtatagagttgttcacggcattgatgtgtttgacccccaaatttaa cattgtgtcaccaggagctgatatgaatctctatttcccatactacgagaaggaaaagagattgacagcatatcaccctgaaattgaggagctgctg tttagtgatgttgagaatgacgaacacatgtatgttactaaactagcaatcctgctgcaaaattatggctaattatgtaaacaagtttgtactgaat agatttgttattcgatcaggtgtgtgctgaagaacaggaataagcctatcatattcactatggctagattggatcgagtgaagaacttaactggact tgtcgagctgtacgccaagaacccacggctaagggagttggttaaccttgtcgtggttggaggagaccgaaggaaagaatccaaagacttggaagaa caggcagagatgaagaagatgtacgaacttataaagactcacaatttgaacggccaattccgatggatttcttcccagatgaaccgcgtgaggaatg gcgaactctacaggtacattgccgatactaggggagctttcgtgcagcctgcattttacgaggcttttggtttgactgttgttgaggccatgacctg tggtttgcctacatttgcaactaatcacggtggtccagctgagatcatcgttcacgggaaatctggtttccacattgatccataccacggggatcag gcagctgaacttctcgctgatttctttgagaaatgtaagaaagaaccttcgcactgggaagccatttccgagggcggccttaagcgtatacaggaga agtaagcaaactgctactcttttcattttgcaaaacctactatgatcattattaagctcattttgcaaaacctacttgctgttgttattgtttgt tgcttccttttcactgttctttgagctgaaggtctatcagaaacagtctctctaccttcacaaggtaggggtaagatctgcgtgcacgttaccctcc tcaaactctacttaattgtgagattacactaggtttgttgttgttgattccttgctaattaattaaaaggtacacatggcaaatatactcggategg
```

```
ttgttgacactggctgctgtatatggattctggaagcatgtttccaagcttgatcgtcttgaaattcgccgttatcttgaaatgttctatgctctca aattccgcaagctggtgagtttcattgctttctgcactcctgcaattgtatag
```

SEQ ID NO: 23: Polypeptide sequence of NtSUS4-S
```
MAERVLTRVHSLRERLDATLAAHRNEILLFLSRIESHGKGILKPHQLLAEFDSIHKEDKNKLNDHAFEEVLKSTQEAIVLSPWVALAIRLRPGVWEY VRVNVNALVVEELTVPEYLQFKEELVNGTSHDNFVLELDFEPFTASFPKPTLTKSIGNGVEFLNRHLSAKMFHDKESMTPLLEFLRVHHYKGKTMML NDRIQDLNTLQNVLRKAEEYLTTLSPETSYSAFEHKFQEIGLERGWGDTAERVLEMICMLLDLLEAPDSCTLEKFLGRIPMVFNVVILSPHGYFAQE NVLGYPDTGGQVVYILDQVPALEREMLKRIKEQGLDIKPRILIVTRLLPDAVGTTCGQRLEKVFGTEHSHILRVPFRTEKGIVRKWISRFEVWPYME TFTEDVAKEIAAELQAKPDLIIGNYSEGNLAASLLAHKLGVTQCTIAHALEKTKYPDSDIYLKKFDEKYHFSAQFTADLIAMNHTDFIITSTFQEIA GSKDTVGQYESHMAFTMPGLYRVVHGIDVFDPKFNIVSPGADMNLYFPYYEKEKRLTAYHPEIEELLFSDVENDEHMCVLKNRNKPIIFTMARLDRV KNLTGLVELYAKNPRLRELVNLVVGGDRRKESKDLEEQAEMKKMYELIKTHNLNGQFRWISSQMNRVRNGELYRYIADTRGAFVQPAFYEAFGLTV VEAMTCGLPTFATNHGGPAEIIVHGKSGFHIDPYHGDQAAELLADFFEKCKKEPSHWEAISEGGLKRIQEKYTWQIYSDRLLTLAAVYGFWKHVSKL

DRLEIRRYLEMFYALKFRKLVSFIAFCTPAIV
```

SEQ ID NO: 24: Polynucleotide sequence of NtSUS4-T
```
atggccgaacgtgtgctaactcgtgttcacagccttcgcgaacgtcttgatgctactttggctgctcatcgcaatgagattttgctgtttctttcaa ggtatagtcttagcagattgttctttgatttagttggtgttatttgccagttctaatgtatggactaatatatgaacaaagtgcgaccatttcaact gacaacttaaaatgtttgagagaatacacgtttatttacttaattatggcttgagcataggaagtgtatcttggcgtaactcgtaaagttgacctca tgtgacaaggaggtcacggtttcgagccgtggaaacagcctcttgcagaaatgcaggtaaggctgcgtgcaatagatcgccttccacggacccgcg catagcgggaacttagtgcaccggttgggctgtccttttttatgtcttcagcacaaaaatttagtttaaacatgtgtatcatggattattcatgctg gttttgccggttgcaggattgaaagccacggaaaagggatattgaaacctcaccagttgctggctgagtttgaatcaattcacaaagaagacaaaaa caaactgaatgatcatgcttttgaagaagtcctgaaatctactcaggtaatttgtggtttagtgttaggtgatggatagcatttattgtcttacta agatcatatatgtgtcagtttgtggctagtatttgaaaagtctggtgtggttgtcatactaggaagcaattgtcttgtcccttggggttgcgcttg ccattcgtctgcggcctggtgtgtgggaatatgttcgtgtgaatgtcaatgcacttattgtcgaggagctgactgtgcctgaatatttgcaattcaa ggaagaacttgttaatggaacgtaagttttaggttcgaaatgatgatttgttaaataatatgttctgaacttttttgattaatgttgtgttttcccct gatgcagctcgaacgataactttgttcttgagctggattttgagcccttcactgcatcatttcccaaaccaaccctcaccaaatcaattggaaatgg agttgaattcctcaaccgacacctctctgccaaaatgttccatgacaaggaaagcatgacccctcttctcgagtttcttcgagttcatcactacaag ggcaaggtaaacttgtttttcctgtttgtctatgaatttagtttctgaaagttgctttgcttcgtgaatttttttagtggcaactgatttatgatttt ctgtgcagacaatgatgctgaatgacagagttcaggacttaaacactctccaaaatgtcctaaggaaggctgaggaatatctcactaccctttcccc tgaaaacttcatactcggtatttgagcacaagttccaagaaattggcctagagaggggctggggtgacaatgctgagcgtgttctagagatgatctgc atgctcctggatctcctcgaggctccagactcatgcactcttgagaagttccttggtagaattcctatggttttttaatgtggtcattcttttcacctc acggatatttcgcccaggaaaatgtcttgggttaccccgatactggtggccaggtgcactgcttatttgtaacaccttacgcttttccctctgaaac ttatttgcggcaagttctaaggtcctccttccttaatttgcaggttgtctatattttggatcaagttccggccttggagcgtgagatgctcaagcgc ataaaggagcaaggacttgatatcaaaccgcgtattcttattgttcgtatctccaataattgcgtttaaacttatgattgtgcaggatttgatctgt tcaaatctaatgactgattttctttttttttttttttcccctcaggttactcggctgctgcctgatgcggttggtaccacttgtggtcagcggcttg agaaagtgtttggaacagagcattcacatattcttagggtcccctttaggaccgagaagggcatcgttcgcaaatggatctctcgctttgaagtctg gccttacatggagacattcactgaggtgaagcaagctttctctattcattttcaatcttccaatctgttttggcagcaatttttcacttactaaca ctttggctttcgctaaaacttcggatttattacattaggatgtggcaaaagaaattgctgcagaactgcaggcaaagccagatcttataatcggca actacagcgagggcaaccttgctgcctccttgttggctcacaagttaggtgtaactcaggtctgtaatgtttgtcacctgttatttcaactttgcat ttcctttcatttgcaactagaagttaagagttctctctcttttatcttttccgtctcattttgccttctgcagtgcaccatagctcatgcgttggaga aaacaaaatatcctgattctgatatctacttgaagaaatttgatgaaaaataccatttctcagcccagtttactgccgatcttattgcaatgaatca caccgatttcataatcaccagcactttccaggagatagcgggaaggtattacatcacaatggatttccgatatgattaaattagttaatttaatcct
```

```
acttcattgtgtttgatcctaaaacttttctaaatttcccagcaaggacactgttggacagtacgagagccacatggctttcacgatgcctggattg tatagagttgttcacggcattgatgtgttcgatcccaaattcaacattgtgtcaccaggagctgatatgaatctctatttcccctacttcgagaagg aaaagcgattgacagcatatcaccctgaaattgaggagctgctgtttagcgatgttgagaatgacgaacacatgtatgttactaaactagcaatcct gctgcaaaattgtggctaattatgtaaaaaagttttactgaatagatttgtgcttctatcaggtgtgtgctgaaggacaggaataagccaattata ttcaccatggctagattggatcgagtgaagaacttaactggacttgtggagttgtacgccaagaacccacggctaagggagttggttaaccttgtcg tggttggtggagaccgaaggaaggaatccaaagatttggaagaacaggcagagatgaagaagatgtatgaacttataaagacgcacaatttaaacgg ccaattccgatggatttcttcccagatgaaccgcgtgaggaatggcgaactctacaggtacattgccgatactagggggagcttttgtgcagcctgca ttttacgaggcttttggtttgactgttgttgaggccatgacctgtggtttgcctacgtttgcaactaatcacggtggtccagctgagatcatcgttc acgggaagtctggttttcacattgatccataccacggcgagcaggcagctgaacttctagctgatttctttgagagatgtaagaaagaaccttcaca ctgggaagccatttccgagggcggccttaagcgtatacaggagaagtaagcaagctgctactcttttcattttttgcaaaacctaccatgatcattat taagctcatttttgcaaaacctacttgttattctttgttgcttccttttccctgtttttttgagccgaggttttatcgaaaacatgctttctaccttc acaaggtaggggtaaggtctgcgtttgttattattgttgttgttgattctctgcgaattaattaaaaggtacacatggcaaatctactcggatcggt tgttgacactggctgctgtttatggattctggaagcatgtttccaaacttgatcgtcttgaaattcgtcgttatcttgaaatgttctatgctctaaa attccgcaaactggtgagtttcactgctttctgcactcttccaattgttagttgagtgcactcatttaaactgtagctaaagctgttgtaaatcttc agttaagcagctgctaatgaagttttttatcttttgtttttggttcaggctgaagctgtcccgttggctgttgagtaa SEQ ID NO: 25: Polypeptide sequence of NtSUS4-T
MAERVLTRVHSLRERLDATLAAHRNEILLFLSRIESHGKGILKPHQLLAEFESIHKEDKNKLNDHAFEEVLKSTQEAIVLSPWVALAIRLRPGVWEY VRVNVNALIVEELTVPEYLQFKEELVNGTSNDNFVLELDFEPPFTASFPKPTLTKSIGNGVEFLNRHLSAKMFHDKESMTPLLEFLRVHHYKGKTMML NDRVQDLNTLQNVLRKAEEYLTTLSPETSYSVFEHKFQEIGLERGWGDNAERVLEMICMLLDLLEAPDSCTLEKFLGRIPMVFNVVILSPHGYFAQE NVLGYPDTGGQVVYILDQVPALEREMLKRIKEQGLDIKPRILIVTRLLPDAVGTTCGQRLEKVFGTEHSHILRVPFRTEKGIVRKWISRFEVWPYME TFTEDVAKEIAAELQAKPDLIIGNYSEGNLAASLLAHKLGVTQCTIAHALEKTKYPDSDIYLKKFDEKYHFSAQFTADLIAMNHTDFIITSTFQEIA GSKDTVGQYESHMAFTMPGLYRVVHGIDVFDPKFNIVSPGADMNLYFPYFEKEKRLTAYHPEIEELLFSDVENDEHMCVLKDRNKPIIFTMARLDRV KNLTGLVELYAKNPRLRELVNLVVVGGDRRKESKDLEEQAEMKKMYELIKTHNLNGQFRWISSQMNRVRNGELYRYIADTRGAFVQPAFYEAFGLTV VEAMTCGLPTFATNHGGPAEIIVHGKSGFHIDPYHGEQAAELLADFFERCKKEPSHWEAISEGGLKRIQEKYTWQIYSDRLLTLAAVYGFWKHVSKL

DRLEIRRYLEMFYALKFRKLAEAVPLAVE

SEQ ID NO: 26: Polynucleotide sequence of NtSUS5-S
atggcctcaacagttgctgatagcatgcctgatgctttgaaacaaagccggtatcatatgaagagatgcttcgctaggtgaacacccttcttttatg tttttttcccctctacgtgtttatgtcaaatttccatgcataatgctaactactttcttcttttttgacttcaaaattggatgtgaaaggttcattgc aatgggaaggaggctaatgaagttgaaacatttaacagaagaaatagaagaaactattgaagacaaggcagaaagaaccaggattttggagggttca cttggaaaaattatgagttccacacaggtcagcaccatttaaccaacttagttgaacaggaaaaaaagaaaaagcaaaagagttattgcaaggcgta acgattttctttgaaattttcaggaggcagctgttgttccaccttatgttgcttttgcagtaaggcacaatcctggcttctgggattatgtcaaagt taacgctgaaactctctctgtggaagctatttcagccagggaatatctcaaattcaaagagatgatctttgacgaagactggtaagtggaaaattgt atcattttaaagagaaacaattttgtaacatacaagaatagtttgatggttgaatgtgcaagcagggcaaaggatgataatgcactggaagtagat tttggtgcttttgactactctaatcctcggttagcccttcctcttctgtcggaaatgggctcaacttatctcaaagttctgtcttcaaagtttg gtggaaagccagaggacgcccagcctttgcttgattacttactagctcttaatcatcaaggagaggtatgaaaatggactacctttgtttcttaaag gtattatataatgatgcgcgttataaagttcctttttaaattgaaactttgcagaatctaatgatcaatgagaatctgaatggtgttgctaagcttc aagcagcattgatagtagctgaagttttgtatcttcctttcccaaagacacacacctataaagactttgagcataagtaagcttctcatatgcttcc attgtcatatgcagtataccaatgacatgctaccgaaaagttgtttatgtttgtgacttgattatgaaaactctaggctcaaagaatggggctttga taaagggtggggtcacaatgcaggaagagtaagagagacaatgagactgcttccgagataatccaagcaccagatcccataaatatggagtcctttt
```

```
ttcagcaagcttcctactacattcaacattgttatcttctccattcatggttactttggccaagcagatgtccttggtctgcccgatactggaggcc
aggtctacatatacagcaatttatctccttttgcctcatattgcttattagcgacacttgcatcattgaaatcagacttttacttcacaggttgttt
atattctggatcaagtaagggctttagaggaggaaatgttacaaagaatcaagcagcaagggctaaacgtgaagcccaagattcttgtggtgagttt
tgcaaaaatatgcttagacaggttttgagattgatcggagaagggattaagatgatcaagatctttgttcctgctttcatgatgtaaacaggtatc
tcgtctcataccagatgctcgagggacaacatgcaatcaggagatgaaccttattcttaactcatcccattctcacatcctgagaattccattcagg
actgagaaggagttcttcgccaatgggtttctcggtttgatatctatccttacttggagaactatgccaaggcaagtcttctaacaaaattaccac
ctattcatacactttatttactttcttgaactaatcgtttggtttgtgacgtatatcattaggatgcttctgctaagatacttgagctcatggaagg
taaaccagacctcataattgggaactacactgatggaaatttagtggcatctctattggccaacaaacttggagttactcaggttccgtagctgatc
atatgatcatattttctacattgtttcttgataattaaatgaaatcttattggatgataacattttagggaaccattgctcatgcattagagaaaa
ctaagtatgaagattctgatgtgaagtggaagcagtttgatcccaagtaccacttttcttgccaatttactgccgatttattggcaatgaatgctgc
tgatttatcattaccagcacatatcaagaaatcgctggaaggttagcactgactctctcagtatatttggcaacttaatgaatttactgcagtggc
caacactaaaagctatcattcgtccttcagcgaaactaggcctggacaatatgaaagtcacacagcatttaccatgccggggctttatagagctgtt
tcaggcatcaatgtatttgatccaaagttcaacattgctgctcctggggctgaacagtctacctatttcccttcactgagaaacagaaacgattca
gcacatttcgtcctgctattaacgaattacttttacagtaatgaggaaaacaatgagcacatgtaagtctaattgcccattttcctaatctaaccatt
gcttaaatcgttctgttttaccggatgtgtggtacttatcagtaacatttttttttggatcagtggatttcttgcagaccggaaaaaaccaattat
attttcaatggcgagatttgatacagtgaagaacctgtcaggcttgactgagtggtatgggaagaataagaagttgcggaacttggtaaaccttgtt
attgttgggggattcttcgatccatcaaaatcaaaagaccgggaggaagcagctgaaatcaagaagatgcatgaattgattgagaaataccagctca
agggacaaatgagatggatagcagctcaaactgataaatatcgaaatagtgagctataccgaactattgctgacactaagggagcttttgtccaacc
ggctttatatgaagcttttggactaaccgttattgaagcaatggattgtggattgcctacgtttgcaactaatcaaggtggacctgcagaaatcatt
gttgatggggtttcaggtttccatattgatccttacaatggggacgaatcaagcaagaaaatagctgatttctttgagaagtgtaaggttgattcta
aatattggaacaggatatctgagggaggtctcaagcgcattgaagaatggtaacaaactagttccaagtttaaaaaatggaaaaatgcttatcatg
ttatattttcgtggttttaagttctgcttcgatgcagttatacgtggaagatttatgcaaacaaagtgttgaatatgggatcaatctatggattttg
gagacaattcaatgtggggcaaaagcaggctaagcaaagatactttgagatgttttacaatcctctcttcaggaaattggtaggttgtatatgttga
atacaatttactaagatcctcaaaatgaccaagaaatatacattgactatgctacttttgtaatttcacaggccaaaagcgtgccgatcccacatga
agagccattgccacttgcaacatcagactctactcaatcccaagaattaaaactaccactaccagttccagcagcagtagctaaagttctgccatta
acaaggcatgcttttaacttaattacttctctacctagagtaactggtaaagtggatgtcaagtga
```

SEQ ID NO: 27: Polypeptide sequence of NtSUS5-S
MASTVADSMPDALKQSRYHMKRCFARFIAMGRRLMKLKHLTEEIEETIEDKAERTRILEGSLGKIMSSTQEAAVVPPYVAFAVRHNPGFWDYVKVNA
ETLSVEAISAREYLKFKEMIFDEDWAKDDNALEVDFGAFDYSNPRLALSSSVGNGLNFISKVLSSKFGGKPEDAQPLLDYLLALNHQGENLMINENL
NGVAKLQAALIVAEVFVSSFPKDTPYKDFEHKLKEWGFDKGWGHNAGRVRETMRLLSEIIQAPDPINMESFFSKLPTTFNIVIFSIHGYFGQADVLG
LPDTGGQVVYILDQVRALEEEMLQRIKQQGLNVKPKILVVSRLIPDARGTTCNQEMEPILNSSHSHILRIPFRTEKGVLRQWDASAKILELMEGKPD
LIIGNYTDGNLVASLLANKLGVTQGTIAHALEKTKYEDSDVKWKQFDPKYHFSCQFTADLLAMNAADFIITSTYQEIAGSETRPGQYESHTAFTMPG
LYRAVSGINVFDPKFNIAAPGAEQSTYFPFTEKQKRFSTFRPAINELLYSNEENNEHIGFLADRKKPIIFSMARFDTVKNLSGLTEWYGKNKKLRNL
VNLVIVGGFFDPSKSKDREEAAEIKKMHELIEKYQLKGQMRWIAAQTDKYRNSELYRTIADTKGAFVQPALYEAFGLTVIEAMDCGLPTFATNQGGP
AEIIVDGVSGFHIDPYNGDESSKKIADFFEKCKVDSKYWNRISEGGLKRIEECYTWKIYANKVLNMGSIYGFWRQFNVGQKQAKQRYFEMFYNPLFR
KLAKSVPIPHEEPLPLATSDSTQSQELKLPLPVPAAVAKVLPLTRHAFNLITSLPRVTGKVDVK SEQ ID NO: 28: Polynucleotide sequence of NtSUS5-T
atggcctcaactgttgctggtagcatgcctgatgctttgaaacaaagccgatatcatatgaagagatgcttcgctaggtgaacaccttcttgttct
ttttgttttttccctctaccatttatgtcaaatttcaatgcataatgctaactactttttttcttttgacttcaaaattggacgtgaaaggtteat
tgcaatgggaaggaggttgatgaagctgaaacattcaacagaagaaatagaaaaaactattgaagacaaggcagaaagaaccaagattttggaggt -continued

SEQUENCE LISTING

```
tcacttggaaaaattatgagttccacacaggtcagcaccatttaaccaacttaattgaataggaagaaaaaaaaaagcaaaagagttattgcaaggc
gtaacgatttcctttgaaattttcaggaggcagctgttgtcccacctatgttgcttttgcagtaaggcacaatcctggcttctgggattatgtcaa
agttgacgctgaaactctctctgtggaagctatttcagccagggactatctcaaattcaaagagatgatctttgatgaagattggtaactggaagat
tgtatcatttaaagaaacaatttttaatattcaagattagttttgatggttgaatgtgcaagcagggcaaaggatgaaaatgcactcgaagtaga
ttttggtgcttttgactactctaatcatcggttagcccttcctcttctgtcggaaatgggctaaacttcatctcgaaagttttgtcttcaaagttt
ggtggaaaggcagaagatgcccagcctttgcttgattacttactagctcttaatcatcaaggagaggtatggaaatggactaccttcctttcttaag
gaattatataatgatgtatgttataaagatcctttttaaacattgacactttgcagaatctaatgatcaatgagaatctgaatggcgtctctaagct
tcaagcagcattgatagtagctgaagttttttgtatcttcctttcccaaagacacaccttataaagactttgagcataagtaagcttttcaaacgctt
ctgttatcatatgcaatataccaagaatatgttgccttttgaaaagttgtttatgtttatgacttgataatgaaaatactaggctcaaagaatgggg
ctttgagaaagggtggggtcacaatgcaggaagagtaagagagacaatgagactgctttccgagataatccaagcgccagatcccataaatatggag
tocttttcagcaggcttoctactacattcaacattgttatottotocattcatggttacttggccaagcagatgtccttggtttgcccgatactg
gaggccaggtttacatacacagcaatttatctccttttgcctcatatttacttattagcgacacttgcattattgaaatcacatttgtatttaacag
gttgtttatattctggatcaagtaagagccttagaggaggaaatgttacaaagaatcaagcagcaagggttaaatgtgaagcccaagattcttgtgg
tgagttatgcaaaaatatgcgtagccaaggttttgaaattgttcagaggggattaagatgategagatatttgtttccttcttccattgatgtgtac
aggtcactcgtctcattccagatgctcgagggactacatgcaatcaggagatggaacctatacttaactcgtcccattctcacatcctgagaattcc
attcaggacagagaaaggagttcttcgccaatgggtttctcggtttgatatctatccttacttggagaactatgccaaggcaagtctcctaccaaaa
ttaccacctattcatacactttattcagttttttgagctaatcattctcatttgtcacgtatgtgattaggatgcttctgctaagatacttgagctc
atggaaggtaaaccagacctcattattgggaactacactgatggaaatttagtggcatctctattggccaacaaacttggagttactcaggttctac
agctgatcatttatctgatcagattttctacattgttttcttgataattaaacgaaatcttatgagattgtaacattttagggaaccattgctcat
gcattagagaaaaccaagtatgaagattctgatgtcaagtggaagcagtttgattccaagtaccacttttcttgccaattcactgccgatttattgg
caatgaatgctgctgatttttatcattaccagcacatatcaagaaatcgcaggaaggttagcactgactctctcagtatatttggcaacttaatgaat
gtactgcttgtggccaacactaaaagctattactcgtccttcagcgaaactaggcctggacaatatgaaagtcacacagcatttaccatgccggggc
tttatagagctgtttcaggcatcaatgtatttgatccaaagttcaacattgctgctcctggggctgaacagtctgcctatttcccttcactgagaa
acagaaacgattcagcgcgtttcgtcctgctattgaggaactactttacagtaatgagcaaaacaacgagcacatgtaagtctaattgccccattt
cctaatctaaccattgcttaaatgttctgttttacttgatatgtggtacttatcagtgatatttttattggaacagtggatttcttgcagaccgt
aaaaaaccaattatattttcaatggcaagatttgatacggtgaagaacttgtcaggcttgactgagtggtatgggaagaataagaagttgcggaact
tggttaacctcgttatcgttggggattcttcgatccatcaaaatcaaaagaccgggaggaagcagctgaaatcaagaagatgcatgaattgattga
gaaatacaagctcaagggacaaatgagatggatagcagctcaaactgataaatatcaaaacagtgagctatatcgaactattgctgacactaaagga
gctttcgtccaaccggctttatatgaagcttttggactaactgttattgaagcaatgaattgtggactgcctacatttgctactaatcaaggcggac
ctgcagaaatcattgttgatggggtttcaggcttccatattgatccttacaatggggatgaatcgagcaagaaaatagctgatttctttgagaagtg
taaggttgattctaaatattggaacaagatatgtggaggaggtctcaagcgcattgaagaatggtaa
```

SEQ ID NO: 29: Polypeptide sequence of NtSUS5-T
MASTVAGSMPDALKQSRYHMKRCFARFIAMGRRLMKLKHLTEEIEKTIEDKAERTKILEGSLGKIMSSTQEAAVVPPYVAFAVRHNPGFWDYVKVDA ETLSVEAISARDYLKFKEMIFDEDWAKDENALEVDFGAFDYSNHRLALSSSVGNGLNFISKVLSSKFGGKAEDAQPLLDYLLALNHQGENLMINENL NGVSKLQAALIVAEVFVSSFPKDTPYKDFEHKLKEWGFEKGWGHNAGRVRETMRLLSEIIQAPDPINMESFFSRLPTTFNIVIFSIHGYFGQADVLG LPDTGGQVVYILDQVRALEEEMLQRIKQQGLNVKPKILVVTRLIPDARGTTCNQEMEPILNSSHSHILRIPFRTEKGVLRQWDASAKILELMEGKPD LIIGNYTDGNLVASLLANKLGVTQGTIAHALEKTKYEDSDVKWKQFDSKYHFSCQFTADLLAMNAADFIITSTYQEIAGSETRPGQYESHTAFTMPG LYRAVSGINVFDPKFNIAAPGAEQSAYFPFTEKQKRFSAFRPAIEELLYSNEQNNEHIGFLADRKKPIIFSMARFDTVKNLSGLTEWYGKNKKLRNL
VNLVIVGGFFDPSKSKDREEAAEIKKMHELIEKYKLKGQMRWIAAQTDKYQNSELYRTIADTKGAFVQPALYEAFGLTVIEAMNCGLPTFATNQGGP
AEIIVDGVSGFHIDPYNGDESSKKIADFFEKCKVDSKYWNKICGGGLKRIEEW SEQ ID NO: 30: Polynucleotide sequence of NtSUS6-S
atggctactgcaccagccctaaatagatcagagtccatagctgatagcatgccagaggccttaaggcaaagccggtaccacatgaagaaatgttttg
ccaagtacatagagcaaggaaagaggatgatgaaacttcataacttgatggatgagttggagaaagtaattgatgatcctgctgaaaggaaccatgt
tttggaaggcttacttggctacatatatgcactacaatggtatagctagattcatatgtacttatgatgcccttatattgtttcctgatgtattac
tcttaaaaccttctttgatcaaatttacaggaggctgcagttgttcctccctacattgcctttgccacgagacagaatcctggattctgggaatatg
tgaaagtgaatgctaatgatctttctgttgagggtattacagctacagaatacttgaaattcaaggaaatgatagttgatgaatgctggtatagtat
acgttgcagcttatcatacctttgtggttttataacttcaatcagaaaactcatcagagttacctttgtgtgaacatgaaatgcagggcaaaagat
gaatatgcactggaaattgattttggagcagtagacttctcaacgcctcgactgacccctatcctcttcaattggcaatggtctcagttatgtttcca
agtttctaacttcaaagctaaatgctacctccgcgagtgcacagtgtctggttgactacttgctcactttgaatcatcaaggagatgtacgtcaaca
aaaatcaaactccataagtaaacttgtcaactctaagaagaaaaaatagggaaaagaagattcacgtaacaaattttctttatgttcaactgcagaaa
ctgatgatcaatgagacactcagcactgtctcaaagcttcaggctgcactggttgtagcagaagcatctatttcctctttaccaacagatacaccat
atgagagctttgagctaaggtgatttgttttttcctctacttccctccacttgtgccatgctacgtagtactaagtaacttcaattcttgtaaagat
tcaaacagtggggttttgagaaaggatggggtgatacagctgaaagggtcagcgacaccatgagaacactgtctgaggtgcttcaggcaccagatcc
attgaacattcagaagttctttggaagggttccaactgttttcaatattgtattgttctctgtccatggatactttggccaagcagatgttcttggc
ttgccagacactggtggtcaggtaagcatttaatagctttacatttaacttctatgcattgacaataaaataatttttaacagtttgaccacttct
gctcttgttcaacaggtagtttatgttttggatcaagttgtagcttttgaagaagaaatgctacaaagaattaaacagcagggctcaatattaagc
ctcaaattcttgtggtgagttcctagacaatcgacgtgactatgcaattatgtagaggctgtttagaaaagttaatatcatatgttgattgcacagt
taacccgactgattccggatgcaaaaggaacaaagtgcaaccaggaactagaaccaatcaagaatacaaaacattcacacatcctcagagttccatt
taggacagaaaaaggagtgcttaatcaatgggtttcacgatttgatatctatccatatctggagagatatactcaggtatgtattttatatcaacc
ttgctcatcaaagatgtgttgtttcctcaattccattttttcccttggcaaaaggatgctgctgacaaaatcgtcgagctaatggaaggcaaacctg
atctaatcattggtaactacactgatgggaatctagtggcttcactaatggctagaaaacttgggataactctggtaacttttcttaatcatatttg
atgttgcttcttctccaagttagttcttaatctccactgacctagaccatctttgcaacagggaactattgctcatgctttggagaagacaaaatat
gaagactctgacataaaattgaaggaactcgatccgaagtaccacttctcttgccaattcacagctgatttgattgcaatgaattcagcagatttca
ttatcactagcacataccaagaaatagctggaaggtaagaattagagctaataagtaatgcattcatatgtatttcagcatcgctctttcaccatca
tcgaatacacaccactactcagtaaatgtatttgctcaaaagtttgcaacttaatggatctcattcttgaatgcttcaacatatgcagcaaagataa
accaggacagtatgagagccatagtgcatttacccttccagggctttacagagttgcttcaggtatcaatgtctttgatccaaaatttaatattgct
gcacctggggcagaccagtcggtgtatttcccttacacagaaaagcagaagcgtttgactgctttccgcccctgccattgaggaactgcttttagta
aagtggacaatgacgagcacgtgtaagtctaagtgttaaacttcagcttagtgcctagaacatcccactgctctatgtattgatgtttcacttgttt
caaacagtggatatttagaagacagaaagaaacctatcctgtttaccatggcaaggctggacacagtgaagaacacatctggactaacagaatggta
tggcaagaacaagaggctcagaagcttagttaaccttgttgtggttggtggttcctttgatcctacaaaatccaaggatagggaagaagcagctgaa
ataaaaaagatgcacatgctgatagagaaataccagcttaagggtcagattagatggatagcagctcagactgacagatacagaaatagtgaactct
accgcacaatagcagattccaaggagcttttgtgcagcctgcattgtatgaagcatttggtctaacagtcattgaggcaatgaactgtggattacc
aaccctttgctaccaaccaaggtggccctgctgagattattgttgatggggtctcaggcttcatattgatccaaataatggggatgaatcaagcaac
aaaattgccaacttttttccaaaaatgcagggaggatcctgagtattggaacaggatttcagtccagggtctaaaccgtatatgaatggtaactca
cagataagccattcaaattgcaaagaggcacatatcttgcagaaaatttcttaatccttaaatcctaatttttgcagttacacatggaagatctat
gcaaacaaggtattgaatatggggtccatctatacttttttggaggacattgtacagagatcagaaacaagcaaagcaaagatacatgagaettttct -continued

SEQUENCE LISTING

```
acaatcttgagtttaggaacttggtatagtgctgcatgacattgacagtataccacaaacatctttatgagatgaattacttttaataaaattgttt
ttaacctttgcttccttaatggcacttattgcaggtaaaaaatgtgcctatcagaaaggacgaaacaccacaaggaccaaaggagagggagaaagtt
aagccacagatatcacaaaggcatgctctaaagcttttgcctacagttttcaagagaccctagtatattctagtactaaattagaattatacagca
tgcagcttttgctgttcacctttctaaatcaccagttgtgtcaatcaagttgacaaaatcaataaattgggattttcccttcctatgcttgattgt
tattactcctactttgtttatggtagtcttccttcattgtttctcctgtacttcttttactacaactgtactgacatactaattatttctgtgtac
caggcgctcacaatcaaggttgcagaagtaagattagataaaattgctactgcatga
```

SEQ ID NO: 31: Polypeptide sequence of NtSUS6-S
```
MATAPALNRSESIADSMPEALRQSRYHMKKCFAKYIEQGKRMMKLHNLMDELEKVIDDPAERNHVLEGLLGYILCTTMEAAVVPPYIAFATRQNPGF
WEYVKVNANDLSVEGITATEYLKFKEMIVDECWAKDEYALEIDFGAVDFSTPRLTLSSSIGNGLSYVSKFLTSKLNATSASAQCLVDYLLTLNHQGD
KLMINETLSTVSKLQAALVVAEASISSLPTDTPYESFELRFKQWGFEKGWGDTAERVSDTMRTLSEVLQAPDPLNIQKFFGRVPTVFNIVLFSVHGY
FGQADVLGLPDTGGQVVYVLDQVVAFEEEMLQRIKQQGLNIKPQILVLTRLIPDAKGTKCNQELEPIKNTKHSHILRVPFRTEKGVLNQWVSRFDIY
PYLERYTQDAADKIVELMEGKPDLIIGNYTDGNLVASLMARKLGITLGTIAHALEKTKYEDSDIKLKELDPKYHFSCQFTADLIAMNSADFIITSTY
QEIAGSKDKPGQYESHSAFTLPGLYRVASGINVFDPKFNIAAPGADQSVYFPYTEKQKRLTAFRPAIEELLFSKVDNDEHVGYLEDRKKPILFTMAR
LDTVKNTSGLTEWYGKNKRLRSLVNLVVVGGSFDPTKSKDREEAAEIKKMHMLIEKYQLKGQIRWIAAQTDRYRNSELYRTIADSKGAFVQPALYEA
FGLTVIEAMNCGLPTFATNQGGPAEIIVDGVSGFHIDPNNGDESSNKIANFFQKCREDPEYWNRISVQGLNRIYECYTWKIYANKVLNMGSIYTFWR
TLYRDQKQAKQRYIETFYNLEFRNLVKNVPIRKDETPQGPKEREKVKPQISQRHALKLLPTVFQETLALTIKVAEVRLDKIATA
```

SEQ ID NO: 32: Polynucleotide sequence of NtSUS6-T
```
atggctactgcaccagccctgaaaagatcagagtccatagctgatagcatgccagaggccttaaggcaaagccggtaccacatgaagaaatgttttg
ccaagtacatagagcaaggcaagaggatgatgaaacttcataacttgatggatgaattggagaaagtaattgatgatcctgctgaaaggaaccatgt
tttggaaggcttacttggctacatatattgtactacaatggtatagctagattcatatgtacttatgatgtccttatattgtttccggaggcattat
tcttaaatccttctttgatcaaatttgtaggaggctgcagttgttcctccctatattgccttcgccacgagacagaatcctggattctgggaatatg
tgaaagtcaatgctaatgatctttctgttgagggtattacagctacagattacttgaaattcaaggaaatgatagttgatgaaagctggtatagaat
actttgcagcttateataccttttgtggttttataatttcaatcagaaaactcatcagagttaccttttgtgtgaacatgacatgcagggcaaaagat
gaatatgcactggaaattgattttggagcagtagacttctcaacgcctcgactgacccctatcctcttcaattggaaatggtctcagttatgtttcca
agtttctaacttcaaagctaaatgctacctcagcgagtgcacagtgtctggttgactacttgctcactttgaatcaccaaggagatgtacgtcaaca
aaaatcaaactccataagtaaacttgtcaactctaagaagtaaaaataggaaaagaagattcatgtaacaaattttctttatgttcaactgtagaaa
ctgatgatcaatgagacactcggcactgtctcaaagcttcaggctgcactggttgtagcagaagcatctatttcctccttaccaacagatacaccat
accagagctttgagctaaggtgatttgttttttcctctacttccttccacttttggtgtgctacatagtactaagtaacttcaattcttgtaaagat
tcaaacagtggggttttgagaaaggatggggtgatacagctgaaagggtccgcgacaccatgagaacactttctgaggtacttcaggcgccagatcc
attgaacattgagaagttctttggagggttccaactgttttcaatattgtattgttctctgttcatggatactttggccaagcaaatgttcttggc
ttgccagacacaggtggtcaggtaagcatctaatagcttttacatttaacttctatgcattgacaataaaataacttctacactaccaaataattttt
tgaaagtttgaccacttcggctcttgttcaacaggtggtttatgttttggatcaagttgtagcttttgaagaagaaatgctccaaagaattaaacag
caggggctcaatattaagcctcaaattcttgtggtgagctcctagacaatgacgtgactatgcaattaagtagaggctgtttagaaaagttaatatc
atatgttgattgcacagttaacccgactgattccggacgccaaaggaacaaagtgcaaccaggaactagaaccaatcaagaatacaaaacattcaca
catcctcagagttccatttaggacagaaaaaggagtgcttaatcaatgggtttcacgatttgatatctatccatatctggagagatatactcaggtg
tgtattttatatcaaccctgctcatcaaagatgtgttgtttcctcaattccattttcgccttgacaaaaggaegetgctgacaaaatcategagc
taatggaaggcaaacctgatctaatcattggtaactacactgatgggaatctagtggcttctctaatggctagaaagcttgggataactctggtaac
ttttcttatcatatttgatgttgtttcttctccaagttggttcttaatgtcaactaacccagaccatctttgtaacagggaactattgctcatgctc
tggagaagacaaaatatgaagactctgacatcaaattgaaggaactcgatccgaagtaccacttttcttgccaattcacagctgatttgattgcaat
```

SEQUENCE LISTING

```
gaattcagcagatttcattatcacaagcacatatcaagaaatagccggaaggtaagaattggaactacggaagcagagagctaataagtagtgcact
catatatttcagcatcgctctttcgcataatcgaatacacaccactactcagtaaatgtacttgctcaaaagtttacaagtttatggatcttattct
tgaatgcttcaacatatgcagcaaagataggccaggacagtatgagagcatagtgcatttaccctttccagggctttacagagttgcttcaggcatc
aatgtctttgatcctaaatttaatattgctgcacctggggcagaccaatcggtgtatttcccttacacagaaaagcagacgcgtttgactgctttcc
gccctgccattgaggaactgcttttagtaaagtggacaatgacgagcacatgtaagtcttagtgttaaacttcagctttcagcttagtgcctagaa
cattccactggctctatgtattaatgtttcacttgtttcaaacacagtggatatttagaagacagaaagaaacctatcctgtttaccatggcaaggc
tggacacagtgaagaacacatctggactaacagaatggtatggcaagaacaagaggctcagaagcttagttaaccttgttgtggttggtggttcctt
tgatcctacaaaatccaaggatagagaagaagcagctgaaataaaaaagatgcacatgctgatagagaaataccagcttaagggtcagatcagatgg
atagcagctcagactgacagatatagaaacagtgaactctaccgcacaatagcagattccaaaggagcttttgtgcagcctgcattatatgaagcat
ttggtctaacagtcattgaggcaatgaactgtggattaccaacctttgctaccaaccaaggtggccctgctgagattattgttgatggggtctcagg
ctttcatattgatccaaataatgggatgaatcaagcaacaaagttgccaacttttccaaaaatgcagggaggatcctgagtattggaacaggatt
tcagtccagggtctaaaccgtatatatgaatggtaactcacagataagccattcaaattgcaaagaggcacatatcttgctgaaaatttcttaatcc
tttaatcctaaaattttgcagttacacatggaagatatgcaaacaaggtattgaatatggggtccatctatacttttggaggacattgtacaga
gatcagaaacaagcaaagcaaagatacatcgagaaettctacaatcttgagtttaggaacttggtatagtgctgcatgacattgacagtataccaca
aacatctttatgagatgaattacttttaataaaattgtttttaacctttgcctccttaatgacacttattgcaggtaaaaaatgtgcctatcagaca
ggacgaaacaccacaaggaccaaaggagaggagggagaaagttaagccacagatatcacaaaggcatgctctaaagcttttgcctatagttttcag
gagaccctagtatattctagtactaaattagaattatacagcatgcagcttgcttctgctgttcacctttctaaatcaccagttatgtcaatcaagt
tgacaaaatcaataaattcggcttttcccttcctatgcttgattgttattactcctacttcgtttatggtagtcttccttcattgttttctcctgt
acttcttttactacaactgtactga
```

SEQ ID NO: 33: Polypeptide sequence of NtSUS6-T
MATAPALKRSESIADSMPEALRQSRYHMKKCFAKYIEQGKRMMKLHNLMDELEKVIDDPAERNHVLEGLLGYILCTTMEAAVVPPYIAFATRQNPGF
WEYVKVNANDLSVEGITATDYLKFKEMIVDESWAKDEYALEIDFGAVDFSTPRLTLSSSIGNGLSYVSKFLTSKLNATSASAQCLVDYLLTLNHQGD
KLMINETLGTVSKLQAALVVAEASISSLPTDTPYQSFELRFKQWGFEKGWGDTAERVRDTMRTLSEVLQAPDPLNIEKFFGRVPTVFNIVLFSVHGY
FGQANVLGLPDTGGQVVYVLDQVVAFEEEMLQRIKQQGLNIKPQILVLTRLIPDAKGTKCNQELEPIKNTKHSHILRVPFRTEKGVLNQWVSRFDIY
PYLERYTQDAADKIIELMEGKPDLIIGNYTDGNLVASLMARKLGITLGTIAHALEKTKYEDSDIKLKELDPKYHFSCQFTADLIAMNSADFIITSTY
QEIAGSKDRPGQYESHSAFTLPGLYRVASGINVFDPKFNIAAPGADQSVYFPYTEKQTRLTAFRPAIEELLFSKVDNDEHIGYLEDRKKPILFTMAR
LDTVKNTSGLTEWYGKNKRLRSLVNLVVVGGSFDPTKSKDREEAAEIKKMHMLIEKYQLKGQIRWIAAQTDRYRNSELYRTIADSKGAFVQPALYEA
FGLTVIEAMNCGLPTFATNQGGPAEIIVDGVSGFHIDPNNGDESSNKVANFFQKCREDPEYWNRISVQGLNRIYECYTWKIYANKVLNMGSIYTFWR
TLYRDQKQAKQRYIETFYNLEFRNLVKNVPIRQDETPQGPKERREKVKPQISQRHALKLLPIVFQETLVYSSTKLELYSMQLASAVHLSKSPVMSIK
LTKSINSAFPFPMLDCYYSYFVYGSLPSLFSPVLLLLQLY

The invention claimed is:

1. A *Nicotiana tabacum* plant cell comprising a non-natural modification to reduce expression or activity of one or both of a polynucleotide having at least 95% sequence identity to SEQ ID NO:5 and a polynucleotide having at least 95% sequence identity to SEQ ID NO:7, as compared to a control plant cell in which the plant cell has not been modified to modulate expression or activity of the one or both polynucleotides.

2. The *Nicotiana tabacum* plant cell of claim 1, wherein the reduced expression or reduced activity reduces the level of one or more of glucose or fructose and/or increases the level of sucrose in cured leaf of a plant comprising the plant cell as compared to the level of the one or more of glucose or fructose in cured leaf of a control plant containing the control plant cell.

3. The *Nicotiana tabacum* plant cell of claim 2, wherein a mid-position cured leaf has reduced levels of glucose of at least about 63% as compared to a control mid-position cured leaf; or
wherein a mid-position cured leaf has reduced levels of fructose of at least about 43%, respectively, as compared to a control mid-position cured leaf, or
wherein a mid-position cured leaf has reduced levels of glucose of at least about 63% and reduced levels of fructose of at least about 43%, respectively, as compared to a control mid-position cured leaf.

4. The *Nicotiana tabacum* plant cell of claim 1, wherein the non-natural modification to the plant cell comprises an edit to a gene encoding the polypeptide having at least 95% sequence identity to SEQ ID NO:6 and/or a gene encoding the polypeptide having at least 95% sequence identity to SEQ ID NO:8.

5. The *Nicotiana tabacum* plant cell of claim 4, wherein the edit to the gene encoding the polypeptide having at least 95% sequence identity to SEQ ID NO: 6 and/or the gene encoding the polypeptide having at least 95% sequence identity to SEQ ID NO:8 comprises an edit introduced by genome editing selected from CRISPR-mediated genome editing, zinc finger nuclease-mediated mutagenesis, chemical or radiation mutagenesis, homologous recombination, oligonucleotide-directed mutagenesis and meganuclease-mediated mutagenesis.

6. The *Nicotiana tabacum* plant cell of claim 1, wherein the non-natural modification comprises introduction of an interference polynucleotide or a polynucleotide encoding the same into the plant cell, wherein the interference polynucleotide has a sequence complementary to at least a portion of an RNA transcript encoding the polypeptide having at least 95% sequence identity to SEQ ID NO: 6 and/or the polypeptide having at least 95% sequence identity to SEQ ID NO: 8.

7. The plant cell according to claim 1, further comprising at least one modification in a NtSUS polynucleotide or polypeptide encoded thereby,
 wherein the NtSUS polynucleotide or polypeptide encoded thereby comprises NtSUS2-T, NtSUS3-S, NtSUS3-T, NtSUS4-S, NtSUS4-T, or a combination of two or more thereof, or
 wherein the NtSUS polynucleotide or polypeptide encoded thereby comprises NtSUS2-S, NtSUS3-S, NtSUS3-T, NtSUS4-S, or a combination of two or more thereof.

8. A plant or part thereof comprising the plant cell according to claim 1.

9. Plant material, cured plant material, or homogenized plant material, derived or obtained from the plant or part thereof of claim 8;
 wherein the plant material comprises biomass, seed, stem, flowers, leaves, or a combination of two or more thereof; or
 wherein the cured plant material comprises flue-cured plant material, sun-cured plant material, air-cured plant material, or a combination of two or more thereof.

10. A tobacco product comprising the plant cell of claim 1.

11. A method for producing the plant of claim 8, comprising the steps of:
 (a) providing the plant cell comprising the at least one modification; and
 (b) propagating the plant cell into a plant.

12. A method for producing cured plant material with a reduced amount of reducing sugars and/or an increased amount of sucrose as compared to control plant material, comprising the steps of:
 (a) providing a plant or part thereof according to claim 8;
 (b) harvesting plant material therefrom; and
 (c) curing the plant material.

13. A method of producing a liquid tobacco extract, the method comprising the steps of:
 (a) preparing a first tobacco starting material from a plant or part thereof containing a plant cell according to claim 1;
 (b) preparing a second tobacco starting material from a plant or part thereof containing a plant cell comprising at least one modification in a NtSUS polynucleotide or polypeptide encoded thereby,
 wherein the NtSUS polynucleotide or polypeptide encoded thereby comprises NtSUS2-T, NtSUS3-S, NtSUS3-T, NtSUS4-S, NtSUS4-T or a combination of two or more thereof, or
 wherein the NtSUS polynucleotide or polypeptide encoded thereby comprises NtSUS2-S, NtSUS3-S, NtSUS3-T and NtSUS4-S or a combination of two or more thereof;
 (c) heating the first tobacco starting material at a first extraction temperature;
 (d) heating the second tobacco starting material at a second extraction temperature;
 (e) collecting one or more volatile compounds released from the first tobacco starting materials and second tobacco starting materials during heating; and
 (f) combining the collected volatile compounds released from the first and second tobacco starting materials and forming a liquid tobacco extract from the combined volatile compounds.

14. A method for producing a *Nicotiana tabacum* plant cell in which the level of one or more reducing sugars is reduced and/or the level of sucrose is increased when the plant or a portion thereof comprising the cell is cured, comprising:
 subjecting the plants to a mutagenesis process to produce mutated plants comprising a mutated cell;
 subjecting the mutated plants or portions thereof to an assay to determine the level or activity of a polypeptide when the plants or portions thereof are cured;
 selecting the mutated plants for which the assay indicates the mutated plants or portions thereof have a reduced level or activity of the polynucleotide or a polypeptide encoded by the polynucleotide when the mutated plants or portions thereof are cured,
 wherein the polynucleotide comprises a sequence having at least 95% sequence identify to SEQ ID NO: 5 or SEQ ID NO:7 or the polypeptide comprises a sequence having at least 95% sequence identity to SEQ ID NO: 6 or at least 95% sequence identity to SEQ ID NO: 8.

15. The method of claim 14, wherein the mutagenesis process comprises introducing an edit into the genome of the one or more cells by genome editing selected from CRISPR-mediated genome editing, zinc finger nuclease-mediated mutagenesis, chemical or radiation mutagenesis, homologous recombination, oligonucleotide-directed mutagenesis and meganuclease-mediated mutagenesis.

16. A method for reducing the levels of reducing sugars and/or increasing sucrose of cured *Nicotiana tabacum* leaf, wherein the method comprises reducing the expression or activity of a polynucleotide, as compared to a control plant cell in which the expression or activity of the polynucleotide has not been modified, wherein the polynucleotide comprises a sequence having at least 95% identity to SEQ ID NO: 5 or SEQ ID NO: 7.

17. The method of claim 16, wherein the polynucleotide comprises a sequence identical to SEQ ID NO: 5 or SEQ ID NO: 7.

18. The method of claim 16, wherein the leaf is a leaf of a *Nicotiana tabacum* plant variety Virginia and dark tobacco.

* * * * *